US010493137B2

(12) United States Patent
Ishibashi et al.

(10) Patent No.: US 10,493,137 B2
(45) Date of Patent: Dec. 3, 2019

(54) IMMUNE RESPONSE INDUCER

(71) Applicant: TORAY INDUSTRIES, INC., Tokyo (JP)

(72) Inventors: Masaki Ishibashi, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 195 days.

(21) Appl. No.: 15/331,491

(22) Filed: Oct. 21, 2016

(65) Prior Publication Data

US 2017/0035868 A1   Feb. 9, 2017

Related U.S. Application Data

(62) Division of application No. 12/739,723, filed as application No. PCT/JP2008/069267 on Oct. 23, 2008, now Pat. No. 9,504,737.

(30) Foreign Application Priority Data

Oct. 25, 2007  (JP) ............... 2007-277240
Oct. 25, 2007  (JP) ............... 2007-277578
Oct. 25, 2007  (JP) ............... 2007-277611
Oct. 26, 2007  (JP) ............... 2007-279113

(51) Int. Cl.
*A61K 39/395*   (2006.01)
*A61K 39/00*    (2006.01)
*A61K 38/20*    (2006.01)
*A61K 38/21*    (2006.01)

(52) U.S. Cl.
CPC ........ *A61K 39/0011* (2013.01); *A61K 38/208* (2013.01); *A61K 38/212* (2013.01); *A61K 38/215* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 5,698,396 | A | 12/1997 | Pfreundschuh |
| 7,745,391 | B2 | 6/2010 | Mintz et al. |
| 2002/0197679 | A1* | 12/2002 | Tang ............. C07K 14/47 435/69.1 |

FOREIGN PATENT DOCUMENTS

| WO | WO 02/083876 A2 | 10/2002 |
|---|---|---|
| WO | WO 03/009814 A2 | 2/2003 |
| WO | WO 2004/024887 A2 | 3/2004 |
| WO | WO 2004/080148 A2 | 3/2004 |
| WO | WO 2005/040414 A1 | 5/2005 |

OTHER PUBLICATIONS

Domingues et al., ImmunoTargets and Therapy, 2018, vol. 7, pp. 35-49.*
Akiyoshi, "Cancer Vaccine Therapy Using Peptide Derived from Tumor-Rejection Antigens", Jpn. J. Cancer and Chemotherapy., vol. 24, No. 5, pp. 511-519, Mar. 1997.
Brass et al., "Translation initiation factor eIF-4gamma is encoded by an amplified gene and induces an immune response in squamous cell lung carcinoma", Human Molecular Genetics, vol. 6, No. 1, pp. 33-39, 1997.
Extended European Search Report issued in European Application No. 08840900.8 dated Dec. 13, 2010.
Gromley et al., "A novel human protein of the maternal centriole is required for the final stages of cytokinesis and entry into S phase", The Journal of Cell Biology, vol. 161, No. 3, pp. 535-545, May 12, 2003.
Guasch et al., "FGFR1 is fused to the centrosome-associated protein CEP110 in the 8p12 stem cell myeloproliferative disorder with t(8;9)(p12;q33)", Blood, vol. 95, No. 5, pp. 1788-1796, Mar. 1, 2000.
Gure et al., "Human Lung Cancer Antigens Recognized by Autologous Antibodies: Definition of a Novel cDNA Derived from the Tumor Suppressor Gene Locus on Chromosome 3p21.3", Cancer Research, vol. 58, pp. 1034-1041, Mar. 1, 1998.
Gure et al., "SSX: A Multigene Family with Several Members Transcribed in Normal Testis and Human Cancer", International Journal of Cancer, vol. 72, pp. 965-971, May 1, 1997.
Infante et al., "GMAP-210, A Cis-Golgi Network-associated Protein, Is a Minus End Microtubule-binding Protein", The Journal of Cell Biology, vol. 145, No. 1, pp. 83-98, Apr. 5, 1999.
Inoue et al., "How far was fertilization elucidated?", Protein, Nucleic Acid and Enzyme, Institute for Microbial Disease, vol. 50, No. 11, pp. 1405-1412, 2005 (Abstract only provided).
International Search Report dated Jan. 6, 2009 for International Application No. PCT/JP2008/069267.
Itoh et al., "Autoantigen frequently eliciting humoral immune response in patients with adult T cell leukemia", Int. J. Oncol., vol. 14, No. 4, pp. 703-708, Apr. 1999 (Abstract only provided).
Lee et al., "Two classes of proteins dependent on either the presence or absence of thyroid hormone for interaction with the thyroid hormone receptor", Mol Endocrinol, vol. 9, No. 2, pp. 243-254, Feb. 9, 1995 (Abstract only provided).
Ou et al., "CEP110 and ninein are located in a specific domain of the centrosome associated with centrosome maturation", Journal of Cell Science, vol. 115, pp. 1825-1835, Feb. 16, 2002.
Scanlan et al., "Characterization of Human Colon Cancer Antigens Recognized by Autologous Antibodies", International Journal of Cancer, vol. 76, pp. 652-658, Jan. 5, 1998.

(Continued)

*Primary Examiner* — Yunsoo Kim
(74) *Attorney, Agent, or Firm* — Birch, Stewart, Kolasch & Birch, LLP

(57) ABSTRACT

An immunity-inducing agent comprising as an effective ingredient a specific polypeptide is disclosed. These polypeptides were isolated, by the SEREX method using a cDNA library derived from canine testis and serum from a cancer-bearing dog, as a polypeptide which binds to an antibody existing specifically in serum derived from a cancer-bearing living body. The polypeptides can induce immunity in a living body and cause regression of a tumor in a cancer-bearing living body. Therefore, these polypeptides are especially effective as a therapeutic and/or prophylactic agent for a cancer(s).

14 Claims, 5 Drawing Sheets

Specification includes a Sequence Listing.

(56) References Cited

OTHER PUBLICATIONS

Tanaka et al., "Cloning and Characterization of the human Calmegin gene encoding putative testis-specific chaperone", Gene, vol. 204, pp. 159-163, 1997.
Tureci et al., "The SSX-2 Gene, Which is Involved in the t(X;18) Translocation of Synovial Sarcomas, Codes for the Human Tumor Antigen HOM-MEL-40", Cancer Research, vol. 56, pp. 4766-4772, Oct. 15, 1996.
U.S. Notice of Allowance for U.S. Appl. No. 12/739,723, dated Jul. 21, 2016.
U.S. Office Action for U.S. Appl. No. 12/739,723, dated Apr. 27, 2012.
U.S. Office Action for U.S. Appl. No. 12/739,723, dated Jan. 23, 2015.
U.S. Office Action for U.S. Appl. No. 12/739,723, dated Jan. 24, 2013.
U.S. Office Action for U.S. Appl. No. 12/739,723, dated Jul. 19, 2012.
U.S. Office Action for U.S. Appl. No. 12/739,723, dated May 27, 2015.
U.S. Office Action for U.S. Appl. No. 12/739,723, dated May 7, 2013.
U.S. Office Action for U.S. Appl. No. 12/739,723, dated May 8, 2014.
U.S. Office Action for U.S. Appl. No. 12/739,723, dated Nov. 13, 2015.
U.S. Office Action for U.S. Appl. No. 12/739,723, dated Sep. 18, 2014.

* cited by examiner

SEQUENCE LISTING

```
<160> NUMBER OF SEQ ID NOS: 47

<210> SEQ ID NO 1
<211> LENGTH: 1508
<212> TYPE: DNA
<213> ORGANISM: Canis familiaris
<220> FEATURE:
<221> NAME/KEY: CDS
<222> LOCATION: (17)..(937)

<400> SEQUENCE: 1
gcggcccggg cgggac atg gcg gcg ctc tac gcc tgc acc aag tgc cac cag        52
               Met Ala Ala Leu Tyr Ala Cys Thr Lys Cys His Gln
                 1               5                  10 cgc ttc ccc ttc gag gcg ctg tct cag ggg cag cag ctg tgc aag gaa         100
Arg Phe Pro Phe Glu Ala Leu Ser Gln Gly Gln Gln Leu Cys Lys Glu
         15                  20                  25 tgt cgg att gca cac cct gtt gtg aag tgc acc tac tgt aga act gag         148
Cys Arg Ile Ala His Pro Val Val Lys Cys Thr Tyr Cys Arg Thr Glu
     30                  35                  40 tac cag caa gag agt aaa acc aat aca ata tgc aaa aaa tgt gct cag         196
Tyr Gln Gln Glu Ser Lys Thr Asn Thr Ile Cys Lys Lys Cys Ala Gln
 45                  50                  55                  60 aat gtg cag tta tat gga acg ccc aaa cct tgt cag tac tgc aac ata         244
Asn Val Gln Leu Tyr Gly Thr Pro Lys Pro Cys Gln Tyr Cys Asn Ile
                 65                  70                  75 att gca gca ttt att ggc aac aaa tgc cag cga tgc acg aat tca gag         292
Ile Ala Ala Phe Ile Gly Asn Lys Cys Gln Arg Cys Thr Asn Ser Glu
             80                  85                  90 aag aag tat gga cca cca tat tca tgt gaa cag tgt aaa caa cag tgt         340
Lys Lys Tyr Gly Pro Pro Tyr Ser Cys Glu Gln Cys Lys Gln Gln Cys
         95                 100                 105 gca ttt gac agg aaa gat gat aga aag aag gta gat ggg aaa ttg ctg         388
Ala Phe Asp Arg Lys Asp Asp Arg Lys Lys Val Asp Gly Lys Leu Leu
     110                 115                 120 tgt tgg ctg tgc aca ctt tca tac aaa cgg gtc ctt caa aag acc aaa         436
Cys Trp Leu Cys Thr Leu Ser Tyr Lys Arg Val Leu Gln Lys Thr Lys
125                 130                 135                 140 gag cag agg aaa cat ctg agc agc tct tcc cgt gcc agc cac cag gag         484
Glu Gln Arg Lys His Leu Ser Ser Ser Ser Arg Ala Ser His Gln Glu
                145                 150                 155 aag gaa cag tat cga ctg agt ggt ggc agc cat tat aac agc cag aaa         532
Lys Glu Gln Tyr Arg Leu Ser Gly Gly Ser His Tyr Asn Ser Gln Lys
            160                 165                 170 aca ctt tct acg tct tca att caa aat gaa atc cca aag aaa aaa tcc         580
Thr Leu Ser Thr Ser Ser Ile Gln Asn Glu Ile Pro Lys Lys Lys Ser
        175                 180                 185 aag ttt gag tca atc aca act aat gga gac agc ttt tcc cca gac ctg         628
Lys Phe Glu Ser Ile Thr Thr Asn Gly Asp Ser Phe Ser Pro Asp Leu
```

-continued

```
                        190                 195                 200
gct ctg gac tca cca ggc act gac cac ttt gtc atc att gcc cag ctg      676
Ala Leu Asp Ser Pro Gly Thr Asp His Phe Val Ile Ile Ala Gln Leu
205                 210                 215                 220 aag gaa gaa gtg gcc act ttg aag aag atg ctg cat caa aag gat caa      724
Lys Glu Glu Val Ala Thr Leu Lys Lys Met Leu His Gln Lys Asp Gln
                225                 230                 235 atg att tta gag aaa gag aag aag atc aca gag ttg aag gct gat ttt      772
Met Ile Leu Glu Lys Glu Lys Lys Ile Thr Glu Leu Lys Ala Asp Phe
            240                 245                 250 caa tac caa gaa tct cag atg aga gcc aaa atg aac cag atg gag aaa      820
Gln Tyr Gln Glu Ser Gln Met Arg Ala Lys Met Asn Gln Met Glu Lys
        255                 260                 265 act cac aaa gaa gtc aca gag caa ttg cag gcc aaa aac cga gaa ctc      868
Thr His Lys Glu Val Thr Glu Gln Leu Gln Ala Lys Asn Arg Glu Leu
    270                 275                 280 ctg aag cag gca gct gcc ttg tcc aag agc aag aag tca gag aag tca      916
Leu Lys Gln Ala Ala Ala Leu Ser Lys Ser Lys Lys Ser Glu Lys Ser
285                 290                 295                 300 gga gct ata act tct cca tga gagaccataa ggaggcttcc agccacagca         967
Gly Ala Ile Thr Ser Pro
                305 aaggggtttc ctgggttagg gttggtggcc tggctgttat ctgggaattg cccacgctcc   1027 cgggaagggc ctgtcccagt cggctctgcc ctaccgccgc agcgtcccca cctggctgaa   1087 gctgacgtcc gacgacgtga aggagcagat ctacaaactg gccaagaagg gtctgactcc   1147 ctcgcagatc ggtgtgatcc tgagagactc ccatggtgtt gcacaagtac gttttgtgac   1207 aggcaataaa atcttgagaa ttcttaagtc caagggactt gcacctgatc tccctgagga   1267 tctgtaccat ttgattaaga agctgttgc tgttcgaaag catcttgaga ggaacagaaa    1327 ggataaggat gccaaattcc gactgattct gattgagagc cgtattcacc gattggctcg   1387 atattataag accaaaagag ttctccctcc caattggaaa tacgagtcat ccacagcctc   1447 tgccctggtc gcataaattt ggctatgtac tcaagcaata aaatcattgt ctactagaaa   1507 a                                                                   1508
```

<210> SEQ ID NO 2
<211> LENGTH: 306
<212> TYPE: PRT
<213> ORGANISM: Canis familiaris

<400> SEQUENCE: 2

```
Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
                20                  25                  30

His Pro Val Val Lys Cys Thr Tyr Cys Arg Thr Glu Tyr Gln Gln Glu
            35                  40                  45

Ser Lys Thr Asn Thr Ile Cys Lys Lys Cys Ala Gln Asn Val Gln Leu
        50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Cys Ala Phe Asp Arg
            100                 105                 110
```

```
Lys Asp Asp Arg Lys Lys Val Asp Gly Lys Leu Leu Cys Trp Leu Cys
            115                 120                 125
Thr Leu Ser Tyr Lys Arg Val Leu Gln Lys Thr Lys Glu Gln Arg Lys
        130                 135                 140
His Leu Ser Ser Ser Arg Ala Ser His Gln Glu Lys Glu Gln Tyr
145                 150                 155                 160
Arg Leu Ser Gly Gly Ser His Tyr Asn Ser Gln Lys Thr Leu Ser Thr
                165                 170                 175
Ser Ser Ile Gln Asn Glu Ile Pro Lys Lys Ser Lys Phe Glu Ser
            180                 185                 190
Ile Thr Thr Asn Gly Asp Ser Phe Ser Pro Asp Leu Ala Leu Asp Ser
        195                 200                 205
Pro Gly Thr Asp His Phe Val Ile Ile Ala Gln Leu Lys Glu Glu Val
    210                 215                 220
Ala Thr Leu Lys Lys Met Leu His Gln Lys Asp Gln Met Ile Leu Glu
225                 230                 235                 240
Lys Glu Lys Lys Ile Thr Glu Leu Lys Ala Asp Phe Gln Tyr Gln Glu
                245                 250                 255
Ser Gln Met Arg Ala Lys Met Asn Gln Met Glu Lys Thr His Lys Glu
            260                 265                 270
Val Thr Glu Gln Leu Gln Ala Lys Asn Arg Glu Leu Leu Lys Gln Ala
        275                 280                 285
Ala Ala Leu Ser Lys Ser Lys Lys Ser Glu Lys Ser Gly Ala Ile Thr
    290                 295                 300
Ser Pro
305

<210> SEQ ID NO 3
<211> LENGTH: 2161
<212> TYPE: DNA
<213> ORGANISM: Homo sapiens
<220> FEATURE:
<221> NAME/KEY: CDS
<222> LOCATION: (103)..(1026)

<400> SEQUENCE: 3
gccgcagcca gcagcctgca gccgccgccg ggttgtgcct cagactgtca gataaatcgg    60
cgggccgggc cggcgggtcg gtgagcgcgg cccgggccgg ac atg gcg gcg ctc     114
                                              Met Ala Ala Leu
                                                1 tac gcc tgc acc aag tgc cac cag cgc ttc ccc ttc gag gcg ctg tct    162
Tyr Ala Cys Thr Lys Cys His Gln Arg Phe Pro Phe Glu Ala Leu Ser
 5                  10                  15                  20 cag ggg cag cag ctg tgc aag gaa tgt cgg att gca cac cct gtt gtg    210
Gln Gly Gln Gln Leu Cys Lys Glu Cys Arg Ile Ala His Pro Val Val
                 25                  30                  35 aag tgc acc tac tgc agg act gag tac cag cag gag agt aaa acc aat    258
Lys Cys Thr Tyr Cys Arg Thr Glu Tyr Gln Gln Glu Ser Lys Thr Asn
             40                  45                  50 aca ata tgc aag aaa tgt gct cag aac gtg cag ttg tat gga acg ccc    306
Thr Ile Cys Lys Lys Cys Ala Gln Asn Val Gln Leu Tyr Gly Thr Pro
         55                  60                  65 aaa cct tgt cag tat tgc aac ata att gca gca ttt att ggg aat aaa    354
Lys Pro Cys Gln Tyr Cys Asn Ile Ile Ala Ala Phe Ile Gly Asn Lys
     70                  75                  80 tgc cag cgc tgc aca aat tca gaa aag aag tat gga cca ccc tat tct    402
Cys Gln Arg Cys Thr Asn Ser Glu Lys Lys Tyr Gly Pro Pro Tyr Ser
 85                  90                  95                 100
```

```
tgt gaa cag tgc aag cag cag tgt gca ttt gac agg aaa gat gat aga      450
Cys Glu Gln Cys Lys Gln Gln Cys Ala Phe Asp Arg Lys Asp Asp Arg
            105                 110                 115 aag aag gta gat ggg aaa ttg ctg tgc tgg ctg tgc aca ctt tca tac      498
Lys Lys Val Asp Gly Lys Leu Leu Cys Trp Leu Cys Thr Leu Ser Tyr
        120                 125                 130 aaa cgg gtc ctt cag aag acc aaa gag cag agg aaa cac ctg agt agc      546
Lys Arg Val Leu Gln Lys Thr Lys Glu Gln Arg Lys His Leu Ser Ser
    135                 140                 145 tct tct cgt gct ggc cac cag gag aag gag cag tat agt cgc ctg agt      594
Ser Ser Arg Ala Gly His Gln Glu Lys Glu Gln Tyr Ser Arg Leu Ser
150                 155                 160 ggt ggt ggc cat tat aac agc cag aaa aca ctt tct aca tct tca att      642
Gly Gly Gly His Tyr Asn Ser Gln Lys Thr Leu Ser Thr Ser Ser Ile
165                 170                 175                 180 caa aat gaa atc cca aag aaa aag tcc aag ttt gag tca atc aca act      690
Gln Asn Glu Ile Pro Lys Lys Lys Ser Lys Phe Glu Ser Ile Thr Thr
                185                 190                 195 aat gga gac agc ttc tcc cca gac ctg gct ctg gac tca cca ggc act      738
Asn Gly Asp Ser Phe Ser Pro Asp Leu Ala Leu Asp Ser Pro Gly Thr
            200                 205                 210 gac cac ttt gtc atc att gcc caa ctg aag gaa gaa gtg gct acc ctg      786
Asp His Phe Val Ile Ile Ala Gln Leu Lys Glu Glu Val Ala Thr Leu
        215                 220                 225 aag aag atg ttg cat caa aag gat caa atg att tta gag aaa gag aag      834
Lys Lys Met Leu His Gln Lys Asp Gln Met Ile Leu Glu Lys Glu Lys
    230                 235                 240 aag att aca gag ttg aag gct gat ttt cag tac cag gaa tcg cag atg      882
Lys Ile Thr Glu Leu Lys Ala Asp Phe Gln Tyr Gln Glu Ser Gln Met
245                 250                 255                 260 aga gcc aaa atg aac cag atg gag aaa acc cac aaa gaa gtc aca gaa      930
Arg Ala Lys Met Asn Gln Met Glu Lys Thr His Lys Glu Val Thr Glu
                265                 270                 275 caa ctg cag gcc aaa aac cga gag ctc ctg aag cag gca gct gct ttg      978
Gln Leu Gln Ala Lys Asn Arg Glu Leu Leu Lys Gln Ala Ala Ala Leu
            280                 285                 290 tcc aag agc aag aag tca gag aag tca gga gct ata acc tct cca tga    1026
Ser Lys Ser Lys Lys Ser Glu Lys Ser Gly Ala Ile Thr Ser Pro
        295                 300                 305 cagacctcaa ggaggctccc tagcaacagc aaatggagtt gtccagggtt agggttggag   1086
acctggctgt tctgtgggaa ttgcaagctt tcttaagaaa tctctatttt attacagtta   1146
tccttctttg tgcgattgca gtgggctgaa tggaaacacc tggtttgtgc tgtgttagac   1206
tgcatgcttg agtgtttggg atttcaagct cgctctcttt ctctcactat taggactttt   1266 cttttcttc ttcctcttct ctctattttg gttctattct ttttttttct ttttctttt    1326 tttttttttt ttttttttttg tggtggtcac tgctcagtgt aatgtgcaga atgatttgtt   1386
ttttgttttt tttttttttt tttggtcctt cattgcatcc tgccataccc atgagcaaac   1446
agtttggcat taattatata tcactgccac cctctgaact ttgaaaactg ccatcttcag   1506
acttggtata atggaagagg ctttctctct ccaataaacc ttttgcttca gggtatactc   1566
ttcggttttt ttccagatgt attatgtatg aactttgtac tatgtatagc cagagtttta   1626
tttatttttt aaaaaagaaa ctttttcttg ataaggaat aatggtggtc tagctagttc    1686
ttgtaaaagt gatgcctctt gaaaaaaaac agtcctattc actagctttt agtaaaagaa   1746
tcagatcttt tctttcttgt taccttggag tcttaaaaac tgattgctaa ggtgaaacaa   1806
```

```
ttcaatgcat aagtatggag ctaagtgcct tttggaggat ttcttggaag agcatttatg    1866
gagatactta agggaggtag caaagatttg aaccgtctgt cttttttaagt aagggcagaa   1926
```
(correcting) 
```
ttcaatgcat aagtatggag ctaagtgcct tttggaggat ttcttggaag agcatttatg    1866
gagatactta agggaggtag caaagatttg aaccgtctgt cttttttaagt aagggcagaa   1926 agcaaggttg tccaggttgt actggacact tctctcccca cccctttcct gattgtttta    1986
tgtgattgat tttaaattct cacactgcca cttctttaaa aaataaaatc ctttatttgc    2046
ttaaaaaaaa aaaaaaaaaa aaaaaaaaaa aaaaaaaaaa aaaaaaaaaa aaaaaaaaaa    2106
aaaaaaaaaa aaaaaaaaaa aaaaaaaaaa aaaaaaaaaa aaaaaaaaaa aaaaa         2161
```

<210> SEQ ID NO 4
<211> LENGTH: 307
<212> TYPE: PRT
<213> ORGANISM: Homo sapiens

<400> SEQUENCE: 4

```
Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
                20                  25                  30

His Pro Val Val Lys Cys Thr Tyr Cys Arg Thr Glu Tyr Gln Gln Glu
            35                  40                  45

Ser Lys Thr Asn Thr Ile Cys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Cys Ala Phe Asp Arg
            100                 105                 110

Lys Asp Asp Arg Lys Lys Val Asp Gly Lys Leu Leu Cys Trp Leu Cys
            115                 120                 125

Thr Leu Ser Tyr Lys Arg Val Leu Gln Lys Thr Lys Glu Gln Arg Lys
130                 135                 140

His Leu Ser Ser Ser Arg Ala Gly His Gln Glu Lys Glu Gln Tyr
145                 150                 155                 160

Ser Arg Leu Ser Gly Gly His Tyr Asn Ser Gln Lys Thr Leu Ser
                165                 170                 175

Thr Ser Ser Ile Gln Asn Glu Ile Pro Lys Lys Ser Lys Phe Glu
            180                 185                 190

Ser Ile Thr Thr Asn Gly Asp Ser Phe Ser Pro Asp Leu Ala Leu Asp
            195                 200                 205

Ser Pro Gly Thr Asp His Phe Val Ile Ile Ala Gln Leu Lys Glu Glu
    210                 215                 220

Val Ala Thr Leu Lys Lys Met Leu His Gln Asp Gln Met Ile Leu
225                 230                 235                 240

Glu Lys Glu Lys Lys Ile Thr Glu Leu Lys Ala Asp Phe Gln Tyr Gln
                245                 250                 255

Glu Ser Gln Met Arg Ala Lys Met Asn Gln Met Glu Lys Thr His Lys
            260                 265                 270

Glu Val Thr Glu Gln Leu Gln Ala Lys Asn Arg Glu Leu Leu Lys Gln
        275                 280                 285

Ala Ala Ala Leu Ser Lys Ser Lys Ser Glu Lys Ser Gly Ala Ile
    290                 295                 300

Thr Ser Pro
305
```

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
aattaaccct cactaaaggg                                               20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
taatacgact cactatagg                                                19

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
agctgtgcaa ggaatgtc                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ccattagttg tgattgac                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 9
gggctgcttt taactctg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 10
ccaggaaatg agcttgac                                                 18

<210> SEQ ID NO 11
<211> LENGTH: 22
<212> TYPE: DNA
<213> ORGANISM: Artificial Sequence
<220> FEATURE:

```
<223> OTHER INFORMATION: Synthetic primer

<400> SEQUENCE: 11
atcatatggc ggcgctctac gc                                               22

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
cgctcgagtg gagaagttat agctc                                            25

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gatatcatgg cggcgctcta cgc                                              23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
gaattctcat ggagaggtta tagc                                             24

<210> SEQ ID NO 15
<211> LENGTH: 2326
<212> TYPE: DNA
<213> ORGANISM: Canis familiaris
<220> FEATURE:
<221> NAME/KEY: CDS
<222> LOCATION: (62)..(1894)

<400> SEQUENCE: 15
cagcgcctcg acatcggag ctgccgctgc cgaacacggg cccgcaacac aggtaatcag        60 t atg cat ttc caa agc ttt tgg cta tgt ctg gga ctt ctg ttc atc tca     109
  Met His Phe Gln Ser Phe Trp Leu Cys Leu Gly Leu Leu Phe Ile Ser
    1               5                  10                  15 gtt aat gca gaa ttt atg gat gat gat gtt gag atg gaa gat ttt gat       157
Val Asn Ala Glu Phe Met Asp Asp Asp Val Glu Met Glu Asp Phe Asp
                20                  25                  30 gaa aat tca gaa gag att gat gtt aat gaa ggt gaa ctc ccc tca gag       205
Glu Asn Ser Glu Glu Ile Asp Val Asn Glu Gly Glu Leu Pro Ser Glu
        35                  40                  45 att aat tat aag aca cct cag cct atg gga gaa gta tat ttt aca gaa       253
Ile Asn Tyr Lys Thr Pro Gln Pro Met Gly Glu Val Tyr Phe Thr Glu
    50                  55                  60 act ttt gat agt gga agg ttg gct ggg tgg gtc tta tca aaa gca aag       301
Thr Phe Asp Ser Gly Arg Leu Ala Gly Trp Val Leu Ser Lys Ala Lys
65                  70                  75                  80 aaa gat gat aca gat gca gag att tcc ata tat gat gga aga tgg gaa       349
Lys Asp Asp Thr Asp Ala Glu Ile Ser Ile Tyr Asp Gly Arg Trp Glu
                85                  90                  95
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ata | gaa | gaa | ttg | aaa | gaa | aac | cga | gtg | cct | ggt | gac | aga | ggg | ctg | gta | 397  |
| Ile | Glu | Glu | Leu | Lys | Glu | Asn | Arg | Val | Pro | Gly | Asp | Arg | Gly | Leu | Val |      |
|     |     |     |     | 100 |     |     |     |     | 105 |     |     |     |     | 110 |     |      |
| ctg | aaa | tct | aga | gca | aag | cat | cat | gca | ata | gct | gct | gta | tta | gca | aaa | 445  |
| Leu | Lys | Ser | Arg | Ala | Lys | His | His | Ala | Ile | Ala | Ala | Val | Leu | Ala | Lys |      |
|     | 115 |     |     |     |     | 120 |     |     |     |     | 125 |     |     |     |     |      |
| ccc | ttc | att | ttt | gct | gac | aaa | ccc | ttg | atc | gtt | caa | tat | gaa | gta | aat | 493  |
| Pro | Phe | Ile | Phe | Ala | Asp | Lys | Pro | Leu | Ile | Val | Gln | Tyr | Glu | Val | Asn |      |
| 130 |     |     |     |     | 135 |     |     |     |     | 140 |     |     |     |     |     |      |
| ttt | caa | gat | ggt | att | gat | tgt | gga | ggt | gca | tac | att | aaa | ctc | cta | gca | 541  |
| Phe | Gln | Asp | Gly | Ile | Asp | Cys | Gly | Gly | Ala | Tyr | Ile | Lys | Leu | Leu | Ala |      |
| 145 |     |     |     |     | 150 |     |     |     |     | 155 |     |     |     |     | 160 |      |
| gac | act | gat | ggt | ttg | aat | ctg | gaa | aac | ttt | tat | gat | aaa | aca | tcc | tat | 589  |
| Asp | Thr | Asp | Gly | Leu | Asn | Leu | Glu | Asn | Phe | Tyr | Asp | Lys | Thr | Ser | Tyr |      |
|     |     |     |     | 165 |     |     |     |     | 170 |     |     |     |     | 175 |     |      |
| acc | att | atg | ttt | gga | cca | gat | aaa | tgt | gga | gaa | gat | tat | aaa | ctt | cat | 637  |
| Thr | Ile | Met | Phe | Gly | Pro | Asp | Lys | Cys | Gly | Glu | Asp | Tyr | Lys | Leu | His |      |
|     |     |     | 180 |     |     |     |     | 185 |     |     |     |     | 190 |     |     |      |
| ttc | atc | ttc | aga | cac | aaa | cat | cct | aaa | act | gga | gtt | ttt | gaa | gag | aaa | 685  |
| Phe | Ile | Phe | Arg | His | Lys | His | Pro | Lys | Thr | Gly | Val | Phe | Glu | Glu | Lys |      |
|     |     | 195 |     |     |     |     | 200 |     |     |     |     | 205 |     |     |     |      |
| cat | gcc | aaa | cct | cca | gat | gta | gac | ctt | aaa | aag | ttc | ttt | aca | gac | agg | 733  |
| His | Ala | Lys | Pro | Pro | Asp | Val | Asp | Leu | Lys | Lys | Phe | Phe | Thr | Asp | Arg |      |
|     | 210 |     |     |     |     | 215 |     |     |     |     | 220 |     |     |     |     |      |
| aag | act | cat | ctt | tat | acc | ctt | gtg | atg | aat | cca | gat | gac | aca | ttt | gaa | 781  |
| Lys | Thr | His | Leu | Tyr | Thr | Leu | Val | Met | Asn | Pro | Asp | Asp | Thr | Phe | Glu |      |
| 225 |     |     |     |     | 230 |     |     |     |     | 235 |     |     |     |     | 240 |      |
| gta | cta | att | gat | caa | gta | gtt | gta | aac | caa | gga | agc | ctc | cta | gaa | gat | 829  |
| Val | Leu | Ile | Asp | Gln | Val | Val | Val | Asn | Gln | Gly | Ser | Leu | Leu | Glu | Asp |      |
|     |     |     |     | 245 |     |     |     |     | 250 |     |     |     |     | 255 |     |      |
| gtg | gtt | cct | cct | atc | aat | cct | ccc | aaa | gaa | att | gaa | gac | ccc | agt | gat | 877  |
| Val | Val | Pro | Pro | Ile | Asn | Pro | Pro | Lys | Glu | Ile | Glu | Asp | Pro | Ser | Asp |      |
|     |     |     | 260 |     |     |     |     | 265 |     |     |     |     | 270 |     |     |      |
| aaa | aag | cct | gat | gaa | tgg | gat | gaa | aga | gca | aaa | atc | cct | gat | cct | tct | 925  |
| Lys | Lys | Pro | Asp | Glu | Trp | Asp | Glu | Arg | Ala | Lys | Ile | Pro | Asp | Pro | Ser |      |
|     |     | 275 |     |     |     |     | 280 |     |     |     |     | 285 |     |     |     |      |
| gct | gtc | aaa | cca | gaa | gac | tgg | gat | gaa | agt | gaa | cct | gcc | caa | ata | gaa | 973  |
| Ala | Val | Lys | Pro | Glu | Asp | Trp | Asp | Glu | Ser | Glu | Pro | Ala | Gln | Ile | Glu |      |
|     | 290 |     |     |     |     | 295 |     |     |     |     | 300 |     |     |     |     |      |
| gat | tta | agt | gtt | gtt | aaa | cct | gat | ggc | tgg | ctt | gat | gat | gaa | cca | aaa | 1021 |
| Asp | Leu | Ser | Val | Val | Lys | Pro | Asp | Gly | Trp | Leu | Asp | Asp | Glu | Pro | Lys |      |
| 305 |     |     |     |     | 310 |     |     |     |     | 315 |     |     |     |     | 320 |      |
| ttt | att | cca | gat | cca | aat | gct | gaa | aaa | cct | gat | gac | tgg | aat | gaa | gac | 1069 |
| Phe | Ile | Pro | Asp | Pro | Asn | Ala | Glu | Lys | Pro | Asp | Asp | Trp | Asn | Glu | Asp |      |
|     |     |     |     | 325 |     |     |     |     | 330 |     |     |     |     | 335 |     |      |
| atg | gat | gga | gaa | tgg | gag | gca | cct | cgt | att | tct | aat | cca | gca | tgt | cga | 1117 |
| Met | Asp | Gly | Glu | Trp | Glu | Ala | Pro | Arg | Ile | Ser | Asn | Pro | Ala | Cys | Arg |      |
|     |     |     | 340 |     |     |     |     | 345 |     |     |     |     | 350 |     |     |      |
| att | ggg | tgt | ggt | gag | tgg | tca | cct | ccc | atg | ata | gat | aat | ccc | aaa | tac | 1165 |
| Ile | Gly | Cys | Gly | Glu | Trp | Ser | Pro | Pro | Met | Ile | Asp | Asn | Pro | Lys | Tyr |      |
|     |     | 355 |     |     |     |     | 360 |     |     |     |     | 365 |     |     |     |      |
| aaa | gga | gta | tgg | aga | cct | cca | atg | ata | gat | aat | cct | aac | tac | cag | gga | 1213 |
| Lys | Gly | Val | Trp | Arg | Pro | Pro | Met | Ile | Asp | Asn | Pro | Asn | Tyr | Gln | Gly |      |
|     | 370 |     |     |     |     | 375 |     |     |     |     | 380 |     |     |     |     |      |
| atc | tgg | agt | cct | cga | aaa | atc | ccg | aat | cca | gat | tat | ttt | gaa | gat | gat | 1261 |
| Ile | Trp | Ser | Pro | Arg | Lys | Ile | Pro | Asn | Pro | Asp | Tyr | Phe | Glu | Asp | Asp |      |
| 385 |     |     |     |     | 390 |     |     |     |     | 395 |     |     |     |     | 400 |      |
| cat | cca | ttt | ctt | ctg | act | tct | ttc | cgt | gct | ctt | ggt | tta | gag | ctt | tgg | 1309 |
| His | Pro | Phe | Leu | Leu | Thr | Ser | Phe | Arg | Ala | Leu | Gly | Leu | Glu | Leu | Trp |      |
|     |     |     |     | 405 |     |     |     |     | 410 |     |     |     |     | 415 |     |      |

```
tct atg acc tct aat att tac ttt gat aat ttt att atc tgc tcg gaa      1357
Ser Met Thr Ser Asn Ile Tyr Phe Asp Asn Phe Ile Ile Cys Ser Glu
        420                 425                 430 aag gaa aca gca gat cgc tgg gct gca gat ggg tgg gga gtg aag ata      1405
Lys Glu Thr Ala Asp Arg Trp Ala Ala Asp Gly Trp Gly Val Lys Ile
        435                 440                 445 ctg gta gca aat gct aac gag cct ggt ata ttt aaa cag tta atg gca      1453
Leu Val Ala Asn Ala Asn Glu Pro Gly Ile Phe Lys Gln Leu Met Ala
        450                 455                 460 gct gct gaa gag cgc cca tgg ctt tgg ctc att tat ttt gtg aca gca      1501
Ala Ala Glu Glu Arg Pro Trp Leu Trp Leu Ile Tyr Phe Val Thr Ala
465                 470                 475                 480 ggg ctt cca ata gca tta att gct tca ttt tgt tgg cca aga aaa gtc      1549
Gly Leu Pro Ile Ala Leu Ile Ala Ser Phe Cys Trp Pro Arg Lys Val
                485                 490                 495 aag aaa aaa tat gaa gat tca gag tat aaa aag act gac ata tgc aag      1597
Lys Lys Lys Tyr Glu Asp Ser Glu Tyr Lys Lys Thr Asp Ile Cys Lys
            500                 505                 510 cca caa aca aag gga gca cta gag caa gaa gtg aag gaa aag aaa gct      1645
Pro Gln Thr Lys Gly Ala Leu Glu Gln Glu Val Lys Glu Lys Lys Ala
        515                 520                 525 gcc ctg gag aaa cca gta gac ttg gaa gaa gaa aaa aag caa agt gat      1693
Ala Leu Glu Lys Pro Val Asp Leu Glu Glu Glu Lys Lys Gln Ser Asp
        530                 535                 540 ggt gaa act gtt gaa aaa gaa gag gaa gct gaa cct gag gaa aag agt      1741
Gly Glu Thr Val Glu Lys Glu Glu Glu Ala Glu Pro Glu Glu Lys Ser
545                 550                 555                 560 gaa gaa gaa att gaa atc ata gaa gga caa gaa gaa ggt aat aaa tca      1789
Glu Glu Glu Ile Glu Ile Ile Glu Gly Gln Glu Glu Gly Asn Lys Ser
                565                 570                 575 aat aag tct gga tca gag gat gag atg aag gaa gcg gat gag agc aca      1837
Asn Lys Ser Gly Ser Glu Asp Glu Met Lys Glu Ala Asp Glu Ser Thr
            580                 585                 590 gga tct gga gat ggg cca gtg aag tca gtg cgc aaa aga aga gta cga      1885
Gly Ser Gly Asp Gly Pro Val Lys Ser Val Arg Lys Arg Arg Val Arg
        595                 600                 605 aag gaa taa actatattca agtattttta attcctgagc gagatatttg              1934
Lys Glu
    610 gcattctaaa atcagtgtgc cagagctgaa cttgagtcag tctgcacatg tttctaatat    1994 ctagcaatgt tattctttca gacacttatt ttagtctttc ttttcaggaa aaaaaaaact    2054 ttcaagttac ctggtctttg gatttagagt aaaaaagagg ggcatgttac gtatcagatt    2114 taagagacta ataccattag aagttaccaa gttttaatag ttggagaaag ttttggtttg    2174 tacagagaaa aataatatgc agcagctttg ctgctgttgg aaaatcagtt attggaattt    2234 cccctttaaac agctatacaa caatattact ggtagttcta taataaaaat gagagtgtgt   2294 tctgttgtac agagctaact gcaaaaaaaa aa                                  2326

<210> SEQ ID NO 16
<211> LENGTH: 610
<212> TYPE: PRT
<213> ORGANISM: Canis familiaris

<400> SEQUENCE: 16

Met His Phe Gln Ser Phe Trp Leu Cys Leu Gly Leu Leu Phe Ile Ser
1               5                   10                  15

Val Asn Ala Glu Phe Met Asp Asp Asp Val Glu Met Glu Asp Phe Asp
```

```
            20                  25                  30
Glu Asn Ser Glu Glu Ile Asp Val Asn Glu Gly Glu Leu Pro Ser Glu
        35                  40                  45

Ile Asn Tyr Lys Thr Pro Gln Pro Met Gly Glu Val Tyr Phe Thr Glu
    50                  55                  60

Thr Phe Asp Ser Gly Arg Leu Ala Gly Trp Val Leu Ser Lys Ala Lys
65                  70                  75                  80

Lys Asp Asp Thr Asp Ala Glu Ile Ser Ile Tyr Asp Gly Arg Trp Glu
                85                  90                  95

Ile Glu Glu Leu Lys Glu Asn Arg Val Pro Gly Asp Arg Gly Leu Val
            100                 105                 110

Leu Lys Ser Arg Ala Lys His His Ala Ile Ala Ala Val Leu Ala Lys
        115                 120                 125

Pro Phe Ile Phe Ala Asp Lys Pro Leu Ile Val Gln Tyr Glu Val Asn
    130                 135                 140

Phe Gln Asp Gly Ile Asp Cys Gly Gly Ala Tyr Ile Lys Leu Leu Ala
145                 150                 155                 160

Asp Thr Asp Gly Leu Asn Leu Glu Asn Phe Tyr Asp Lys Thr Ser Tyr
                165                 170                 175

Thr Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
        195                 200                 205

His Ala Lys Pro Pro Asp Val Asp Leu Lys Lys Phe Phe Thr Asp Arg
    210                 215                 220

Lys Thr His Leu Tyr Thr Leu Val Met Asn Pro Asp Asp Thr Phe Glu
225                 230                 235                 240

Val Leu Ile Asp Gln Val Val Val Asn Gln Gly Ser Leu Leu Glu Asp
                245                 250                 255

Val Val Pro Pro Ile Asn Pro Pro Lys Glu Ile Glu Asp Pro Ser Asp
            260                 265                 270

Lys Lys Pro Asp Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
    290                 295                 300

Asp Leu Ser Val Val Lys Pro Asp Gly Trp Leu Asp Asp Glu Pro Lys
305                 310                 315                 320

Phe Ile Pro Asp Pro Asn Ala Glu Lys Pro Asp Asp Trp Asn Glu Asp
                325                 330                 335

Met Asp Gly Glu Trp Glu Ala Pro Arg Ile Ser Asn Pro Ala Cys Arg
            340                 345                 350

Ile Gly Cys Gly Glu Trp Ser Pro Met Ile Asp Asn Pro Lys Tyr
        355                 360                 365

Lys Gly Val Trp Arg Pro Pro Met Ile Asp Asn Pro Asn Tyr Gln Gly
    370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Arg Ala Leu Gly Leu Glu Leu Trp
                405                 410                 415

Ser Met Thr Ser Asn Ile Tyr Phe Asp Asn Phe Ile Ile Cys Ser Glu
            420                 425                 430

Lys Glu Thr Ala Asp Arg Trp Ala Ala Asp Gly Trp Gly Val Lys Ile
        435                 440                 445
```

```
Leu Val Ala Asn Ala Asn Glu Pro Gly Ile Phe Lys Gln Leu Met Ala
    450                 455                 460
Ala Ala Glu Glu Arg Pro Trp Leu Trp Leu Ile Tyr Phe Val Thr Ala
465                 470                 475                 480
Gly Leu Pro Ile Ala Leu Ile Ala Ser Phe Cys Trp Pro Arg Lys Val
                485                 490                 495
Lys Lys Lys Tyr Glu Asp Ser Glu Tyr Lys Lys Thr Asp Ile Cys Lys
            500                 505                 510
Pro Gln Thr Lys Gly Ala Leu Glu Gln Glu Val Lys Glu Lys Lys Ala
        515                 520                 525
Ala Leu Glu Lys Pro Val Asp Leu Glu Glu Glu Lys Lys Gln Ser Asp
    530                 535                 540
Gly Glu Thr Val Glu Lys Glu Glu Glu Ala Glu Pro Glu Glu Lys Ser
545                 550                 555                 560
Glu Glu Glu Ile Glu Ile Ile Glu Gly Gln Glu Glu Gly Asn Lys Ser
                565                 570                 575
Asn Lys Ser Gly Ser Glu Asp Glu Met Lys Glu Ala Asp Glu Ser Thr
            580                 585                 590
Gly Ser Gly Asp Gly Pro Val Lys Ser Val Arg Lys Arg Val Arg
        595                 600                 605
Lys Glu
    610

<210> SEQ ID NO 17
<211> LENGTH: 2710
<212> TYPE: DNA
<213> ORGANISM: Homo sapiens
<220> FEATURE:
<221> NAME/KEY: CDS
<222> LOCATION: (102)..(1934)

<400> SEQUENCE: 17
cgccggcggg actggtctga agagacgcgg ggacaaagtg caacgactt ggacatctga      60 gctgtcactg ccgaaaacag gccgcaagag agataatcaa t atg cat ttc caa gcc    116
                                             Met His Phe Gln Ala
                                             1               5 ttt tgg cta tgt ttg ggt ctt ctg ttc atc tca att aat gca gaa ttt     164
Phe Trp Leu Cys Leu Gly Leu Leu Phe Ile Ser Ile Asn Ala Glu Phe
        10                  15                  20 atg gat gat gat gtt gag acg gaa gac ttt gaa gaa aat tca gaa gaa     212
Met Asp Asp Asp Val Glu Thr Glu Asp Phe Glu Glu Asn Ser Glu Glu
            25                  30                  35 att gat gtt aat gaa agt gaa ctt tcc tca gag att aaa tat aag aca     260
Ile Asp Val Asn Glu Ser Glu Leu Ser Ser Glu Ile Lys Tyr Lys Thr
        40                  45                  50 cct caa cct ata gga gaa gta tat ttt gca gaa act ttt gat agt gga     308
Pro Gln Pro Ile Gly Glu Val Tyr Phe Ala Glu Thr Phe Asp Ser Gly
    55                  60                  65 agg ttg gct gga tgg gtc tta tca aaa gca aag aaa gat gac atg gat     356
Arg Leu Ala Gly Trp Val Leu Ser Lys Ala Lys Lys Asp Asp Met Asp
70                  75                  80                  85 gag gaa att tca ata tac gat gga aga tgg gaa att gaa gag ttg aaa     404
Glu Glu Ile Ser Ile Tyr Asp Gly Arg Trp Glu Ile Glu Glu Leu Lys
                90                  95                  100 gaa aac cag gta cct ggt gac aga gga ctg gta tta aaa tct aga gca     452
Glu Asn Gln Val Pro Gly Asp Arg Gly Leu Val Leu Lys Ser Arg Ala
            105                 110                 115
```

```
aag cat cat gca ata tct gct gta tta gca aaa cca ttc att ttt gct      500
Lys His His Ala Ile Ser Ala Val Leu Ala Lys Pro Phe Ile Phe Ala
        120                 125                 130 gat aaa ccc ttg ata gtt caa tat gaa gta aat ttt caa gat ggt att      548
Asp Lys Pro Leu Ile Val Gln Tyr Glu Val Asn Phe Gln Asp Gly Ile
    135                 140                 145 gat tgt gga ggt gca tac att aaa ctc cta gca gac act gat gat ttg      596
Asp Cys Gly Gly Ala Tyr Ile Lys Leu Leu Ala Asp Thr Asp Asp Leu
150                 155                 160                 165 att ctg gaa aac ttt tat gat aaa aca tcc tat atc att atg ttt gga      644
Ile Leu Glu Asn Phe Tyr Asp Lys Thr Ser Tyr Ile Ile Met Phe Gly
            170                 175                 180 cca gat aaa tgt gga gaa gat tat aaa ctt cat ttt atc ttc aga cat      692
Pro Asp Lys Cys Gly Glu Asp Tyr Lys Leu His Phe Ile Phe Arg His
        185                 190                 195 aaa cat ccc aaa act gga gtt ttc gaa gag aaa cat gcc aaa cct cca      740
Lys His Pro Lys Thr Gly Val Phe Glu Glu Lys His Ala Lys Pro Pro
    200                 205                 210 gat gta gac ctt aaa aag ttc ttt aca gac agg aag act cat ctt tat      788
Asp Val Asp Leu Lys Lys Phe Phe Thr Asp Arg Lys Thr His Leu Tyr
215                 220                 225 acc ctt gtg atg aat cca gat gac aca ttt gag gtg tta gtt gat caa      836
Thr Leu Val Met Asn Pro Asp Asp Thr Phe Glu Val Leu Val Asp Gln
230                 235                 240                 245 aca gtt gta aac aaa gga agc ctc cta gag gat gtg gtt cct cct atc      884
Thr Val Val Asn Lys Gly Ser Leu Leu Glu Asp Val Val Pro Pro Ile
            250                 255                 260 aaa cct ccc aaa gaa att gaa gat ccc aat gat aaa aaa cct gag gaa      932
Lys Pro Pro Lys Glu Ile Glu Asp Pro Asn Asp Lys Lys Pro Glu Glu
        265                 270                 275 tgg gat gaa aga gca aaa att cct gat cct tct gcc gtc aaa cca gaa      980
Trp Asp Glu Arg Ala Lys Ile Pro Asp Pro Ser Ala Val Lys Pro Glu
    280                 285                 290 gac tgg gat gaa agt gaa cct gcc caa ata gaa gat tca agt gtt gtt     1028
Asp Trp Asp Glu Ser Glu Pro Ala Gln Ile Glu Asp Ser Ser Val Val
295                 300                 305 aaa cct gct ggc tgg ctt gat gat gaa cca aaa ttt atc cct gat cct     1076
Lys Pro Ala Gly Trp Leu Asp Asp Glu Pro Lys Phe Ile Pro Asp Pro
310                 315                 320                 325 aat gct gaa aaa cct gat gac tgg aat gaa gac acg gat gga gaa tgg     1124
Asn Ala Glu Lys Pro Asp Asp Trp Asn Glu Asp Thr Asp Gly Glu Trp
            330                 335                 340 gag gca cct cag att ctt aat cca gca tgt cgg att ggg tgt ggt gag     1172
Glu Ala Pro Gln Ile Leu Asn Pro Ala Cys Arg Ile Gly Cys Gly Glu
        345                 350                 355 tgg aaa cct ccc atg ata gat aac cca aaa tac aaa gga gta tgg aga     1220
Trp Lys Pro Pro Met Ile Asp Asn Pro Lys Tyr Lys Gly Val Trp Arg
    360                 365                 370 cct cca ctg gtc gat aat cct aac tat cag gga atc tgg agt cct cga     1268
Pro Pro Leu Val Asp Asn Pro Asn Tyr Gln Gly Ile Trp Ser Pro Arg
375                 380                 385 aaa att cct aat cca gat tat ttc gaa gat gat cat cca ttt ctt ctg     1316
Lys Ile Pro Asn Pro Asp Tyr Phe Glu Asp Asp His Pro Phe Leu Leu
390                 395                 400                 405 act tct ttc agt gct ctt ggt tta gag ctt tgg tct atg acc tct gat     1364
Thr Ser Phe Ser Ala Leu Gly Leu Glu Leu Trp Ser Met Thr Ser Asp
            410                 415                 420 atc tac ttt gat aat ttt att atc tgt tcg gaa aag gaa gta gca gat     1412
Ile Tyr Phe Asp Asn Phe Ile Ile Cys Ser Glu Lys Glu Val Ala Asp
        425                 430                 435
```

```
cac tgg gct gca gat ggt tgg aga tgg aaa ata atg ata gca aat gct      1460
His Trp Ala Ala Asp Gly Trp Arg Trp Lys Ile Met Ile Ala Asn Ala
        440                 445                 450 aat aag cct ggt gta tta aaa cag tta atg gca gct gct gaa ggg cac      1508
Asn Lys Pro Gly Val Leu Lys Gln Leu Met Ala Ala Ala Glu Gly His
    455                 460                 465 cca tgg ctt tgg ttg att tat ctt gtg aca gca gga gtg cca ata gca      1556
Pro Trp Leu Trp Leu Ile Tyr Leu Val Thr Ala Gly Val Pro Ile Ala
470                 475                 480                 485 tta att act tca ttt tgt tgg cca aga aaa gta aag aaa aaa cat aaa      1604
Leu Ile Thr Ser Phe Cys Trp Pro Arg Lys Val Lys Lys Lys His Lys
                490                 495                 500 gat aca gag tat aaa aaa acc gac ata tgt ata cca caa aca aaa gga      1652
Asp Thr Glu Tyr Lys Lys Thr Asp Ile Cys Ile Pro Gln Thr Lys Gly
            505                 510                 515 gta cta gag caa gaa gaa aag gaa gag aaa gca gcc ctg gaa aaa cca      1700
Val Leu Glu Gln Glu Glu Lys Glu Glu Lys Ala Ala Leu Glu Lys Pro
        520                 525                 530 atg gac ctg gaa gag gaa aaa aag caa aat gat ggt gaa atg ctt gaa      1748
Met Asp Leu Glu Glu Glu Lys Lys Gln Asn Asp Gly Glu Met Leu Glu
535                 540                 545 aaa gaa gag gaa agt gaa cct gag gaa aag agt gaa gaa gaa att gaa      1796
Lys Glu Glu Glu Ser Glu Pro Glu Glu Lys Ser Glu Glu Glu Ile Glu
550                 555                 560                 565 atc ata gaa ggg caa gaa gaa agt aat caa tca aat aag tct ggg tca      1844
Ile Ile Glu Gly Gln Glu Glu Ser Asn Gln Ser Asn Lys Ser Gly Ser
                570                 575                 580 gag gat gag atg aaa gaa gca gat gag agc aca gga tct gga gat ggg      1892
Glu Asp Glu Met Lys Glu Ala Asp Glu Ser Thr Gly Ser Gly Asp Gly
            585                 590                 595 ccg ata aag tca gta cgc aaa aga aga gta cga aag gac taa              1934
Pro Ile Lys Ser Val Arg Lys Arg Arg Val Arg Lys Asp
        600                 605                 610 actagattga aatattttta attcccgaga ggatgtttgg cattgtaaaa atcagcatgc    1994
cagacctgaa ctttaatcag tctgcacatc ctgtttctaa tatctagcaa cattatattc    2054
tttcagacat ttattttagt ccttcatttc cgaggaaaaa gaagcaactt tgaagttacc    2114
tcatctttga atttagaata aaagtggcac attacatatc ggatctaaga gattaatacc    2174
attagaagtt acacagtttt agttgtttgg agatagtttt ggtttgtaca gaacaaaata    2234
atatgtagca gcttcattgc tattggaaaa atcagttatt ggaatttcca cttaaatggc    2294
tatacaacaa tataactggt agttctataa taaaaatgag catatgttct gttgtgaaga    2354
gctaaatgca ataaagtttc tgtatggttg tttgattcta tcaacaattg aaagtgttgt    2414
atatgaccca catttaccta gtttgtgtca aattatagtt acagtgagtt gtttgcttaa    2474
attatagatt cctttaagga catgccttgt tcataaaatc actggattat attgcagcat    2534 atttacatt tgaatacaag gataatgggt tttatcaaaa caaatgatg tacagatttt      2594 ttttcaagtt tttatagttg ctttatgcca gagtggttta ccccattcac aaaatttctt    2654
atgcatacat tgctattgaa aataaaattt aaatattttt tcatcctgaa aaaaa         2710

<210> SEQ ID NO 18
<211> LENGTH: 610
<212> TYPE: PRT
<213> ORGANISM: Homo sapiens

<400> SEQUENCE: 18
```

Met His Phe Gln Ala Phe Trp Leu Cys Leu Gly Leu Leu Phe Ile Ser
1               5                   10                  15

Ile Asn Ala Glu Phe Met Asp Asp Val Glu Thr Glu Asp Phe Glu
        20                  25                  30

Glu Asn Ser Glu Glu Ile Asp Val Asn Glu Ser Glu Leu Ser Ser Glu
            35                  40                  45

Ile Lys Tyr Lys Thr Pro Gln Pro Ile Gly Glu Val Tyr Phe Ala Glu
50                  55                  60

Thr Phe Asp Ser Gly Arg Leu Ala Gly Trp Val Leu Ser Lys Ala Lys
65                  70                  75                  80

Lys Asp Asp Met Asp Glu Glu Ile Ser Ile Tyr Asp Gly Arg Trp Glu
                85                  90                  95

Ile Glu Glu Leu Lys Glu Asn Gln Val Pro Gly Asp Arg Gly Leu Val
            100                 105                 110

Leu Lys Ser Arg Ala Lys His His Ala Ile Ser Ala Val Leu Ala Lys
        115                 120                 125

Pro Phe Ile Phe Ala Asp Lys Pro Leu Ile Val Gln Tyr Glu Val Asn
    130                 135                 140

Phe Gln Asp Gly Ile Asp Cys Gly Gly Ala Tyr Ile Lys Leu Leu Ala
145                 150                 155                 160

Asp Thr Asp Asp Leu Ile Leu Glu Asn Phe Tyr Asp Lys Thr Ser Tyr
                165                 170                 175

Ile Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
        195                 200                 205

His Ala Lys Pro Pro Asp Val Asp Leu Lys Lys Phe Phe Thr Asp Arg
    210                 215                 220

Lys Thr His Leu Tyr Thr Leu Val Met Asn Pro Asp Asp Thr Phe Glu
225                 230                 235                 240

Val Leu Val Asp Gln Thr Val Val Asn Lys Gly Ser Leu Leu Glu Asp
                245                 250                 255

Val Val Pro Pro Ile Lys Pro Pro Lys Glu Ile Glu Asp Pro Asn Asp
            260                 265                 270

Lys Lys Pro Glu Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
    290                 295                 300

Asp Ser Ser Val Val Lys Pro Ala Gly Trp Leu Asp Asp Glu Pro Lys
305                 310                 315                 320

Phe Ile Pro Asp Pro Asn Ala Glu Lys Pro Asp Asp Trp Asn Glu Asp
                325                 330                 335

Thr Asp Gly Glu Trp Glu Ala Pro Gln Ile Leu Asn Pro Ala Cys Arg
            340                 345                 350

Ile Gly Cys Gly Glu Trp Lys Pro Pro Met Ile Asp Asn Pro Lys Tyr
        355                 360                 365

Lys Gly Val Trp Arg Pro Pro Leu Val Asp Asn Pro Asn Tyr Gln Gly
    370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Ser Ala Leu Gly Leu Glu Leu Trp
                405                 410                 415

Ser Met Thr Ser Asp Ile Tyr Phe Asp Asn Phe Ile Ile Cys Ser Glu

```
            420             425             430
Lys Glu Val Ala Asp His Trp Ala Ala Asp Gly Trp Arg Trp Lys Ile
        435                 440                 445
Met Ile Ala Asn Ala Asn Lys Pro Gly Val Leu Lys Gln Leu Met Ala
    450                 455                 460
Ala Ala Glu Gly His Pro Trp Leu Trp Leu Ile Tyr Leu Val Thr Ala
465                 470                 475                 480
Gly Val Pro Ile Ala Leu Ile Thr Ser Phe Cys Trp Pro Arg Lys Val
                485                 490                 495
Lys Lys Lys His Lys Asp Thr Glu Tyr Lys Lys Thr Asp Ile Cys Ile
            500                 505                 510
Pro Gln Thr Lys Gly Val Leu Glu Gln Glu Lys Glu Glu Lys Ala
        515                 520                 525
Ala Leu Glu Lys Pro Met Asp Leu Glu Glu Glu Lys Lys Gln Asn Asp
    530                 535                 540
Gly Glu Met Leu Glu Lys Glu Glu Ser Glu Pro Glu Glu Lys Ser
545                 550                 555                 560
Glu Glu Glu Ile Glu Ile Ile Glu Gly Gln Glu Glu Ser Asn Gln Ser
                565                 570                 575
Asn Lys Ser Gly Ser Glu Asp Glu Met Lys Glu Ala Asp Glu Ser Thr
            580                 585                 590
Gly Ser Gly Asp Gly Pro Ile Lys Ser Val Arg Lys Arg Val Arg
        595                 600                 605
Lys Asp
    610

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gtgatgaatc cagatgac                                              18

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
ggtcatagac caaagctc                                              18

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
aaggatccat gcatttccaa agc                                        23

<210> SEQ ID NO 22
<211> LENGTH: 25
<212> TYPE: DNA
<213> ORGANISM: Artificial Sequence
```

-continued

```
<220> FEATURE:
<223> OTHER INFORMATION: Synthetic primer

<400> SEQUENCE: 22
ccgaattctt attcctttcg tactc                                            25

<210> SEQ ID NO 23
<211> LENGTH: 26
<212> TYPE: DNA
<213> ORGANISM: Artificial Sequence
<220> FEATURE:
<223> OTHER INFORMATION: Synthetic primer

<400> SEQUENCE: 23
gaattcatgc atttccaagc cttttg                                           26

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
ctcgagttag tcctttcgta ctc                                              23

<210> SEQ ID NO 25
<211> LENGTH: 7353
<212> TYPE: DNA
<213> ORGANISM: Canis familiaris
<220> FEATURE:
<221> NAME/KEY: CDS
<222> LOCATION: (1)..(7020)

<400> SEQUENCE: 25 atg aag aaa ggt tct cag caa aag ttt ttg aaa gca aag atg cca cca        48
Met Lys Lys Gly Ser Gln Gln Lys Phe Leu Lys Ala Lys Met Pro Pro
1               5                   10                  15 tca tct cac tct cct agt cca cca tcc ctt acg tcc aat atg aga tct        96
Ser Ser His Ser Pro Ser Pro Pro Ser Leu Thr Ser Asn Met Arg Ser
            20                  25                  30 agg tca ctt tcg cct cta agt gga tct gag act ctg cct ttt cat ttt       144
Arg Ser Leu Ser Pro Leu Ser Gly Ser Glu Thr Leu Pro Phe His Phe
        35                  40                  45 gga gga ccg tgg cat gag caa gtt gag att aca gat gaa agc aca gtg       192
Gly Gly Pro Trp His Glu Gln Val Glu Ile Thr Asp Glu Ser Thr Val
    50                  55                  60 gtt tta gac tac caa gac cat aaa gaa gct gat tca cat gca gga gtc       240
Val Leu Asp Tyr Gln Asp His Lys Glu Ala Asp Ser His Ala Gly Val
65                  70                  75                  80 cga tat att aca gag gcc ctt gtt aga aaa ctt act aaa cag gac aat       288
Arg Tyr Ile Thr Glu Ala Leu Val Arg Lys Leu Thr Lys Gln Asp Asn
                85                  90                  95 ttg gcc ttg gta aaa tct ctg aac ctt tca ctt gct aaa ggt ggt ggc       336
Leu Ala Leu Val Lys Ser Leu Asn Leu Ser Leu Ala Lys Gly Gly Gly
            100                 105                 110 aag aaa ttc agg tgt atc gaa aat ttg gaa aaa tgt gtt aaa ctt gaa       384
Lys Lys Phe Arg Cys Ile Glu Asn Leu Glu Lys Cys Val Lys Leu Glu
        115                 120                 125 gta ctg aat ctc agc tat aat cta ata gga aag att gag aaa gtg gac       432
Val Leu Asn Leu Ser Tyr Asn Leu Ile Gly Lys Ile Glu Lys Val Asp
    130                 135                 140 aaa ctg tta aaa tta cgt gaa ctc aac tta tcg tat aac aaa atc cgc       480
```

```
Lys Leu Leu Lys Leu Arg Glu Leu Asn Leu Ser Tyr Asn Lys Ile Arg
145                 150                 155                 160 aaa att gaa ggc ata gaa aat tta tat aat ctg caa aag ctg aac ctt    528
Lys Ile Glu Gly Ile Glu Asn Leu Tyr Asn Leu Gln Lys Leu Asn Leu
                165                 170                 175 gca gga aat gaa atc gaa cat atc cca gta tgg tta ggg aag aag tta    576
Ala Gly Asn Glu Ile Glu His Ile Pro Val Trp Leu Gly Lys Lys Leu
            180                 185                 190 aaa tct ttg cga atc ctg aat ctg aaa ggc aac aag ata tca tcg ctc    624
Lys Ser Leu Arg Ile Leu Asn Leu Lys Gly Asn Lys Ile Ser Ser Leu
        195                 200                 205 caa gat gta agc aag ttg aaa cca ctt caa gat ttg act tct ctg atc    672
Gln Asp Val Ser Lys Leu Lys Pro Leu Gln Asp Leu Thr Ser Leu Ile
210                 215                 220 cta ctt gaa aat cca gtt gcg acc ctt cct cat tat atc cag ttt acc    720
Leu Leu Glu Asn Pro Val Ala Thr Leu Pro His Tyr Ile Gln Phe Thr
225                 230                 235                 240 att ttt cac ctt cgc tca ttg gaa agt ttg gaa ggt cag cca gta act    768
Ile Phe His Leu Arg Ser Leu Glu Ser Leu Glu Gly Gln Pro Val Thr
                245                 250                 255 agt cag gac aga caa gaa gct ttt gcg aga ttc agt tta gat gag gta    816
Ser Gln Asp Arg Gln Glu Ala Phe Ala Arg Phe Ser Leu Asp Glu Val
            260                 265                 270 gaa aga ctg gaa aga gac ctg gag aag aag aca atg gaa act gaa gag    864
Glu Arg Leu Glu Arg Asp Leu Glu Lys Lys Thr Met Glu Thr Glu Glu
        275                 280                 285 ctt agg agt gag cag aca agg ttc ctt gag gaa att aaa agt cag gat    912
Leu Arg Ser Glu Gln Thr Arg Phe Leu Glu Glu Ile Lys Ser Gln Asp
290                 295                 300 aaa ttg aac aaa tca ctg aaa gag gag gcc aga cta caa aaa cag agc    960
Lys Leu Asn Lys Ser Leu Lys Glu Glu Ala Arg Leu Gln Lys Gln Ser
305                 310                 315                 320 tat gag gag ctg gag agt aac cta aac acc aaa aat gaa ttg cta aaa    1008
Tyr Glu Glu Leu Glu Ser Asn Leu Asn Thr Lys Asn Glu Leu Leu Lys
                325                 330                 335 cag aag acc atg gaa cta atg cga gca tgt cag aaa cag tat gag atg    1056
Gln Lys Thr Met Glu Leu Met Arg Ala Cys Gln Lys Gln Tyr Glu Met
            340                 345                 350 gaa cag gag ttg gcc ttt tat aaa att gat gcc aaa ttt gaa cca cta    1104
Glu Gln Glu Leu Ala Phe Tyr Lys Ile Asp Ala Lys Phe Glu Pro Leu
        355                 360                 365 aat tat tac cca tca gag tat gtc gaa att gat aaa acc cca gat gaa    1152
Asn Tyr Tyr Pro Ser Glu Tyr Val Glu Ile Asp Lys Thr Pro Asp Glu
370                 375                 380 agc cct tac att ggc aaa tcc aga tac aag aga aat atg ttc act aca    1200
Ser Pro Tyr Ile Gly Lys Ser Arg Tyr Lys Arg Asn Met Phe Thr Thr
385                 390                 395                 400 gag agt tat att att gca aat gcc cag aca gta aag atc aag aag atg    1248
Glu Ser Tyr Ile Ile Ala Asn Ala Gln Thr Val Lys Ile Lys Lys Met
                405                 410                 415 gag cta gat gaa ggg gaa caa ctc aga aat gag cac gtg aac ttg gga    1296
Glu Leu Asp Glu Gly Glu Gln Leu Arg Asn Glu His Val Asn Leu Gly
            420                 425                 430 gca tcg cca aca gac ata caa ctg gaa gac aaa gaa aaa aaa ata agt    1344
Ala Ser Pro Thr Asp Ile Gln Leu Glu Asp Lys Glu Lys Lys Ile Ser
        435                 440                 445 gca gca caa act cga cta tca gaa cta cat gat gaa ata gaa aag gca    1392
Ala Ala Gln Thr Arg Leu Ser Glu Leu His Asp Glu Ile Glu Lys Ala
450                 455                 460
```

-continued

| | | |
|---|---|---|
| gaa caa caa att tta aga gcc act gaa gaa ttt aaa caa ctg gaa gaa<br>Glu Gln Gln Ile Leu Arg Ala Thr Glu Glu Phe Lys Gln Leu Glu Glu<br>465                                  470                            475                         480 | 1440 |
| gct ata caa ctt aaa aaa att tca gaa gcg gag aaa gac ctt ctt ttc<br>Ala Ile Gln Leu Lys Lys Ile Ser Glu Ala Glu Lys Asp Leu Leu Phe<br>                 485                            490                          495 | 1488 |
| aag cag ttg agt ggt agg ata cag ctt ctc aat aaa tta cgc caa gaa<br>Lys Gln Leu Ser Gly Arg Ile Gln Leu Leu Asn Lys Leu Arg Gln Glu<br>                       500                            505                        510 | 1536 |
| gct gtg gat cta gaa aca cag atg gaa aag caa agg caa gaa att ggt<br>Ala Val Asp Leu Glu Thr Gln Met Glu Lys Gln Arg Gln Glu Ile Gly<br>              515                          520                        525 | 1584 |
| gaa aag cag aat gag atc aag gac ctg gaa ata gtc aca gat agc ctg<br>Glu Lys Gln Asn Glu Ile Lys Asp Leu Glu Ile Val Thr Asp Ser Leu<br>530                                  535                            540 | 1632 |
| gat tcc aga gac cca aaa cat tgc cat atg aag gct cag aaa aga ggt<br>Asp Ser Arg Asp Pro Lys His Cys His Met Lys Ala Gln Lys Arg Gly<br>545                                  550                            555                        560 | 1680 |
| aaa gaa caa caa ctt gac att atg aac aag cag tac aaa cag ctt gaa<br>Lys Glu Gln Gln Leu Asp Ile Met Asn Lys Gln Tyr Lys Gln Leu Glu<br>                     565                            570                        575 | 1728 |
| agc cgt ttg gat gag ata ctt tct aga att gcc aaa gaa act gaa gag<br>Ser Arg Leu Asp Glu Ile Leu Ser Arg Ile Ala Lys Glu Thr Glu Glu<br>              580                          585                        590 | 1776 |
| att aag gac ctt gaa gaa cag ctt act gaa gga caa ata gcc gca aac<br>Ile Lys Asp Leu Glu Glu Gln Leu Thr Glu Gly Gln Ile Ala Ala Asn<br>                 595                          600                        605 | 1824 |
| gaa gcc ctg aag aag gac tta gaa agt gtc atc agt ggg ttg caa gaa<br>Glu Ala Leu Lys Lys Asp Leu Glu Ser Val Ile Ser Gly Leu Gln Glu<br>610                                  615                            620 | 1872 |
| tac ctg gag act gtc aaa ggt cag gcc cgt cag gcc cag aat gag tgc<br>Tyr Leu Glu Thr Val Lys Gly Gln Ala Arg Gln Ala Gln Asn Glu Cys<br>625                                  630                            635                        640 | 1920 |
| aga aag cta cag gat gag aag gag aca ttg ctg cag aga ttg agt gag<br>Arg Lys Leu Gln Asp Glu Lys Glu Thr Leu Leu Gln Arg Leu Ser Glu<br>                     645                            650                        655 | 1968 |
| gtc gag cag gag agg gac caa ctg gaa ata gtg gcc ata gat gca gaa<br>Val Glu Gln Glu Arg Asp Gln Leu Glu Ile Val Ala Ile Asp Ala Glu<br>              660                          665                        670 | 2016 |
| aat atg agg aag gag ctc gca gaa ctg gag aat gcc ctc cag gag cag<br>Asn Met Arg Lys Glu Leu Ala Glu Leu Glu Asn Ala Leu Gln Glu Gln<br>         675                            680                        685 | 2064 |
| cat gag gtg aat ata tct ctg cag cag acc cag gga gat ctc agt gcc<br>His Glu Val Asn Ile Ser Leu Gln Gln Thr Gln Gly Asp Leu Ser Ala<br>690                                  695                            700 | 2112 |
| tat gag gct gag cta gag gct cag ctg aaa ata cgg gat gct gaa gcc<br>Tyr Glu Ala Glu Leu Glu Ala Gln Leu Lys Ile Arg Asp Ala Glu Ala<br>705                                  710                            715                        720 | 2160 |
| aac cag ctc aag gag gag ttg gaa aaa ctt aga agg ttg agc cag tta<br>Asn Gln Leu Lys Glu Glu Leu Glu Lys Leu Arg Arg Leu Ser Gln Leu<br>                     725                            730                        735 | 2208 |
| gaa caa tcg gcc ctt caa gca gag ctt gag aag gaa aag caa gcc ttc<br>Glu Gln Ser Ala Leu Gln Ala Glu Leu Glu Lys Glu Lys Gln Ala Phe<br>              740                          745                        750 | 2256 |
| aag act gct gtc aaa aaa gcc cag ctc tca gaa gga aag gac caa gaa<br>Lys Thr Ala Val Lys Lys Ala Gln Leu Ser Glu Gly Lys Asp Gln Glu<br>                 755                          760                        765 | 2304 |
| aat agt gag ctc cgc aca caa ctc caa cag ctg cag gat gac aat gac<br>Asn Ser Glu Leu Arg Thr Gln Leu Gln Gln Leu Gln Asp Asp Asn Asp<br>770                                  775                            780 | 2352 |

| | |
|---|---|
| cta ttg aaa cag caa ctt aaa gat ttc cag agt cac ctt aac cat gtg<br>Leu Leu Lys Gln Gln Leu Lys Asp Phe Gln Ser His Leu Asn His Val<br>785                     790                       795                     800 | 2400 |
| gtt gat ggt ttg att cgt cca gaa gaa gtg gca gct tgt gtg gat gag<br>Val Asp Gly Leu Ile Arg Pro Glu Glu Val Ala Ala Cys Val Asp Glu<br>                  805                       810                     815 | 2448 |
| cta agg aaa aaa ctg aag tca gga gct ggg gaa atg aga atc cat act<br>Leu Arg Lys Lys Leu Lys Ser Gly Ala Gly Glu Met Arg Ile His Thr<br>         820                       825                     830 | 2496 |
| cct tca gat gtc tta ggg aaa agt ctt gct gac ttg cag aag caa ttc<br>Pro Ser Asp Val Leu Gly Lys Ser Leu Ala Asp Leu Gln Lys Gln Phe<br>         835                       840                     845 | 2544 |
| agt gag atc ctg gca cgc tcc cag tgg gaa aga cag gaa gca caa gtg<br>Ser Glu Ile Leu Ala Arg Ser Gln Trp Glu Arg Gln Glu Ala Gln Val<br>850                     855                       860 | 2592 |
| aga gag aga aaa ctc cag gag gaa atg gct ctg caa caa gag aaa ctg<br>Arg Glu Arg Lys Leu Gln Glu Glu Met Ala Leu Gln Gln Glu Lys Leu<br>865                     870                       875                     880 | 2640 |
| gcg agc gga caa gag gag ttc agg cac gcc tgc gag agg gcc ctg gaa<br>Ala Ser Gly Gln Glu Glu Phe Arg His Ala Cys Glu Arg Ala Leu Glu<br>                       885                     890                     895 | 2688 |
| gcc cga att agt ttt gat aag agg cag cac gaa gca aga atc cag cag<br>Ala Arg Ile Ser Phe Asp Lys Arg Gln His Glu Ala Arg Ile Gln Gln<br>         900                       905                     910 | 2736 |
| ttg gag aat gaa att cac tat ttg caa gaa aat cta aaa agt atg gag<br>Leu Glu Asn Glu Ile His Tyr Leu Gln Glu Asn Leu Lys Ser Met Glu<br>                 915                     920                     925 | 2784 |
| gaa atc caa ggt ctc aca gac ctc caa ctt cag gaa gct gat gaa gag<br>Glu Ile Gln Gly Leu Thr Asp Leu Gln Leu Gln Glu Ala Asp Glu Glu<br>         930                       935                     940 | 2832 |
| aag gag aga att ctg gcc caa ctc cgg gag tta gag aaa aag aag aaa<br>Lys Glu Arg Ile Leu Ala Gln Leu Arg Glu Leu Glu Lys Lys Lys Lys<br>945                   950                       955                     960 | 2880 |
| ctt gag gat gcc aag tct cag gag cag ttt ctt gga tta gat aga gaa<br>Leu Glu Asp Ala Lys Ser Gln Glu Gln Phe Leu Gly Leu Asp Arg Glu<br>                       965                     970                     975 | 2928 |
| ttg aag aag cta aag aaa gct gtg gct gcc tct gat aag ctg gcc aca<br>Leu Lys Lys Leu Lys Lys Ala Val Ala Ala Ser Asp Lys Leu Ala Thr<br>         980                       985                     990 | 2976 |
| gct gag ctc acc att gcc aaa gac cag ctc aag tcc ctt cat gga act<br>Ala Glu Leu Thr Ile Ala Lys Asp Gln Leu Lys Ser Leu His Gly Thr<br>               995                    1000                  1005 | 3024 |
| gtg atg aaa att aac cag gag cga gca gag gag ctg cag gag acg<br>Val Met Lys Ile Asn Gln Glu Arg Ala Glu Glu Leu Gln Glu Thr<br>        1010                  1015                  1020 | 3069 |
| gag agg ttc agc aga aag gca gca caa gca gct agg gat ctg atc<br>Glu Arg Phe Ser Arg Lys Ala Ala Gln Ala Ala Arg Asp Leu Ile<br>1025                  1030                  1035 | 3114 |
| cga gca gaa gcg gag att gaa ctc ctg cag aag ctt ctc aga gat<br>Arg Ala Glu Ala Glu Ile Glu Leu Leu Gln Lys Leu Leu Arg Asp<br>1040                  1045                  1050 | 3159 |
| aaa gag gag cag ttt cga aat gag att gag aaa gta gat gtc ggc<br>Lys Glu Glu Gln Phe Arg Asn Glu Ile Glu Lys Val Asp Val Gly<br>1055                  1060                  1065 | 3204 |
| tct gga gga gca aag tca cag atg ctg gag atg gag aaa cta aat<br>Ser Gly Gly Ala Lys Ser Gln Met Leu Glu Met Glu Lys Leu Asn<br>1070                  1075                  1080 | 3249 |
| gag aca atg gag agg caa aga aca gag att gct agg ctg agg aat<br>Glu Thr Met Glu Arg Gln Arg Thr Glu Ile Ala Arg Leu Arg Asn | 3294 |

-continued

```
              1085                1090                1095
tta cta gac ctc acc ggg gct gat aac aaa gga aac ttt gaa aat    3339
Leu Leu Asp Leu Thr Gly Ala Asp Asn Lys Gly Asn Phe Glu Asn
    1100                1105                1110 gtt ttg gaa gaa att gct gaa ctt cga cgt gaa gtt tct cat cag    3384
Val Leu Glu Glu Ile Ala Glu Leu Arg Arg Glu Val Ser His Gln
    1115                1120                1125 aat gat tac atc agc agc atg aca gat cct ttc aaa aga cga ggc    3429
Asn Asp Tyr Ile Ser Ser Met Thr Asp Pro Phe Lys Arg Arg Gly
    1130                1135                1140 tat tgg tac ttt atg cca cca cca tca tca tca aaa gtt tcc agc    3474
Tyr Trp Tyr Phe Met Pro Pro Pro Ser Ser Ser Lys Val Ser Ser
    1145                1150                1155 cac agt tcc cag gcc acc aag gac tct ggt gtt ggc cta aag tac    3519
His Ser Ser Gln Ala Thr Lys Asp Ser Gly Val Gly Leu Lys Tyr
    1160                1165                1170 aca gcc tcc act ccg gtt aga aaa cca cat cgt gga cgg cag gat    3564
Thr Ala Ser Thr Pro Val Arg Lys Pro His Arg Gly Arg Gln Asp
    1175                1180                1185 gga aag gag aac agt ggg cct cca cct gcc tca gga tac tgg gtg    3609
Gly Lys Glu Asn Ser Gly Pro Pro Pro Ala Ser Gly Tyr Trp Val
    1190                1195                1200 tat tct cct atc agg agt ggg tta cat aaa tcg ttc tca aat aga    3654
Tyr Ser Pro Ile Arg Ser Gly Leu His Lys Ser Phe Ser Asn Arg
    1205                1210                1215 gac gca gac agt gga gga gat agc cag gaa gag agc gag cta gat    3699
Asp Ala Asp Ser Gly Gly Asp Ser Gln Glu Glu Ser Glu Leu Asp
    1220                1225                1230 gac caa gaa gac cac cca ttt gta cct cct cct gga tac atg atg    3744
Asp Gln Glu Asp His Pro Phe Val Pro Pro Pro Gly Tyr Met Met
    1235                1240                1245 tac act gtg ttt cct gat ggt tct cct gta ccc cag ggc atg gcc    3789
Tyr Thr Val Phe Pro Asp Gly Ser Pro Val Pro Gln Gly Met Ala
    1250                1255                1260 ctg tat gca ccc cct cct ccc ttg ccc aac aat agc cag cct ctt    3834
Leu Tyr Ala Pro Pro Pro Pro Leu Pro Asn Asn Ser Gln Pro Leu
    1265                1270                1275 gac ctt ggc act gtt gtt tat ggc cca cct cct gtt ggg gct ccc    3879
Asp Leu Gly Thr Val Val Tyr Gly Pro Pro Pro Val Gly Ala Pro
    1280                1285                1290 atc gtg tat ggg cct cca cct ccc aac ttc tcc gta ccc ctc atc    3924
Ile Val Tyr Gly Pro Pro Pro Pro Asn Phe Ser Val Pro Leu Ile
    1295                1300                1305 ccc gtg ggt gtg ctg cac tgc aat gtc cca gaa cac cat aac ttg    3969
Pro Val Gly Val Leu His Cys Asn Val Pro Glu His His Asn Leu
    1310                1315                1320 gag aat gaa gtt tct aga tta gaa gac ata atg cag cat tta aaa    4014
Glu Asn Glu Val Ser Arg Leu Glu Asp Ile Met Gln His Leu Lys
    1325                1330                1335 tct ggg aaa cgg gaa cag tgc atg aaa aca ccc aag ctg cag tcg    4059
Ser Gly Lys Arg Glu Gln Cys Met Lys Thr Pro Lys Leu Gln Ser
    1340                1345                1350 gag aaa gaa ctc gca gag ctg cag cat aac att gat ggt ctt ttg    4104
Glu Lys Glu Leu Ala Glu Leu Gln His Asn Ile Asp Gly Leu Leu
    1355                1360                1365 caa gag aag aaa gac tta gag cat gaa gta gaa gaa tta cat aga    4149
Gln Glu Lys Lys Asp Leu Glu His Glu Val Glu Glu Leu His Arg
    1370                1375                1380 acc atc caa aaa cat caa cag cga aaa gat ttc att gat gga aac    4194
```

```
Thr Ile Gln Lys His Gln Gln Arg Lys Asp Phe Ile Asp Gly Asn
    1385            1390            1395 gtt gag agt ctt gtg aat gat cta gaa ata gag aag tca ctc aaa    4239
Val Glu Ser Leu Val Asn Asp Leu Glu Ile Glu Lys Ser Leu Lys
1400            1405            1410 cac cat gaa gat att gtt gat gaa att gaa tgt att gag agg acc    4284
His His Glu Asp Ile Val Asp Glu Ile Glu Cys Ile Glu Arg Thr
    1415            1420            1425 ctt ctg aag cgc cgt gca gag ctc agg gaa gcc gac cgg ctg ctg    4329
Leu Leu Lys Arg Arg Ala Glu Leu Arg Glu Ala Asp Arg Leu Leu
1430            1435            1440 acg gag gct gaa agt gaa ctt tca tgc acg aaa gag aaa aca aaa    4374
Thr Glu Ala Glu Ser Glu Leu Ser Cys Thr Lys Glu Lys Thr Lys
    1445            1450            1455 cat gct gtt gag aag ttc act gat gcc aag aga aat tta ttg caa    4419
His Ala Val Glu Lys Phe Thr Asp Ala Lys Arg Asn Leu Leu Gln
1460            1465            1470 act gag aaa gat gct gag gag tta gaa agg aga gcc cag gaa act    4464
Thr Glu Lys Asp Ala Glu Glu Leu Glu Arg Arg Ala Gln Glu Thr
    1475            1480            1485 gcc att aac ctc gtc aaa gcc gac cag cag ctg aga ttg ctc cag    4509
Ala Ile Asn Leu Val Lys Ala Asp Gln Gln Leu Arg Leu Leu Gln
1490            1495            1500 gct gac acg aag gat ttg gag cag cac aaa atg gag caa gag gaa    4554
Ala Asp Thr Lys Asp Leu Glu Gln His Lys Met Glu Gln Glu Glu
    1505            1510            1515 atc ttg aaa gaa ata aac aaa gtt gtt gca gca aaa gac tca gac    4599
Ile Leu Lys Glu Ile Asn Lys Val Val Ala Ala Lys Asp Ser Asp
1520            1525            1530 ttc cag agc cta aac aag aag aag gaa gta ctg aca gga gag ctg    4644
Phe Gln Ser Leu Asn Lys Lys Lys Glu Val Leu Thr Gly Glu Leu
    1535            1540            1545 cag aaa ctc cag aag gac att gag act gca cgg cac aat gag gat    4689
Gln Lys Leu Gln Lys Asp Ile Glu Thr Ala Arg His Asn Glu Asp
1550            1555            1560 cag cac ctg cag gtc ctt aaa gag tcg gag acc ctc ctg cag gcc    4734
Gln His Leu Gln Val Leu Lys Glu Ser Glu Thr Leu Leu Gln Ala
    1565            1570            1575 aag aaa gct gag ctg gaa aat ctg aaa agc cag gtg tca gga cag    4779
Lys Lys Ala Glu Leu Glu Asn Leu Lys Ser Gln Val Ser Gly Gln
1580            1585            1590 cag cag gag atg gcc gtc ttg gac agg gag tta gga cac aag aag    4824
Gln Gln Glu Met Ala Val Leu Asp Arg Glu Leu Gly His Lys Lys
    1595            1600            1605 gaa gag ctg cat ctc ctc cag gaa agc atg gtc cag gcc aaa gct    4869
Glu Glu Leu His Leu Leu Gln Glu Ser Met Val Gln Ala Lys Ala
1610            1615            1620 gac ctc cag gaa gca ctg aga cta gga gaa agc gaa gta act gag    4914
Asp Leu Gln Glu Ala Leu Arg Leu Gly Glu Ser Glu Val Thr Glu
    1625            1630            1635 aag tgc aat cac att agg gaa gta aaa tct ctt ctg gaa gaa ctc    4959
Lys Cys Asn His Ile Arg Glu Val Lys Ser Leu Leu Glu Glu Leu
1640            1645            1650 agt ttt cag aaa gga gaa ctg aat gtc cag atc agt gaa aaa aaa    5004
Ser Phe Gln Lys Gly Glu Leu Asn Val Gln Ile Ser Glu Lys Lys
    1655            1660            1665 act caa ctt gca ctc ata aag cag gaa att gaa aaa gag gaa gac    5049
Thr Gln Leu Ala Leu Ile Lys Gln Glu Ile Glu Lys Glu Glu Asp
1670            1675            1680
```

```
aat ctt cag gta gtt tta ggg caa atg tct aaa cat aaa act gaa       5094
Asn Leu Gln Val Val Leu Gly Gln Met Ser Lys His Lys Thr Glu
    1685            1690                1695 cta aag aat att ctg gac atg ttg caa ctt gaa aat aat gag ctg       5139
Leu Lys Asn Ile Leu Asp Met Leu Gln Leu Glu Asn Asn Glu Leu
    1700            1705                1710 caa ggt ttg aag ctc caa cat gac caa aag atg tct gaa tta gag       5184
Gln Gly Leu Lys Leu Gln His Asp Gln Lys Met Ser Glu Leu Glu
    1715            1720                1725 aag act cgg gtt gaa gtg ctg gag gag aaa ctg gag tta gag agt       5229
Lys Thr Arg Val Glu Val Leu Glu Glu Lys Leu Glu Leu Glu Ser
    1730            1735                1740 ctg cag cag gca gcc ctg cga cag aga ggg gag ata gag tgg cag       5274
Leu Gln Gln Ala Ala Leu Arg Gln Arg Gly Glu Ile Glu Trp Gln
    1745            1750                1755 aag cag ctc ctc cag agg aac aca cag gaa gta gag cgg atg act       5319
Lys Gln Leu Leu Gln Arg Asn Thr Gln Glu Val Glu Arg Met Thr
    1760            1765                1770 gct gag acc cga gca tta cag tcg tgt gtt gag tct ttg tgc aaa       5364
Ala Glu Thr Arg Ala Leu Gln Ser Cys Val Glu Ser Leu Cys Lys
    1775            1780                1785 gaa aag caa gat ctc gaa gaa aaa cag gac agc tgg gaa aag aag       5409
Glu Lys Gln Asp Leu Glu Glu Lys Gln Asp Ser Trp Glu Lys Lys
    1790            1795                1800 ttg gca cag acc aaa cgg gtt cta gca gct gca gaa gag gac agc       5454
Leu Ala Gln Thr Lys Arg Val Leu Ala Ala Ala Glu Glu Asp Ser
    1805            1810                1815 gag atg gag cgg gca cgc tta gaa aag ttg gaa ctg gac gcc agg       5499
Glu Met Glu Arg Ala Arg Leu Glu Lys Leu Glu Leu Asp Ala Arg
    1820            1825                1830 aag ctg cag cag gag ttg gac caa cga aac agg gag aag ctc tcc       5544
Lys Leu Gln Gln Glu Leu Asp Gln Arg Asn Arg Glu Lys Leu Ser
    1835            1840                1845 ctg cat caa gac ctg gca gtg gtg cag cag cag cta caa gaa aaa       5589
Leu His Gln Asp Leu Ala Val Val Gln Gln Gln Leu Gln Glu Lys
    1850            1855                1860 cag gaa gca gta aac tca tta cag aag gaa cta act gat gtc cag       5634
Gln Glu Ala Val Asn Ser Leu Gln Lys Glu Leu Thr Asp Val Gln
    1865            1870                1875 gag cat ttg gac cta gca gaa cag gag gtg ctc tgc acc acc aag       5679
Glu His Leu Asp Leu Ala Glu Gln Glu Val Leu Cys Thr Thr Lys
    1880            1885                1890 cgc aag gac gca ctc ctc agc gaa cag acc agg ctc gag aag gac       5724
Arg Lys Asp Ala Leu Leu Ser Glu Gln Thr Arg Leu Glu Lys Asp
    1895            1900                1905 gtg ggt gaa tgg acg aag aag ttt gaa gac tgc cag aaa gaa ggg       5769
Val Gly Glu Trp Thr Lys Lys Phe Glu Asp Cys Gln Lys Glu Gly
    1910            1915                1920 gag aca aag cag caa cag ctt caa ggg ctt cag aag gag att gaa       5814
Glu Thr Lys Gln Gln Gln Leu Gln Gly Leu Gln Lys Glu Ile Glu
    1925            1930                1935 gga aac gag gcg aag cta gcc caa caa gaa atg atg ttt cag aga       5859
Gly Asn Glu Ala Lys Leu Ala Gln Gln Glu Met Met Phe Gln Arg
    1940            1945                1950 ctc cag aaa gag cga gaa tgt gaa gaa aaa aag tta gaa gct agt       5904
Leu Gln Lys Glu Arg Glu Cys Glu Glu Lys Lys Leu Glu Ala Ser
    1955            1960                1965 aaa gtg act ctg aag gag cag cag caa cag ctg gaa aag gaa ttg       5949
Lys Val Thr Leu Lys Glu Gln Gln Gln Gln Leu Glu Lys Glu Leu
    1970            1975                1980
```

```
atg gag cag aaa ggc aag ctg gac cag gtg ctc gct aag ctc ttg                5994
Met Glu Gln Lys Gly Lys Leu Asp Gln Val Leu Ala Lys Leu Leu
    1985            1990                1995 gtg gct gag gag cgt gtc agg acc ttg cag gag gag gga agg tgg                6039
Val Ala Glu Glu Arg Val Arg Thr Leu Gln Glu Glu Gly Arg Trp
        2000            2005                2010 agc gag acc ctg gag aag acg ctc tcc cag acc aag cga cag ctt                6084
Ser Glu Thr Leu Glu Lys Thr Leu Ser Gln Thr Lys Arg Gln Leu
    2015            2020                2025 tca gaa cgg gag cag cag tta ctg gcc aag tca gac gag ctg ctg                6129
Ser Glu Arg Glu Gln Gln Leu Leu Ala Lys Ser Asp Glu Leu Leu
        2030            2035                2040 gcc ctg cag aag gag acg gac tcc atg agg gcg gac ttc agc ctc                6174
Ala Leu Gln Lys Glu Thr Asp Ser Met Arg Ala Asp Phe Ser Leu
    2045            2050                2055 ttg cgc aac cag ttc ctg aca gaa aga aag aaa gcc gag aag cag                6219
Leu Arg Asn Gln Phe Leu Thr Glu Arg Lys Lys Ala Glu Lys Gln
        2060            2065                2070 gtg gcc agc ctg aag gaa gcc ctt aag atc cag cgg agc caa ctg                6264
Val Ala Ser Leu Lys Glu Ala Leu Lys Ile Gln Arg Ser Gln Leu
    2075            2080                2085 gag aag aac ctt ctg gag caa aag cag gag aac agc tgc atg cag                6309
Glu Lys Asn Leu Leu Glu Gln Lys Gln Glu Asn Ser Cys Met Gln
        2090            2095                2100 agg gag atg gca acc atc gaa cag gtg gcc cag gac aac cac gag                6354
Arg Glu Met Ala Thr Ile Glu Gln Val Ala Gln Asp Asn His Glu
    2105            2110                2115 cgg gcc cgg cgc cta atg agg gag ctc aac cag atg cag cgc gag                6399
Arg Ala Arg Arg Leu Met Arg Glu Leu Asn Gln Met Gln Arg Glu
        2120            2125                2130 tac gtg gag ctc agg aaa cag atg aca aac caa aag gat ttg gaa                6444
Tyr Val Glu Leu Arg Lys Gln Met Thr Asn Gln Lys Asp Leu Glu
    2135            2140                2145 aga aga cag atg gaa atc agt gat gcg atg caa gca ctt aaa tgt                6489
Arg Arg Gln Met Glu Ile Ser Asp Ala Met Gln Ala Leu Lys Cys
        2150            2155                2160 gag gtg aaa gat gaa atc cga acc agc ctg aag aat ctc aac cag                6534
Glu Val Lys Asp Glu Ile Arg Thr Ser Leu Lys Asn Leu Asn Gln
    2165            2170                2175 ttt ctt cca gaa ctg cca gcg gac ctg gag gcc ctt ctg gaa agg                6579
Phe Leu Pro Glu Leu Pro Ala Asp Leu Glu Ala Leu Leu Glu Arg
        2180            2185                2190 aat gag aac ctt gga gga ggc ttg gag agc ttg aaa gag aat ttc                6624
Asn Glu Asn Leu Gly Gly Gly Leu Glu Ser Leu Lys Glu Asn Phe
    2195            2200                2205 ccg ttt acc gtg agc gac aga cca tca tct tgc gaa gag aaa ctg                6669
Pro Phe Thr Val Ser Asp Arg Pro Ser Ser Cys Glu Glu Lys Leu
        2210            2215                2220 aat ttt ggc cag gct cac gtg gcg gat gaa cag tgg cgg gga gag                6714
Asn Phe Gly Gln Ala His Val Ala Asp Glu Gln Trp Arg Gly Glu
    2225            2230                2235 gca ctc cgg gag aag ctg cgc cac cgc gag gac cgg ctc aag gcc                6759
Ala Leu Arg Glu Lys Leu Arg His Arg Glu Asp Arg Leu Lys Ala
        2240            2245                2250 cag ctg cgc cgc tgc atg tcc aag cag gcc gag gtg ctg agc gag                6804
Gln Leu Arg Arg Cys Met Ser Lys Gln Ala Glu Val Leu Ser Glu
    2255            2260                2265 ggc cgg cgg cgc acg gag ggg acc ctg cac agc ctg cgg cgg cag                6849
Gly Arg Arg Arg Thr Glu Gly Thr Leu His Ser Leu Arg Arg Gln
```

```
                    2270                2275                2280
gtg  gac  gcc  ctg  ggc  gag  ctg  gtc  acc  agc  act  tcc  ggg  gac  tcc      6894
Val  Asp  Ala  Leu  Gly  Glu  Leu  Val  Thr  Ser  Thr  Ser  Gly  Asp  Ser
     2285                2290                2295 gcg  tcc  acc  cgc  agt  ctg  tcg  cgc  acc  gag  ggc  tcg  ctc  gcc  gag      6939
Ala  Ser  Thr  Arg  Ser  Leu  Ser  Arg  Thr  Glu  Gly  Ser  Leu  Ala  Glu
2300                2305                2310 gac  gaa  ccg  ccg  ggg  ccc  agc  cag  agc  tcc  cgg  cgg  ctc  ccc  cga      6984
Asp  Glu  Pro  Pro  Gly  Pro  Ser  Gln  Ser  Ser  Arg  Arg  Leu  Pro  Arg
     2315                2320                2325 ggc  ccg  tcg  ccg  cgg  ctg  gac  gcg  cac  cga  ccc  tga ggacccggag          7030
Gly  Pro  Ser  Pro  Arg  Leu  Asp  Ala  His  Arg  Pro
2330                2335 gacccggagg cccggcgtcc cctcggaacg cttcctccgc gtccgcggac accaggctca              7090
cgggaaggcg cgtccatgcg ggaagagccg cgagcggaac ccggatgccc gggctggtct              7150
ctgggccttg gaaacgtgtt gccgtaaaag cagcgcccgc ggctgcggac ttgaagcccc              7210
gaactggtaa actcggcggc tgccgggcga actgtactca ggacttttt  cacggacacc              7270 gtcagatttt attttggaa  atctattttc atatgaaaat aaaagataaa agcgcctgaa              7330
aaaaaaaaaa aaaaaaaact agt                                                      7353

<210> SEQ ID NO 26
<211> LENGTH: 2339
<212> TYPE: PRT
<213> ORGANISM: Canis familiaris

<400> SEQUENCE: 26

Met Lys Lys Gly Ser Gln Gln Lys Phe Leu Lys Ala Lys Met Pro Pro
1               5                   10                  15

Ser Ser His Ser Pro Ser Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45

Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220
```

```
Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
            245                 250                 255

Ser Gln Asp Arg Gln Glu Ala Phe Ala Arg Phe Ser Leu Asp Glu Val
                260                 265                 270

Glu Arg Leu Glu Arg Asp Leu Glu Lys Lys Thr Met Glu Thr Glu Glu
            275                 280                 285

Leu Arg Ser Glu Gln Thr Arg Phe Leu Glu Glu Ile Lys Ser Gln Asp
        290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
370                 375                 380

Ser Pro Tyr Ile Gly Lys Ser Arg Tyr Lys Arg Asn Met Phe Thr Thr
385                 390                 395                 400

Glu Ser Tyr Ile Ile Ala Asn Ala Gln Thr Val Lys Ile Lys Lys Met
                405                 410                 415

Glu Leu Asp Glu Gly Glu Gln Leu Arg Asn Glu His Val Asn Leu Gly
            420                 425                 430

Ala Ser Pro Thr Asp Ile Gln Leu Glu Asp Lys Glu Lys Lys Ile Ser
        435                 440                 445

Ala Ala Gln Thr Arg Leu Ser Glu Leu His Asp Glu Ile Glu Lys Ala
        450                 455                 460

Glu Gln Gln Ile Leu Arg Ala Thr Glu Glu Phe Lys Gln Leu Glu Glu
465                 470                 475                 480

Ala Ile Gln Leu Lys Lys Ile Ser Glu Ala Glu Lys Asp Leu Leu Phe
                485                 490                 495

Lys Gln Leu Ser Gly Arg Ile Gln Leu Leu Asn Lys Leu Arg Gln Glu
            500                 505                 510

Ala Val Asp Leu Glu Thr Gln Met Glu Lys Gln Arg Gln Glu Ile Gly
        515                 520                 525

Glu Lys Gln Asn Glu Ile Lys Asp Leu Glu Ile Val Thr Asp Ser Leu
530                 535                 540

Asp Ser Arg Asp Pro Lys His Cys His Met Lys Ala Gln Lys Arg Gly
545                 550                 555                 560

Lys Glu Gln Gln Leu Asp Ile Met Asn Lys Gln Tyr Lys Gln Leu Glu
                565                 570                 575

Ser Arg Leu Asp Glu Ile Leu Ser Arg Ile Ala Lys Glu Thr Glu Glu
            580                 585                 590

Ile Lys Asp Leu Glu Glu Gln Leu Thr Glu Gly Gln Ile Ala Ala Asn
        595                 600                 605

Glu Ala Leu Lys Lys Asp Leu Glu Ser Val Ile Ser Gly Leu Gln Glu
610                 615                 620

Tyr Leu Glu Thr Val Lys Gly Gln Ala Arg Gln Ala Gln Asn Glu Cys
625                 630                 635                 640
```

-continued

```
Arg Lys Leu Gln Asp Glu Lys Glu Thr Leu Leu Gln Arg Leu Ser Glu
                645                 650                 655
Val Glu Gln Glu Arg Asp Gln Leu Glu Ile Val Ala Ile Asp Ala Glu
            660                 665                 670
Asn Met Arg Lys Glu Leu Ala Glu Leu Glu Asn Ala Leu Gln Glu Gln
            675                 680                 685
His Glu Val Asn Ile Ser Leu Gln Gln Thr Gln Gly Asp Leu Ser Ala
        690                 695                 700
Tyr Glu Ala Glu Leu Glu Ala Gln Leu Lys Ile Arg Asp Ala Glu Ala
705                 710                 715                 720
Asn Gln Leu Lys Glu Glu Leu Glu Lys Leu Arg Arg Leu Ser Gln Leu
                725                 730                 735
Glu Gln Ser Ala Leu Gln Ala Glu Leu Glu Lys Glu Lys Gln Ala Phe
            740                 745                 750
Lys Thr Ala Val Lys Lys Ala Gln Leu Ser Glu Gly Lys Asp Gln Glu
            755                 760                 765
Asn Ser Glu Leu Arg Thr Gln Leu Gln Gln Leu Gln Asp Asp Asn Asp
        770                 775                 780
Leu Leu Lys Gln Gln Leu Lys Asp Phe Gln Ser His Leu Asn His Val
785                 790                 795                 800
Val Asp Gly Leu Ile Arg Pro Glu Val Ala Ala Cys Val Asp Glu
            805                 810                 815
Leu Arg Lys Lys Leu Lys Ser Gly Ala Gly Glu Met Arg Ile His Thr
            820                 825                 830
Pro Ser Asp Val Leu Gly Lys Ser Leu Ala Asp Leu Gln Lys Gln Phe
        835                 840                 845
Ser Glu Ile Leu Ala Arg Ser Gln Trp Glu Arg Gln Glu Ala Gln Val
    850                 855                 860
Arg Glu Arg Lys Leu Gln Glu Glu Met Ala Leu Gln Gln Glu Lys Leu
865                 870                 875                 880
Ala Ser Gly Gln Glu Glu Phe Arg His Ala Cys Glu Arg Ala Leu Glu
                885                 890                 895
Ala Arg Ile Ser Phe Asp Lys Arg Gln His Glu Ala Arg Ile Gln Gln
            900                 905                 910
Leu Glu Asn Glu Ile His Tyr Leu Gln Glu Asn Leu Lys Ser Met Glu
            915                 920                 925
Glu Ile Gln Gly Leu Thr Asp Leu Gln Leu Gln Glu Ala Asp Glu Glu
        930                 935                 940
Lys Glu Arg Ile Leu Ala Gln Leu Arg Glu Leu Glu Lys Lys Lys Lys
945                 950                 955                 960
Leu Glu Asp Ala Lys Ser Gln Glu Gln Phe Leu Gly Leu Asp Arg Glu
                965                 970                 975
Leu Lys Lys Leu Lys Lys Ala Val Ala Ala Ser Asp Lys Leu Ala Thr
            980                 985                 990
Ala Glu Leu Thr Ile Ala Lys Asp Gln Leu Lys Ser Leu His Gly Thr
            995                1000                1005
Val Met Lys Ile Asn Gln Glu Arg Ala Glu Glu Leu Gln Glu Thr
        1010                1015                1020
Glu Arg Phe Ser Arg Lys Ala Ala Gln Ala Ala Arg Asp Leu Ile
    1025                1030                1035
Arg Ala Glu Ala Glu Ile Glu Leu Leu Gln Lys Leu Leu Arg Asp
    1040                1045                1050
Lys Glu Glu Gln Phe Arg Asn Glu Ile Glu Lys Val Asp Val Gly
```

```
       1055               1060                1065
Ser Gly Gly Ala Lys Ser Gln Met Leu Glu Met Glu Lys Leu Asn
       1070               1075                1080

Glu Thr Met Glu Arg Gln Arg Thr Glu Ile Ala Arg Leu Arg Asn
       1085               1090                1095

Leu Leu Asp Leu Thr Gly Ala Asp Asn Lys Gly Asn Phe Glu Asn
       1100               1105                1110

Val Leu Glu Glu Ile Ala Glu Leu Arg Arg Glu Val Ser His Gln
       1115               1120                1125

Asn Asp Tyr Ile Ser Ser Met Thr Asp Pro Phe Lys Arg Arg Gly
       1130               1135                1140

Tyr Trp Tyr Phe Met Pro Pro Ser Ser Lys Val Ser Ser
       1145               1150                1155

His Ser Ser Gln Ala Thr Lys Asp Ser Gly Val Gly Leu Lys Tyr
       1160               1165                1170

Thr Ala Ser Thr Pro Val Arg Lys Pro His Arg Gly Arg Gln Asp
       1175               1180                1185

Gly Lys Glu Asn Ser Gly Pro Pro Ala Ser Gly Tyr Trp Val
       1190               1195                1200

Tyr Ser Pro Ile Arg Ser Gly Leu His Lys Ser Phe Ser Asn Arg
       1205               1210                1215

Asp Ala Asp Ser Gly Gly Asp Ser Gln Glu Glu Ser Glu Leu Asp
       1220               1225                1230

Asp Gln Glu Asp His Pro Phe Val Pro Pro Gly Tyr Met Met
       1235               1240                1245

Tyr Thr Val Phe Pro Asp Gly Ser Pro Val Pro Gln Gly Met Ala
       1250               1255                1260

Leu Tyr Ala Pro Pro Pro Pro Leu Pro Asn Asn Ser Gln Pro Leu
       1265               1270                1275

Asp Leu Gly Thr Val Val Tyr Gly Pro Pro Pro Val Gly Ala Pro
       1280               1285                1290

Ile Val Tyr Gly Pro Pro Pro Pro Asn Phe Ser Val Pro Leu Ile
       1295               1300                1305

Pro Val Gly Val Leu His Cys Asn Val Pro Glu His His Asn Leu
       1310               1315                1320

Glu Asn Glu Val Ser Arg Leu Glu Asp Ile Met Gln His Leu Lys
       1325               1330                1335

Ser Gly Lys Arg Glu Gln Cys Met Lys Thr Pro Lys Leu Gln Ser
       1340               1345                1350

Glu Lys Glu Leu Ala Glu Leu Gln His Asn Ile Asp Gly Leu Leu
       1355               1360                1365

Gln Glu Lys Lys Asp Leu Glu His Glu Val Glu Glu Leu His Arg
       1370               1375                1380

Thr Ile Gln Lys His Gln Gln Arg Lys Asp Phe Ile Asp Gly Asn
       1385               1390                1395

Val Glu Ser Leu Val Asn Asp Leu Glu Ile Glu Lys Ser Leu Lys
       1400               1405                1410

His His Glu Asp Ile Val Asp Glu Ile Glu Cys Ile Glu Arg Thr
       1415               1420                1425

Leu Leu Lys Arg Arg Ala Glu Leu Arg Glu Ala Asp Arg Leu Leu
       1430               1435                1440

Thr Glu Ala Glu Ser Glu Leu Ser Cys Thr Lys Glu Lys Thr Lys
       1445               1450                1455
```

-continued

```
His Ala Val Glu Lys Phe Thr Asp Ala Lys Arg Asn  Leu Leu Gln
    1460                1465                1470

Thr Glu Lys Asp Ala Glu Glu Leu Glu Arg Arg Ala  Gln Glu Thr
    1475                1480                1485

Ala Ile Asn Leu Val Lys Ala Asp Gln Gln Leu Arg  Leu Leu Gln
    1490                1495                1500

Ala Asp Thr Lys Asp Leu Glu Gln His Lys Met Glu  Gln Glu Glu
    1505                1510                1515

Ile Leu Lys Glu Ile Asn Lys Val Val Ala Ala Lys  Asp Ser Asp
    1520                1525                1530

Phe Gln Ser Leu Asn Lys Lys Glu Val Leu Thr  Gly Glu Leu
    1535                1540                1545

Gln Lys Leu Gln Lys Asp Ile Glu Thr Ala Arg His  Asn Glu Asp
    1550                1555                1560

Gln His Leu Gln Val Leu Lys Glu Ser Glu Thr Leu  Leu Gln Ala
    1565                1570                1575

Lys Lys Ala Glu Leu Glu Asn Leu Lys Ser Gln Val  Ser Gly Gln
    1580                1585                1590

Gln Gln Glu Met Ala Val Leu Asp Arg Glu Leu Gly  His Lys Lys
    1595                1600                1605

Glu Glu Leu His Leu Leu Gln Glu Ser Met Val Gln  Ala Lys Ala
    1610                1615                1620

Asp Leu Gln Glu Ala Leu Arg Leu Gly Glu Ser Glu  Val Thr Glu
    1625                1630                1635

Lys Cys Asn His Ile Arg Glu Val Lys Ser Leu Leu  Glu Glu Leu
    1640                1645                1650

Ser Phe Gln Lys Gly Glu Leu Asn Val Gln Ile Ser  Glu Lys Lys
    1655                1660                1665

Thr Gln Leu Ala Leu Ile Lys Gln Glu Ile Glu Lys  Glu Glu Asp
    1670                1675                1680

Asn Leu Gln Val Val Leu Gly Gln Met Ser Lys His  Lys Thr Glu
    1685                1690                1695

Leu Lys Asn Ile Leu Asp Met Leu Gln Leu Glu Asn  Asn Glu Leu
    1700                1705                1710

Gln Gly Leu Lys Leu Gln His Asp Gln Lys Met Ser  Glu Leu Glu
    1715                1720                1725

Lys Thr Arg Val Glu Val Leu Glu Glu Lys Leu Glu  Leu Glu Ser
    1730                1735                1740

Leu Gln Gln Ala Ala Leu Arg Gln Arg Gly Glu Ile  Glu Trp Gln
    1745                1750                1755

Lys Gln Leu Leu Gln Arg Asn Thr Gln Glu Val Glu  Arg Met Thr
    1760                1765                1770

Ala Glu Thr Arg Ala Leu Gln Ser Cys Val Glu Ser  Leu Cys Lys
    1775                1780                1785

Glu Lys Gln Asp Leu Glu Glu Lys Gln Asp Ser Trp  Glu Lys Lys
    1790                1795                1800

Leu Ala Gln Thr Lys Arg Val Leu Ala Ala Ala Glu  Glu Asp Ser
    1805                1810                1815

Glu Met Glu Arg Ala Arg Leu Glu Lys Leu Glu Leu  Asp Ala Arg
    1820                1825                1830

Lys Leu Gln Gln Glu Leu Asp Gln Arg Asn Arg Glu  Lys Leu Ser
    1835                1840                1845
```

```
Leu His Gln Asp Leu Ala Val  Val Gln Gln Gln Leu  Gln Glu Lys
    1850             1855              1860

Gln Glu Ala Val Asn Ser Leu  Gln Lys Glu Leu Thr  Asp Val Gln
    1865             1870              1875

Glu His Leu Asp Leu Ala Glu  Gln Glu Val Leu Cys  Thr Thr Lys
    1880             1885              1890

Arg Lys Asp Ala Leu Leu Ser  Glu Gln Thr Arg Leu  Glu Lys Asp
    1895             1900              1905

Val Gly Glu Trp Thr Lys Lys  Phe Glu Asp Cys Gln  Lys Glu Gly
    1910             1915              1920

Glu Thr Lys Gln Gln Gln Leu  Gln Gly Leu Gln Lys  Glu Ile Glu
    1925             1930              1935

Gly Asn Glu Ala Lys Leu Ala  Gln Gln Glu Met Met  Phe Gln Arg
    1940             1945              1950

Leu Gln Lys Glu Arg Glu Cys  Glu Glu Lys Lys Leu  Glu Ala Ser
    1955             1960              1965

Lys Val Thr Leu Lys Glu Gln  Gln Gln Gln Leu Glu  Lys Glu Leu
    1970             1975              1980

Met Glu Gln Lys Gly Lys Leu  Asp Gln Val Leu Ala  Lys Leu Leu
    1985             1990              1995

Val Ala Glu Glu Arg Val Arg  Thr Leu Gln Glu Glu  Gly Arg Trp
    2000             2005              2010

Ser Glu Thr Leu Glu Lys Thr  Leu Ser Gln Thr Lys  Arg Gln Leu
    2015             2020              2025

Ser Glu Arg Glu Gln Gln Leu  Leu Ala Lys Ser Asp  Glu Leu Leu
    2030             2035              2040

Ala Leu Gln Lys Glu Thr Asp  Ser Met Arg Ala Asp  Phe Ser Leu
    2045             2050              2055

Leu Arg Asn Gln Phe Leu Thr  Glu Arg Lys Lys Ala  Glu Lys Gln
    2060             2065              2070

Val Ala Ser Leu Lys Glu Ala  Leu Lys Ile Gln Arg  Ser Gln Leu
    2075             2080              2085

Glu Lys Asn Leu Leu Glu Gln  Lys Gln Glu Asn Ser  Cys Met Gln
    2090             2095              2100

Arg Glu Met Ala Thr Ile Glu  Gln Val Ala Gln Asp  Asn His Glu
    2105             2110              2115

Arg Ala Arg Arg Leu Met Arg  Glu Leu Asn Gln Met  Gln Arg Glu
    2120             2125              2130

Tyr Val Glu Leu Arg Lys Gln  Met Thr Asn Gln Lys  Asp Leu Glu
    2135             2140              2145

Arg Arg Gln Met Glu Ile Ser  Asp Ala Met Gln Ala  Leu Lys Cys
    2150             2155              2160

Glu Val Lys Asp Glu Ile Arg  Thr Ser Leu Lys Asn  Leu Asn Gln
    2165             2170              2175

Phe Leu Pro Glu Leu Pro Ala  Asp Leu Glu Ala Leu  Leu Glu Arg
    2180             2185              2190

Asn Glu Asn Leu Gly Gly Gly  Leu Glu Ser Leu Lys  Glu Asn Phe
    2195             2200              2205

Pro Phe Thr Val Ser Asp Arg  Pro Ser Ser Cys Glu  Glu Lys Leu
    2210             2215              2220

Asn Phe Gly Gln Ala His Val  Ala Asp Glu Gln Trp  Arg Gly Glu
    2225             2230              2235

Ala Leu Arg Glu Lys Leu Arg  His Arg Glu Asp Arg  Leu Lys Ala
```

```
                2240                2245                2250
Gln Leu Arg Arg Cys Met Ser Lys Gln Ala Glu Val Leu Ser Glu
        2255                2260                2265

Gly Arg Arg Arg Thr Glu Gly Thr Leu His Ser Leu Arg Arg Gln
    2270                2275                2280

Val Asp Ala Leu Gly Glu Leu Val Thr Ser Thr Ser Gly Asp Ser
        2285                2290                2295

Ala Ser Thr Arg Ser Leu Ser Arg Thr Glu Gly Ser Leu Ala Glu
        2300                2305                2310

Asp Glu Pro Pro Gly Pro Ser Gln Ser Ser Arg Arg Leu Pro Arg
        2315                2320                2325

Gly Pro Ser Pro Arg Leu Asp Ala His Arg Pro
        2330                2335

<210> SEQ ID NO 27
<211> LENGTH: 7770
<212> TYPE: DNA
<213> ORGANISM: Canis familiaris
<220> FEATURE:
<221> NAME/KEY: CDS
<222> LOCATION: (1)..(7770)

<400> SEQUENCE: 27 atg aag aaa ggt tct cag caa aag ttt ttg aaa gca aag atg cca cca      48
Met Lys Lys Gly Ser Gln Gln Lys Phe Leu Lys Ala Lys Met Pro Pro
1               5                   10                  15 tca tct cac tct cct agt cca cca tcc ctt acg tcc aat atg aga tct     96
Ser Ser His Ser Pro Ser Pro Pro Ser Leu Thr Ser Asn Met Arg Ser
                20                  25                  30 agg tca ctt tcg cct cta agt gga tct gag act ctg cct ttt cat ttt    144
Arg Ser Leu Ser Pro Leu Ser Gly Ser Glu Thr Leu Pro Phe His Phe
            35                  40                  45 gga gga ccg tgg cat gag caa gtt gag att aca gat gaa agc aca gtg    192
Gly Gly Pro Trp His Glu Gln Val Glu Ile Thr Asp Glu Ser Thr Val
        50                  55                  60 gtt tta gac tac caa gac cat aaa gaa gct gat tca cat gca gga gtc    240
Val Leu Asp Tyr Gln Asp His Lys Glu Ala Asp Ser His Ala Gly Val
65                  70                  75                  80 cga tat att aca gag gcc ctt gtt aga aaa ctt act aaa cag gac aat    288
Arg Tyr Ile Thr Glu Ala Leu Val Arg Lys Leu Thr Lys Gln Asp Asn
                85                  90                  95 ttg gcc ttg gta aaa tct ctg aac ctt tca ctt gct aaa ggt ggt ggc    336
Leu Ala Leu Val Lys Ser Leu Asn Leu Ser Leu Ala Lys Gly Gly Gly
                100                 105                 110 aag aaa ttc agg tgt atc gaa aat ttg gaa aaa tgt gtt aaa ctt gaa    384
Lys Lys Phe Arg Cys Ile Glu Asn Leu Glu Lys Cys Val Lys Leu Glu
            115                 120                 125 gta ctg aat ctc agc tat aat cta ata gga aag att gag aaa gtg gac    432
Val Leu Asn Leu Ser Tyr Asn Leu Ile Gly Lys Ile Glu Lys Val Asp
        130                 135                 140 aaa ctg tta aaa tta cgt gaa ctc aac tta tcg tat aac aaa atc cgc    480
Lys Leu Leu Lys Leu Arg Glu Leu Asn Leu Ser Tyr Asn Lys Ile Arg
145                 150                 155                 160 aaa att gaa ggc ata gaa aat tta tat aat ctg caa aag ctg aac ctt    528
Lys Ile Glu Gly Ile Glu Asn Leu Tyr Asn Leu Gln Lys Leu Asn Leu
                165                 170                 175 gca gga aat gaa atc gaa cat atc cca gta tgg tta ggg aag aag tta    576
Ala Gly Asn Glu Ile Glu His Ile Pro Val Trp Leu Gly Lys Lys Leu
                180                 185                 190
```

```
aaa tct ttg cga atc ctg aat ctg aaa ggc aac aag ata tca tcg ctc       624
Lys Ser Leu Arg Ile Leu Asn Leu Lys Gly Asn Lys Ile Ser Ser Leu
        195                 200                 205 caa gat gta agc aag ttg aaa cca ctt caa gat ttg act tct ctg atc       672
Gln Asp Val Ser Lys Leu Lys Pro Leu Gln Asp Leu Thr Ser Leu Ile
210                 215                 220 cta ctt gaa aat cca gtt gcg acc ctt cct cat tat atc cag ttt acc       720
Leu Leu Glu Asn Pro Val Ala Thr Leu Pro His Tyr Ile Gln Phe Thr
225                 230                 235                 240 att ttt cac ctt cgc tca ttg gaa agt ttg gaa ggt cag cca gta act       768
Ile Phe His Leu Arg Ser Leu Glu Ser Leu Glu Gly Gln Pro Val Thr
                245                 250                 255 agt cag gac aga caa gaa gct ttt gcg aga ttc agt tta gat gag gta       816
Ser Gln Asp Arg Gln Glu Ala Phe Ala Arg Phe Ser Leu Asp Glu Val
            260                 265                 270 gaa aga ctg gaa aga gac ctg gag aag aag aca atg gaa act gaa gag       864
Glu Arg Leu Glu Arg Asp Leu Glu Lys Lys Thr Met Glu Thr Glu Glu
        275                 280                 285 ctt agg agt gag cag aca agg ttc ctt gag gaa att aaa agt cag gat       912
Leu Arg Ser Glu Gln Thr Arg Phe Leu Glu Glu Ile Lys Ser Gln Asp
290                 295                 300 aaa ttg aac aaa tca ctg aaa gag gag gcc aga cta caa aaa cag agc       960
Lys Leu Asn Lys Ser Leu Lys Glu Glu Ala Arg Leu Gln Lys Gln Ser
305                 310                 315                 320 tat gag gag ctg gag agt aac cta aac acc aaa aat gaa ttg cta aaa      1008
Tyr Glu Glu Leu Glu Ser Asn Leu Asn Thr Lys Asn Glu Leu Leu Lys
                325                 330                 335 cag aag acc atg gaa cta atg cga gca tgt cag aaa cag tat gag atg      1056
Gln Lys Thr Met Glu Leu Met Arg Ala Cys Gln Lys Gln Tyr Glu Met
            340                 345                 350 gaa cag gag ttg gcc ttt tat aaa att gat gcc aaa ttt gaa cca cta      1104
Glu Gln Glu Leu Ala Phe Tyr Lys Ile Asp Ala Lys Phe Glu Pro Leu
        355                 360                 365 aat tat tac cca tca gag tat gtc gaa att gat aaa acc cca gat gaa      1152
Asn Tyr Tyr Pro Ser Glu Tyr Val Glu Ile Asp Lys Thr Pro Asp Glu
370                 375                 380 agc cct tac att ggc aaa tcc aga tac aag aga aat atg ttc act aca      1200
Ser Pro Tyr Ile Gly Lys Ser Arg Tyr Lys Arg Asn Met Phe Thr Thr
385                 390                 395                 400 gag agt tat att att gca aat gcc cag aca gta aag atc aag aag atg      1248
Glu Ser Tyr Ile Ile Ala Asn Ala Gln Thr Val Lys Ile Lys Lys Met
                405                 410                 415 gag cta gat gaa ggg gaa caa ctc aga aat gag cac gtg aac ttg gga      1296
Glu Leu Asp Glu Gly Glu Gln Leu Arg Asn Glu His Val Asn Leu Gly
            420                 425                 430 gca tcg cca aca gac ata caa ctg gaa gac aaa gaa aaa aaa ata agt      1344
Ala Ser Pro Thr Asp Ile Gln Leu Glu Asp Lys Glu Lys Lys Ile Ser
        435                 440                 445 gca gca caa act cga cta tca gaa cta cat gat gaa ata gaa aag gca      1392
Ala Ala Gln Thr Arg Leu Ser Glu Leu His Asp Glu Ile Glu Lys Ala
450                 455                 460 gaa caa caa att tta aga gcc act gaa gaa ttt aaa caa ctg gaa gaa      1440
Glu Gln Gln Ile Leu Arg Ala Thr Glu Glu Phe Lys Gln Leu Glu Glu
465                 470                 475                 480 gct ata caa ctt aaa aaa att tca gaa gcg gag aaa gac ctt ctt ttc      1488
Ala Ile Gln Leu Lys Lys Ile Ser Glu Ala Glu Lys Asp Leu Leu Phe
                485                 490                 495 aag cag ttg agt ggt agg ata cag ctt ctc aat aaa tta cgc caa gaa      1536
Lys Gln Leu Ser Gly Arg Ile Gln Leu Leu Asn Lys Leu Arg Gln Glu
            500                 505                 510
```

-continued

```
gct gtg gat cta gaa aca cag atg gaa aag caa agg caa gaa att ggt    1584
Ala Val Asp Leu Glu Thr Gln Met Glu Lys Gln Arg Gln Glu Ile Gly
        515                 520                 525 gaa aag cag aat gag atc aag gac ctg gaa ata gtc aca gat agc ctg    1632
Glu Lys Gln Asn Glu Ile Lys Asp Leu Glu Ile Val Thr Asp Ser Leu
    530                 535                 540 gat tcc aga gac cca aaa cat tgc cat atg aag gct cag aaa aga ggt    1680
Asp Ser Arg Asp Pro Lys His Cys His Met Lys Ala Gln Lys Arg Gly
545                 550                 555                 560 aaa gaa caa caa ctt gac att atg aac aag cag tac aaa cag ctt gaa    1728
Lys Glu Gln Gln Leu Asp Ile Met Asn Lys Gln Tyr Lys Gln Leu Glu
                565                 570                 575 agc cgt ttg gat gag ata ctt tct aga att gcc aaa gaa act gaa gag    1776
Ser Arg Leu Asp Glu Ile Leu Ser Arg Ile Ala Lys Glu Thr Glu Glu
            580                 585                 590 att aag gac ctt gaa gaa cag ctt act gaa gga caa ata gcc gca aac    1824
Ile Lys Asp Leu Glu Glu Gln Leu Thr Glu Gly Gln Ile Ala Ala Asn
        595                 600                 605 gaa gcc ctg aag aag gac tta gaa agt gtc atc agt ggg ttg caa gaa    1872
Glu Ala Leu Lys Lys Asp Leu Glu Ser Val Ile Ser Gly Leu Gln Glu
    610                 615                 620 tac ctg gag act gtc aaa ggt cag gcc cgt cag gcc cag aat gag tgc    1920
Tyr Leu Glu Thr Val Lys Gly Gln Ala Arg Gln Ala Gln Asn Glu Cys
625                 630                 635                 640 aga aag cta cag gat gag aag gag aca ttg ctg cag aga ttg agt gag    1968
Arg Lys Leu Gln Asp Glu Lys Glu Thr Leu Leu Gln Arg Leu Ser Glu
                645                 650                 655 gtc gag cag gag agg gac caa ctg gaa ata gtg gcc ata gat gca gaa    2016
Val Glu Gln Glu Arg Asp Gln Leu Glu Ile Val Ala Ile Asp Ala Glu
            660                 665                 670 aat atg agg aag gag ctc gca gaa ctg gag aat gcc ctc cag gag cag    2064
Asn Met Arg Lys Glu Leu Ala Glu Leu Glu Asn Ala Leu Gln Glu Gln
        675                 680                 685 cat gag gtg aat ata tct ctg cag cag acc cag gga gat ctc agt gcc    2112
His Glu Val Asn Ile Ser Leu Gln Gln Thr Gln Gly Asp Leu Ser Ala
    690                 695                 700 tat gag gct gag cta gag gct cag ctg aaa ata cgg gat gct gaa gcc    2160
Tyr Glu Ala Glu Leu Glu Ala Gln Leu Lys Ile Arg Asp Ala Glu Ala
705                 710                 715                 720 aac cag ctc aag gag gag ttg gaa aaa ctt aga agg ttg agc cag tta    2208
Asn Gln Leu Lys Glu Glu Leu Glu Lys Leu Arg Arg Leu Ser Gln Leu
                725                 730                 735 gaa caa tcg gcc ctt caa gca gag ctt gag aag gaa aag caa gcc ttc    2256
Glu Gln Ser Ala Leu Gln Ala Glu Leu Glu Lys Glu Lys Gln Ala Phe
            740                 745                 750 aag act gct gtc aaa aaa gcc cag ctc tca gaa gga aag gac caa gaa    2304
Lys Thr Ala Val Lys Lys Ala Gln Leu Ser Glu Gly Lys Asp Gln Glu
        755                 760                 765 aat agt gag ctc cgc aca caa ctc caa cag ctg cag gat gac aat gac    2352
Asn Ser Glu Leu Arg Thr Gln Leu Gln Gln Leu Gln Asp Asp Asn Asp
    770                 775                 780 cta ttg aaa cag caa ctt aaa gat ttc cag agt cac ctt aac cat gtg    2400
Leu Leu Lys Gln Gln Leu Lys Asp Phe Gln Ser His Leu Asn His Val
785                 790                 795                 800 gtt gat ggt ttg att cgt cca gaa gaa gtg gca gct tgt gtg gat gag    2448
Val Asp Gly Leu Ile Arg Pro Glu Glu Val Ala Ala Cys Val Asp Glu
                805                 810                 815 cta agg aaa aaa ctg aag tca gga gct ggg gaa atg aga atc cat act    2496
Leu Arg Lys Lys Leu Lys Ser Gly Ala Gly Glu Met Arg Ile His Thr
```

-continued

```
                820                 825                 830
cct tca gat gtc tta ggg aaa agt ctt gct gac ttg cag aag caa ttc    2544
Pro Ser Asp Val Leu Gly Lys Ser Leu Ala Asp Leu Gln Lys Gln Phe
        835                 840                 845 agt gag atc ctg gca cgc tcc cag tgg gaa aga cag gaa gca caa gtg    2592
Ser Glu Ile Leu Ala Arg Ser Gln Trp Glu Arg Gln Glu Ala Gln Val
850                 855                 860 aga gag aga aaa ctc cag gag gaa atg gct ctg caa caa gag aaa ctg    2640
Arg Glu Arg Lys Leu Gln Glu Glu Met Ala Leu Gln Gln Glu Lys Leu
865                 870                 875                 880 gcg agc gga caa gag gag ttc agg cac gcc tgc gag agg gcc ctg gaa    2688
Ala Ser Gly Gln Glu Glu Phe Arg His Ala Cys Glu Arg Ala Leu Glu
            885                 890                 895 gcc cga att agt ttt gat aag agg cag cac gaa gca aga atc cag cag    2736
Ala Arg Ile Ser Phe Asp Lys Arg Gln His Glu Ala Arg Ile Gln Gln
        900                 905                 910 ttg gag aat gaa att cac tat ttg caa gaa aat cta aaa agt atg gag    2784
Leu Glu Asn Glu Ile His Tyr Leu Gln Glu Asn Leu Lys Ser Met Glu
    915                 920                 925 gaa atc caa ggt ctc aca gac ctc caa ctt cag gaa gct gat gaa gag    2832
Glu Ile Gln Gly Leu Thr Asp Leu Gln Leu Gln Glu Ala Asp Glu Glu
930                 935                 940 aag gag aga att ctg gcc caa ctc cgg gag tta gag aaa aag aag aaa    2880
Lys Glu Arg Ile Leu Ala Gln Leu Arg Glu Leu Glu Lys Lys Lys Lys
945                 950                 955                 960 ctt gag gat gcc aag tct cag gag cag ttt ctt gga tta gat aga gaa    2928
Leu Glu Asp Ala Lys Ser Gln Glu Gln Phe Leu Gly Leu Asp Arg Glu
            965                 970                 975 ttg aag aag cta aag aaa gct gtg gct gcc tct gat aag ctg gcc aca    2976
Leu Lys Lys Leu Lys Lys Ala Val Ala Ala Ser Asp Lys Leu Ala Thr
        980                 985                 990 gct gag ctc acc att gcc aaa gac cag ctc aag tcc ctt cat gga act    3024
Ala Glu Leu Thr Ile Ala Lys Asp Gln Leu Lys Ser Leu His Gly Thr
    995                 1000                1005 gtg atg aaa att aac cag gag cga gca gag gag ctg cag gag acg        3069
Val Met Lys Ile Asn Gln Glu Arg Ala Glu Glu Leu Gln Glu Thr
    1010                1015                1020 gag agg ttc agc aga aag gca gca caa gca gct agg gat ctg atc        3114
Glu Arg Phe Ser Arg Lys Ala Ala Gln Ala Ala Arg Asp Leu Ile
    1025                1030                1035 cga gca gaa gcg gag att gaa ctc ctg cag aag ctt ctc aga gat        3159
Arg Ala Glu Ala Glu Ile Glu Leu Leu Gln Lys Leu Leu Arg Asp
    1040                1045                1050 aaa gag gag cag ttt cga aat gag att gag aaa gta gat gtc ggc        3204
Lys Glu Glu Gln Phe Arg Asn Glu Ile Glu Lys Val Asp Val Gly
    1055                1060                1065 tct gga gga gca aag tca cag atg ctg gag atg gag aaa cta aat        3249
Ser Gly Gly Ala Lys Ser Gln Met Leu Glu Met Glu Lys Leu Asn
    1070                1075                1080 gag aca atg gag agg caa aga aca gag att gct agg ctg agg aat        3294
Glu Thr Met Glu Arg Gln Arg Thr Glu Ile Ala Arg Leu Arg Asn
    1085                1090                1095 tta cta gac ctc acc ggg gct gat aac aaa gga aac ttt gaa aat        3339
Leu Leu Asp Leu Thr Gly Ala Asp Asn Lys Gly Asn Phe Glu Asn
    1100                1105                1110 gtt ttg gaa gaa att gct gaa ctt cga cgt gaa gtt tct cat cag        3384
Val Leu Glu Glu Ile Ala Glu Leu Arg Arg Glu Val Ser His Gln
    1115                1120                1125 aat gat tac atc agc agc atg aca gat cct ttc aaa aga cga ggc        3429
```

```
        Asn Asp Tyr Ile Ser Ser Met Thr Asp Pro Phe Lys Arg Arg Gly
            1130                1135                1140 tat tgg tac ttt atg cca cca cca tca tca aaa gtt tcc agc           3474
Tyr Trp Tyr Phe Met Pro Pro Pro Ser Ser Ser Lys Val Ser Ser
1145                1150                1155 cac agt tcc cag gcc acc aag gac tct ggt gtt ggc cta aag tac       3519
His Ser Ser Gln Ala Thr Lys Asp Ser Gly Val Gly Leu Lys Tyr
1160                1165                1170 aca gcc tcc act ccg gtt aga aaa cca cat cgt gga cgg cag gat       3564
Thr Ala Ser Thr Pro Val Arg Lys Pro His Arg Gly Arg Gln Asp
1175                1180                1185 gga aag gag aac agt ggg cct cca cct gcc tca gga tac tgg gtg       3609
Gly Lys Glu Asn Ser Gly Pro Pro Pro Ala Ser Gly Tyr Trp Val
1190                1195                1200 tat tct cct atc agg agt ggg tta cat aaa tcg ttc tca aat aga       3654
Tyr Ser Pro Ile Arg Ser Gly Leu His Lys Ser Phe Ser Asn Arg
1205                1210                1215 gac gca gac agt gga gga gat agc cag gaa gag agc gag cta gat       3699
Asp Ala Asp Ser Gly Gly Asp Ser Gln Glu Glu Ser Glu Leu Asp
1220                1225                1230 gac caa gaa gac cac cca ttt gta cct cct cct gga tac atg atg       3744
Asp Gln Glu Asp His Pro Phe Val Pro Pro Pro Gly Tyr Met Met
1235                1240                1245 tac act gtg ttt cct gat ggt tct cct gta ccc cag ggc atg gcc       3789
Tyr Thr Val Phe Pro Asp Gly Ser Pro Val Pro Gln Gly Met Ala
1250                1255                1260 ctg tat gca ccc cct cct ccc ttg ccc aac aat agc cag cct ctt       3834
Leu Tyr Ala Pro Pro Pro Pro Leu Pro Asn Asn Ser Gln Pro Leu
1265                1270                1275 gac ctt ggc act gtt gtt tat ggc cca cct cct gtt ggg gct ccc       3879
Asp Leu Gly Thr Val Val Tyr Gly Pro Pro Pro Val Gly Ala Pro
1280                1285                1290 atc gtg tat ggg cct cca cct ccc aac ttc tcc gta ccc ctc atc       3924
Ile Val Tyr Gly Pro Pro Pro Asn Phe Ser Val Pro Leu Ile
1295                1300                1305 ccc gtg ggt gtg ctg cac tgc aat gtc cca gaa cac cat aac ttg       3969
Pro Val Gly Val Leu His Cys Asn Val Pro Glu His His Asn Leu
1310                1315                1320 gag aat gaa gtt tct aga tta gaa gac ata atg cag cat tta aaa       4014
Glu Asn Glu Val Ser Arg Leu Glu Asp Ile Met Gln His Leu Lys
1325                1330                1335 tct ggg aaa cgg gaa cag tgc atg aaa aca ccc aag ctg cag tcg       4059
Ser Gly Lys Arg Glu Gln Cys Met Lys Thr Pro Lys Leu Gln Ser
1340                1345                1350 gag aaa gaa ctc gca gag ctg cag cat aac att gat ggt ctt ttg       4104
Glu Lys Glu Leu Ala Glu Leu Gln His Asn Ile Asp Gly Leu Leu
1355                1360                1365 caa gag aag aaa gac tta gag cat gaa gta gaa gaa tta cat aga       4149
Gln Glu Lys Lys Asp Leu Glu His Glu Val Glu Glu Leu His Arg
1370                1375                1380 acc atc caa aaa cat caa cag cga aaa gat ttc att gat gga aac       4194
Thr Ile Gln Lys His Gln Gln Arg Lys Asp Phe Ile Asp Gly Asn
1385                1390                1395 gtt gag agt ctt gtg aat gat cta gaa ata gag aag tca ctc aaa       4239
Val Glu Ser Leu Val Asn Asp Leu Glu Ile Glu Lys Ser Leu Lys
1400                1405                1410 cac cat gaa gat att gtt gat gaa att gaa tgt att gag agg acc       4284
His His Glu Asp Ile Val Asp Glu Ile Glu Cys Ile Glu Arg Thr
1415                1420                1425
```

```
ctt ctg aag cgc cgt gca gag ctc agg gaa gcc gac cgg ctg ctg      4329
Leu Leu Lys Arg Arg Ala Glu Leu Arg Glu Ala Asp Arg Leu Leu
    1430                1435                1440 acg gag gct gaa agt gaa ctt tca tgc acg aaa gag aaa aca aaa      4374
Thr Glu Ala Glu Ser Glu Leu Ser Cys Thr Lys Glu Lys Thr Lys
1445                1450                1455 cat gct gtt gag aag ttc act gat gcc aag aga aat tta ttg caa      4419
His Ala Val Glu Lys Phe Thr Asp Ala Lys Arg Asn Leu Leu Gln
    1460                1465                1470 act gag aaa gat gct gag gag tta gaa agg aga gcc cag gaa act      4464
Thr Glu Lys Asp Ala Glu Glu Leu Glu Arg Arg Ala Gln Glu Thr
1475                1480                1485 gcc att aac ctc gtc aaa gcc gac cag cag ctg aga ttg ctc cag      4509
Ala Ile Asn Leu Val Lys Ala Asp Gln Gln Leu Arg Leu Leu Gln
    1490                1495                1500 gct gac acg aag gat ttg gag cag cac aaa atg gag caa gag gaa      4554
Ala Asp Thr Lys Asp Leu Glu Gln His Lys Met Glu Gln Glu Glu
1505                1510                1515 atc ttg aaa gaa ata aac aaa gtt gtt gca gca aaa gac tca gac      4599
Ile Leu Lys Glu Ile Asn Lys Val Val Ala Ala Lys Asp Ser Asp
    1520                1525                1530 ttc cag agc cta aac aag aag aag gaa gta ctg aca gga gag ctg      4644
Phe Gln Ser Leu Asn Lys Lys Lys Glu Val Leu Thr Gly Glu Leu
1535                1540                1545 cag aaa ctc cag aag gac att gag act gca cgg cac aat gag gat      4689
Gln Lys Leu Gln Lys Asp Ile Glu Thr Ala Arg His Asn Glu Asp
    1550                1555                1560 cag cac ctg cag gtc ctt aaa gag tcg gag acc ctc ctg cag gcc      4734
Gln His Leu Gln Val Leu Lys Glu Ser Glu Thr Leu Leu Gln Ala
1565                1570                1575 aag aaa gct gag ctg gaa aat ctg aaa agc cag gtg tca gga cag      4779
Lys Lys Ala Glu Leu Glu Asn Leu Lys Ser Gln Val Ser Gly Gln
    1580                1585                1590 cag cag gag atg gcc gtc ttg gac agg gag tta gga cac aag aag      4824
Gln Gln Glu Met Ala Val Leu Asp Arg Glu Leu Gly His Lys Lys
1595                1600                1605 gaa gag ctg cat ctc ctc cag gaa agc atg gtc cag gcc aaa gct      4869
Glu Glu Leu His Leu Leu Gln Glu Ser Met Val Gln Ala Lys Ala
    1610                1615                1620 gac ctc cag gaa gca ctg aga cta gga gaa agt gaa gta act gag      4914
Asp Leu Gln Glu Ala Leu Arg Leu Gly Glu Ser Glu Val Thr Glu
1625                1630                1635 aag tgc aat cac att agg gaa gta aaa tct ctt ctg gaa gaa ctc      4959
Lys Cys Asn His Ile Arg Glu Val Lys Ser Leu Leu Glu Glu Leu
    1640                1645                1650 agt ttt cag aaa gga gaa ctg aat gtc cag atc agt gaa aaa aaa      5004
Ser Phe Gln Lys Gly Glu Leu Asn Val Gln Ile Ser Glu Lys Lys
1655                1660                1665 act caa ctt gca ctc ata aag cag gaa att gaa aaa gag gaa gac      5049
Thr Gln Leu Ala Leu Ile Lys Gln Glu Ile Glu Lys Glu Glu Asp
    1670                1675                1680 aat ctt cag gta gtt tta ggg caa atg tct aaa cat aaa act gaa      5094
Asn Leu Gln Val Val Leu Gly Gln Met Ser Lys His Lys Thr Glu
1685                1690                1695 cta aag aat att ctg gac atg ttg caa ctt gaa aat aat gag ctg      5139
Leu Lys Asn Ile Leu Asp Met Leu Gln Leu Glu Asn Asn Glu Leu
    1700                1705                1710 caa ggt ttg aag ctc caa cat gac caa aag atg tct gaa tta gag      5184
Gln Gly Leu Lys Leu Gln His Asp Gln Lys Met Ser Glu Leu Glu
1715                1720                1725
```

-continued

| | | | | | | | | | | | | | | |
|---|---|---|---|---|---|---|---|---|---|---|---|---|---|---|
| aag | act | cgg | gtt | gaa | gtg | ctg | gag | gag | aaa | ctg | gag | tta | gag | agt | 5229 |
| Lys | Thr | Arg | Val | Glu | Val | Leu | Glu | Glu | Lys | Leu | Glu | Leu | Glu | Ser | |
| | 1730 | | | | 1735 | | | | | 1740 | | | | | |
| ctg | cag | cag | gca | gcc | ctg | cga | cag | aga | ggg | gag | ata | gag | tgg | cag | 5274 |
| Leu | Gln | Gln | Ala | Ala | Leu | Arg | Gln | Arg | Gly | Glu | Ile | Glu | Trp | Gln | |
| 1745 | | | | | 1750 | | | | | 1755 | | | | | |
| aag | cag | ctc | ctc | cag | agg | aac | aca | cag | gaa | gta | gag | cgg | atg | act | 5319 |
| Lys | Gln | Leu | Leu | Gln | Arg | Asn | Thr | Gln | Glu | Val | Glu | Arg | Met | Thr | |
| 1760 | | | | | 1765 | | | | | 1770 | | | | | |
| gct | gag | acc | cga | gca | tta | cag | tca | tgt | gtt | gag | tct | ttg | tgc | aaa | 5364 |
| Ala | Glu | Thr | Arg | Ala | Leu | Gln | Ser | Cys | Val | Glu | Ser | Leu | Cys | Lys | |
| 1775 | | | | | 1780 | | | | | 1785 | | | | | |
| gaa | aag | caa | gat | ctc | gaa | gaa | aaa | cag | gac | agc | tgg | gaa | aag | aag | 5409 |
| Glu | Lys | Gln | Asp | Leu | Glu | Glu | Lys | Gln | Asp | Ser | Trp | Glu | Lys | Lys | |
| | 1790 | | | | 1795 | | | | | 1800 | | | | | |
| ttg | gca | cag | acc | aaa | cgg | gtt | cta | gca | gct | gca | gaa | gag | gac | agc | 5454 |
| Leu | Ala | Gln | Thr | Lys | Arg | Val | Leu | Ala | Ala | Ala | Glu | Glu | Asp | Ser | |
| 1805 | | | | | 1810 | | | | | 1815 | | | | | |
| gag | atg | gag | cgg | gca | cgc | tta | gaa | aag | ttg | gaa | ctg | gac | gcc | agg | 5499 |
| Glu | Met | Glu | Arg | Ala | Arg | Leu | Glu | Lys | Leu | Glu | Leu | Asp | Ala | Arg | |
| | 1820 | | | | 1825 | | | | | 1830 | | | | | |
| aag | ctg | cag | cag | gag | ttg | gac | caa | cga | aac | agg | gag | aag | ctc | tcc | 5544 |
| Lys | Leu | Gln | Gln | Glu | Leu | Asp | Gln | Arg | Asn | Arg | Glu | Lys | Leu | Ser | |
| 1835 | | | | | 1840 | | | | | 1845 | | | | | |
| ctg | cat | caa | gac | ctg | gca | gtg | gtg | cag | cag | cag | cta | caa | gaa | aaa | 5589 |
| Leu | His | Gln | Asp | Leu | Ala | Val | Val | Gln | Gln | Gln | Leu | Gln | Glu | Lys | |
| 1850 | | | | | 1855 | | | | | 1860 | | | | | |
| cag | gaa | gca | gta | aac | tca | tta | cag | aag | gaa | cta | gct | gat | gtc | cag | 5634 |
| Gln | Glu | Ala | Val | Asn | Ser | Leu | Gln | Lys | Glu | Leu | Ala | Asp | Val | Gln | |
| 1865 | | | | | 1870 | | | | | 1875 | | | | | |
| gag | cat | ttg | gac | cta | gca | gaa | cag | gag | gtg | ctc | tgc | acc | acc | aag | 5679 |
| Glu | His | Leu | Asp | Leu | Ala | Glu | Gln | Glu | Val | Leu | Cys | Thr | Thr | Lys | |
| 1880 | | | | | 1885 | | | | | 1890 | | | | | |
| cgc | aag | gac | gca | ctg | ctc | agc | gaa | cag | acc | agg | ctc | gag | aag | gac | 5724 |
| Arg | Lys | Asp | Ala | Leu | Leu | Ser | Glu | Gln | Thr | Arg | Leu | Glu | Lys | Asp | |
| 1895 | | | | | 1900 | | | | | 1905 | | | | | |
| gtg | ggt | gaa | tgg | acg | aag | aag | ttt | gaa | gac | tgc | cag | aaa | gaa | ggg | 5769 |
| Val | Gly | Glu | Trp | Thr | Lys | Lys | Phe | Glu | Asp | Cys | Gln | Lys | Glu | Gly | |
| 1910 | | | | | 1915 | | | | | 1920 | | | | | |
| gag | aca | aag | cag | caa | cag | ctt | caa | ggg | ctt | cag | aag | gag | att | gaa | 5814 |
| Glu | Thr | Lys | Gln | Gln | Gln | Leu | Gln | Gly | Leu | Gln | Lys | Glu | Ile | Glu | |
| 1925 | | | | | 1930 | | | | | 1935 | | | | | |
| gga | aac | gag | gcg | aag | cta | gcc | caa | caa | gaa | atg | atg | ttt | cag | aga | 5859 |
| Gly | Asn | Glu | Ala | Lys | Leu | Ala | Gln | Gln | Glu | Met | Met | Phe | Gln | Arg | |
| 1940 | | | | | 1945 | | | | | 1950 | | | | | |
| ctc | cag | aaa | gag | cga | gaa | tgt | gaa | gaa | aaa | aag | tta | gaa | gct | agt | 5904 |
| Leu | Gln | Lys | Glu | Arg | Glu | Cys | Glu | Glu | Lys | Lys | Leu | Glu | Ala | Ser | |
| 1955 | | | | | 1960 | | | | | 1965 | | | | | |
| aaa | gtg | act | ctg | aag | gag | cag | cag | caa | cag | ctg | gaa | aag | gaa | ttg | 5949 |
| Lys | Val | Thr | Leu | Lys | Glu | Gln | Gln | Gln | Gln | Leu | Glu | Lys | Glu | Leu | |
| 1970 | | | | | 1975 | | | | | 1980 | | | | | |
| atg | gag | cag | aaa | ggc | aag | ctg | gac | cag | gtg | ctc | gct | aag | ctc | ttg | 5994 |
| Met | Glu | Gln | Lys | Gly | Lys | Leu | Asp | Gln | Val | Leu | Ala | Lys | Leu | Leu | |
| 1985 | | | | | 1990 | | | | | 1995 | | | | | |
| gtg | gct | gag | gag | cgt | gtc | agg | acc | ttg | cag | gag | gag | gga | agg | tgg | 6039 |
| Val | Ala | Glu | Glu | Arg | Val | Arg | Thr | Leu | Gln | Glu | Glu | Gly | Arg | Trp | |
| | 2000 | | | | 2005 | | | | | 2010 | | | | | |
| agc | gag | acc | ctg | gag | aag | acg | ctc | tcc | cag | acc | aag | cga | cag | ctt | 6084 |
| Ser | Glu | Thr | Leu | Glu | Lys | Thr | Leu | Ser | Gln | Thr | Lys | Arg | Gln | Leu | |

```
                 2015                2020                2025
tca gaa  cgg gag  cag cag  tta ctg  gcc aag  tca gac  gag ctg  ctg         6129
Ser Glu  Arg Glu  Gln Gln  Leu Leu  Ala Lys  Ser Asp  Glu Leu  Leu
         2030                2035                2040 gcc ctg  cag aag  gag acg  gac tcc  atg agg  gcg gac  ttc agc  ctc         6174
Ala Leu  Gln Lys  Glu Thr  Asp Ser  Met Arg  Ala Asp  Phe Ser  Leu
         2045                2050                2055 ttg cgc  aac cag  ttc ctg  aca gaa  aga aag  aaa gcc  gag aag  cag         6219
Leu Arg  Asn Gln  Phe Leu  Thr Glu  Arg Lys  Lys Ala  Glu Lys  Gln
         2060                2065                2070 gtg gcc  agc ctg  aag gaa  gcc ctt  aag atc  cag cgg  agc caa  ctg         6264
Val Ala  Ser Leu  Lys Glu  Ala Leu  Lys Ile  Gln Arg  Ser Gln  Leu
         2075                2080                2085 gag aag  aac ctt  ctg gag  caa aag  cag gag  aac agc  tgc atg  cag         6309
Glu Lys  Asn Leu  Leu Glu  Gln Lys  Gln Glu  Asn Ser  Cys Met  Gln
         2090                2095                2100 agg gag  atg gca  acc atc  gaa cag  gtg gcc  cag gac  aac cac  gag         6354
Arg Glu  Met Ala  Thr Ile  Glu Gln  Val Ala  Gln Asp  Asn His  Glu
         2105                2110                2115 cgg gcc  cgg cgc  ctg atg  agg gag  ctc aac  cag atg  cag cgc  gag         6399
Arg Ala  Arg Arg  Leu Met  Arg Glu  Leu Asn  Gln Met  Gln Arg  Glu
         2120                2125                2130 tac gtg  gag ctc  agg aaa  cag atg  aca aac  caa aag  gat ttg  gaa         6444
Tyr Val  Glu Leu  Arg Lys  Gln Met  Thr Asn  Gln Lys  Asp Leu  Glu
         2135                2140                2145 aga aga  cag atg  gaa atc  agt gat  gcg atg  caa gca  ctt aaa  tgt         6489
Arg Arg  Gln Met  Glu Ile  Ser Asp  Ala Met  Gln Ala  Leu Lys  Cys
         2150                2155                2160 gag gtg  aaa gat  gaa atc  cga acc  agc ctg  aag aat  ctc aac  cag         6534
Glu Val  Lys Asp  Glu Ile  Arg Thr  Ser Leu  Lys Asn  Leu Asn  Gln
         2165                2170                2175 ttt ctt  cca gag  ctg cca  gcg gac  ctg gag  gcc ctt  ctg gaa  agg         6579
Phe Leu  Pro Glu  Leu Pro  Ala Asp  Leu Glu  Ala Leu  Leu Glu  Arg
         2180                2185                2190 aat gag  aac ctt  gga gga  ggc ttg  gag agc  ttg aaa  gag aat  ttc         6624
Asn Glu  Asn Leu  Gly Gly  Gly Leu  Glu Ser  Leu Lys  Glu Asn  Phe
         2195                2200                2205 ccg ttt  acc gtg  agc gac  aga cca  tca tct  tgc gaa  gag aaa  ctg         6669
Pro Phe  Thr Val  Ser Asp  Arg Pro  Ser Ser  Cys Glu  Glu Lys  Leu
         2210                2215                2220 aat ttt  ggc cag  gct cac  gtg gcg  gat gaa  cag tgg  cgg gga  gag         6714
Asn Phe  Gly Gln  Ala His  Val Ala  Asp Glu  Gln Trp  Arg Gly  Glu
         2225                2230                2235 gca ctc  cgg gag  aag ctg  cgc cac  cgc gag  gac cgg  ctc aag  gcc         6759
Ala Leu  Arg Glu  Lys Leu  Arg His  Arg Glu  Asp Arg  Leu Lys  Ala
         2240                2245                2250 cag ctg  cgc cgc  tgc atg  tcc aag  cag gcc  gag gtg  ctg agc  gag         6804
Gln Leu  Arg Arg  Cys Met  Ser Lys  Gln Ala  Glu Val  Leu Ser  Glu
         2255                2260                2265 ggc cgg  cgg cgc  acg gag  ggg acc  ctg cac  agc ctg  cgg cgg  cag         6849
Gly Arg  Arg Arg  Thr Glu  Gly Thr  Leu His  Ser Leu  Arg Arg  Gln
         2270                2275                2280 gtg gac  gcc ctg  ggc gag  ctg gtc  acc agc  act tcc  ggg gac  tcc         6894
Val Asp  Ala Leu  Gly Glu  Leu Val  Thr Ser  Thr Ser  Gly Asp  Ser
         2285                2290                2295 gcg tcc  acc cgc  agt ctg  tcg cgc  acc gag  ggc tcg  ctc gcc  gag         6939
Ala Ser  Thr Arg  Ser Leu  Ser Arg  Thr Glu  Gly Ser  Leu Ala  Glu
         2300                2305                2310 gac gaa  ccg ccg  ggg ccc  agc cag  gag ctg  cac gtg  ctg ggg  tcg         6984
```

```
Asp Glu Pro Pro Gly Pro Ser Gln Glu Leu His Val Leu Gly Ser
    2315                2320                2325 ggc ggc agc gac cga ggt gga gga cgg ggc ggg ggc agg aag ggc      7029
Gly Gly Ser Asp Arg Gly Gly Gly Arg Gly Gly Gly Arg Lys Gly
2330                2335                2340 ctt tcc cga cgc cgc cgc tgg aac cac gga gaa gcg cgc ctc ggc      7074
Leu Ser Arg Arg Arg Arg Trp Asn His Gly Glu Ala Arg Leu Gly
    2345                2350                2355 ccg cgg agg ccc cca cgg gag ggg gca ggg cgg ggc gcg gcc ttc      7119
Pro Arg Arg Pro Pro Arg Glu Gly Ala Gly Arg Gly Ala Ala Phe
2360                2365                2370 cga gcc ttg gtc tcc tgc tcc cgc cct gca gag ctc ccg gcg gct      7164
Arg Ala Leu Val Ser Cys Ser Arg Pro Ala Glu Leu Pro Ala Ala
    2375                2380                2385 ccc ccg agg ccc gtc gcc gcg gct gga cgc gca ccg acc ctg agg      7209
Pro Pro Arg Pro Val Ala Ala Ala Gly Arg Ala Pro Thr Leu Arg
2390                2395                2400 acc cgg agg acc cgg agg ccc ggc gtc ccc tcg gaa cgc ttc ctc      7254
Thr Arg Arg Thr Arg Arg Pro Gly Val Pro Ser Glu Arg Phe Leu
    2405                2410                2415 cgc gtc cgc gga cac cag gct cac ggg aag gcg cgt cca tgc ggg      7299
Arg Val Arg Gly His Gln Ala His Gly Lys Ala Arg Pro Cys Gly
2420                2425                2430 aag agc cgc gag cgg aac ccg gat gcc cgg gct ggt ctc tgg gcc      7344
Lys Ser Arg Glu Arg Asn Pro Asp Ala Arg Ala Gly Leu Trp Ala
    2435                2440                2445 ttg gaa acg tgt tgc cgt aaa agc agc gcc cgc ggc tgc gga ctt      7389
Leu Glu Thr Cys Cys Arg Lys Ser Ser Ala Arg Gly Cys Gly Leu
2450                2455                2460 gaa gcc ccg aac tgc cgc cgt gcc cgg tgc gga gcg agc gtg cgg      7434
Glu Ala Pro Asn Cys Arg Arg Ala Arg Cys Gly Ala Ser Val Arg
    2465                2470                2475 tac cct ctc gtg cct cgg ggc cgg act gga cga ggg gcc gtg acc      7479
Tyr Pro Leu Val Pro Arg Gly Arg Thr Gly Arg Gly Ala Val Thr
2480                2485                2490 ccg tgg ggc cgc ctg cag tcc cga ggg acg cgg acc acc ccc cgg      7524
Pro Trp Gly Arg Leu Gln Ser Arg Gly Thr Arg Thr Thr Pro Arg
    2495                2500                2505 ccg gtg cga cgg gag cat ccc cag cac cag gaa agg ccc cca ggg      7569
Pro Val Arg Arg Glu His Pro Gln His Gln Glu Arg Pro Pro Gly
2510                2515                2520 cgc gtt acc gcg gcc cac act gag acc gcc cct ccc cgc cgg gtg      7614
Arg Val Thr Ala Ala His Thr Glu Thr Ala Pro Pro Arg Arg Val
    2525                2530                2535 ttc cac gcg cga gta gca gtc ggg gag gtc agc ctc ggg ccc ggc      7659
Phe His Ala Arg Val Ala Val Gly Glu Val Ser Leu Gly Pro Gly
2540                2545                2550 cgc ggt ctc gag cga aca cgg ggc ggg ggc ggg ggg gcg ggg gcg      7704
Arg Gly Leu Glu Arg Thr Arg Gly Gly Gly Gly Gly Ala Gly Ala
    2555                2560                2565 gga ctc ctc gca gag gcc gcg gcc acg gcc cgg tgc gca gac ccc      7749
Gly Leu Leu Ala Glu Ala Ala Ala Thr Ala Arg Cys Ala Asp Pro
2570                2575                2580 tcc aca gac ccc tcc gca tag                                      7770
Ser Thr Asp Pro Ser Ala
    2585

<210> SEQ ID NO 28
<211> LENGTH: 2589
<212> TYPE: PRT
```

<213> ORGANISM: Canis familiaris

<400> SEQUENCE: 28

Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45

Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285

Leu Arg Ser Glu Gln Thr Arg Phe Leu Glu Glu Ile Lys Ser Gln Asp
    290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
    370                 375                 380

Ser Pro Tyr Ile Gly Lys Ser Arg Tyr Lys Arg Asn Met Phe Thr Thr
385                 390                 395                 400

-continued

```
Glu Ser Tyr Ile Ile Ala Asn Ala Gln Thr Val Lys Ile Lys Lys Met
                405                 410                 415
Glu Leu Asp Glu Gly Glu Gln Leu Arg Asn Glu His Val Asn Leu Gly
            420                 425                 430
Ala Ser Pro Thr Asp Ile Gln Leu Glu Asp Lys Glu Lys Lys Ile Ser
        435                 440                 445
Ala Ala Gln Thr Arg Leu Ser Glu Leu His Asp Glu Ile Glu Lys Ala
    450                 455                 460
Glu Gln Gln Ile Leu Arg Ala Thr Glu Glu Phe Lys Gln Leu Glu Glu
465                 470                 475                 480
Ala Ile Gln Leu Lys Lys Ile Ser Glu Ala Glu Lys Asp Leu Leu Phe
                485                 490                 495
Lys Gln Leu Ser Gly Arg Ile Gln Leu Leu Asn Lys Leu Arg Gln Glu
            500                 505                 510
Ala Val Asp Leu Glu Thr Gln Met Glu Lys Gln Arg Gln Glu Ile Gly
        515                 520                 525
Glu Lys Gln Asn Glu Ile Lys Asp Leu Glu Ile Val Thr Asp Ser Leu
    530                 535                 540
Asp Ser Arg Asp Pro Lys His Cys His Met Lys Ala Gln Lys Arg Gly
545                 550                 555                 560
Lys Glu Gln Gln Leu Asp Ile Met Asn Lys Gln Tyr Lys Gln Leu Glu
                565                 570                 575
Ser Arg Leu Asp Glu Ile Leu Ser Arg Ile Ala Lys Glu Thr Glu Glu
            580                 585                 590
Ile Lys Asp Leu Glu Glu Gln Leu Thr Glu Gly Gln Ile Ala Ala Asn
        595                 600                 605
Glu Ala Leu Lys Lys Asp Leu Glu Ser Val Ile Ser Gly Leu Gln Glu
    610                 615                 620
Tyr Leu Glu Thr Val Lys Gly Gln Ala Arg Gln Ala Gln Asn Glu Cys
625                 630                 635                 640
Arg Lys Leu Gln Asp Glu Lys Glu Thr Leu Leu Gln Arg Leu Ser Glu
                645                 650                 655
Val Glu Gln Glu Arg Asp Gln Leu Glu Ile Val Ala Ile Asp Ala Glu
            660                 665                 670
Asn Met Arg Lys Glu Leu Ala Glu Leu Glu Asn Ala Leu Gln Glu Gln
        675                 680                 685
His Glu Val Asn Ile Ser Leu Gln Gln Thr Gln Gly Asp Leu Ser Ala
    690                 695                 700
Tyr Glu Ala Glu Leu Glu Ala Gln Leu Lys Ile Arg Asp Ala Glu Ala
705                 710                 715                 720
Asn Gln Leu Lys Glu Glu Leu Glu Lys Leu Arg Arg Leu Ser Gln Leu
                725                 730                 735
Glu Gln Ser Ala Leu Gln Ala Glu Leu Glu Lys Glu Lys Gln Ala Phe
            740                 745                 750
Lys Thr Ala Val Lys Ala Gln Leu Ser Glu Gly Lys Asp Gln Glu
        755                 760                 765
Asn Ser Glu Leu Arg Thr Gln Leu Gln Leu Gln Asp Asp Asn Asp
    770                 775                 780
Leu Leu Lys Gln Gln Leu Lys Asp Phe Gln Ser His Leu Asn His Val
785                 790                 795                 800
Val Asp Gly Leu Ile Arg Pro Glu Glu Val Ala Ala Cys Val Asp Glu
                805                 810                 815
Leu Arg Lys Lys Leu Lys Ser Gly Ala Gly Glu Met Arg Ile His Thr
```

```
                820              825                830
Pro Ser Asp Val Leu Gly Lys Ser Leu Ala Asp Leu Gln Lys Gln Phe
            835              840                845

Ser Glu Ile Leu Ala Arg Ser Gln Trp Glu Arg Gln Glu Ala Gln Val
        850              855                860

Arg Glu Arg Lys Leu Gln Glu Glu Met Ala Leu Gln Gln Glu Lys Leu
865             870              875                880

Ala Ser Gly Gln Glu Glu Phe Arg His Ala Cys Glu Arg Ala Leu Glu
                885              890                895

Ala Arg Ile Ser Phe Asp Lys Arg Gln His Glu Ala Arg Ile Gln Gln
            900              905                910

Leu Glu Asn Glu Ile His Tyr Leu Gln Glu Asn Leu Lys Ser Met Glu
        915              920                925

Glu Ile Gln Gly Leu Thr Asp Leu Gln Leu Gln Glu Ala Asp Glu Glu
        930              935                940

Lys Glu Arg Ile Leu Ala Gln Leu Arg Glu Leu Glu Lys Lys Lys Lys
945             950              955                960

Leu Glu Asp Ala Lys Ser Gln Glu Gln Phe Leu Gly Leu Asp Arg Glu
            965              970                975

Leu Lys Lys Leu Lys Lys Ala Val Ala Ala Ser Asp Lys Leu Ala Thr
        980              985                990

Ala Glu Leu Thr Ile Ala Lys Asp Gln Leu Lys Ser Leu His Gly Thr
        995              1000               1005

Val Met Lys Ile Asn Gln Glu Arg Ala Glu Glu Leu Gln Glu Thr
        1010             1015               1020

Glu Arg Phe Ser Arg Lys Ala Ala Gln Ala Ala Arg Asp Leu Ile
        1025             1030               1035

Arg Ala Glu Ala Glu Ile Glu Leu Leu Gln Lys Leu Leu Arg Asp
        1040             1045               1050

Lys Glu Glu Gln Phe Arg Asn Glu Ile Glu Lys Val Asp Val Gly
        1055             1060               1065

Ser Gly Gly Ala Lys Ser Gln Met Leu Glu Met Glu Lys Leu Asn
        1070             1075               1080

Glu Thr Met Glu Arg Gln Arg Thr Glu Ile Ala Arg Leu Arg Asn
        1085             1090               1095

Leu Leu Asp Leu Thr Gly Ala Asp Asn Lys Gly Asn Phe Glu Asn
        1100             1105               1110

Val Leu Glu Glu Ile Ala Glu Leu Arg Arg Glu Val Ser His Gln
        1115             1120               1125

Asn Asp Tyr Ile Ser Ser Met Thr Asp Pro Phe Lys Arg Arg Gly
        1130             1135               1140

Tyr Trp Tyr Phe Met Pro Pro Ser Ser Lys Val Ser Ser
        1145             1150               1155

His Ser Ser Gln Ala Thr Lys Asp Ser Gly Val Gly Leu Lys Tyr
        1160             1165               1170

Thr Ala Ser Thr Pro Val Arg Lys Pro His Arg Gly Arg Gln Asp
        1175             1180               1185

Gly Lys Glu Asn Ser Gly Pro Pro Ala Ser Gly Tyr Trp Val
        1190             1195               1200

Tyr Ser Pro Ile Arg Ser Gly Leu His Lys Ser Phe Ser Asn Arg
        1205             1210               1215

Asp Ala Asp Ser Gly Gly Asp Ser Gln Glu Glu Ser Glu Leu Asp
        1220             1225               1230
```

-continued

Asp Gln Glu Asp His Pro Phe Val Pro Pro Gly Tyr Met Met
1235                1240                1245

Tyr Thr Val Phe Pro Asp Gly Ser Pro Val Pro Gln Gly Met Ala
1250                1255                1260

Leu Tyr Ala Pro Pro Pro Leu Pro Asn Asn Ser Gln Pro Leu
    1265                1270                1275

Asp Leu Gly Thr Val Val Tyr Gly Pro Pro Val Gly Ala Pro
    1280                1285                1290

Ile Val Tyr Gly Pro Pro Pro Asn Phe Ser Val Pro Leu Ile
    1295                1300                1305

Pro Val Gly Val Leu His Cys Asn Val Pro Glu His His Asn Leu
1310                1315                1320

Glu Asn Glu Val Ser Arg Leu Glu Asp Ile Met Gln His Leu Lys
1325                1330                1335

Ser Gly Lys Arg Glu Gln Cys Met Lys Thr Pro Lys Leu Gln Ser
1340                1345                1350

Glu Lys Glu Leu Ala Glu Leu Gln His Asn Ile Asp Gly Leu Leu
1355                1360                1365

Gln Glu Lys Lys Asp Leu Glu His Glu Val Glu Glu Leu His Arg
1370                1375                1380

Thr Ile Gln Lys His Gln Gln Arg Lys Asp Phe Ile Asp Gly Asn
1385                1390                1395

Val Glu Ser Leu Val Asn Asp Leu Glu Ile Glu Lys Ser Leu Lys
1400                1405                1410

His His Glu Asp Ile Val Asp Glu Ile Glu Cys Ile Glu Arg Thr
1415                1420                1425

Leu Leu Lys Arg Arg Ala Glu Leu Arg Glu Ala Asp Arg Leu Leu
1430                1435                1440

Thr Glu Ala Glu Ser Glu Leu Ser Cys Thr Lys Glu Lys Thr Lys
1445                1450                1455

His Ala Val Glu Lys Phe Thr Asp Ala Lys Arg Asn Leu Leu Gln
1460                1465                1470

Thr Glu Lys Asp Ala Glu Glu Leu Glu Arg Arg Ala Gln Glu Thr
1475                1480                1485

Ala Ile Asn Leu Val Lys Ala Asp Gln Gln Leu Arg Leu Leu Gln
1490                1495                1500

Ala Asp Thr Lys Asp Leu Glu Gln His Lys Met Glu Gln Glu Glu
1505                1510                1515

Ile Leu Lys Glu Ile Asn Lys Val Val Ala Ala Lys Asp Ser Asp
1520                1525                1530

Phe Gln Ser Leu Asn Lys Lys Glu Val Leu Thr Gly Glu Leu
    1535                1540                1545

Gln Lys Leu Gln Lys Asp Ile Glu Thr Ala Arg His Asn Glu Asp
1550                1555                1560

Gln His Leu Gln Val Leu Lys Glu Ser Glu Thr Leu Leu Gln Ala
1565                1570                1575

Lys Lys Ala Glu Leu Glu Asn Leu Lys Ser Gln Val Ser Gly Gln
1580                1585                1590

Gln Gln Glu Met Ala Val Leu Asp Arg Glu Leu Gly His Lys Lys
1595                1600                1605

Glu Glu Leu His Leu Leu Gln Glu Ser Met Val Gln Ala Lys Ala
1610                1615                1620

```
Asp Leu Gln Glu Ala Leu Arg Leu Gly Glu Ser Glu Val Thr Glu
1625                1630                1635

Lys Cys Asn His Ile Arg Glu Val Lys Ser Leu Leu Glu Glu Leu
1640                1645                1650

Ser Phe Gln Lys Gly Glu Leu Asn Val Gln Ile Ser Glu Lys Lys
1655                1660                1665

Thr Gln Leu Ala Leu Ile Lys Gln Glu Ile Glu Lys Glu Glu Asp
1670                1675                1680

Asn Leu Gln Val Val Leu Gly Gln Met Ser Lys His Lys Thr Glu
1685                1690                1695

Leu Lys Asn Ile Leu Asp Met Leu Gln Leu Glu Asn Asn Glu Leu
1700                1705                1710

Gln Gly Leu Lys Leu Gln His Asp Gln Lys Met Ser Glu Leu Glu
1715                1720                1725

Lys Thr Arg Val Glu Val Leu Glu Glu Lys Leu Glu Leu Glu Ser
1730                1735                1740

Leu Gln Gln Ala Ala Leu Arg Gln Arg Gly Glu Ile Glu Trp Gln
1745                1750                1755

Lys Gln Leu Leu Gln Arg Asn Thr Gln Glu Val Glu Arg Met Thr
1760                1765                1770

Ala Glu Thr Arg Ala Leu Gln Ser Cys Val Glu Ser Leu Cys Lys
1775                1780                1785

Glu Lys Gln Asp Leu Glu Glu Lys Gln Asp Ser Trp Glu Lys Lys
1790                1795                1800

Leu Ala Gln Thr Lys Arg Val Leu Ala Ala Ala Glu Glu Asp Ser
1805                1810                1815

Glu Met Glu Arg Ala Arg Leu Glu Lys Leu Glu Leu Asp Ala Arg
1820                1825                1830

Lys Leu Gln Gln Glu Leu Asp Gln Arg Asn Arg Glu Lys Leu Ser
1835                1840                1845

Leu His Gln Asp Leu Ala Val Val Gln Gln Gln Leu Gln Glu Lys
1850                1855                1860

Gln Glu Ala Val Asn Ser Leu Gln Lys Glu Leu Ala Asp Val Gln
1865                1870                1875

Glu His Leu Asp Leu Ala Glu Gln Glu Val Leu Cys Thr Thr Lys
1880                1885                1890

Arg Lys Asp Ala Leu Leu Ser Glu Gln Thr Arg Leu Glu Lys Asp
1895                1900                1905

Val Gly Glu Trp Thr Lys Lys Phe Glu Asp Cys Gln Lys Glu Gly
1910                1915                1920

Glu Thr Lys Gln Gln Gln Leu Gln Gly Leu Gln Lys Glu Ile Glu
1925                1930                1935

Gly Asn Glu Ala Lys Leu Ala Gln Gln Glu Met Met Phe Gln Arg
1940                1945                1950

Leu Gln Lys Glu Arg Glu Cys Glu Glu Lys Lys Leu Glu Ala Ser
1955                1960                1965

Lys Val Thr Leu Lys Glu Gln Gln Gln Leu Glu Lys Glu Leu
1970                1975                1980

Met Glu Gln Lys Gly Lys Leu Asp Gln Val Leu Ala Lys Leu Leu
1985                1990                1995

Val Ala Glu Glu Arg Val Arg Thr Leu Gln Glu Glu Gly Arg Trp
2000                2005                2010

Ser Glu Thr Leu Glu Lys Thr Leu Ser Gln Thr Lys Arg Gln Leu
```

-continued

```
                2015                2020                2025

Ser Glu Arg Glu Gln Gln Leu Leu Ala Lys Ser Asp Glu Leu Leu
        2030                2035                2040

Ala Leu Gln Lys Glu Thr Asp Ser Met Arg Ala Asp Phe Ser Leu
        2045                2050                2055

Leu Arg Asn Gln Phe Leu Thr Glu Arg Lys Lys Ala Glu Lys Gln
        2060                2065                2070

Val Ala Ser Leu Lys Glu Ala Leu Lys Ile Gln Arg Ser Gln Leu
        2075                2080                2085

Glu Lys Asn Leu Leu Glu Gln Lys Gln Glu Asn Ser Cys Met Gln
        2090                2095                2100

Arg Glu Met Ala Thr Ile Glu Gln Val Ala Gln Asp Asn His Glu
        2105                2110                2115

Arg Ala Arg Arg Leu Met Arg Glu Leu Asn Gln Met Gln Arg Glu
        2120                2125                2130

Tyr Val Glu Leu Arg Lys Gln Met Thr Asn Gln Lys Asp Leu Glu
        2135                2140                2145

Arg Arg Gln Met Glu Ile Ser Asp Ala Met Gln Ala Leu Lys Cys
        2150                2155                2160

Glu Val Lys Asp Glu Ile Arg Thr Ser Leu Lys Asn Leu Asn Gln
        2165                2170                2175

Phe Leu Pro Glu Leu Pro Ala Asp Leu Glu Ala Leu Leu Glu Arg
        2180                2185                2190

Asn Glu Asn Leu Gly Gly Gly Leu Glu Ser Leu Lys Glu Asn Phe
        2195                2200                2205

Pro Phe Thr Val Ser Asp Arg Pro Ser Ser Cys Glu Glu Lys Leu
        2210                2215                2220

Asn Phe Gly Gln Ala His Val Ala Asp Glu Gln Trp Arg Gly Glu
        2225                2230                2235

Ala Leu Arg Glu Lys Leu Arg His Arg Glu Asp Arg Leu Lys Ala
        2240                2245                2250

Gln Leu Arg Arg Cys Met Ser Lys Gln Ala Glu Val Leu Ser Glu
        2255                2260                2265

Gly Arg Arg Arg Thr Glu Gly Thr Leu His Ser Leu Arg Arg Gln
        2270                2275                2280

Val Asp Ala Leu Gly Glu Leu Val Thr Ser Thr Ser Gly Asp Ser
        2285                2290                2295

Ala Ser Thr Arg Ser Leu Ser Arg Thr Glu Gly Ser Leu Ala Glu
        2300                2305                2310

Asp Glu Pro Pro Gly Pro Ser Gln Glu Leu His Val Leu Gly Ser
        2315                2320                2325

Gly Gly Ser Asp Arg Gly Gly Gly Arg Gly Gly Arg Lys Gly
        2330                2335                2340

Leu Ser Arg Arg Arg Arg Trp Asn His Gly Glu Ala Arg Leu Gly
        2345                2350                2355

Pro Arg Arg Pro Pro Arg Glu Gly Ala Gly Arg Gly Ala Ala Phe
        2360                2365                2370

Arg Ala Leu Val Ser Cys Ser Arg Pro Ala Glu Leu Pro Ala Ala
        2375                2380                2385

Pro Pro Arg Pro Val Ala Ala Gly Arg Ala Pro Thr Leu Arg
        2390                2395                2400

Thr Arg Arg Thr Arg Arg Pro Gly Val Pro Ser Glu Arg Phe Leu
        2405                2410                2415
```

-continued

```
Arg Val Arg Gly His Gln Ala His Gly Lys Ala Arg Pro Cys Gly
            2420                2425                2430

Lys Ser Arg Glu Arg Asn Pro Asp Ala Arg Ala Gly Leu Trp Ala
        2435                2440                2445

Leu Glu Thr Cys Cys Arg Lys Ser Ser Ala Arg Gly Cys Gly Leu
    2450                2455                2460

Glu Ala Pro Asn Cys Arg Arg Ala Arg Cys Gly Ala Ser Val Arg
2465                2470                2475

Tyr Pro Leu Val Pro Arg Gly Arg Thr Gly Arg Gly Ala Val Thr
            2480                2485                2490

Pro Trp Gly Arg Leu Gln Ser Arg Gly Thr Arg Thr Thr Pro Arg
        2495                2500                2505

Pro Val Arg Arg Glu His Pro Gln His Gln Glu Arg Pro Pro Gly
    2510                2515                2520

Arg Val Thr Ala Ala His Thr Glu Thr Ala Pro Pro Arg Arg Val
2525                2530                2535

Phe His Ala Arg Val Ala Val Gly Glu Val Ser Leu Gly Pro Gly
            2540                2545                2550

Arg Gly Leu Glu Arg Thr Arg Gly Gly Gly Gly Gly Ala Gly Ala
        2555                2560                2565

Gly Leu Leu Ala Glu Ala Ala Ala Thr Ala Arg Cys Ala Asp Pro
    2570                2575                2580

Ser Thr Asp Pro Ser Ala
2585

<210> SEQ ID NO 29
<211> LENGTH: 7431
<212> TYPE: DNA
<213> ORGANISM: Homo sapiens
<220> FEATURE:
<221> NAME/KEY: CDS
<222> LOCATION: (32)..(7009)

<400> SEQUENCE: 29
gttttgatga cacctggct ttattcttgc a atg aag aaa ggt tct caa caa       52
                                  Met Lys Lys Gly Ser Gln Gln
                                   1               5 aaa ata ttc tcc aaa gca aag ata cca tca tca tct cac tct cct atc      100
Lys Ile Phe Ser Lys Ala Lys Ile Pro Ser Ser Ser His Ser Pro Ile
         10                  15                  20 cca tca tct atg tcc aat atg aga tct agg tca ctt tca cct ttg att      148
Pro Ser Ser Met Ser Asn Met Arg Ser Arg Ser Leu Ser Pro Leu Ile
 25                  30                  35 gga tca gag act cta cct ttt cat tct gga gga cag tgg tgt gag caa      196
Gly Ser Glu Thr Leu Pro Phe His Ser Gly Gly Gln Trp Cys Glu Gln
40                  45                  50                  55 gtt gag att gca gat gaa aac aat atg ctt ttg gac tat caa gac cat      244
Val Glu Ile Ala Asp Glu Asn Asn Met Leu Leu Asp Tyr Gln Asp His
                 60                  65                  70 aaa gga gct gat tca cat gca gga gtt aga tat att aca gag gcc ctc      292
Lys Gly Ala Asp Ser His Ala Gly Val Arg Tyr Ile Thr Glu Ala Leu
             75                  80                  85 att aaa aaa ctt act aaa cag gat aat ttg gct ttg ata aaa tct ctg      340
Ile Lys Lys Leu Thr Lys Gln Asp Asn Leu Ala Leu Ile Lys Ser Leu
         90                  95                 100 aac ctt tca ctt tct aaa gac ggt ggc aag aaa ttt aag tat att gag      388
Asn Leu Ser Leu Ser Lys Asp Gly Gly Lys Lys Phe Lys Tyr Ile Glu
 105                 110                 115
```

```
aat ttg gaa aaa tgt gtt aaa ctt gaa gta ctg aat ctc agc tat aat      436
Asn Leu Glu Lys Cys Val Lys Leu Glu Val Leu Asn Leu Ser Tyr Asn
120             125                 130                 135 cta ata ggg aag att gaa aag ttg gac aag ctg tta aaa tta cgt gaa      484
Leu Ile Gly Lys Ile Glu Lys Leu Asp Lys Leu Leu Lys Leu Arg Glu
            140                 145                 150 ctc aac tta tca tat aac aaa atc agc aaa att gaa ggc ata gaa aat      532
Leu Asn Leu Ser Tyr Asn Lys Ile Ser Lys Ile Glu Gly Ile Glu Asn
                155                 160                 165 atg tgt aat ctg caa aag ctt aac ctt gca gga aat gaa att gag cat      580
Met Cys Asn Leu Gln Lys Leu Asn Leu Ala Gly Asn Glu Ile Glu His
        170                 175                 180 att cca gta tgg tta ggg aag aag tta aaa tct ttg cga gtc ctc aat      628
Ile Pro Val Trp Leu Gly Lys Lys Leu Lys Ser Leu Arg Val Leu Asn
    185                 190                 195 ttg aaa ggc aac aag ata tca tcg ctc caa gat ata agc aag ttg aaa      676
Leu Lys Gly Asn Lys Ile Ser Ser Leu Gln Asp Ile Ser Lys Leu Lys
200                 205                 210                 215 ccg ctt caa gat ttg att tct ctg atc cta gtt gaa aat cca gtt gtg      724
Pro Leu Gln Asp Leu Ile Ser Leu Ile Leu Val Glu Asn Pro Val Val
                220                 225                 230 acc ctt cct cat tac ctc cag ttt acc att ttc cac ctc cgt tca ttg      772
Thr Leu Pro His Tyr Leu Gln Phe Thr Ile Phe His Leu Arg Ser Leu
            235                 240                 245 gaa agt ttg gaa ggt cag cca gta acc act cag gat aga cag gag gct      820
Glu Ser Leu Glu Gly Gln Pro Val Thr Thr Gln Asp Arg Gln Glu Ala
                250                 255                 260 ttt gag aga ttc agt tta gaa gag gta gaa aga ctg gaa aga gac cta      868
Phe Glu Arg Phe Ser Leu Glu Glu Val Glu Arg Leu Glu Arg Asp Leu
265                 270                 275 gaa aaa aag atg ata gaa act gaa gag ctt aag agc aaa caa aca agg      916
Glu Lys Lys Met Ile Glu Thr Glu Glu Leu Lys Ser Lys Gln Thr Arg
280             285                 290                 295 ttc ctt gag gaa att aaa aat caa gat aaa ttg aat aaa tca tta aaa      964
Phe Leu Glu Glu Ile Lys Asn Gln Asp Lys Leu Asn Lys Ser Leu Lys
                300                 305                 310 gag gag gcc atg tta cag aaa cag agc tgt gag gaa ctc aag agt gac     1012
Glu Glu Ala Met Leu Gln Lys Gln Ser Cys Glu Glu Leu Lys Ser Asp
            315                 320                 325 tta aac aca aaa aat gaa ttg cta aaa cag aag acc ata gaa tta aca     1060
Leu Asn Thr Lys Asn Glu Leu Leu Lys Gln Lys Thr Ile Glu Leu Thr
                330                 335                 340 cga gca tgt cag aag caa tat gag ctg gaa cag gaa ttg gcc ttt tat     1108
Arg Ala Cys Gln Lys Gln Tyr Glu Leu Glu Gln Glu Leu Ala Phe Tyr
345                 350                 355 aaa att gat gct aaa ttt gag cca cta aat tat tat cca tca gag tat     1156
Lys Ile Asp Ala Lys Phe Glu Pro Leu Asn Tyr Tyr Pro Ser Glu Tyr
360                 365                 370                 375 gct gaa att gat aaa gcc cca gat gaa agc cct tac att ggc aaa tcc     1204
Ala Glu Ile Asp Lys Ala Pro Asp Glu Ser Pro Tyr Ile Gly Lys Ser
            380                 385                 390 aga tac aag aga aat atg ttt gcc aca gag agt tat att att gac agt     1252
Arg Tyr Lys Arg Asn Met Phe Ala Thr Glu Ser Tyr Ile Ile Asp Ser
                395                 400                 405 gct cag gca gta cag atc aag aag atg gag cca gat gaa caa ctt aga     1300
Ala Gln Ala Val Gln Ile Lys Lys Met Glu Pro Asp Glu Gln Leu Arg
            410                 415                 420 aat gat cac atg aac ttg aga ggc cac aca cca ctg gac acg caa ctg     1348
Asn Asp His Met Asn Leu Arg Gly His Thr Pro Leu Asp Thr Gln Leu
```

-continued

|  |  |
|---|---|
| 425 430 435 | |
| gaa gac aaa gaa aaa aaa ata agt gca gca caa act cga cta tca gaa<br>Glu Asp Lys Glu Lys Lys Ile Ser Ala Ala Gln Thr Arg Leu Ser Glu<br>440 445 450 455 | 1396 |
| ctg cat gat gaa ata gaa aag gca gaa caa caa att ttg aga gct act<br>Leu His Asp Glu Ile Glu Lys Ala Glu Gln Gln Ile Leu Arg Ala Thr<br>460 465 470 | 1444 |
| gaa gaa ttt aaa caa ctg gaa gaa gct ata caa cta aaa aag att tca<br>Glu Glu Phe Lys Gln Leu Glu Glu Ala Ile Gln Leu Lys Lys Ile Ser<br>475 480 485 | 1492 |
| gaa gca ggg aaa gac ctt ctt tac aag cag ttg agt ggt aga cta caa<br>Glu Ala Gly Lys Asp Leu Leu Tyr Lys Gln Leu Ser Gly Arg Leu Gln<br>490 495 500 | 1540 |
| ctt gta aat aaa tta cgc cag gaa gct ctg gat cta gaa ctg cag atg<br>Leu Val Asn Lys Leu Arg Gln Glu Ala Leu Asp Leu Glu Leu Gln Met<br>505 510 515 | 1588 |
| gaa aag caa aag cag gaa att gcc gga aag cag aag gag att aag gac<br>Glu Lys Gln Lys Gln Glu Ile Ala Gly Lys Gln Lys Glu Ile Lys Asp<br>520 525 530 535 | 1636 |
| ctg caa ata gcc ata gat agc ctg gat tcc aaa gac cca aaa cat tcc<br>Leu Gln Ile Ala Ile Asp Ser Leu Asp Ser Lys Asp Pro Lys His Ser<br>540 545 550 | 1684 |
| cat atg aag gct caa aag agc ggt aaa gaa caa cag ctt gac att atg<br>His Met Lys Ala Gln Lys Ser Gly Lys Glu Gln Gln Leu Asp Ile Met<br>555 560 565 | 1732 |
| aac aag cag tac caa caa ctt gaa agt cgt ttg gat gag ata ctt tct<br>Asn Lys Gln Tyr Gln Gln Leu Glu Ser Arg Leu Asp Glu Ile Leu Ser<br>570 575 580 | 1780 |
| aga att gct aag gaa acg gaa gag att aag gac ctt gaa gaa cag ctt<br>Arg Ile Ala Lys Glu Thr Glu Glu Ile Lys Asp Leu Glu Glu Gln Leu<br>585 590 595 | 1828 |
| act gaa ggc cag ata gca gca aat gaa gcc ctg aag aag gat tta gaa<br>Thr Glu Gly Gln Ile Ala Ala Asn Glu Ala Leu Lys Lys Asp Leu Glu<br>600 605 610 615 | 1876 |
| ggt gtt atc agt ggg ttg caa gaa tac ctg ggg acc att aaa ggc cag<br>Gly Val Ile Ser Gly Leu Gln Glu Tyr Leu Gly Thr Ile Lys Gly Gln<br>620 625 630 | 1924 |
| gca act cag gcc cag aat gag tgc agg aag ctg cgg gat gag aaa gag<br>Ala Thr Gln Ala Gln Asn Glu Cys Arg Lys Leu Arg Asp Glu Lys Glu<br>635 640 645 | 1972 |
| aca ttg ttg cag aga ttg aca gaa gtc gag cag gag aga gac cag ctg<br>Thr Leu Leu Gln Arg Leu Thr Glu Val Glu Gln Glu Arg Asp Gln Leu<br>650 655 660 | 2020 |
| gaa ata gtt gcc atg gat gca gaa aat atg agg aag gag ctt gca gag<br>Glu Ile Val Ala Met Asp Ala Glu Asn Met Arg Lys Glu Leu Ala Glu<br>665 670 675 | 2068 |
| cta gaa agt gcc ctc caa gag cag cat gag gtg aat gca tct ttg cag<br>Leu Glu Ser Ala Leu Gln Glu Gln His Glu Val Asn Ala Ser Leu Gln<br>680 685 690 695 | 2116 |
| cag acc cag gga gat ctc agt gcc tat gaa gct gag cta gag gct cgg<br>Gln Thr Gln Gly Asp Leu Ser Ala Tyr Glu Ala Glu Leu Glu Ala Arg<br>700 705 710 | 2164 |
| cta aac cta agg gat gct gaa gcc aac cag ctc aag gaa gag ttg gaa<br>Leu Asn Leu Arg Asp Ala Glu Ala Asn Gln Leu Lys Glu Glu Leu Glu<br>715 720 725 | 2212 |
| aaa gta aca aga ctt acc cag tta gaa caa tca gcc ctt caa gca gaa<br>Lys Val Thr Arg Leu Thr Gln Leu Glu Gln Ser Ala Leu Gln Ala Glu<br>730 735 740 | 2260 |
| ctt gag aag gaa agg caa gcc ctc aag aat gcc ctt gga aaa gcc cag | 2308 |

-continued

| | |
|---|---|
| Leu Glu Lys Glu Arg Gln Ala Leu Lys Asn Ala Leu Gly Lys Ala Gln<br>    745                          750                      755 | |
| ttc tca gaa gaa aag gag caa gag aac agt gag ctc cat gca aaa ctt<br>Phe Ser Glu Glu Lys Glu Gln Glu Asn Ser Glu Leu His Ala Lys Leu<br>760                    765                  770                  775 | 2356 |
| aaa cac ttg cag gat gac aat aat ctg tta aaa cag caa ctt aaa gat<br>Lys His Leu Gln Asp Asp Asn Asn Leu Leu Lys Gln Gln Leu Lys Asp<br>                        780                        785                        790 | 2404 |
| ttc cag aat cac ctt aac cat gtg gtt gat ggt ttg gtt cgt cca gaa<br>Phe Gln Asn His Leu Asn His Val Val Asp Gly Leu Val Arg Pro Glu<br>                795                  800                  805 | 2452 |
| gaa gtg gca gct cgt gtg gat gag cta aga aga aaa ctg aaa tta gga<br>Glu Val Ala Ala Arg Val Asp Glu Leu Arg Arg Lys Leu Lys Leu Gly<br>        810                      815                        820 | 2500 |
| act ggg gaa atg aac atc cat agt cct tca gat gtc tta ggg aaa agt<br>Thr Gly Glu Met Asn Ile His Ser Pro Ser Asp Val Leu Gly Lys Ser<br>        825                      830                        835 | 2548 |
| ctt gct gat tta cag aaa caa ttc agt gaa att ctt gca cgc tcc aag<br>Leu Ala Asp Leu Gln Lys Gln Phe Ser Glu Ile Leu Ala Arg Ser Lys<br>840                    845                  850                  855 | 2596 |
| tgg gaa aga gat gaa gca caa gtt aga gag aga aaa ctc caa gaa gaa<br>Trp Glu Arg Asp Glu Ala Gln Val Arg Glu Arg Lys Leu Gln Glu Glu<br>                        860                        865                  870 | 2644 |
| atg gct ctg cag caa gag aaa ctg gca act gga caa gaa gag ttc agg<br>Met Ala Leu Gln Gln Glu Lys Leu Ala Thr Gly Gln Glu Glu Phe Arg<br>        875                      880                        885 | 2692 |
| cag gcc tgt gag aga gcc ctg gaa gca aga atg aat ttt gat aag agg<br>Gln Ala Cys Glu Arg Ala Leu Glu Ala Arg Met Asn Phe Asp Lys Arg<br>                890                        895                  900 | 2740 |
| caa cat gaa gca aga atc cag caa atg gag aat gaa att cac tat ttg<br>Gln His Glu Ala Arg Ile Gln Gln Met Glu Asn Glu Ile His Tyr Leu<br>905                    910                  915 | 2788 |
| caa gaa aat cta aaa agt atg gag gaa atc caa ggc ctt aca gat ctc<br>Gln Glu Asn Leu Lys Ser Met Glu Glu Ile Gln Gly Leu Thr Asp Leu<br>920                    925                  930                  935 | 2836 |
| caa ctt cag gaa gct gat gaa gag aag gag aga att ctg gcc caa ctc<br>Gln Leu Gln Glu Ala Asp Glu Glu Lys Glu Arg Ile Leu Ala Gln Leu<br>                940                        945                  950 | 2884 |
| cga gag tta gag aaa aag aag aaa ctt gaa gat gcc aaa tct cag gag<br>Arg Glu Leu Glu Lys Lys Lys Lys Leu Glu Asp Ala Lys Ser Gln Glu<br>        955                      960                        965 | 2932 |
| caa gtt ttt ggt tta gat aaa gaa ctg aag aaa cta aag aaa gcc gtg<br>Gln Val Phe Gly Leu Asp Lys Glu Leu Lys Lys Leu Lys Lys Ala Val<br>        970                      975                        980 | 2980 |
| gcc acc tct gat aag cta gcc aca gct gag ctc acc att gcc aaa gac<br>Ala Thr Ser Asp Lys Leu Ala Thr Ala Glu Leu Thr Ile Ala Lys Asp<br>985                    990                  995 | 3028 |
| cag ctg aag tcc ctt cat gga act gtt atg aaa att aac cag gag<br>Gln Leu Lys Ser Leu His Gly Thr Val Met Lys Ile Asn Gln Glu<br>1000                   1005                  1010 | 3073 |
| cga gca gag gag ttg cag gaa gca gag agg ttc agc aga aag gca<br>Arg Ala Glu Glu Leu Gln Glu Ala Glu Arg Phe Ser Arg Lys Ala<br>1015                   1020                  1025 | 3118 |
| gca caa gca gcc aga gat ctc acc cga gca gaa gct gag atc gaa<br>Ala Gln Ala Ala Arg Asp Leu Thr Arg Ala Glu Ala Glu Ile Glu<br>1030                   1035                  1040 | 3163 |
| ctc ctg cag aat ctc ctc agg cag aag ggg gag cag ttt cga ctt<br>Leu Leu Gln Asn Leu Leu Arg Gln Lys Gly Glu Gln Phe Arg Leu<br>1045                   1050                  1055 | 3208 |

| | | | | | | | | | | | | | |
|---|---|---|---|---|---|---|---|---|---|---|---|---|---|
| gag | atg | gag | aaa | aca | ggt | gta | ggt | act | gga | gca | aac | tca | cag gtc | 3253 |
| Glu | Met | Glu | Lys | Thr | Gly | Val | Gly | Thr | Gly | Ala | Asn | Ser | Gln Val | |
| 1060 | | | | | 1065 | | | | | 1070 | | | | |

| | | | | | | | | | | | | | |
|---|---|---|---|---|---|---|---|---|---|---|---|---|---|
| cta | gaa | att | gag | aaa | ctg | aat | gag | aca | atg | gaa | cga | caa | agg aca | 3298 |
| Leu | Glu | Ile | Glu | Lys | Leu | Asn | Glu | Thr | Met | Glu | Arg | Gln | Arg Thr | |
| 1075 | | | | | 1080 | | | | | 1085 | | | | |

| | | | | | | | | | | | | | |
|---|---|---|---|---|---|---|---|---|---|---|---|---|---|
| gag | att | gca | agg | ctg | cag | aat | gta | cta | gac | ctc | act | gga | agt gac | 3343 |
| Glu | Ile | Ala | Arg | Leu | Gln | Asn | Val | Leu | Asp | Leu | Thr | Gly | Ser Asp | |
| 1090 | | | | | 1095 | | | | | 1100 | | | | |

| | | | | | | | | | | | | | |
|---|---|---|---|---|---|---|---|---|---|---|---|---|---|
| aac | aaa | gga | ggc | ttt | gaa | aat | gtt | tta | gaa | gaa | att | gct | gaa ctt | 3388 |
| Asn | Lys | Gly | Gly | Phe | Glu | Asn | Val | Leu | Glu | Glu | Ile | Ala | Glu Leu | |
| 1105 | | | | | 1110 | | | | | 1115 | | | | |

| | | | | | | | | | | | | | |
|---|---|---|---|---|---|---|---|---|---|---|---|---|---|
| cga | cgt | gaa | gtt | tct | tat | cag | aat | gat | tac | ata | agc | agc | atg gca | 3433 |
| Arg | Arg | Glu | Val | Ser | Tyr | Gln | Asn | Asp | Tyr | Ile | Ser | Ser | Met Ala | |
| 1120 | | | | | 1125 | | | | | 1130 | | | | |

| | | | | | | | | | | | | | |
|---|---|---|---|---|---|---|---|---|---|---|---|---|---|
| gat | cct | ttc | aaa | aga | cga | ggc | tat | tgg | tac | ttt | atg | cca | cca cca | 3478 |
| Asp | Pro | Phe | Lys | Arg | Arg | Gly | Tyr | Trp | Tyr | Phe | Met | Pro | Pro Pro | |
| 1135 | | | | | 1140 | | | | | 1145 | | | | |

| | | | | | | | | | | | | | |
|---|---|---|---|---|---|---|---|---|---|---|---|---|---|
| cca | tca | tca | aaa | gtt | tcc | agc | cat | agt | tcc | cag | gcc | acc | aag gac | 3523 |
| Pro | Ser | Ser | Lys | Val | Ser | Ser | His | Ser | Ser | Gln | Ala | Thr | Lys Asp | |
| 1150 | | | | | 1155 | | | | | 1160 | | | | |

| | | | | | | | | | | | | | |
|---|---|---|---|---|---|---|---|---|---|---|---|---|---|
| tct | ggt | gtt | ggc | ctt | aag | tac | tca | gcc | tca | act | cct | gtt | aga aaa | 3568 |
| Ser | Gly | Val | Gly | Leu | Lys | Tyr | Ser | Ala | Ser | Thr | Pro | Val | Arg Lys | |
| 1165 | | | | | 1170 | | | | | 1175 | | | | |

| | | | | | | | | | | | | | |
|---|---|---|---|---|---|---|---|---|---|---|---|---|---|
| cca | cgc | cct | ggg | cag | cag | gat | ggg | aag | gaa | ggc | agt | caa | cct ccc | 3613 |
| Pro | Arg | Pro | Gly | Gln | Gln | Asp | Gly | Lys | Glu | Gly | Ser | Gln | Pro Pro | |
| 1180 | | | | | 1185 | | | | | 1190 | | | | |

| | | | | | | | | | | | | | |
|---|---|---|---|---|---|---|---|---|---|---|---|---|---|
| cct | gcc | tca | gga | tac | tgg | gtt | tat | tct | ccc | atc | agg | agt | ggg tta | 3658 |
| Pro | Ala | Ser | Gly | Tyr | Trp | Val | Tyr | Ser | Pro | Ile | Arg | Ser | Gly Leu | |
| 1195 | | | | | 1200 | | | | | 1205 | | | | |

| | | | | | | | | | | | | | |
|---|---|---|---|---|---|---|---|---|---|---|---|---|---|
| cat | aaa | ctg | ttt | cca | agt | aga | gat | gca | gac | agt | gga | gga | gat agt | 3703 |
| His | Lys | Leu | Phe | Pro | Ser | Arg | Asp | Ala | Asp | Ser | Gly | Gly | Asp Ser | |
| 1210 | | | | | 1215 | | | | | 1220 | | | | |

| | | | | | | | | | | | | | |
|---|---|---|---|---|---|---|---|---|---|---|---|---|---|
| cag | gaa | gag | agt | gag | ctg | gat | gac | caa | gaa | gaa | ccc | cca | ttt gtg | 3748 |
| Gln | Glu | Glu | Ser | Glu | Leu | Asp | Asp | Gln | Glu | Glu | Pro | Pro | Phe Val | |
| 1225 | | | | | 1230 | | | | | 1235 | | | | |

| | | | | | | | | | | | | | |
|---|---|---|---|---|---|---|---|---|---|---|---|---|---|
| cct | cct | cct | gga | tac | atg | atg | tat | act | gtg | ctt | cct | gat | ggt tct | 3793 |
| Pro | Pro | Pro | Gly | Tyr | Met | Met | Tyr | Thr | Val | Leu | Pro | Asp | Gly Ser | |
| 1240 | | | | | 1245 | | | | | 1250 | | | | |

| | | | | | | | | | | | | | |
|---|---|---|---|---|---|---|---|---|---|---|---|---|---|
| cct | gta | ccc | cag | ggc | atg | gcc | ctg | tat | gca | cca | cct | cct | ccc ttg | 3838 |
| Pro | Val | Pro | Gln | Gly | Met | Ala | Leu | Tyr | Ala | Pro | Pro | Pro | Pro Leu | |
| 1255 | | | | | 1260 | | | | | 1265 | | | | |

| | | | | | | | | | | | | | |
|---|---|---|---|---|---|---|---|---|---|---|---|---|---|
| cca | aac | aat | agc | cga | cct | ctc | acc | cct | ggc | act | gtt | gtt | tat ggc | 3883 |
| Pro | Asn | Asn | Ser | Arg | Pro | Leu | Thr | Pro | Gly | Thr | Val | Val | Tyr Gly | |
| 1270 | | | | | 1275 | | | | | 1280 | | | | |

| | | | | | | | | | | | | | |
|---|---|---|---|---|---|---|---|---|---|---|---|---|---|
| cca | cct | cct | gct | ggg | gcc | ccc | atg | gtg | tat | ggg | cct | cca | ccc ccc | 3928 |
| Pro | Pro | Pro | Ala | Gly | Ala | Pro | Met | Val | Tyr | Gly | Pro | Pro | Pro Pro | |
| 1285 | | | | | 1290 | | | | | 1295 | | | | |

| | | | | | | | | | | | | | |
|---|---|---|---|---|---|---|---|---|---|---|---|---|---|
| aac | ttc | tcc | atc | ccc | ttc | atc | cct | atg | ggt | gtg | ctg | cat | tgc aac | 3973 |
| Asn | Phe | Ser | Ile | Pro | Phe | Ile | Pro | Met | Gly | Val | Leu | His | Cys Asn | |
| 1300 | | | | | 1305 | | | | | 1310 | | | | |

| | | | | | | | | | | | | | |
|---|---|---|---|---|---|---|---|---|---|---|---|---|---|
| gtc | cct | gaa | cac | cat | aac | tta | gag | aat | gaa | gtt | tct | aga | tta gaa | 4018 |
| Val | Pro | Glu | His | His | Asn | Leu | Glu | Asn | Glu | Val | Ser | Arg | Leu Glu | |
| 1315 | | | | | 1320 | | | | | 1325 | | | | |

| | | | | | | | | | | | | | |
|---|---|---|---|---|---|---|---|---|---|---|---|---|---|
| gac | ata | atg | cag | cat | tta | aaa | tca | aag | aag | cgg | gaa | gaa | agg tgg | 4063 |
| Asp | Ile | Met | Gln | His | Leu | Lys | Ser | Lys | Lys | Arg | Glu | Glu | Arg Trp | |
| 1330 | | | | | 1335 | | | | | 1340 | | | | |

| | | | | | | | | | | | | | |
|---|---|---|---|---|---|---|---|---|---|---|---|---|---|
| atg | aga | gca | tcc | aag | cgg | cag | tcg | gag | aaa | gaa | atg | gaa | gaa ctg | 4108 |
| Met | Arg | Ala | Ser | Lys | Arg | Gln | Ser | Glu | Lys | Glu | Met | Glu | Glu Leu | |
| 1345 | | | | | 1350 | | | | | 1355 | | | | |

-continued

| | | |
|---|---|---|
| cat cat aat att gat gat ctt ttg caa gag aag aaa agc tta gag<br>His His Asn Ile Asp Asp Leu Leu Gln Glu Lys Lys Ser Leu Glu<br>1360                          1365                        1370 | 4153 | |
| tgt gaa gta gaa gaa tta cat aga act gtc cag aaa cgt caa cag<br>Cys Glu Val Glu Glu Leu His Arg Thr Val Gln Lys Arg Gln Gln<br>1375                          1380                        1385 | 4198 | |
| caa aag gac ttc att gat gga aat gtt gag agt ctt atg act gaa<br>Gln Lys Asp Phe Ile Asp Gly Asn Val Glu Ser Leu Met Thr Glu<br>1390                          1395                        1400 | 4243 | |
| cta gaa ata gaa aaa tca ctc aaa cat cat gaa gat att gta gat<br>Leu Glu Ile Glu Lys Ser Leu Lys His His Glu Asp Ile Val Asp<br>1405                          1410                        1415 | 4288 | |
| gaa att gag tgc att gag aag act ctt ctg aaa cgt cgc tca gag<br>Glu Ile Glu Cys Ile Glu Lys Thr Leu Leu Lys Arg Arg Ser Glu<br>1420                          1425                        1430 | 4333 | |
| ctc agg gaa gct gac cga ctc ctg gca gag gct gag agt gaa ctt<br>Leu Arg Glu Ala Asp Arg Leu Leu Ala Glu Ala Glu Ser Glu Leu<br>1435                          1440                        1445 | 4378 | |
| tca tgc act aaa gaa aag aca aaa aat gct gtt gaa aag ttc act<br>Ser Cys Thr Lys Glu Lys Thr Lys Asn Ala Val Glu Lys Phe Thr<br>1450                          1455                        1460 | 4423 | |
| gat gcc aag aga agt tta ttg caa act gag tca gat gct gag gaa<br>Asp Ala Lys Arg Ser Leu Leu Gln Thr Glu Ser Asp Ala Glu Glu<br>1465                          1470                        1475 | 4468 | |
| tta gaa agg aga gct cag gaa act gct gtt aac ctc gtc aaa gct<br>Leu Glu Arg Arg Ala Gln Glu Thr Ala Val Asn Leu Val Lys Ala<br>1480                          1485                        1490 | 4513 | |
| gat cag cag cta aga tcg ctc cag gct gat gca aag gat ttg gag<br>Asp Gln Gln Leu Arg Ser Leu Gln Ala Asp Ala Lys Asp Leu Glu<br>1495                          1500                        1505 | 4558 | |
| cag cac aaa atc aag caa gaa gaa atc ttg aaa gaa ata aac aaa<br>Gln His Lys Ile Lys Gln Glu Glu Ile Leu Lys Glu Ile Asn Lys<br>1510                          1515                        1520 | 4603 | |
| att gta gca gca aaa gac tca gac ttc caa tgt tta agc aag aag<br>Ile Val Ala Ala Lys Asp Ser Asp Phe Gln Cys Leu Ser Lys Lys<br>1525                          1530                        1535 | 4648 | |
| aag gaa aaa ctg aca gaa gag ctt cag aaa cta cag aaa gac ata<br>Lys Glu Lys Leu Thr Glu Glu Leu Gln Lys Leu Gln Lys Asp Ile<br>1540                          1545                        1550 | 4693 | |
| gag atg gca gaa cgc aat gag gat cac cac ctg cag gtc ctt aaa<br>Glu Met Ala Glu Arg Asn Glu Asp His His Leu Gln Val Leu Lys<br>1555                          1560                        1565 | 4738 | |
| gaa tct gag gtg ctt ctt cag gcc aaa aga gcc gag ctg gaa aag<br>Glu Ser Glu Val Leu Leu Gln Ala Lys Arg Ala Glu Leu Glu Lys<br>1570                          1575                        1580 | 4783 | |
| ctg aaa agc cag gtg aca agt cag cag cag gag atg gct gtc ttg<br>Leu Lys Ser Gln Val Thr Ser Gln Gln Gln Glu Met Ala Val Leu<br>1585                          1590                        1595 | 4828 | |
| gac agg cag tta ggg cat aaa aag gag gag ctg cat cta ctc caa<br>Asp Arg Gln Leu Gly His Lys Lys Glu Glu Leu His Leu Leu Gln<br>1600                          1605                        1610 | 4873 | |
| gga agc atg gtc cag gca aaa gct gac ctc cag gaa gct ctg aga<br>Gly Ser Met Val Gln Ala Lys Ala Asp Leu Gln Glu Ala Leu Arg<br>1615                          1620                        1625 | 4918 | |
| ctg gga gag act gaa gta act gag aag tgc aat cac att agg gaa<br>Leu Gly Glu Thr Glu Val Thr Glu Lys Cys Asn His Ile Arg Glu<br>1630                          1635                        1640 | 4963 | |
| gta aaa tct ctt ctg gaa gaa ctg agt ttt cag aaa gga gaa cta<br>Val Lys Ser Leu Leu Glu Glu Leu Ser Phe Gln Lys Gly Glu Leu | 5008 | |

|   |   |   |   |   |   |   |   |   |   |   |   |   |   |
|---|---|---|---|---|---|---|---|---|---|---|---|---|---|
| | | 1645 | | | | 1650 | | | | 1655 | | | |
| aat | gtt | cag | att | agt | gaa | aga | aaa | act | caa | ctt | aca | ctt | ata | aag | 5053 |
| Asn | Val | Gln | Ile | Ser | Glu | Arg | Lys | Thr | Gln | Leu | Thr | Leu | Ile | Lys | |
| 1660 | | | | | 1665 | | | | | 1670 | | | | | |
| cag | gaa | att | gaa | aaa | gag | gaa | gaa | aat | ctt | cag | gtt | gtt | tta | agg | 5098 |
| Gln | Glu | Ile | Glu | Lys | Glu | Glu | Glu | Asn | Leu | Gln | Val | Val | Leu | Arg | |
| 1675 | | | | | 1680 | | | | | 1685 | | | | | |
| cag | atg | tct | aaa | cat | aaa | acc | gaa | cta | aag | aat | att | ctg | gac | atg | 5143 |
| Gln | Met | Ser | Lys | His | Lys | Thr | Glu | Leu | Lys | Asn | Ile | Leu | Asp | Met | |
| 1690 | | | | | 1695 | | | | | 1700 | | | | | |
| ttg | caa | ctt | gaa | aac | cat | gag | cta | caa | ggt | ttg | aag | cta | caa | cat | 5188 |
| Leu | Gln | Leu | Glu | Asn | His | Glu | Leu | Gln | Gly | Leu | Lys | Leu | Gln | His | |
| 1705 | | | | | 1710 | | | | | 1715 | | | | | |
| gac | caa | agg | gta | tct | gaa | tta | gag | aag | act | cag | gtg | gca | gtg | cta | 5233 |
| Asp | Gln | Arg | Val | Ser | Glu | Leu | Glu | Lys | Thr | Gln | Val | Ala | Val | Leu | |
| 1720 | | | | | 1725 | | | | | 1730 | | | | | |
| gag | gag | aaa | ctg | gag | tta | gag | aat | ttg | cag | cag | ata | tcc | cag | cag | 5278 |
| Glu | Glu | Lys | Leu | Glu | Leu | Glu | Asn | Leu | Gln | Gln | Ile | Ser | Gln | Gln | |
| 1735 | | | | | 1740 | | | | | 1745 | | | | | |
| cag | aaa | ggg | gaa | ata | gag | tgg | cag | aag | cag | ctc | ctt | gag | agg | gat | 5323 |
| Gln | Lys | Gly | Glu | Ile | Glu | Trp | Gln | Lys | Gln | Leu | Leu | Glu | Arg | Asp | |
| 1750 | | | | | 1755 | | | | | 1760 | | | | | |
| aaa | cga | gaa | ata | gaa | cga | atg | act | gct | gag | tcc | cga | gct | tta | caa | 5368 |
| Lys | Arg | Glu | Ile | Glu | Arg | Met | Thr | Ala | Glu | Ser | Arg | Ala | Leu | Gln | |
| 1765 | | | | | 1770 | | | | | 1775 | | | | | |
| tcg | tgt | gtt | gag | tgt | ttg | agc | aaa | gaa | aag | gaa | gat | ctc | caa | gag | 5413 |
| Ser | Cys | Val | Glu | Cys | Leu | Ser | Lys | Glu | Lys | Glu | Asp | Leu | Gln | Glu | |
| 1780 | | | | | 1785 | | | | | 1790 | | | | | |
| aaa | tgt | gac | att | tgg | gaa | aaa | aag | ttg | gca | caa | acc | aaa | agg | gtt | 5458 |
| Lys | Cys | Asp | Ile | Trp | Glu | Lys | Lys | Leu | Ala | Gln | Thr | Lys | Arg | Val | |
| 1795 | | | | | 1800 | | | | | 1805 | | | | | |
| tta | gca | gca | gca | gaa | gaa | aat | agc | aaa | atg | gag | caa | tca | aac | tta | 5503 |
| Leu | Ala | Ala | Ala | Glu | Glu | Asn | Ser | Lys | Met | Glu | Gln | Ser | Asn | Leu | |
| 1810 | | | | | 1815 | | | | | 1820 | | | | | |
| gaa | aag | ttg | gaa | ttg | aat | gtc | aga | aaa | ctg | cag | cag | gaa | cta | gac | 5548 |
| Glu | Lys | Leu | Glu | Leu | Asn | Val | Arg | Lys | Leu | Gln | Gln | Glu | Leu | Asp | |
| 1825 | | | | | 1830 | | | | | 1835 | | | | | |
| caa | cta | aac | aga | gac | aag | ttg | tca | ctg | cat | aac | gac | att | tca | gca | 5593 |
| Gln | Leu | Asn | Arg | Asp | Lys | Leu | Ser | Leu | His | Asn | Asp | Ile | Ser | Ala | |
| 1840 | | | | | 1845 | | | | | 1850 | | | | | |
| atg | caa | cag | cag | ctc | caa | gaa | aaa | cga | gaa | gca | gta | aac | tca | ctg | 5638 |
| Met | Gln | Gln | Gln | Leu | Gln | Glu | Lys | Arg | Glu | Ala | Val | Asn | Ser | Leu | |
| 1855 | | | | | 1860 | | | | | 1865 | | | | | |
| cag | gag | gaa | cta | gct | aat | gtc | caa | gac | cat | ttg | aac | cta | gca | aaa | 5683 |
| Gln | Glu | Glu | Leu | Ala | Asn | Val | Gln | Asp | His | Leu | Asn | Leu | Ala | Lys | |
| 1870 | | | | | 1875 | | | | | 1880 | | | | | |
| cag | gac | ctg | ctt | cac | acc | acc | aag | cat | cag | gat | gtg | ttg | ctc | agt | 5728 |
| Gln | Asp | Leu | Leu | His | Thr | Thr | Lys | His | Gln | Asp | Val | Leu | Leu | Ser | |
| 1885 | | | | | 1890 | | | | | 1895 | | | | | |
| gag | cag | acc | cga | ctc | cag | aag | gac | atc | agt | gaa | tgg | gca | aat | agg | 5773 |
| Glu | Gln | Thr | Arg | Leu | Gln | Lys | Asp | Ile | Ser | Glu | Trp | Ala | Asn | Arg | |
| 1900 | | | | | 1905 | | | | | 1910 | | | | | |
| ttt | gaa | gac | tgt | cag | aaa | gaa | gag | gag | aca | aaa | caa | caa | caa | ctt | 5818 |
| Phe | Glu | Asp | Cys | Gln | Lys | Glu | Glu | Glu | Thr | Lys | Gln | Gln | Gln | Leu | |
| 1915 | | | | | 1920 | | | | | 1925 | | | | | |
| caa | gtg | ctt | cag | aat | gag | att | gaa | gaa | aac | aag | ctc | aaa | cta | gtc | 5863 |
| Gln | Val | Leu | Gln | Asn | Glu | Ile | Glu | Glu | Asn | Lys | Leu | Lys | Leu | Val | |
| 1930 | | | | | 1935 | | | | | 1940 | | | | | |
| caa | caa | gaa | atg | atg | ttt | cag | aga | ctc | cag | aaa | gag | aga | gaa | agt | 5908 |

```
                Gln Gln Glu Met Met Phe Gln Arg Leu Gln Lys Glu Arg Glu Ser
                1945                1950                1955 gaa gaa agc aaa tta gaa acc agt aaa gtg aca ctg aag gag caa       5953
Glu Glu Ser Lys Leu Glu Thr Ser Lys Val Thr Leu Lys Glu Gln
1960                1965                1970 cag cac cag ctg gaa aag gaa tta aca gac cag aaa agc aaa ctg       5998
Gln His Gln Leu Glu Lys Glu Leu Thr Asp Gln Lys Ser Lys Leu
1975                1980                1985 gac caa gtg ctc tca aag gtg ctg gca gct gaa gag cgt gtt agg       6043
Asp Gln Val Leu Ser Lys Val Leu Ala Ala Glu Glu Arg Val Arg
1990                1995                2000 act ctg cag gaa gag gag agg tgg tgt gag agc ctg gag aag aca       6088
Thr Leu Gln Glu Glu Glu Arg Trp Cys Glu Ser Leu Glu Lys Thr
2005                2010                2015 ctc tcc caa act aaa cgg cag ctt tca gaa agg gag cag caa ttg       6133
Leu Ser Gln Thr Lys Arg Gln Leu Ser Glu Arg Glu Gln Gln Leu
2020                2025                2030 gtg gag aaa tca ggt gag ctg ttg gcc ctc cag aaa gag gca gat       6178
Val Glu Lys Ser Gly Glu Leu Leu Ala Leu Gln Lys Glu Ala Asp
2035                2040                2045 tct atg agg gca gac ttc agc ctt ctg cgg aac cag ttc ttg aca       6223
Ser Met Arg Ala Asp Phe Ser Leu Leu Arg Asn Gln Phe Leu Thr
2050                2055                2060 gaa aga aag aaa gct gag aag cag gtg gcc agc ctg aag gaa gca       6268
Glu Arg Lys Lys Ala Glu Lys Gln Val Ala Ser Leu Lys Glu Ala
2065                2070                2075 ctt aag atc cag cgg agc cag ctg gag aaa aac ctt ctt gag caa       6313
Leu Lys Ile Gln Arg Ser Gln Leu Glu Lys Asn Leu Leu Glu Gln
2080                2085                2090 aaa cag gag aac agc tgc ata caa aag gaa atg gca aca att gaa       6358
Lys Gln Glu Asn Ser Cys Ile Gln Lys Glu Met Ala Thr Ile Glu
2095                2100                2105 ctg gta gcc cag gac aac cat gag cgg gcc agg cgc ctg atg aag       6403
Leu Val Ala Gln Asp Asn His Glu Arg Ala Arg Arg Leu Met Lys
2110                2115                2120 gag ctc aac cag atg cag tat gag tac acg gag ctc aag aaa cag       6448
Glu Leu Asn Gln Met Gln Tyr Glu Tyr Thr Glu Leu Lys Lys Gln
2125                2130                2135 atg gca aac caa aaa gat ttg gag aga aga caa atg gaa atc agt       6493
Met Ala Asn Gln Lys Asp Leu Glu Arg Arg Gln Met Glu Ile Ser
2140                2145                2150 gat gca atg agg aca ctt aaa tct gag gtg aag gat gaa atc aga       6538
Asp Ala Met Arg Thr Leu Lys Ser Glu Val Lys Asp Glu Ile Arg
2155                2160                2165 acc agc ttg aag aat ctt aat cag ttt ctt cca gaa cta cca gca       6583
Thr Ser Leu Lys Asn Leu Asn Gln Phe Leu Pro Glu Leu Pro Ala
2170                2175                2180 gat cta gaa gct att ttg gaa aga aac gaa aac cta gaa gga gaa       6628
Asp Leu Glu Ala Ile Leu Glu Arg Asn Glu Asn Leu Glu Gly Glu
2185                2190                2195 ttg gaa agc ttg aaa gag aac ctt cca ttt acc atg aat gag gga       6673
Leu Glu Ser Leu Lys Glu Asn Leu Pro Phe Thr Met Asn Glu Gly
2200                2205                2210 cct ttt gaa gaa aaa ctg aac ttt tcc caa gtt cac ata atg gat       6718
Pro Phe Glu Glu Lys Leu Asn Phe Ser Gln Val His Ile Met Asp
2215                2220                2225 gaa cac tgg cgt gga gaa gca ctc cgg gag aaa ctg cgt cac cgg       6763
Glu His Trp Arg Gly Glu Ala Leu Arg Glu Lys Leu Arg His Arg
2230                2235                2240
```

```
gaa  gac  cga  ctc  aag  gcc  caa  ctc  cga  cac  tgt  atg  tcc  aag  caa        6808
Glu  Asp  Arg  Leu  Lys  Ala  Gln  Leu  Arg  His  Cys  Met  Ser  Lys  Gln
2245                2250                2255 gca  gaa  gta  tta  att  aaa  gga  aag  cgg  cag  aca  gag  ggc  act  tta        6853
Ala  Glu  Val  Leu  Ile  Lys  Gly  Lys  Arg  Gln  Thr  Glu  Gly  Thr  Leu
2260                2265                2270 cac  agt  ttg  agg  aga  caa  gta  gat  gct  tta  ggg  gaa  ttg  gtc  acc        6898
His  Ser  Leu  Arg  Arg  Gln  Val  Asp  Ala  Leu  Gly  Glu  Leu  Val  Thr
2275                2280                2285 agc  acc  tct  gca  gat  tca  gcg  tca  tca  ccc  agt  ctg  tct  cag  ctg        6943
Ser  Thr  Ser  Ala  Asp  Ser  Ala  Ser  Ser  Pro  Ser  Leu  Ser  Gln  Leu
2290                2295                2300 gag  tct  tcc  ctc  aca  gag  gac  tct  caa  ctt  gga  caa  aat  cag  gaa        6988
Glu  Ser  Ser  Leu  Thr  Glu  Asp  Ser  Gln  Leu  Gly  Gln  Asn  Gln  Glu
2305                2310                2315 aag  aat  gcc  tca  gcc  aga  tga ggatactgt cttgtgtaaa tatattcaag               7039
Lys  Asn  Ala  Ser  Ala  Arg
2320                2325 gaaaacacct ccactacctc actgacttca taattggaat gtcacatggt ttttttaatc                7099
aagatgcagt gaactgagat tctgaaactc cactgtagtt tactttgcct gtaccattaa                7159
tgccaatgtt tttataaatc acttgtacat agtacatatg ggaatagttg catatgggaa                7219
tttaaaccaa catgtggctg agccttttt tttttaatct tcgtaacatg tttaaaaaaa                  7279
aacagtgatt ttaactgcat atttgaacct acaaactggt aaatcttatt aacaaaaga                 7339 atgtacttaa ggccctcttt atttatagtg tcgagttatt tttgaatttt gcttaaaatc                7399
tatttttcat atgaaaataa aagataacaa tc                                              7431

<210> SEQ ID NO 30
<211> LENGTH: 2325
<212> TYPE: PRT
<213> ORGANISM: Homo sapiens

<400> SEQUENCE: 30

Met Lys Lys Gly Ser Gln Gln Lys Ile Phe Ser Lys Ala Lys Ile Pro
1               5                   10                  15

Ser Ser Ser His Ser Pro Ile Pro Ser Ser Met Ser Asn Met Arg Ser
            20                  25                  30

Arg Ser Leu Ser Pro Leu Ile Gly Ser Glu Thr Leu Pro Phe His Ser
        35                  40                  45

Gly Gly Gln Trp Cys Glu Gln Val Glu Ile Ala Asp Glu Asn Asn Met
    50                  55                  60

Leu Leu Asp Tyr Gln Asp His Lys Gly Ala Asp Ser His Ala Gly Val
65                  70                  75                  80

Arg Tyr Ile Thr Glu Ala Leu Ile Lys Lys Leu Thr Lys Gln Asp Asn
                85                  90                  95

Leu Ala Leu Ile Lys Ser Leu Asn Leu Ser Leu Ser Lys Asp Gly Gly
            100                 105                 110

Lys Lys Phe Lys Tyr Ile Glu Asn Leu Glu Lys Cys Val Lys Leu Glu
        115                 120                 125

Val Leu Asn Leu Ser Tyr Asn Leu Ile Gly Lys Ile Glu Lys Leu Asp
    130                 135                 140

Lys Leu Leu Lys Leu Arg Glu Leu Asn Leu Ser Tyr Asn Lys Ile Ser
145                 150                 155                 160

Lys Ile Glu Gly Ile Glu Asn Met Cys Asn Leu Gln Lys Leu Asn Leu
                165                 170                 175
```

```
Ala Gly Asn Glu Ile Glu His Ile Pro Val Trp Leu Gly Lys Lys Leu
            180                 185                 190

Lys Ser Leu Arg Val Leu Asn Leu Lys Gly Asn Lys Ile Ser Ser Leu
        195                 200                 205

Gln Asp Ile Ser Lys Leu Lys Pro Leu Gln Asp Leu Ile Ser Leu Ile
    210                 215                 220

Leu Val Glu Asn Pro Val Val Thr Leu Pro His Tyr Leu Gln Phe Thr
225                 230                 235                 240

Ile Phe His Leu Arg Ser Leu Glu Ser Leu Gly Gln Pro Val Thr
                245                 250                 255

Thr Gln Asp Arg Gln Glu Ala Phe Glu Arg Phe Ser Leu Glu Glu Val
        260                 265                 270

Glu Arg Leu Glu Arg Asp Leu Glu Lys Lys Met Ile Glu Thr Glu Glu
        275                 280                 285

Leu Lys Ser Lys Gln Thr Arg Phe Leu Glu Glu Ile Lys Asn Gln Asp
290                 295                 300

Lys Leu Asn Lys Ser Leu Lys Glu Glu Ala Met Leu Gln Lys Gln Ser
305                 310                 315                 320

Cys Glu Glu Leu Lys Ser Asp Leu Asn Thr Lys Asn Glu Leu Leu Lys
                325                 330                 335

Gln Lys Thr Ile Glu Leu Thr Arg Ala Cys Gln Lys Gln Tyr Glu Leu
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Ala Glu Ile Asp Lys Ala Pro Asp Glu
    370                 375                 380

Ser Pro Tyr Ile Gly Lys Ser Arg Tyr Lys Arg Asn Met Phe Ala Thr
385                 390                 395                 400

Glu Ser Tyr Ile Ile Asp Ser Ala Gln Ala Val Gln Ile Lys Lys Met
                405                 410                 415

Glu Pro Asp Glu Gln Leu Arg Asn Asp His Met Asn Leu Arg Gly His
            420                 425                 430

Thr Pro Leu Asp Thr Gln Leu Glu Asp Lys Glu Lys Lys Ile Ser Ala
        435                 440                 445

Ala Gln Thr Arg Leu Ser Glu Leu His Asp Glu Ile Glu Lys Ala Glu
    450                 455                 460

Gln Gln Ile Leu Arg Ala Thr Glu Glu Phe Lys Gln Leu Glu Glu Ala
465                 470                 475                 480

Ile Gln Leu Lys Lys Ile Ser Glu Ala Gly Lys Asp Leu Leu Tyr Lys
                485                 490                 495

Gln Leu Ser Gly Arg Leu Gln Leu Val Asn Lys Leu Arg Gln Glu Ala
            500                 505                 510

Leu Asp Leu Glu Leu Gln Met Glu Lys Gln Lys Gln Glu Ile Ala Gly
        515                 520                 525

Lys Gln Lys Glu Ile Lys Asp Leu Gln Ile Ala Ile Asp Ser Leu Asp
    530                 535                 540

Ser Lys Asp Pro Lys His Ser His Met Lys Ala Gln Lys Ser Gly Lys
545                 550                 555                 560

Glu Gln Gln Leu Asp Ile Met Asn Lys Gln Tyr Gln Gln Leu Glu Ser
                565                 570                 575

Arg Leu Asp Glu Ile Leu Ser Arg Ile Ala Lys Glu Thr Glu Glu Ile
            580                 585                 590

Lys Asp Leu Glu Glu Gln Leu Thr Glu Gly Gln Ile Ala Ala Asn Glu
```

```
                595                 600                 605
Ala Leu Lys Lys Asp Leu Glu Gly Val Ile Ser Gly Leu Gln Glu Tyr
610                 615                 620

Leu Gly Thr Ile Lys Gly Gln Ala Thr Gln Ala Gln Asn Glu Cys Arg
625                 630                 635                 640

Lys Leu Arg Asp Glu Lys Glu Thr Leu Leu Gln Arg Leu Thr Glu Val
                645                 650                 655

Glu Gln Glu Arg Asp Gln Leu Glu Ile Val Ala Met Asp Ala Glu Asn
                660                 665                 670

Met Arg Lys Glu Leu Ala Glu Leu Glu Ser Ala Leu Gln Glu Gln His
                675                 680                 685

Glu Val Asn Ala Ser Leu Gln Gln Thr Gln Gly Asp Leu Ser Ala Tyr
690                 695                 700

Glu Ala Glu Leu Glu Ala Arg Leu Asn Leu Arg Asp Ala Glu Ala Asn
705                 710                 715                 720

Gln Leu Lys Glu Glu Leu Glu Lys Val Thr Arg Leu Thr Gln Leu Glu
                725                 730                 735

Gln Ser Ala Leu Gln Ala Glu Leu Glu Lys Glu Arg Gln Ala Leu Lys
                740                 745                 750

Asn Ala Leu Gly Lys Ala Gln Phe Ser Glu Glu Lys Glu Gln Glu Asn
                755                 760                 765

Ser Glu Leu His Ala Lys Leu Lys His Leu Gln Asp Asp Asn Asn Leu
770                 775                 780

Leu Lys Gln Gln Leu Lys Asp Phe Gln Asn His Leu Asn His Val Val
785                 790                 795                 800

Asp Gly Leu Val Arg Pro Glu Val Ala Ala Arg Val Asp Glu Leu
                805                 810                 815

Arg Arg Lys Leu Lys Leu Gly Thr Gly Glu Met Asn Ile His Ser Pro
                820                 825                 830

Ser Asp Val Leu Gly Lys Ser Leu Ala Asp Leu Gln Lys Gln Phe Ser
                835                 840                 845

Glu Ile Leu Ala Arg Ser Lys Trp Glu Arg Asp Glu Ala Gln Val Arg
850                 855                 860

Glu Arg Lys Leu Gln Glu Glu Met Ala Leu Gln Gln Glu Lys Leu Ala
865                 870                 875                 880

Thr Gly Gln Glu Glu Phe Arg Gln Ala Cys Glu Arg Ala Leu Glu Ala
                885                 890                 895

Arg Met Asn Phe Asp Lys Arg Gln His Glu Ala Arg Ile Gln Gln Met
                900                 905                 910

Glu Asn Glu Ile His Tyr Leu Gln Glu Asn Leu Lys Ser Met Glu Glu
                915                 920                 925

Ile Gln Gly Leu Thr Asp Leu Gln Leu Gln Glu Ala Asp Glu Glu Lys
930                 935                 940

Glu Arg Ile Leu Ala Gln Leu Arg Glu Leu Glu Lys Lys Lys Lys Leu
945                 950                 955                 960

Glu Asp Ala Lys Ser Gln Glu Gln Val Phe Gly Leu Asp Lys Glu Leu
                965                 970                 975

Lys Lys Leu Lys Lys Ala Val Ala Thr Ser Asp Lys Leu Ala Thr Ala
                980                 985                 990

Glu Leu Thr Ile Ala Lys Asp Gln Leu Lys Ser Leu His Gly Thr Val
                995                 1000                1005

Met Lys Ile Asn Gln Glu Arg Ala Glu Glu Leu Gln Glu Ala Glu
   1010                 1015                1020
```

-continued

Arg Phe Ser Arg Lys Ala Ala Gln Ala Ala Arg Asp Leu Thr Arg
1025                1030                1035

Ala Glu Ala Glu Ile Glu Leu Leu Gln Asn Leu Leu Arg Gln Lys
1040                1045                1050

Gly Glu Gln Phe Arg Leu Glu Met Glu Lys Thr Gly Val Gly Thr
1055                1060                1065

Gly Ala Asn Ser Gln Val Leu Glu Ile Glu Lys Leu Asn Glu Thr
1070                1075                1080

Met Glu Arg Gln Arg Thr Glu Ile Ala Arg Leu Gln Asn Val Leu
1085                1090                1095

Asp Leu Thr Gly Ser Asp Asn Lys Gly Gly Phe Glu Asn Val Leu
1100                1105                1110

Glu Glu Ile Ala Glu Leu Arg Arg Glu Val Ser Tyr Gln Asn Asp
1115                1120                1125

Tyr Ile Ser Ser Met Ala Asp Pro Phe Lys Arg Arg Gly Tyr Trp
1130                1135                1140

Tyr Phe Met Pro Pro Pro Ser Ser Lys Val Ser Ser His Ser
1145                1150                1155

Ser Gln Ala Thr Lys Asp Ser Gly Val Gly Leu Lys Tyr Ser Ala
1160                1165                1170

Ser Thr Pro Val Arg Lys Pro Arg Pro Gly Gln Gln Asp Gly Lys
1175                1180                1185

Glu Gly Ser Gln Pro Pro Pro Ala Ser Gly Tyr Trp Val Tyr Ser
1190                1195                1200

Pro Ile Arg Ser Gly Leu His Lys Leu Phe Pro Ser Arg Asp Ala
1205                1210                1215

Asp Ser Gly Gly Asp Ser Gln Glu Glu Ser Glu Leu Asp Asp Gln
1220                1225                1230

Glu Glu Pro Pro Phe Val Pro Pro Gly Tyr Met Met Tyr Thr
1235                1240                1245

Val Leu Pro Asp Gly Ser Pro Val Pro Gln Gly Met Ala Leu Tyr
1250                1255                1260

Ala Pro Pro Pro Pro Leu Pro Asn Asn Ser Arg Pro Leu Thr Pro
1265                1270                1275

Gly Thr Val Val Tyr Gly Pro Pro Ala Gly Ala Pro Met Val
1280                1285                1290

Tyr Gly Pro Pro Pro Asn Phe Ser Ile Pro Phe Ile Pro Met
1295                1300                1305

Gly Val Leu His Cys Asn Val Pro Glu His His Asn Leu Glu Asn
1310                1315                1320

Glu Val Ser Arg Leu Glu Asp Ile Met Gln His Leu Lys Ser Lys
1325                1330                1335

Lys Arg Glu Glu Arg Trp Met Arg Ala Ser Lys Arg Gln Ser Glu
1340                1345                1350

Lys Glu Met Glu Glu Leu His His Asn Ile Asp Asp Leu Leu Gln
1355                1360                1365

Glu Lys Lys Ser Leu Glu Cys Glu Val Glu Glu Leu His Arg Thr
1370                1375                1380

Val Gln Lys Arg Gln Gln Gln Lys Asp Phe Ile Asp Gly Asn Val
1385                1390                1395

Glu Ser Leu Met Thr Glu Leu Glu Ile Glu Lys Ser Leu Lys His
1400                1405                1410

```
His Glu Asp Ile Val Asp Glu Ile Glu Cys Ile Glu Lys Thr Leu
    1415            1420            1425

Leu Lys Arg Arg Ser Glu Leu Arg Glu Ala Asp Arg Leu Leu Ala
    1430            1435            1440

Glu Ala Glu Ser Glu Leu Ser Cys Thr Lys Glu Lys Thr Lys Asn
    1445            1450            1455

Ala Val Glu Lys Phe Thr Asp Ala Lys Arg Ser Leu Leu Gln Thr
    1460            1465            1470

Glu Ser Asp Ala Glu Glu Leu Glu Arg Arg Ala Gln Glu Thr Ala
    1475            1480            1485

Val Asn Leu Val Lys Ala Asp Gln Gln Leu Arg Ser Leu Gln Ala
    1490            1495            1500

Asp Ala Lys Asp Leu Glu Gln His Lys Ile Lys Gln Glu Glu Ile
    1505            1510            1515

Leu Lys Glu Ile Asn Lys Ile Val Ala Ala Lys Asp Ser Asp Phe
    1520            1525            1530

Gln Cys Leu Ser Lys Lys Lys Glu Lys Leu Thr Glu Glu Leu Gln
    1535            1540            1545

Lys Leu Gln Lys Asp Ile Glu Met Ala Glu Arg Asn Glu Asp His
    1550            1555            1560

His Leu Gln Val Leu Lys Glu Ser Glu Val Leu Leu Gln Ala Lys
    1565            1570            1575

Arg Ala Glu Leu Glu Lys Leu Lys Ser Gln Val Thr Ser Gln Gln
    1580            1585            1590

Gln Glu Met Ala Val Leu Asp Arg Gln Leu Gly His Lys Lys Glu
    1595            1600            1605

Glu Leu His Leu Leu Gln Gly Ser Met Val Gln Ala Lys Ala Asp
    1610            1615            1620

Leu Gln Glu Ala Leu Arg Leu Gly Glu Thr Glu Val Thr Glu Lys
    1625            1630            1635

Cys Asn His Ile Arg Glu Val Lys Ser Leu Leu Glu Glu Leu Ser
    1640            1645            1650

Phe Gln Lys Gly Glu Leu Asn Val Gln Ile Ser Glu Arg Lys Thr
    1655            1660            1665

Gln Leu Thr Leu Ile Lys Gln Glu Ile Glu Lys Glu Glu Glu Asn
    1670            1675            1680

Leu Gln Val Val Leu Arg Gln Met Ser Lys His Lys Thr Glu Leu
    1685            1690            1695

Lys Asn Ile Leu Asp Met Leu Gln Leu Glu Asn His Glu Leu Gln
    1700            1705            1710

Gly Leu Lys Leu Gln His Asp Gln Arg Val Ser Glu Leu Glu Lys
    1715            1720            1725

Thr Gln Val Ala Val Leu Glu Glu Lys Leu Glu Leu Glu Asn Leu
    1730            1735            1740

Gln Gln Ile Ser Gln Gln Gln Lys Gly Glu Ile Glu Trp Gln Lys
    1745            1750            1755

Gln Leu Leu Glu Arg Asp Lys Arg Glu Ile Glu Arg Met Thr Ala
    1760            1765            1770

Glu Ser Arg Ala Leu Gln Ser Cys Val Glu Cys Leu Ser Lys Glu
    1775            1780            1785

Lys Glu Asp Leu Gln Glu Lys Cys Asp Ile Trp Glu Lys Lys Leu
    1790            1795            1800

Ala Gln Thr Lys Arg Val Leu Ala Ala Ala Glu Glu Asn Ser Lys
```

```
            1805                1810                1815

Met Glu Gln Ser Asn Leu Glu Lys Leu Glu Leu Asn Val Arg Lys
            1820                1825                1830

Leu Gln Gln Glu Leu Asp Gln Leu Asn Arg Asp Lys Leu Ser Leu
            1835                1840                1845

His Asn Asp Ile Ser Ala Met Gln Gln Gln Leu Gln Glu Lys Arg
            1850                1855                1860

Glu Ala Val Asn Ser Leu Gln Glu Glu Leu Ala Asn Val Gln Asp
            1865                1870                1875

His Leu Asn Leu Ala Lys Gln Asp Leu Leu His Thr Thr Lys His
            1880                1885                1890

Gln Asp Val Leu Leu Ser Glu Gln Thr Arg Leu Gln Lys Asp Ile
            1895                1900                1905

Ser Glu Trp Ala Asn Arg Phe Glu Asp Cys Gln Lys Glu Glu Glu
            1910                1915                1920

Thr Lys Gln Gln Gln Leu Gln Val Leu Gln Asn Glu Ile Glu Glu
            1925                1930                1935

Asn Lys Leu Lys Leu Val Gln Gln Glu Met Met Phe Gln Arg Leu
            1940                1945                1950

Gln Lys Glu Arg Glu Ser Glu Glu Ser Lys Leu Glu Thr Ser Lys
            1955                1960                1965

Val Thr Leu Lys Glu Gln Gln His Gln Leu Glu Lys Glu Leu Thr
            1970                1975                1980

Asp Gln Lys Ser Lys Leu Asp Gln Val Leu Ser Lys Val Leu Ala
            1985                1990                1995

Ala Glu Glu Arg Val Arg Thr Leu Gln Glu Glu Glu Arg Trp Cys
            2000                2005                2010

Glu Ser Leu Glu Lys Thr Leu Ser Gln Thr Lys Arg Gln Leu Ser
            2015                2020                2025

Glu Arg Glu Gln Gln Leu Val Glu Lys Ser Gly Glu Leu Leu Ala
            2030                2035                2040

Leu Gln Lys Glu Ala Asp Ser Met Arg Ala Asp Phe Ser Leu Leu
            2045                2050                2055

Arg Asn Gln Phe Leu Thr Glu Arg Lys Lys Ala Glu Lys Gln Val
            2060                2065                2070

Ala Ser Leu Lys Glu Ala Leu Lys Ile Gln Arg Ser Gln Leu Glu
            2075                2080                2085

Lys Asn Leu Leu Glu Gln Lys Gln Glu Asn Ser Cys Ile Gln Lys
            2090                2095                2100

Glu Met Ala Thr Ile Glu Leu Val Ala Gln Asp Asn His Glu Arg
            2105                2110                2115

Ala Arg Arg Leu Met Lys Glu Leu Asn Gln Met Gln Tyr Glu Tyr
            2120                2125                2130

Thr Glu Leu Lys Lys Gln Met Ala Asn Gln Lys Asp Leu Glu Arg
            2135                2140                2145

Arg Gln Met Glu Ile Ser Asp Ala Met Arg Thr Leu Lys Ser Glu
            2150                2155                2160

Val Lys Asp Glu Ile Arg Thr Ser Leu Lys Asn Leu Asn Gln Phe
            2165                2170                2175

Leu Pro Glu Leu Pro Ala Asp Leu Glu Ala Ile Leu Glu Arg Asn
            2180                2185                2190

Glu Asn Leu Glu Gly Glu Leu Glu Ser Leu Lys Glu Asn Leu Pro
            2195                2200                2205
```

-continued

```
Phe Thr Met Asn Glu Gly Pro Phe Glu Lys Leu Asn Phe Ser
    2210            2215               2220

Gln Val His Ile Met Asp Glu His Trp Arg Gly Glu Ala Leu Arg
2225            2230               2235

Glu Lys Leu Arg His Arg Glu Asp Arg Leu Lys Ala Gln Leu Arg
    2240            2245               2250

His Cys Met Ser Lys Gln Ala Glu Val Leu Ile Lys Gly Lys Arg
    2255            2260               2265

Gln Thr Glu Gly Thr Leu His Ser Leu Arg Arg Gln Val Asp Ala
    2270            2275               2280

Leu Gly Glu Leu Val Thr Ser Thr Ser Ala Asp Ser Ala Ser Ser
    2285            2290               2295

Pro Ser Leu Ser Gln Leu Glu Ser Ser Leu Thr Glu Asp Ser Gln
    2300            2305               2310

Leu Gly Gln Asn Gln Glu Lys Asn Ala Ser Ala Arg
    2315            2320               2325

<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31
gcagcaaaag actcagac                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32
aagttgcaac atgtccag                                                 18

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
ggatccatga agaaaggttc tcag                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
gtcgactcag ggtcggtgcg cgtc                                          24

<210> SEQ ID NO 35
<211> LENGTH: 23
<212> TYPE: DNA
<213> ORGANISM: Artificial Sequence
<220> FEATURE:
```

```
<223> OTHER INFORMATION: Synthetic primer

<400> SEQUENCE: 35
gtcgacctat gcggaggggt ctg                                              23

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
ggatccatga agaaaggttc tcaac                                            25

<210> SEQ ID NO 37
<211> LENGTH: 25
<212> TYPE: DNA
<213> ORGANISM: Artificial Sequence
<220> FEATURE:
<223> OTHER INFORMATION: Synthetic primer

<400> SEQUENCE: 37
gtcgactcat ctggctgagg cattc                                            25

<210> SEQ ID NO 38
<211> LENGTH: 6046
<212> TYPE: DNA
<213> ORGANISM: Canis familiaris
<220> FEATURE:
<221> NAME/KEY: CDS
<222> LOCATION: (1)..(5934)

<400> SEQUENCE: 38
```

| | | | | | | | | | | | | | | | | |
|---|---|---|---|---|---|---|---|---|---|---|---|---|---|---|---|---|
| atg | tcg | tcc | tgg | ctc | ggg | ggc | ctg | ggc | tcc | ggc | ctg | ggc | cag | tcg | ctg | 48 |
| Met | Ser | Ser | Trp | Leu | Gly | Gly | Leu | Gly | Ser | Gly | Leu | Gly | Gln | Ser | Leu | |
| 1 | | | | 5 | | | | | 10 | | | | | 15 | | |
| ggg | caa | gtc | gga | ggc | agc | ctg | gcc | tcc | ctc | act | ggc | cag | att | tca | aac | 96 |
| Gly | Gln | Val | Gly | Gly | Ser | Leu | Ala | Ser | Leu | Thr | Gly | Gln | Ile | Ser | Asn | |
| | | 20 | | | | | 25 | | | | | 30 | | | | |
| ttt | acg | aag | gac | atg | ctg | atg | gag | ggc | acg | gag | gag | gtg | gaa | gca | gaa | 144 |
| Phe | Thr | Lys | Asp | Met | Leu | Met | Glu | Gly | Thr | Glu | Glu | Val | Glu | Ala | Glu | |
| | | | 35 | | | | | 40 | | | | | 45 | | | |
| tta | cct | aat | tct | agg | aga | aag | gaa | gtt | gaa | gcc | att | cat | gca | atc | tta | 192 |
| Leu | Pro | Asn | Ser | Arg | Arg | Lys | Glu | Val | Glu | Ala | Ile | His | Ala | Ile | Leu | |
| | 50 | | | | | 55 | | | | | 60 | | | | | |
| aga | tca | gag | aat | gag | aga | ctc | aaa | gaa | ctt | tgt | act | gat | tta | gaa | gag | 240 |
| Arg | Ser | Glu | Asn | Glu | Arg | Leu | Lys | Glu | Leu | Cys | Thr | Asp | Leu | Glu | Glu | |
| 65 | | | | | 70 | | | | | 75 | | | | | 80 | |
| aag | cat | gaa | gca | tca | gag | ctt | caa | ata | aag | caa | caa | tct | aca | aat | tac | 288 |
| Lys | His | Glu | Ala | Ser | Glu | Leu | Gln | Ile | Lys | Gln | Gln | Ser | Thr | Asn | Tyr | |
| | | | | 85 | | | | | 90 | | | | | 95 | | |
| cga | aat | caa | cta | caa | cag | aaa | gag | gta | gaa | atc | agc | cat | ctt | aaa | gca | 336 |
| Arg | Asn | Gln | Leu | Gln | Gln | Lys | Glu | Val | Glu | Ile | Ser | His | Leu | Lys | Ala | |
| | | | 100 | | | | | 105 | | | | | 110 | | | |
| aga | cag | att | gca | ctg | cag | gat | cag | ttg | ctg | aag | ctg | cag | tca | gct | gct | 384 |
| Arg | Gln | Ile | Ala | Leu | Gln | Asp | Gln | Leu | Leu | Lys | Leu | Gln | Ser | Ala | Ala | |
| | | | | 115 | | | | | 120 | | | | | 125 | | |
| cag | tct | gca | cat | tca | gga | gct | agc | agc | gta | cca | gca | gcc | ctg | gca | tca | 432 |
| Gln | Ser | Ala | His | Ser | Gly | Ala | Ser | Ser | Val | Pro | Ala | Ala | Leu | Ala | Ser | |
| | 130 | | | | | 135 | | | | | 140 | | | | | |
| tct | ccg | ttc | agc | tat | tct | gtc | agt | cat | cat | gct | tca | gct | ttc | cat | gac | 480 |
| Ser | Pro | Phe | Ser | Tyr | Ser | Val | Ser | His | His | Ala | Ser | Ala | Phe | His | Asp | |

-continued

| 145 | | | 150 | | | | 155 | | | 160 | | | |
|---|---|---|---|---|---|---|---|---|---|---|---|---|---|

```
gat gac atg gac ttc agt gac ata att tca tca caa caa gaa ata aac    528
Asp Asp Met Asp Phe Ser Asp Ile Ile Ser Ser Gln Gln Glu Ile Asn
                165                 170                 175 aga tta tca aat gaa gtt tca aga ctt gag tct gag gtt ggc cat tgg    576
Arg Leu Ser Asn Glu Val Ser Arg Leu Glu Ser Glu Val Gly His Trp
            180                 185                 190 agg cat att gct cag act tct aaa gca caa gga tca aat agc tct gat    624
Arg His Ile Ala Gln Thr Ser Lys Ala Gln Gly Ser Asn Ser Ser Asp
        195                 200                 205 caa agt gaa atc tgt aaa cta caa agt atc att aag gaa ctc aaa cag    672
Gln Ser Glu Ile Cys Lys Leu Gln Ser Ile Ile Lys Glu Leu Lys Gln
    210                 215                 220 att cga agt cag gaa atc gat gac cat caa cat gaa atg tca gtg ttg    720
Ile Arg Ser Gln Glu Ile Asp Asp His Gln His Glu Met Ser Val Leu
225                 230                 235                 240 cag aat gca cat caa cag aag ttg aca gat ata agt cgt cgg cat cga    768
Gln Asn Ala His Gln Gln Lys Leu Thr Asp Ile Ser Arg Arg His Arg
                245                 250                 255 gaa gaa tta cgt gac tat gaa gaa cga att gaa gaa ctg gaa aat ctg    816
Glu Glu Leu Arg Asp Tyr Glu Glu Arg Ile Glu Glu Leu Glu Asn Leu
            260                 265                 270 tta gaa caa ggt ggc tca gga att gta ata cct gat cac tca aaa atc    864
Leu Glu Gln Gly Gly Ser Gly Ile Val Ile Pro Asp His Ser Lys Ile
        275                 280                 285 cat gag atg caa aaa act att cag aat cta caa act gaa aaa gta gca    912
His Glu Met Gln Lys Thr Ile Gln Asn Leu Gln Thr Glu Lys Val Ala
    290                 295                 300 tct ata aaa aaa att gaa gaa ctt gag gat aaa ata aaa gac ata gat    960
Ser Ile Lys Lys Ile Glu Glu Leu Glu Asp Lys Ile Lys Asp Ile Asp
305                 310                 315                 320 aaa aaa ttg tct tct gca gaa aat gac aga gat gtt ttg agg aag gag   1008
Lys Lys Leu Ser Ser Ala Glu Asn Asp Arg Asp Val Leu Arg Lys Glu
                325                 330                 335 aaa gaa tgc cta aat gtt gaa aac aga caa ata aca gaa caa tgt gaa   1056
Lys Glu Cys Leu Asn Val Glu Asn Arg Gln Ile Thr Glu Gln Cys Glu
            340                 345                 350 agc ttg aaa ctg gaa tgt aaa ttg cag cat gat gct gag aag caa ggt   1104
Ser Leu Lys Leu Glu Cys Lys Leu Gln His Asp Ala Glu Lys Gln Gly
        355                 360                 365 gat act gtg aca gaa aaa gaa aga atc ctt cca cag agt aca tca gtg   1152
Asp Thr Val Thr Glu Lys Glu Arg Ile Leu Pro Gln Ser Thr Ser Val
    370                 375                 380 gaa gag gaa gtg ctc aaa ctg cag caa gca ctg tct gat gcg gaa aat   1200
Glu Glu Glu Val Leu Lys Leu Gln Gln Ala Leu Ser Asp Ala Glu Asn
385                 390                 395                 400 gaa att atg aga ctg agt aat tta tac cag gat aac agt ctc act gaa   1248
Glu Ile Met Arg Leu Ser Asn Leu Tyr Gln Asp Asn Ser Leu Thr Glu
                405                 410                 415 gat aat ttg aaa ctt aaa atg cat gtc gaa ttt tta gaa aaa cag aag   1296
Asp Asn Leu Lys Leu Lys Met His Val Glu Phe Leu Glu Lys Gln Lys
            420                 425                 430 tcc tta ttg agt caa gaa aag gaa gag ctt caa cta tca ctt tta aag   1344
Ser Leu Leu Ser Gln Glu Lys Glu Glu Leu Gln Leu Ser Leu Leu Lys
        435                 440                 445 ttg aac aat gaa tat gaa gtg att aaa agt aca gct gtg aga gac atg   1392
Leu Asn Asn Glu Tyr Glu Val Ile Lys Ser Thr Ala Val Arg Asp Met
    450                 455                 460 gat atg gat tca aca tta tgt gat tta aga ctg acc ttg gag gca aag   1440
```

```
                                                         -continued

Asp Met Asp Ser Thr Leu Cys Asp Leu Arg Leu Thr Leu Glu Ala Lys
465                 470                 475                 480 gac cag gaa ctc aat cag agt ctc act gag aag gaa ata ttg gtt gct    1488
Asp Gln Glu Leu Asn Gln Ser Leu Thr Glu Lys Glu Ile Leu Val Ala
                    485                 490                 495 gag tta gag gaa ttg gac aga caa aac caa gaa gct aca aag cac atg    1536
Glu Leu Glu Glu Leu Asp Arg Gln Asn Gln Glu Ala Thr Lys His Met
                500                 505                 510 att ctg ata aaa gat cag cta tca aaa caa caa agt gag gga gaa act    1584
Ile Leu Ile Lys Asp Gln Leu Ser Lys Gln Gln Ser Glu Gly Glu Thr
            515                 520                 525 atc att agt aaa ctg aga aaa gat cta aat gat gaa aac aag aga gtc    1632
Ile Ile Ser Lys Leu Arg Lys Asp Leu Asn Asp Glu Asn Lys Arg Val
        530                 535                 540 cat caa ctt gaa gat gat aaa aag aat atg act aaa gaa cta aat gtg    1680
His Gln Leu Glu Asp Asp Lys Lys Asn Met Thr Lys Glu Leu Asn Val
545                 550                 555                 560 cag aaa gag aag tta gtt caa agt gaa ctc gtc cta aat ggc ttg cat    1728
Gln Lys Glu Lys Leu Val Gln Ser Glu Leu Val Leu Asn Gly Leu His
                565                 570                 575 tta gcc aag cag aag ctt gag gag aaa gta gaa gat tta gtg gat cag    1776
Leu Ala Lys Gln Lys Leu Glu Glu Lys Val Glu Asp Leu Val Asp Gln
                580                 585                 590 cta aat aaa tca caa aaa agt aat tta aac atg cag aag gag aac ttt    1824
Leu Asn Lys Ser Gln Lys Ser Asn Leu Asn Met Gln Lys Glu Asn Phe
            595                 600                 605 gga ctt aag gaa cat att aaa caa aat gag gaa gag ctt tct aga gtc    1872
Gly Leu Lys Glu His Ile Lys Gln Asn Glu Glu Glu Leu Ser Arg Val
        610                 615                 620 agg gat gag tta act cag tct cta agt cga gac tct ggc agt gat ttt    1920
Arg Asp Glu Leu Thr Gln Ser Leu Ser Arg Asp Ser Gly Ser Asp Phe
625                 630                 635                 640 aag gat gac tta ctt aaa gaa agg gaa gct gaa gtc aga aac tta aaa    1968
Lys Asp Asp Leu Leu Lys Glu Arg Glu Ala Glu Val Arg Asn Leu Lys
                645                 650                 655 caa aat ctt tca gaa ata gaa cag ctc aat gac agt tta aac aaa gtt    2016
Gln Asn Leu Ser Glu Ile Glu Gln Leu Asn Asp Ser Leu Asn Lys Val
                660                 665                 670 gcc ttt gat ctc aaa atg gaa aat gaa aag ttg gtc tta gcg tgt gaa    2064
Ala Phe Asp Leu Lys Met Glu Asn Glu Lys Leu Val Leu Ala Cys Glu
            675                 680                 685 gat ata aga cat cag ttg gaa gaa tca att gtt ggc agc aat cag atg    2112
Asp Ile Arg His Gln Leu Glu Glu Ser Ile Val Gly Ser Asn Gln Met
        690                 695                 700 tct ctg gaa aga aac act att gtg gag gct cta aaa atg gaa aaa gga    2160
Ser Leu Glu Arg Asn Thr Ile Val Glu Ala Leu Lys Met Glu Lys Gly
705                 710                 715                 720 cag tta gaa gca gaa ttg agt cga gct gac caa agg ctg ttg gaa gaa    2208
Gln Leu Glu Ala Glu Leu Ser Arg Ala Asp Gln Arg Leu Leu Glu Glu
                725                 730                 735 gcc agt aag tat gaa cag acg att caa gag cta tca aag gca cgt gat    2256
Ala Ser Lys Tyr Glu Gln Thr Ile Gln Glu Leu Ser Lys Ala Arg Asp
                740                 745                 750 ttg agg acc tct gct tta cag ctg gag cag cag cat tta atg aaa ctc    2304
Leu Arg Thr Ser Ala Leu Gln Leu Glu Gln Gln His Leu Met Lys Leu
            755                 760                 765 agt caa gag aag gac ttc gaa ata gca gaa ctt aaa aag aac att gaa    2352
Ser Gln Glu Lys Asp Phe Glu Ile Ala Glu Leu Lys Lys Asn Ile Glu
770                 775                 780
```

-continued

| | |
|---|---|
| cag atg gat act gat cat aaa gaa act aag gca att ttg tca tct att<br>Gln Met Asp Thr Asp His Lys Glu Thr Lys Ala Ile Leu Ser Ser Ile<br>785                       790                   795                 800 | 2400 |
| tta gaa gag cag aag caa ttg acg caa ctt ata agt gag aag gaa att<br>Leu Glu Glu Gln Lys Gln Leu Thr Gln Leu Ile Ser Glu Lys Glu Ile<br>             805                   810                   815 | 2448 |
| ttt att gag aaa ctt aaa gaa aga agt tca gag ctt cag gag gaa tta<br>Phe Ile Glu Lys Leu Lys Glu Arg Ser Ser Glu Leu Gln Glu Glu Leu<br>820                       825                   830 | 2496 |
| gag aaa tct act cag gcc tca agg aaa att gaa att tta aag caa acc<br>Glu Lys Ser Thr Gln Ala Ser Arg Lys Ile Glu Ile Leu Lys Gln Thr<br>             835                   840                   845 | 2544 |
| att gag gag aaa gac aga agt ctt ggg tcc atg aaa gaa gaa aac aat<br>Ile Glu Glu Lys Asp Arg Ser Leu Gly Ser Met Lys Glu Glu Asn Asn<br>850                       855                   860 | 2592 |
| cat ctg aaa gaa gaa ctg gaa cgg ctc cgt gaa cag cag agt cga gcc<br>His Leu Lys Glu Glu Leu Glu Arg Leu Arg Glu Gln Gln Ser Arg Ala<br>865                       870                   875                 880 | 2640 |
| gtg cct gtg gtg gag cct aaa ccc ctg gat agt gtt aca gag cta gaa<br>Val Pro Val Val Glu Pro Lys Pro Leu Asp Ser Val Thr Glu Leu Glu<br>                   885                   890                   895 | 2688 |
| tct gag gtg ttg cag cta aat ata gta aag agg aat ctt gag gag gaa<br>Ser Glu Val Leu Gln Leu Asn Ile Val Lys Arg Asn Leu Glu Glu Glu<br>900                       905                   910 | 2736 |
| ata aaa cgt cat cag aag att ata gaa gat caa aac cag agt aaa atg<br>Ile Lys Arg His Gln Lys Ile Ile Glu Asp Gln Asn Gln Ser Lys Met<br>             915                   920                   925 | 2784 |
| cag ctg ctt cag tct cta gag gag cag aag aag gaa atg gat gaa ttt<br>Gln Leu Leu Gln Ser Leu Glu Glu Gln Lys Lys Glu Met Asp Glu Phe<br>930                       935                   940 | 2832 |
| aag tgc cag cat gag caa atg aac gtc aca cac acc caa ctc ttc tta<br>Lys Cys Gln His Glu Gln Met Asn Val Thr His Thr Gln Leu Phe Leu<br>945                       950                   955                 960 | 2880 |
| gag aaa gat gag gag att aag aat ttg caa aaa aca att gaa caa atc<br>Glu Lys Asp Glu Glu Ile Lys Asn Leu Gln Lys Thr Ile Glu Gln Ile<br>                   965                   970                   975 | 2928 |
| aaa acc caa tgg cat gaa gaa aga cag gac gtt caa atg gag aat tct<br>Lys Thr Gln Trp His Glu Glu Arg Gln Asp Val Gln Met Glu Asn Ser<br>             980                   985                   990 | 2976 |
| gag ttc ttt caa gaa aca aaa gtg  cag agc ctt aat cta  gaa aat ggc<br>Glu Phe Phe Gln Glu Thr Lys Val  Gln Ser Leu Asn Leu  Glu Asn Gly<br>             995                   1000                 1005 | 3024 |
| agt gaa  aag cat gat tta tcg  aaa gcc gaa act gag  agg tta gta<br>Ser Glu  Lys His Asp Leu Ser  Lys Ala Glu Thr Glu  Arg Leu Val<br>1010                       1015                    1020 | 3069 |
| aaa gga  ata aaa gaa cga gag  ctg gag att aaa ctt  cta aat gaa<br>Lys Gly  Ile Lys Glu Arg Glu  Leu Glu Ile Lys Leu  Leu Asn Glu<br>1025                       1030                    1035 | 3114 |
| aag aat  ata tct tta aca aaa  caa att gat cag ctg  tcc aaa gat<br>Lys Asn  Ile Ser Leu Thr Lys  Gln Ile Asp Gln Leu  Ser Lys Asp<br>1040                       1045                    1050 | 3159 |
| gag gtt  ggt aaa ctc act cag  atc atc cag cag aaa  gac tta gag<br>Glu Val  Gly Lys Leu Thr Gln  Ile Ile Gln Gln Lys  Asp Leu Glu<br>1055                       1060                    1065 | 3204 |
| ata caa  gct ctt cat gct agg  att tct tca gct tcc  tac acc cag<br>Ile Gln  Ala Leu His Ala Arg  Ile Ser Ser Ala Ser  Tyr Thr Gln<br>1070                       1075                    1080 | 3249 |
| gat gtt  gtc tac ctt cag cag  cag ctg cag gcc tat  gct atg gag<br>Asp Val  Val Tyr Leu Gln Gln  Gln Leu Gln Ala Tyr  Ala Met Glu<br>1085                       1090                    1095 | 3294 |

```
aga gaa caa gta tta gct gtt ttg agt gag aag acc agg gaa aat      3339
Arg Glu Gln Val Leu Ala Val Leu Ser Glu Lys Thr Arg Glu Asn
    1100                1105                1110 agc cat ctg aaa aca gaa tac cac aaa atg atg gat atc gtt gct      3384
Ser His Leu Lys Thr Glu Tyr His Lys Met Met Asp Ile Val Ala
    1115                1120                1125 gct aaa gaa gca gct ctc att aag ctg caa gat gaa aat aaa aaa      3429
Ala Lys Glu Ala Ala Leu Ile Lys Leu Gln Asp Glu Asn Lys Lys
    1130                1135                1140 ttg tct gct aga tcc gaa ggt ggt ggc cag gat atg ttt aga gag      3474
Leu Ser Ala Arg Ser Glu Gly Gly Gly Gln Asp Met Phe Arg Glu
    1145                1150                1155 act gtc cag aat tta tca cgt atc att cga gaa aaa gac att gag      3519
Thr Val Gln Asn Leu Ser Arg Ile Ile Arg Glu Lys Asp Ile Glu
    1160                1165                1170 ata gat gcg tta agt cag aag tgc cag acc tta ttg aca gtt tta      3564
Ile Asp Ala Leu Ser Gln Lys Cys Gln Thr Leu Leu Thr Val Leu
    1175                1180                1185 caa aca tcg agc act ggg aat gag gtt gga ggc gtt aat agc aat      3609
Gln Thr Ser Ser Thr Gly Asn Glu Val Gly Gly Val Asn Ser Asn
    1190                1195                1200 cag ttt gag gag ctt cta cag gaa cgc gac aaa tta aaa caa caa      3654
Gln Phe Glu Glu Leu Leu Gln Glu Arg Asp Lys Leu Lys Gln Gln
    1205                1210                1215 gta aag aag atg gaa gag tgg aaa cag cag gtg atg acc aca gtt      3699
Val Lys Lys Met Glu Glu Trp Lys Gln Gln Val Met Thr Thr Val
    1220                1225                1230 cag aat atg cag cat gag tca gcc cag ctt caa gaa gaa ctt cat      3744
Gln Asn Met Gln His Glu Ser Ala Gln Leu Gln Glu Glu Leu His
    1235                1240                1245 cag ctt cag gca caa gtt ttg gtt gac agt gat aat aat tct aaa      3789
Gln Leu Gln Ala Gln Val Leu Val Asp Ser Asp Asn Asn Ser Lys
    1250                1255                1260 tta caa gtg gat tat act ggc ctg atc caa agt tat gag cag aat      3834
Leu Gln Val Asp Tyr Thr Gly Leu Ile Gln Ser Tyr Glu Gln Asn
    1265                1270                1275 gaa act aaa ctc aaa aat ttt ggg cag gag cta gca caa gtt cag      3879
Glu Thr Lys Leu Lys Asn Phe Gly Gln Glu Leu Ala Gln Val Gln
    1280                1285                1290 cac agc ata ggg cag ctg tac agt acc aaa gac ctt ctc tta gga      3924
His Ser Ile Gly Gln Leu Tyr Ser Thr Lys Asp Leu Leu Leu Gly
    1295                1300                1305 aaa ctt gat att att tct cct caa ctc ccc tcc gga tca tcg cct      3969
Lys Leu Asp Ile Ile Ser Pro Gln Leu Pro Ser Gly Ser Ser Pro
    1310                1315                1320 cct tcc cag tca gca gag tct ctt gga atg gat aag cgt gat aca      4014
Pro Ser Gln Ser Ala Glu Ser Leu Gly Met Asp Lys Arg Asp Thr
    1325                1330                1335 tca agt gag tct tca aaa cag gag cta gaa gag cta aga aag tca      4059
Ser Ser Glu Ser Ser Lys Gln Glu Leu Glu Glu Leu Arg Lys Ser
    1340                1345                1350 ctg cag gaa aaa gat gca acg att aaa aca ctc cag gaa aat aac      4104
Leu Gln Glu Lys Asp Ala Thr Ile Lys Thr Leu Gln Glu Asn Asn
    1355                1360                1365 cac aga ttg tcc gat tca att gct gcc acc tca gag cta gaa aga      4149
His Arg Leu Ser Asp Ser Ile Ala Ala Thr Ser Glu Leu Glu Arg
    1370                1375                1380 aaa gaa cac gaa cag act gat tca gaa att aag cag cta aag gag      4194
Lys Glu His Glu Gln Thr Asp Ser Glu Ile Lys Gln Leu Lys Glu
```

-continued

| | | | | | | | | | | | | | | |
|---|---|---|---|---|---|---|---|---|---|---|---|---|---|---|

```
                     1385                1390                1395
aaa  caa  gat  gtt  tta  caa  aag  tca  ctt  aag  gag  aaa  gac  ctc  tta     4239
Lys  Gln  Asp  Val  Leu  Gln  Lys  Ser  Leu  Lys  Glu  Lys  Asp  Leu  Leu
     1400                1405                1410 atc  aaa  gcc  aaa  agt  gat  cag  tta  ctt  tct  tta  aat  gaa  aat  ttc     4284
Ile  Lys  Ala  Lys  Ser  Asp  Gln  Leu  Leu  Ser  Leu  Asn  Glu  Asn  Phe
     1415                1420                1425 acc  aac  aaa  gtg  aat  gaa  aat  gaa  ctc  ttg  agg  cag  gca  gta  acc     4329
Thr  Asn  Lys  Val  Asn  Glu  Asn  Glu  Leu  Leu  Arg  Gln  Ala  Val  Thr
     1430                1435                1440 aac  ctg  aag  gag  cgg  gta  tta  att  tta  gaa  atg  gac  att  ggt  aaa     4374
Asn  Leu  Lys  Glu  Arg  Val  Leu  Ile  Leu  Glu  Met  Asp  Ile  Gly  Lys
     1445                1450                1455 cta  aaa  gaa  gaa  aat  gaa  aaa  ata  gtt  gaa  aga  acc  agg  gaa  aag     4419
Leu  Lys  Glu  Glu  Asn  Glu  Lys  Ile  Val  Glu  Arg  Thr  Arg  Glu  Lys
     1460                1465                1470 gaa  acg  gag  tat  caa  gca  tta  cag  gag  act  aat  atg  aag  ttt  tcc     4464
Glu  Thr  Glu  Tyr  Gln  Ala  Leu  Gln  Glu  Thr  Asn  Met  Lys  Phe  Ser
     1475                1480                1485 atg  atg  ctt  cga  gaa  aaa  gag  ttt  gag  tgc  cat  tca  atg  aag  gaa     4509
Met  Met  Leu  Arg  Glu  Lys  Glu  Phe  Glu  Cys  His  Ser  Met  Lys  Glu
     1490                1495                1500 aaa  tct  ctt  gca  ttt  gag  cag  cta  ctg  aaa  gaa  aaa  gag  cag  ggc     4554
Lys  Ser  Leu  Ala  Phe  Glu  Gln  Leu  Leu  Lys  Glu  Lys  Glu  Gln  Gly
     1505                1510                1515 aag  act  ggg  gag  tta  aat  caa  ctt  tta  aat  gca  gtt  aag  tca  atg     4599
Lys  Thr  Gly  Glu  Leu  Asn  Gln  Leu  Leu  Asn  Ala  Val  Lys  Ser  Met
     1520                1525                1530 cag  gag  aag  aca  gtt  aag  ttt  caa  caa  gag  aga  gac  cag  gtc  atg     4644
Gln  Glu  Lys  Thr  Val  Lys  Phe  Gln  Gln  Glu  Arg  Asp  Gln  Val  Met
     1535                1540                1545 ttg  gcc  ctg  aaa  cag  aaa  caa  atg  gaa  aac  agt  gct  tta  cag  aat     4689
Leu  Ala  Leu  Lys  Gln  Lys  Gln  Met  Glu  Asn  Ser  Ala  Leu  Gln  Asn
     1550                1555                1560 gag  gtt  caa  cat  tta  cgc  gac  aaa  gaa  tta  cgc  tta  aac  cag  gag     4734
Glu  Val  Gln  His  Leu  Arg  Asp  Lys  Glu  Leu  Arg  Leu  Asn  Gln  Glu
     1565                1570                1575 cta  gag  aga  ttg  cgt  aac  cat  ctt  tta  gaa  tca  gag  gat  tct  tac     4779
Leu  Glu  Arg  Leu  Arg  Asn  His  Leu  Leu  Glu  Ser  Glu  Asp  Ser  Tyr
     1580                1585                1590 acc  cgt  gaa  gct  ttg  gct  gca  gaa  gag  aga  gag  gcc  aaa  ctg  aga     4824
Thr  Arg  Glu  Ala  Leu  Ala  Ala  Glu  Glu  Arg  Glu  Ala  Lys  Leu  Arg
     1595                1600                1605 agg  aaa  gtc  aca  gta  ttg  gag  gaa  aag  cta  gtt  tca  tct  tct  aat     4869
Arg  Lys  Val  Thr  Val  Leu  Glu  Glu  Lys  Leu  Val  Ser  Ser  Ser  Asn
     1610                1615                1620 gca  atg  gaa  aat  gca  agc  cat  cag  gcc  agt  ttg  cag  gta  gag  tca     4914
Ala  Met  Glu  Asn  Ala  Ser  His  Gln  Ala  Ser  Leu  Gln  Val  Glu  Ser
     1625                1630                1635 ctg  cag  gag  cag  ctg  aat  gtg  gtc  tct  aag  cag  agg  gat  gaa  acc     4959
Leu  Gln  Glu  Gln  Leu  Asn  Val  Val  Ser  Lys  Gln  Arg  Asp  Glu  Thr
     1640                1645                1650 gcc  ctg  cag  ctc  tct  gtg  tct  cgg  gaa  caa  gta  aag  cag  tat  gct     5004
Ala  Leu  Gln  Leu  Ser  Val  Ser  Arg  Glu  Gln  Val  Lys  Gln  Tyr  Ala
     1655                1660                1665 ctc  tca  ctc  tcc  aac  ctg  cag  atg  gta  cta  gag  cat  ttc  cag  caa     5049
Leu  Ser  Leu  Ser  Asn  Leu  Gln  Met  Val  Leu  Glu  His  Phe  Gln  Gln
     1670                1675                1680 gag  gaa  aaa  gct  gtg  tat  tct  gct  gaa  cta  gaa  aag  cac  aaa  cag     5094
```

```
                Glu Glu Lys Ala Val Tyr Ser Ala Glu Leu Glu Lys His Lys Gln
                    1685                1690                1695 ctt gta gct gaa tgg aag aaa aag gca gaa aat ctg gaa gga aaa        5139
Leu Val Ala Glu Trp Lys Lys Lys Ala Glu Asn Leu Glu Gly Lys
    1700                1705                1710 ctg atg tca tta cag gag cgt ttt gat gaa gca aat gct gcg ttg        5184
Leu Met Ser Leu Gln Glu Arg Phe Asp Glu Ala Asn Ala Ala Leu
    1715                1720                1725 gat tca gca tca aga ctt aca gag cag tta gat tta aag gaa gaa        5229
Asp Ser Ala Ser Arg Leu Thr Glu Gln Leu Asp Leu Lys Glu Glu
    1730                1735                1740 caa att gaa gaa ctt aaa aaa caa aat gaa ctc cga caa gaa atg        5274
Gln Ile Glu Glu Leu Lys Lys Gln Asn Glu Leu Arg Gln Glu Met
    1745                1750                1755 ctg gat gat gta caa aag aaa ttg atg aac tta gta aac agc aca        5319
Leu Asp Asp Val Gln Lys Lys Leu Met Asn Leu Val Asn Ser Thr
    1760                1765                1770 gaa gga aaa gtg gac aaa gtc cta atg aga aac ctc ttc att gga        5364
Glu Gly Lys Val Asp Lys Val Leu Met Arg Asn Leu Phe Ile Gly
    1775                1780                1785 cat ttc cac aca cca aag cat cag cgc cac gag gtg tta cga tta        5409
His Phe His Thr Pro Lys His Gln Arg His Glu Val Leu Arg Leu
    1790                1795                1800 atg gga agc atc ctt ggt atc aag agg gag gaa atg gaa cag ttg        5454
Met Gly Ser Ile Leu Gly Ile Lys Arg Glu Glu Met Glu Gln Leu
    1805                1810                1815 ctt cat gaa gat cag ggt ggt gtt acc agg tgg atg act gga tgg        5499
Leu His Glu Asp Gln Gly Gly Val Thr Arg Trp Met Thr Gly Trp
    1820                1825                1830 ctt gga gga gga tca aaa agt gtc ccc aac aca cct ctg aga cca        5544
Leu Gly Gly Gly Ser Lys Ser Val Pro Asn Thr Pro Leu Arg Pro
    1835                1840                1845 aat caa caa tct gtg ctt aat agc tct ttt tca gaa ctt ttt gtt        5589
Asn Gln Gln Ser Val Leu Asn Ser Ser Phe Ser Glu Leu Phe Val
    1850                1855                1860 aaa ttt cta gaa aca gaa tct cat cca tct gtt cca cca cca aag        5634
Lys Phe Leu Glu Thr Glu Ser His Pro Ser Val Pro Pro Pro Lys
    1865                1870                1875 ctt tct gtt cat gat atg aaa cct ctg gat tca cca gga agg aga        5679
Leu Ser Val His Asp Met Lys Pro Leu Asp Ser Pro Gly Arg Arg
    1880                1885                1890 aaa gta gtc ata cat gta tca gaa agt ttt aaa gaa acc aca gag        5724
Lys Val Val Ile His Val Ser Glu Ser Phe Lys Glu Thr Thr Glu
    1895                1900                1905 tcc aga tgt gga agg aga aca gat gtg aat cca ttc ttg gct ccc        5769
Ser Arg Cys Gly Arg Arg Thr Asp Val Asn Pro Phe Leu Ala Pro
    1910                1915                1920 cgc tct gca gct gtg cct ctc att aac cca gct gga ctt gga cct        5814
Arg Ser Ala Ala Val Pro Leu Ile Asn Pro Ala Gly Leu Gly Pro
    1925                1930                1935 ggt ggg cct ggg cat ctt ctt ttg aag ccc atc tca gac gtg ttg        5859
Gly Gly Pro Gly His Leu Leu Leu Lys Pro Ile Ser Asp Val Leu
    1940                1945                1950 ccc aca ttt aca cct ttg ccg gtg tca cct gac aac agt gct gga        5904
Pro Thr Phe Thr Pro Leu Pro Val Ser Pro Asp Asn Ser Ala Gly
    1955                1960                1965 gtt gtg ttg aaa gac ctt tta aag caa tag atgattctca agccagagac      5954
Val Val Leu Lys Asp Leu Leu Lys Gln
    1970                1975
```

-continued

```
aacatatgta gcactttaaa gaaaccatga acactatgtg tatgtacttt atcacaaagt      6014
ggcctttcag aaaaagtcat gtgtttgttt gc                                   6046
```

<210> SEQ ID NO 39
<211> LENGTH: 1977
<212> TYPE: PRT
<213> ORGANISM: Canis familiaris

<400> SEQUENCE: 39

```
Met Ser Ser Trp Leu Gly Gly Leu Gly Ser Gly Leu Gly Gln Ser Leu
1               5                   10                  15

Gly Gln Val Gly Gly Ser Leu Ala Ser Leu Thr Gly Gln Ile Ser Asn
            20                  25                  30

Phe Thr Lys Asp Met Leu Met Glu Gly Thr Glu Glu Val Glu Ala Glu
        35                  40                  45

Leu Pro Asn Ser Arg Arg Lys Glu Val Glu Ala Ile His Ala Ile Leu
    50                  55                  60

Arg Ser Glu Asn Glu Arg Leu Lys Glu Leu Cys Thr Asp Leu Glu Glu
65                  70                  75                  80

Lys His Glu Ala Ser Glu Leu Gln Ile Lys Gln Gln Ser Thr Asn Tyr
                85                  90                  95

Arg Asn Gln Leu Gln Gln Lys Glu Val Glu Ile Ser His Leu Lys Ala
            100                 105                 110

Arg Gln Ile Ala Leu Gln Asp Gln Leu Leu Lys Leu Gln Ser Ala Ala
        115                 120                 125

Gln Ser Ala His Ser Gly Ala Ser Ser Val Pro Ala Ala Leu Ala Ser
    130                 135                 140

Ser Pro Phe Ser Tyr Ser Val Ser His His Ala Ser Ala Phe His Asp
145                 150                 155                 160

Asp Asp Met Asp Phe Ser Asp Ile Ile Ser Ser Gln Glu Ile Asn
                165                 170                 175

Arg Leu Ser Asn Glu Val Ser Arg Leu Glu Ser Glu Val Gly His Trp
            180                 185                 190

Arg His Ile Ala Gln Thr Ser Lys Ala Gln Gly Ser Asn Ser Ser Asp
        195                 200                 205

Gln Ser Glu Ile Cys Lys Leu Gln Ser Ile Ile Lys Glu Leu Lys Gln
    210                 215                 220

Ile Arg Ser Gln Glu Ile Asp Asp His Gln His Glu Met Ser Val Leu
225                 230                 235                 240

Gln Asn Ala His Gln Gln Lys Leu Thr Asp Ile Ser Arg Arg His Arg
                245                 250                 255

Glu Glu Leu Arg Asp Tyr Glu Glu Arg Ile Glu Glu Leu Glu Asn Leu
            260                 265                 270

Leu Glu Gln Gly Gly Ser Gly Ile Val Ile Pro Asp His Ser Lys Ile
        275                 280                 285

His Glu Met Gln Lys Thr Ile Gln Asn Leu Gln Thr Glu Lys Val Ala
    290                 295                 300

Ser Ile Lys Lys Ile Glu Glu Leu Glu Asp Lys Ile Lys Asp Ile Asp
305                 310                 315                 320

Lys Lys Leu Ser Ser Ala Glu Asn Asp Arg Asp Val Leu Arg Lys Glu
                325                 330                 335

Lys Glu Cys Leu Asn Val Glu Asn Arg Gln Ile Thr Glu Gln Cys Glu
            340                 345                 350

Ser Leu Lys Leu Glu Cys Lys Leu Gln His Asp Ala Glu Lys Gln Gly
```

-continued

```
            355                 360                 365
Asp Thr Val Thr Glu Lys Glu Arg Ile Leu Pro Gln Ser Thr Ser Val
            370                 375                 380
Glu Glu Glu Val Leu Lys Leu Gln Gln Ala Leu Ser Asp Ala Glu Asn
385                 390                 395                 400
Glu Ile Met Arg Leu Ser Asn Leu Tyr Gln Asp Asn Ser Leu Thr Glu
                405                 410                 415
Asp Asn Leu Lys Leu Lys Met His Val Glu Phe Leu Glu Lys Gln Lys
                420                 425                 430
Ser Leu Leu Ser Gln Glu Lys Glu Glu Leu Gln Leu Ser Leu Leu Lys
            435                 440                 445
Leu Asn Asn Glu Tyr Glu Val Ile Lys Ser Thr Ala Val Arg Asp Met
            450                 455                 460
Asp Met Asp Ser Thr Leu Cys Asp Leu Arg Leu Thr Leu Glu Ala Lys
465                 470                 475                 480
Asp Gln Glu Leu Asn Gln Ser Leu Thr Glu Lys Glu Ile Leu Val Ala
                485                 490                 495
Glu Leu Glu Glu Leu Asp Arg Gln Asn Gln Glu Ala Thr Lys His Met
                500                 505                 510
Ile Leu Ile Lys Asp Gln Leu Ser Lys Gln Gln Ser Glu Gly Glu Thr
            515                 520                 525
Ile Ile Ser Lys Leu Arg Lys Asp Leu Asn Asp Glu Asn Lys Arg Val
            530                 535                 540
His Gln Leu Glu Asp Asp Lys Lys Asn Met Thr Lys Glu Leu Asn Val
545                 550                 555                 560
Gln Lys Glu Lys Leu Val Gln Ser Glu Leu Val Leu Asn Gly Leu His
                565                 570                 575
Leu Ala Lys Gln Lys Leu Glu Glu Lys Val Glu Asp Leu Val Asp Gln
                580                 585                 590
Leu Asn Lys Ser Gln Lys Ser Asn Leu Asn Met Gln Lys Glu Asn Phe
            595                 600                 605
Gly Leu Lys Glu His Ile Lys Gln Asn Glu Glu Leu Ser Arg Val
            610                 615                 620
Arg Asp Glu Leu Thr Gln Ser Leu Ser Arg Asp Ser Gly Ser Asp Phe
625                 630                 635                 640
Lys Asp Asp Leu Leu Lys Glu Arg Glu Ala Glu Val Arg Asn Leu Lys
                645                 650                 655
Gln Asn Leu Ser Glu Ile Glu Gln Leu Asn Asp Ser Leu Asn Lys Val
                660                 665                 670
Ala Phe Asp Leu Lys Met Glu Asn Glu Lys Leu Val Leu Ala Cys Glu
                675                 680                 685
Asp Ile Arg His Gln Leu Glu Ser Ile Val Gly Ser Asn Gln Met
            690                 695                 700
Ser Leu Glu Arg Asn Thr Ile Val Glu Ala Leu Lys Met Glu Lys Gly
705                 710                 715                 720
Gln Leu Glu Ala Glu Leu Ser Arg Ala Asp Gln Arg Leu Leu Glu Glu
            725                 730                 735
Ala Ser Lys Tyr Glu Gln Thr Ile Gln Glu Leu Ser Lys Ala Arg Asp
            740                 745                 750
Leu Arg Thr Ser Ala Leu Gln Leu Gln Gln His Leu Met Lys Leu
            755                 760                 765
Ser Gln Glu Lys Asp Phe Glu Ile Ala Glu Leu Lys Lys Asn Ile Glu
770                 775                 780
```

```
Gln Met Asp Thr Asp His Lys Glu Thr Lys Ala Ile Leu Ser Ser Ile
785                 790                 795                 800

Leu Glu Glu Gln Lys Gln Leu Thr Gln Leu Ile Ser Glu Lys Glu Ile
            805                 810                 815

Phe Ile Glu Lys Leu Lys Glu Arg Ser Ser Glu Leu Gln Glu Glu Leu
        820                 825                 830

Glu Lys Ser Thr Gln Ala Ser Arg Lys Ile Glu Ile Leu Lys Gln Thr
    835                 840                 845

Ile Glu Glu Lys Asp Arg Ser Leu Gly Ser Met Lys Glu Glu Asn Asn
850                 855                 860

His Leu Lys Glu Glu Leu Glu Arg Leu Arg Glu Gln Gln Ser Arg Ala
865                 870                 875                 880

Val Pro Val Val Glu Pro Lys Pro Leu Asp Ser Val Thr Glu Leu Glu
            885                 890                 895

Ser Glu Val Leu Gln Leu Asn Ile Val Lys Arg Asn Leu Glu Glu Glu
        900                 905                 910

Ile Lys Arg His Gln Lys Ile Ile Glu Asp Gln Asn Gln Ser Lys Met
    915                 920                 925

Gln Leu Leu Gln Ser Leu Glu Glu Gln Lys Lys Glu Met Asp Glu Phe
930                 935                 940

Lys Cys Gln His Glu Gln Met Asn Val Thr His Thr Gln Leu Phe Leu
945                 950                 955                 960

Glu Lys Asp Glu Glu Ile Lys Asn Leu Gln Lys Thr Ile Glu Gln Ile
            965                 970                 975

Lys Thr Gln Trp His Glu Arg Gln Asp Val Gln Met Glu Asn Ser
        980                 985                 990

Glu Phe Phe Gln Glu Thr Lys Val  Gln Ser Leu Asn Leu  Glu Asn Gly
        995                 1000                1005

Ser Glu  Lys His Asp Leu Ser  Lys Ala Glu Thr Glu  Arg Leu Val
    1010                1015                1020

Lys Gly  Ile Lys Glu Arg Glu  Leu Glu Ile Lys Leu  Leu Asn Glu
    1025                1030                1035

Lys Asn  Ile Ser Leu Thr Lys  Gln Ile Asp Gln Leu  Ser Lys Asp
    1040                1045                1050

Glu Val  Gly Lys Leu Thr Gln  Ile Ile Gln Gln Lys  Asp Leu Glu
    1055                1060                1065

Ile Gln  Ala Leu His Ala Arg  Ile Ser Ser Ala Ser  Tyr Thr Gln
    1070                1075                1080

Asp Val  Val Tyr Leu Gln Gln  Gln Leu Gln Ala Tyr  Ala Met Glu
    1085                1090                1095

Arg Glu  Gln Val Leu Ala Val  Leu Ser Glu Lys Thr  Arg Glu Asn
    1100                1105                1110

Ser His  Leu Lys Thr Glu Tyr  His Lys Met Met Asp  Ile Val Ala
    1115                1120                1125

Ala Lys  Glu Ala Ala Leu Ile  Lys Leu Gln Asp Glu  Asn Lys Lys
    1130                1135                1140

Leu Ser  Ala Arg Ser Glu Gly  Gly Gly Gln Asp Met  Phe Arg Glu
    1145                1150                1155

Thr Val  Gln Asn Leu Ser Arg  Ile Ile Arg Glu Lys  Asp Ile Glu
    1160                1165                1170

Ile Asp  Ala Leu Ser Gln Lys  Cys Gln Thr Leu Leu  Thr Val Leu
    1175                1180                1185
```

```
Gln Thr Ser Ser Thr Gly Asn Glu Val Gly Gly Val Asn Ser Asn
    1190                1195                1200

Gln Phe Glu Glu Leu Leu Gln Glu Arg Asp Lys Leu Lys Gln Gln
    1205                1210                1215

Val Lys Lys Met Glu Glu Trp Lys Gln Gln Val Met Thr Thr Val
    1220                1225                1230

Gln Asn Met Gln His Glu Ser Ala Gln Leu Gln Glu Glu Leu His
    1235                1240                1245

Gln Leu Gln Ala Gln Val Leu Val Asp Ser Asp Asn Asn Ser Lys
    1250                1255                1260

Leu Gln Val Asp Tyr Thr Gly Leu Ile Gln Ser Tyr Glu Gln Asn
    1265                1270                1275

Glu Thr Lys Leu Lys Asn Phe Gly Gln Glu Leu Ala Gln Val Gln
    1280                1285                1290

His Ser Ile Gly Gln Leu Tyr Ser Thr Lys Asp Leu Leu Leu Gly
    1295                1300                1305

Lys Leu Asp Ile Ile Ser Pro Gln Leu Pro Ser Gly Ser Ser Pro
    1310                1315                1320

Pro Ser Gln Ser Ala Glu Ser Leu Gly Met Asp Lys Arg Asp Thr
    1325                1330                1335

Ser Ser Glu Ser Ser Lys Gln Glu Leu Glu Glu Leu Arg Lys Ser
    1340                1345                1350

Leu Gln Glu Lys Asp Ala Thr Ile Lys Thr Leu Gln Glu Asn Asn
    1355                1360                1365

His Arg Leu Ser Asp Ser Ile Ala Ala Thr Ser Glu Leu Glu Arg
    1370                1375                1380

Lys Glu His Glu Gln Thr Asp Ser Glu Ile Lys Gln Leu Lys Glu
    1385                1390                1395

Lys Gln Asp Val Leu Gln Lys Ser Leu Lys Glu Lys Asp Leu Leu
    1400                1405                1410

Ile Lys Ala Lys Ser Asp Gln Leu Leu Ser Leu Asn Glu Asn Phe
    1415                1420                1425

Thr Asn Lys Val Asn Glu Asn Glu Leu Leu Arg Gln Ala Val Thr
    1430                1435                1440

Asn Leu Lys Glu Arg Val Leu Ile Leu Glu Met Asp Ile Gly Lys
    1445                1450                1455

Leu Lys Glu Glu Asn Glu Lys Ile Val Glu Arg Thr Arg Glu Lys
    1460                1465                1470

Glu Thr Glu Tyr Gln Ala Leu Gln Glu Thr Asn Met Lys Phe Ser
    1475                1480                1485

Met Met Leu Arg Glu Lys Glu Phe Glu Cys His Ser Met Lys Glu
    1490                1495                1500

Lys Ser Leu Ala Phe Glu Gln Leu Leu Lys Glu Lys Glu Gln Gly
    1505                1510                1515

Lys Thr Gly Glu Leu Asn Gln Leu Leu Asn Ala Val Lys Ser Met
    1520                1525                1530

Gln Glu Lys Thr Val Lys Phe Gln Gln Glu Arg Asp Gln Val Met
    1535                1540                1545

Leu Ala Leu Lys Gln Lys Gln Met Glu Asn Ser Ala Leu Gln Asn
    1550                1555                1560

Glu Val Gln His Leu Arg Asp Lys Glu Leu Arg Leu Asn Gln Glu
    1565                1570                1575

Leu Glu Arg Leu Arg Asn His Leu Leu Glu Ser Glu Asp Ser Tyr
```

-continued

```
            1580                1585                1590
Thr Arg Glu Ala Leu Ala Ala Glu Glu Arg Glu Ala Lys Leu Arg
    1595                1600                1605
Arg Lys Val Thr Val Leu Glu Glu Lys Leu Val Ser Ser Ser Asn
    1610                1615                1620
Ala Met Glu Asn Ala Ser His Gln Ala Ser Leu Gln Val Glu Ser
    1625                1630                1635
Leu Gln Glu Gln Leu Asn Val Val Ser Lys Gln Arg Asp Glu Thr
    1640                1645                1650
Ala Leu Gln Leu Ser Val Ser Arg Glu Gln Val Lys Gln Tyr Ala
    1655                1660                1665
Leu Ser Leu Ser Asn Leu Gln Met Val Leu Glu His Phe Gln Gln
    1670                1675                1680
Glu Glu Lys Ala Val Tyr Ser Ala Glu Leu Glu Lys His Lys Gln
    1685                1690                1695
Leu Val Ala Glu Trp Lys Lys Lys Ala Glu Asn Leu Glu Gly Lys
    1700                1705                1710
Leu Met Ser Leu Gln Glu Arg Phe Asp Glu Ala Asn Ala Ala Leu
    1715                1720                1725
Asp Ser Ala Ser Arg Leu Thr Glu Gln Leu Asp Leu Lys Glu Glu
    1730                1735                1740
Gln Ile Glu Glu Leu Lys Lys Gln Asn Glu Leu Arg Gln Glu Met
    1745                1750                1755
Leu Asp Asp Val Gln Lys Lys Leu Met Asn Leu Val Asn Ser Thr
    1760                1765                1770
Glu Gly Lys Val Asp Lys Val Leu Met Arg Asn Leu Phe Ile Gly
    1775                1780                1785
His Phe His Thr Pro Lys His Gln Arg His Glu Val Leu Arg Leu
    1790                1795                1800
Met Gly Ser Ile Leu Gly Ile Lys Arg Glu Glu Met Glu Gln Leu
    1805                1810                1815
Leu His Glu Asp Gln Gly Gly Val Thr Arg Trp Met Thr Gly Trp
    1820                1825                1830
Leu Gly Gly Gly Ser Lys Ser Val Pro Asn Thr Pro Leu Arg Pro
    1835                1840                1845
Asn Gln Gln Ser Val Leu Asn Ser Ser Phe Ser Glu Leu Phe Val
    1850                1855                1860
Lys Phe Leu Glu Thr Glu Ser His Pro Ser Val Pro Pro Pro Lys
    1865                1870                1875
Leu Ser Val His Asp Met Lys Pro Leu Asp Ser Pro Gly Arg Arg
    1880                1885                1890
Lys Val Val Ile His Val Ser Glu Ser Phe Lys Glu Thr Thr Glu
    1895                1900                1905
Ser Arg Cys Gly Arg Arg Thr Asp Val Asn Pro Phe Leu Ala Pro
    1910                1915                1920
Arg Ser Ala Ala Val Pro Leu Ile Asn Pro Ala Gly Leu Gly Pro
    1925                1930                1935
Gly Gly Pro Gly His Leu Leu Leu Lys Pro Ile Ser Asp Val Leu
    1940                1945                1950
Pro Thr Phe Thr Pro Leu Pro Val Ser Pro Asp Asn Ser Ala Gly
    1955                1960                1965
Val Val Leu Lys Asp Leu Leu Lys Gln
    1970                1975
```

```
<210> SEQ ID NO 40
<211> LENGTH: 6452
<212> TYPE: DNA
<213> ORGANISM: Homo sapiens
<220> FEATURE:
<221> NAME/KEY: CDS
<222> LOCATION: (357)..(6296)

<400> SEQUENCE: 40
cgagcgagtg tcatggcggc cggcgtcgag ttggcaggag taacccacgg aactgaggaa      60
agtcattaga gctgagaaag aagtggccca atctggacgg tgggaattcg tgggaatgag     120
cagaaggccc tccgtagtga ctgtgtcact agaggcgggc ccctggtaaa attccaggcc     180
aggcctctgc gtttctaggc agaacctgga gtcggccttg cctgagaacc cagctttgtg     240
ttatcgtatc ctgtctcgcg aaggcaggcg ttcaaggata tttggtcgga tcgcccggcg     300
gcgctaaacg ttttctttt tccgagcgga ccgggtcgtt ctctaaactc gccgcg atg      359
                                                                Met
                                                                  1 tcg tcc tgg ctt ggg ggc ctc ggc tcc gga ttg ggc cag tct ctg ggt       407
Ser Ser Trp Leu Gly Gly Leu Gly Ser Gly Leu Gly Gln Ser Leu Gly
         5                  10                  15 caa gtc ggg ggc agc ctg gct tcc ctc act ggc cag ata tca aac ttt       455
Gln Val Gly Gly Ser Leu Ala Ser Leu Thr Gly Gln Ile Ser Asn Phe
     20                  25                  30 aca aag gat atg ctg atg gag ggc acg gag gaa gtg gaa gca gaa tta       503
Thr Lys Asp Met Leu Met Glu Gly Thr Glu Glu Val Glu Ala Glu Leu
 35                  40                  45 cct gat tct agg aca aag gaa att gaa gcc att cat gca atc ttg aga       551
Pro Asp Ser Arg Thr Lys Glu Ile Glu Ala Ile His Ala Ile Leu Arg
50                  55                  60                  65 tca gag aat gaa agg ctt aag aaa ctt tgt act gat cta gaa gag aaa       599
Ser Glu Asn Glu Arg Leu Lys Lys Leu Cys Thr Asp Leu Glu Glu Lys
                 70                  75                  80 cat gaa gca tca gag att caa ata aag cag caa tct aca agt tac cga       647
His Glu Ala Ser Glu Ile Gln Ile Lys Gln Gln Ser Thr Ser Tyr Arg
             85                  90                  95 aat caa ctt caa caa aaa gag gta gaa atc agc cat ctt aaa gcc aga       695
Asn Gln Leu Gln Gln Lys Glu Val Glu Ile Ser His Leu Lys Ala Arg
        100                 105                 110 cag att gca ctc cag gat cag ttg ctg aaa ctg cag tca gct gct cag       743
Gln Ile Ala Leu Gln Asp Gln Leu Leu Lys Leu Gln Ser Ala Ala Gln
    115                 120                 125 tca gta cct tca gga gct ggt gta cca gca acc act gca tca tct tca       791
Ser Val Pro Ser Gly Ala Gly Val Pro Ala Thr Thr Ala Ser Ser Ser
130                 135                 140                 145 ttc gct tat ggg att agt cat cat cct tca gct ttc cat gac gat gac       839
Phe Ala Tyr Gly Ile Ser His His Pro Ser Ala Phe His Asp Asp Asp
                150                 155                 160 atg gac ttt ggt gat ata att tca tcc caa caa gaa ata aac cga ctc       887
Met Asp Phe Gly Asp Ile Ile Ser Ser Gln Gln Glu Ile Asn Arg Leu
            165                 170                 175 tca aat gaa gtt tca aga ctt gag tct gaa gtt ggc cat tgg agg cat       935
Ser Asn Glu Val Ser Arg Leu Glu Ser Glu Val Gly His Trp Arg His
        180                 185                 190 att gct cag act tcc aaa gca caa gga aca gat aac tct gat caa agt       983
Ile Ala Gln Thr Ser Lys Ala Gln Gly Thr Asp Asn Ser Asp Gln Ser
    195                 200                 205 gaa ata tgt aaa cta caa aat atc att aag gaa cta aaa cag aac cga      1031
```

```
Glu Ile Cys Lys Leu Gln Asn Ile Ile Lys Glu Leu Lys Gln Asn Arg
210             215                 220                 225 agt cag gaa att gat gac cat caa cat gaa atg tca gta ctg cag aat     1079
Ser Gln Glu Ile Asp Asp His Gln His Glu Met Ser Val Leu Gln Asn
            230                 235                 240 gca cac caa cag aaa ttg aca gaa ata agt cga cga cat cga gaa gaa     1127
Ala His Gln Gln Lys Leu Thr Glu Ile Ser Arg Arg His Arg Glu Glu
                245                 250                 255 tta agt gac tat gaa gaa cga att gaa gaa ctt gaa aat ctg tta caa     1175
Leu Ser Asp Tyr Glu Glu Arg Ile Glu Glu Leu Glu Asn Leu Leu Gln
        260                 265                 270 caa ggt ggc tct gga gtt ata gaa act gat ctc tct aaa atc tat gag     1223
Gln Gly Gly Ser Gly Val Ile Glu Thr Asp Leu Ser Lys Ile Tyr Glu
    275                 280                 285 atg caa aaa act att caa gtt cta caa ata gaa aaa gtg gag tct acc     1271
Met Gln Lys Thr Ile Gln Val Leu Gln Ile Glu Lys Val Glu Ser Thr
290                 295                 300                 305 aaa aaa atg gaa caa ctt gag gat aaa ata aaa gat ata aat aaa aaa     1319
Lys Lys Met Glu Gln Leu Glu Asp Lys Ile Lys Asp Ile Asn Lys Lys
                310                 315                 320 tta tct tct gca gaa aat gac aga gat att ttg agg agg gaa caa gaa     1367
Leu Ser Ser Ala Glu Asn Asp Arg Asp Ile Leu Arg Arg Glu Gln Glu
            325                 330                 335 cag cta aat gtg gaa aag aga caa ata atg gaa gaa tgt gaa aac ttg     1415
Gln Leu Asn Val Glu Lys Arg Gln Ile Met Glu Glu Cys Glu Asn Leu
        340                 345                 350 aaa ttg gaa tgt agt aaa ttg cag cct tct gct gtg aag caa agt gat     1463
Lys Leu Glu Cys Ser Lys Leu Gln Pro Ser Ala Val Lys Gln Ser Asp
    355                 360                 365 act atg aca gaa aag gaa aga att ctt gcc cag agt gca tca gtg gaa     1511
Thr Met Thr Glu Lys Glu Arg Ile Leu Ala Gln Ser Ala Ser Val Glu
370                 375                 380                 385 gaa gtg ttc aga cta caa caa gca ctg tct gat gcc gaa aat gaa ata     1559
Glu Val Phe Arg Leu Gln Gln Ala Leu Ser Asp Ala Glu Asn Glu Ile
                390                 395                 400 atg aga ttg agt agt tta aac cag gat aac agt ctt gct gaa gac aat     1607
Met Arg Leu Ser Ser Leu Asn Gln Asp Asn Ser Leu Ala Glu Asp Asn
            405                 410                 415 ctg aaa ctt aaa atg cgt atc gaa gtt tta gaa aaa gag aag tca tta     1655
Leu Lys Leu Lys Met Arg Ile Glu Val Leu Glu Lys Glu Lys Ser Leu
        420                 425                 430 ctg agt caa gaa aag gaa gaa ctt cag atg tca ctt tta aaa ttg aac     1703
Leu Ser Gln Glu Lys Glu Glu Leu Gln Met Ser Leu Leu Lys Leu Asn
    435                 440                 445 aat gaa tat gaa gta att aaa agt aca gct aca aga gac ata agt ttg     1751
Asn Glu Tyr Glu Val Ile Lys Ser Thr Ala Thr Arg Asp Ile Ser Leu
450                 455                 460                 465 gat tca gaa tta cat gac tta aga ctt aat ttg gag gca aag gaa caa     1799
Asp Ser Glu Leu His Asp Leu Arg Leu Asn Leu Glu Ala Lys Glu Gln
                470                 475                 480 gaa ctc aat cag agt att agt gaa aag gaa aca ctg ata gct gag ata     1847
Glu Leu Asn Gln Ser Ile Ser Glu Lys Glu Thr Leu Ile Ala Glu Ile
            485                 490                 495 gaa gaa ttg gac aga cag aat caa gaa gct aca aag cac atg att ttg     1895
Glu Glu Leu Asp Arg Gln Asn Gln Glu Ala Thr Lys His Met Ile Leu
        500                 505                 510 ata aaa gat cag cta tca aaa caa caa aat gaa gga gat agc atc atc     1943
Ile Lys Asp Gln Leu Ser Lys Gln Gln Asn Glu Gly Asp Ser Ile Ile
    515                 520                 525
```

```
                                        -continued agt aaa ctg aaa caa gat cta aat gat gaa aaa aag aga gtt cat caa    1991
Ser Lys Leu Lys Gln Asp Leu Asn Asp Glu Lys Lys Arg Val His Gln
530             535                 540                 545 ctt gaa gat gat aaa atg gac att act aaa gag tta gat gta cag aaa    2039
Leu Glu Asp Asp Lys Met Asp Ile Thr Lys Glu Leu Asp Val Gln Lys
            550                 555                 560 gaa aag cta att caa agt gaa gtg gcc cta aat gat tta cat tta acc    2087
Glu Lys Leu Ile Gln Ser Glu Val Ala Leu Asn Asp Leu His Leu Thr
565                 570                 575 aag cag aaa ctt gag gac aaa gta gaa aat tta gta gat cag cta aat    2135
Lys Gln Lys Leu Glu Asp Lys Val Glu Asn Leu Val Asp Gln Leu Asn
        580                 585                 590 aaa tca caa gaa agt aat gta agc atc cag aag gag aat tta gaa ctt    2183
Lys Ser Gln Glu Ser Asn Val Ser Ile Gln Lys Glu Asn Leu Glu Leu
595                 600                 605 aag gag cat att aga caa aat gag gag gag ctt tct aga ata agg aat    2231
Lys Glu His Ile Arg Gln Asn Glu Glu Glu Leu Ser Arg Ile Arg Asn
610             615                 620                 625 gag tta atg cag tct cta aat caa gac tct aat agt aat ttt aag gat    2279
Glu Leu Met Gln Ser Leu Asn Gln Asp Ser Asn Ser Asn Phe Lys Asp
            630                 635                 640 acc tta ctt aaa gaa aga gaa gct gaa gtt aga aac tta aag caa aat    2327
Thr Leu Leu Lys Glu Arg Glu Ala Glu Val Arg Asn Leu Lys Gln Asn
                645                 650                 655 ctt tca gaa tta gaa cag ctc aat gaa aat tta aag aaa gtt gct ttt    2375
Leu Ser Glu Leu Glu Gln Leu Asn Glu Asn Leu Lys Lys Val Ala Phe
            660                 665                 670 gat gtc aaa atg gaa aat gaa aag tta gtt tta gca tgt gaa gat gtg    2423
Asp Val Lys Met Glu Asn Glu Lys Leu Val Leu Ala Cys Glu Asp Val
675                 680                 685 agg cat cag tta gaa gaa tgt ctt gct ggt aac aat cag ctt tct ctg    2471
Arg His Gln Leu Glu Glu Cys Leu Ala Gly Asn Asn Gln Leu Ser Leu
690             695                 700                 705 gaa aaa aac act att gtg gag act cta aaa atg gaa aaa gga gag ata    2519
Glu Lys Asn Thr Ile Val Glu Thr Leu Lys Met Glu Lys Gly Glu Ile
                710                 715                 720 gag gca gaa ttg tgt tgg gct aaa aag agg ctg ttg gaa gaa gca aac    2567
Glu Ala Glu Leu Cys Trp Ala Lys Lys Arg Leu Leu Glu Glu Ala Asn
            725                 730                 735 aag tat gag aaa acc att gaa gaa ctg tca aat gca cgt aat ttg aat    2615
Lys Tyr Glu Lys Thr Ile Glu Glu Leu Ser Asn Ala Arg Asn Leu Asn
        740                 745                 750 acc tct gcc tta cag ctg gaa cat gag cat tta att aaa ctc aat caa    2663
Thr Ser Ala Leu Gln Leu Glu His Glu His Leu Ile Lys Leu Asn Gln
755                 760                 765 aag aaa gac atg gaa ata gca gaa ctc aaa aag aat att gaa caa atg    2711
Lys Lys Asp Met Glu Ile Ala Glu Leu Lys Lys Asn Ile Glu Gln Met
770                 775                 780                 785 gat act gac cat aaa gaa act aag gac gtt ttg tca tct agt tta gaa    2759
Asp Thr Asp His Lys Glu Thr Lys Asp Val Leu Ser Ser Ser Leu Glu
            790                 795                 800 gag cag aag cag ttg aca caa ctt ata aac aag aaa gaa att ttt att    2807
Glu Gln Lys Gln Leu Thr Gln Leu Ile Asn Lys Lys Glu Ile Phe Ile
                805                 810                 815 gaa aag ctt aaa gaa aga agt tca aag ctg cag gag gaa ttg gat aaa    2855
Glu Lys Leu Lys Glu Arg Ser Ser Lys Leu Gln Glu Glu Leu Asp Lys
            820                 825                 830 tat tct cag gcc tta aga aaa aat gaa att tta aga cag acc ata gag    2903
Tyr Ser Gln Ala Leu Arg Lys Asn Glu Ile Leu Arg Gln Thr Ile Glu
835                 840                 845
```

| | |
|---|---|
| gaa aaa gac cga agt ctt gga tcc atg aaa gag gaa aat aat cat ctg<br>Glu Lys Asp Arg Ser Leu Gly Ser Met Lys Glu Glu Asn Asn His Leu<br>850                       855                     860                    865 | 2951 |
| caa gaa gaa ttg gaa cga ctc agg gaa gag cag agt cga acc gca cct<br>Gln Glu Glu Leu Glu Arg Leu Arg Glu Glu Gln Ser Arg Thr Ala Pro<br>                 870                     875                    880 | 2999 |
| gtg gct gac cct aaa acc ctt gat agt gtt act gaa cta gca tct gag<br>Val Ala Asp Pro Lys Thr Leu Asp Ser Val Thr Glu Leu Ala Ser Glu<br>                 885                     890                    895 | 3047 |
| gta tct caa ctg aac acg atc aag gaa cat ctt gaa gag gaa att aaa<br>Val Ser Gln Leu Asn Thr Ile Lys Glu His Leu Glu Glu Glu Ile Lys<br>         900                     905                    910 | 3095 |
| cat cat caa aag ata att gaa gat caa aac cag agt aag atg caa cta<br>His His Gln Lys Ile Ile Glu Asp Gln Asn Gln Ser Lys Met Gln Leu<br>         915                     920                    925 | 3143 |
| ctt cag tct tta caa gag caa aag aag gaa atg gat gag ttt aga tac<br>Leu Gln Ser Leu Gln Glu Gln Lys Lys Glu Met Asp Glu Phe Arg Tyr<br>930                       935                     940                    945 | 3191 |
| cag cat gag caa atg aac gcc aca cac acc cag ctc ttt tta gag aag<br>Gln His Glu Gln Met Asn Ala Thr His Thr Gln Leu Phe Leu Glu Lys<br>                 950                     955                    960 | 3239 |
| gat gag gaa att aag agt ttg caa aaa aca att gaa caa atc aaa acc<br>Asp Glu Glu Ile Lys Ser Leu Gln Lys Thr Ile Glu Gln Ile Lys Thr<br>         965                     970                    975 | 3287 |
| cag ttg cat gaa gaa aga cag gac att caa aca gat aac tct gat att<br>Gln Leu His Glu Glu Arg Gln Asp Ile Gln Thr Asp Asn Ser Asp Ile<br>         980                     985                    990 | 3335 |
| ttt caa gaa aca aaa gtt cag agc ctt aat ata gaa aat gga agt gaa<br>Phe Gln Glu Thr Lys Val Gln Ser Leu Asn Ile Glu Asn Gly Ser Glu<br>         995                    1000                 1005 | 3383 |
| aag cat gat tta tct aaa gct gaa acg gaa aga tta gtg aaa gga<br>Lys His Asp Leu Ser Lys Ala Glu Thr Glu Arg Leu Val Lys Gly<br>1010                     1015                    1020 | 3428 |
| ata aaa gag cga gaa ctg gag att aaa ctt cta aat gaa aag aat<br>Ile Lys Glu Arg Glu Leu Glu Ile Lys Leu Leu Asn Glu Lys Asn<br>1025                     1030                    1035 | 3473 |
| ata tct tta act aaa cag att gat cag ttg tcc aaa gat gaa gtt<br>Ile Ser Leu Thr Lys Gln Ile Asp Gln Leu Ser Lys Asp Glu Val<br>1040                     1045                    1050 | 3518 |
| ggt aaa cta act cag att att cag cag aaa gat ttg gag ata caa<br>Gly Lys Leu Thr Gln Ile Ile Gln Gln Lys Asp Leu Glu Ile Gln<br>1055                     1060                    1065 | 3563 |
| gct ctt cat gct aga att tct tca act tcc cat act caa gat gtt<br>Ala Leu His Ala Arg Ile Ser Ser Thr Ser His Thr Gln Asp Val<br>1070                     1075                    1080 | 3608 |
| gtt tac ctt caa cag caa ctg cag gct tat gct atg gaa aga gaa<br>Val Tyr Leu Gln Gln Gln Leu Gln Ala Tyr Ala Met Glu Arg Glu<br>1085                     1090                    1095 | 3653 |
| aag gta ttt gct gtt ttg aat gag aag act agg gaa aat agc cat<br>Lys Val Phe Ala Val Leu Asn Glu Lys Thr Arg Glu Asn Ser His<br>1100                     1105                    1110 | 3698 |
| cta aaa aca gaa tat cac aaa atg atg gat att gtt gct gcc aag<br>Leu Lys Thr Glu Tyr His Lys Met Met Asp Ile Val Ala Ala Lys<br>1115                     1120                    1125 | 3743 |
| gaa gca gct ctt atc aaa ctg caa gat gaa aat aaa aaa ttg tcc<br>Glu Ala Ala Leu Ile Lys Leu Gln Asp Glu Asn Lys Lys Leu Ser<br>1130                     1135                    1140 | 3788 |
| act aga ttt gaa agt agt ggc caa gat atg ttt aga gaa act att<br>Thr Arg Phe Glu Ser Ser Gly Gln Asp Met Phe Arg Glu Thr Ile | 3833 |

| | | | | | | | | | | |
|---|---|---|---|---|---|---|---|---|---|---|
| | | 1145 | | | 1150 | | | 1155 | | |
| cag | aat | tta | tca | cgt | atc | att | cga | gaa | aaa | gac | atc | gaa | ata | gat | 3878 |
| Gln | Asn | Leu | Ser | Arg | Ile | Ile | Arg | Glu | Lys | Asp | Ile | Glu | Ile | Asp | |
| 1160 | | | | | 1165 | | | | | 1170 | | | | | |
| gca | cta | agt | cag | aaa | tgt | cag | act | tta | ttg | gca | gtt | tta | caa | aca | 3923 |
| Ala | Leu | Ser | Gln | Lys | Cys | Gln | Thr | Leu | Leu | Ala | Val | Leu | Gln | Thr | |
| 1175 | | | | | 1180 | | | | | 1185 | | | | | |
| tcc | agc | act | ggt | aat | gag | gct | gga | ggt | gtt | aat | agt | cat | caa | ttt | 3968 |
| Ser | Ser | Thr | Gly | Asn | Glu | Ala | Gly | Gly | Val | Asn | Ser | His | Gln | Phe | |
| 1190 | | | | | 1195 | | | | | 1200 | | | | | |
| gag | gag | ctt | cta | cag | gaa | cgt | gac | aag | tta | aaa | cag | caa | gta | aag | 4013 |
| Glu | Glu | Leu | Leu | Gln | Glu | Arg | Asp | Lys | Leu | Lys | Gln | Gln | Val | Lys | |
| 1205 | | | | | 1210 | | | | | 1215 | | | | | |
| aaa | atg | gaa | gag | tgg | aag | cag | cag | gtg | atg | acc | aca | gta | caa | aat | 4058 |
| Lys | Met | Glu | Glu | Trp | Lys | Gln | Gln | Val | Met | Thr | Thr | Val | Gln | Asn | |
| 1220 | | | | | 1225 | | | | | 1230 | | | | | |
| atg | caa | cac | gag | tca | gcc | cag | ctt | cag | gaa | gag | ctt | cac | caa | ctt | 4103 |
| Met | Gln | His | Glu | Ser | Ala | Gln | Leu | Gln | Glu | Glu | Leu | His | Gln | Leu | |
| 1235 | | | | | 1240 | | | | | 1245 | | | | | |
| caa | gca | cag | gtt | ttg | gtt | gac | agt | gat | aat | aat | tct | aaa | tta | caa | 4148 |
| Gln | Ala | Gln | Val | Leu | Val | Asp | Ser | Asp | Asn | Asn | Ser | Lys | Leu | Gln | |
| 1250 | | | | | 1255 | | | | | 1260 | | | | | |
| gtg | gac | tat | act | ggc | ctg | atc | caa | agt | tat | gag | cag | aat | gaa | acc | 4193 |
| Val | Asp | Tyr | Thr | Gly | Leu | Ile | Gln | Ser | Tyr | Glu | Gln | Asn | Glu | Thr | |
| 1265 | | | | | 1270 | | | | | 1275 | | | | | |
| aaa | ctc | aaa | aat | ttt | ggg | cag | gaa | tta | gca | caa | gtt | cag | cac | agc | 4238 |
| Lys | Leu | Lys | Asn | Phe | Gly | Gln | Glu | Leu | Ala | Gln | Val | Gln | His | Ser | |
| 1280 | | | | | 1285 | | | | | 1290 | | | | | |
| att | ggg | cag | ctt | tgc | aat | acc | aag | gat | ctt | ctt | tta | gga | aaa | ctt | 4283 |
| Ile | Gly | Gln | Leu | Cys | Asn | Thr | Lys | Asp | Leu | Leu | Leu | Gly | Lys | Leu | |
| 1295 | | | | | 1300 | | | | | 1305 | | | | | |
| gat | att | att | tca | ccc | cag | ctg | tct | tct | gca | tca | ttg | ctt | act | ccc | 4328 |
| Asp | Ile | Ile | Ser | Pro | Gln | Leu | Ser | Ser | Ala | Ser | Leu | Leu | Thr | Pro | |
| 1310 | | | | | 1315 | | | | | 1320 | | | | | |
| cag | tct | gca | gag | tgt | ctt | aga | gca | agt | aag | tct | gaa | gta | ttg | agt | 4373 |
| Gln | Ser | Ala | Glu | Cys | Leu | Arg | Ala | Ser | Lys | Ser | Glu | Val | Leu | Ser | |
| 1325 | | | | | 1330 | | | | | 1335 | | | | | |
| gaa | tct | tct | gaa | ttg | ctt | cag | caa | gag | tta | gaa | gag | cta | aga | aaa | 4418 |
| Glu | Ser | Ser | Glu | Leu | Leu | Gln | Gln | Glu | Leu | Glu | Glu | Leu | Arg | Lys | |
| 1340 | | | | | 1345 | | | | | 1350 | | | | | |
| tca | cta | cag | gaa | aaa | gat | gca | aca | att | aga | act | ctc | cag | gaa | aat | 4463 |
| Ser | Leu | Gln | Glu | Lys | Asp | Ala | Thr | Ile | Arg | Thr | Leu | Gln | Glu | Asn | |
| 1355 | | | | | 1360 | | | | | 1365 | | | | | |
| aac | cac | aga | ttg | tct | gat | tcg | att | gct | gcc | acc | tca | gag | cta | gaa | 4508 |
| Asn | His | Arg | Leu | Ser | Asp | Ser | Ile | Ala | Ala | Thr | Ser | Glu | Leu | Glu | |
| 1370 | | | | | 1375 | | | | | 1380 | | | | | |
| aga | aaa | gaa | cac | gaa | caa | acc | gat | tca | gaa | atc | aag | cag | cta | aag | 4553 |
| Arg | Lys | Glu | His | Glu | Gln | Thr | Asp | Ser | Glu | Ile | Lys | Gln | Leu | Lys | |
| 1385 | | | | | 1390 | | | | | 1395 | | | | | |
| gag | aaa | caa | gat | gtt | ttg | caa | aag | tta | ctt | aag | gaa | aaa | gac | ctc | 4598 |
| Glu | Lys | Gln | Asp | Val | Leu | Gln | Lys | Leu | Leu | Lys | Glu | Lys | Asp | Leu | |
| 1400 | | | | | 1405 | | | | | 1410 | | | | | |
| tta | atc | aaa | gcc | aaa | agt | gat | caa | cta | ctt | tct | tcc | aat | gaa | aat | 4643 |
| Leu | Ile | Lys | Ala | Lys | Ser | Asp | Gln | Leu | Leu | Ser | Ser | Asn | Glu | Asn | |
| 1415 | | | | | 1420 | | | | | 1425 | | | | | |
| ttc | act | aac | aaa | gta | aat | gaa | aac | gaa | ctt | ttg | agg | cag | gca | gta | 4688 |
| Phe | Thr | Asn | Lys | Val | Asn | Glu | Asn | Glu | Leu | Leu | Arg | Gln | Ala | Val | |
| 1430 | | | | | 1435 | | | | | 1440 | | | | | |
| aca | aac | ctg | aag | gag | aga | ata | tta | att | cta | gag | atg | gac | att | ggc | 4733 |

```
Thr Asn Leu Lys Glu Arg Ile Leu Ile Leu Glu Met Asp Ile Gly
1445                1450                1455 aaa cta aaa gga gaa aat gaa aaa ata gtg gaa aca tac agg gga    4778
Lys Leu Lys Gly Glu Asn Glu Lys Ile Val Glu Thr Tyr Arg Gly
1460                1465                1470 aag gaa aca gaa tat caa gcg tta caa gag act aac atg aag ttt    4823
Lys Glu Thr Glu Tyr Gln Ala Leu Gln Glu Thr Asn Met Lys Phe
1475                1480                1485 tct atg atg ctg cga gaa aaa gag ttt gag tgc cac tca atg aag    4868
Ser Met Met Leu Arg Glu Lys Glu Phe Glu Cys His Ser Met Lys
1490                1495                1500 gag aag gct ctt gct ttt gaa cag cta ttg aaa gag aaa gaa cag    4913
Glu Lys Ala Leu Ala Phe Glu Gln Leu Leu Lys Glu Lys Glu Gln
1505                1510                1515 ggc aag act gga gag tta aat cag ctt tta aat gca gtt aaa tca    4958
Gly Lys Thr Gly Glu Leu Asn Gln Leu Leu Asn Ala Val Lys Ser
1520                1525                1530 atg cag gag aag aca gtt gtg ttt caa cag gag aga gac caa gtc    5003
Met Gln Glu Lys Thr Val Val Phe Gln Gln Glu Arg Asp Gln Val
1535                1540                1545 atg ttg gcc ctg aaa caa aaa caa atg gaa aat act gcc cta cag    5048
Met Leu Ala Leu Lys Gln Lys Gln Met Glu Asn Thr Ala Leu Gln
1550                1555                1560 aat gag gtt caa cgt tta cgt gac aaa gaa ttt cgt tca aac caa    5093
Asn Glu Val Gln Arg Leu Arg Asp Lys Glu Phe Arg Ser Asn Gln
1565                1570                1575 gag cta gag aga ttg cgt aat cat ctt tta gaa tca gaa gat tct    5138
Glu Leu Glu Arg Leu Arg Asn His Leu Leu Glu Ser Glu Asp Ser
1580                1585                1590 tat acc cgt gaa gct ttg gct gca gaa gat aga gag gct aaa cta    5183
Tyr Thr Arg Glu Ala Leu Ala Ala Glu Asp Arg Glu Ala Lys Leu
1595                1600                1605 aga aag aaa gtc aca gta ttg gag gaa aag cta gtt tca tcc tct    5228
Arg Lys Lys Val Thr Val Leu Glu Glu Lys Leu Val Ser Ser Ser
1610                1615                1620 aat gca atg gaa aat gca agc cat caa gcc agt gtg cag gta gag    5273
Asn Ala Met Glu Asn Ala Ser His Gln Ala Ser Val Gln Val Glu
1625                1630                1635 tca ttg caa gaa cag ttg aat gta gtt tcc aag caa agg gat gaa    5318
Ser Leu Gln Glu Gln Leu Asn Val Val Ser Lys Gln Arg Asp Glu
1640                1645                1650 act gcg ctg cag ctt tct gtc tct cag gaa caa gta aag cag tat    5363
Thr Ala Leu Gln Leu Ser Val Ser Gln Glu Gln Val Lys Gln Tyr
1655                1660                1665 gct ctg tca ctg gcc aac ctg cag atg gta cta gag cat ttc caa    5408
Ala Leu Ser Leu Ala Asn Leu Gln Met Val Leu Glu His Phe Gln
1670                1675                1680 caa gag gaa aaa gct atg tat tct gct gaa ctc gaa aag caa aaa    5453
Gln Glu Glu Lys Ala Met Tyr Ser Ala Glu Leu Glu Lys Gln Lys
1685                1690                1695 cag ctt ata gct gaa tgg aag aaa aac gca gaa aat ctg gaa gga    5498
Gln Leu Ile Ala Glu Trp Lys Lys Asn Ala Glu Asn Leu Glu Gly
1700                1705                1710 aaa gtg ata tca tta cag gaa tgt ttg gat gaa gca aat gct gca    5543
Lys Val Ile Ser Leu Gln Glu Cys Leu Asp Glu Ala Asn Ala Ala
1715                1720                1725 ttg gat tca gca tca aga ctt aca gaa cag tta gat gta aaa gaa    5588
Leu Asp Ser Ala Ser Arg Leu Thr Glu Gln Leu Asp Val Lys Glu
1730                1735                1740
```

```
gaa caa att gaa gaa ctt aaa aga caa aat gag ctc cga caa gaa      5633
Glu Gln Ile Glu Glu Leu Lys Arg Gln Asn Glu Leu Arg Gln Glu
1745                1750                1755 atg ctg gat gat gta caa aag aaa ttg atg agc tta gca aac agc      5678
Met Leu Asp Asp Val Gln Lys Lys Leu Met Ser Leu Ala Asn Ser
1760                1765                1770 tca gaa gga aaa gta gac aaa gtc cta atg aga aac ctc ttc att      5723
Ser Glu Gly Lys Val Asp Lys Val Leu Met Arg Asn Leu Phe Ile
1775                1780                1785 ggt cat ttc cac aca ccg aaa aat cag cgt cat gaa gtg tta cgg      5768
Gly His Phe His Thr Pro Lys Asn Gln Arg His Glu Val Leu Arg
1790                1795                1800 tta atg ggg agc atc ctg ggc gtc aga agg gag gag atg gag cag      5813
Leu Met Gly Ser Ile Leu Gly Val Arg Arg Glu Glu Met Glu Gln
1805                1810                1815 ttg ttt cat gac gat cag ggc agt gtt acc agg tgg atg act ggg      5858
Leu Phe His Asp Asp Gln Gly Ser Val Thr Arg Trp Met Thr Gly
1820                1825                1830 tgg ctt gga gga gga tca aaa agt gtt ccc aac aca cct ttg aga      5903
Trp Leu Gly Gly Gly Ser Lys Ser Val Pro Asn Thr Pro Leu Arg
1835                1840                1845 cca aat cag caa tct gtg gtt aat agt tct ttt tca gaa ctt ttt      5948
Pro Asn Gln Gln Ser Val Val Asn Ser Ser Phe Ser Glu Leu Phe
1850                1855                1860 gtt aaa ttt cta gaa aca gaa tct cat cca tcc att cca cca cca      5993
Val Lys Phe Leu Glu Thr Glu Ser His Pro Ser Ile Pro Pro Pro
1865                1870                1875 aag ctt tct gtt cat gat atg aaa cct ctg gat tca cca gga aga      6038
Lys Leu Ser Val His Asp Met Lys Pro Leu Asp Ser Pro Gly Arg
1880                1885                1890 aga aaa aga gat aca aat gca cca gaa agt ttt aaa gat aca gca      6083
Arg Lys Arg Asp Thr Asn Ala Pro Glu Ser Phe Lys Asp Thr Ala
1895                1900                1905 gaa tcc agg tct ggt aga aga aca gat gta aat ccg ttt ttg gct      6128
Glu Ser Arg Ser Gly Arg Arg Thr Asp Val Asn Pro Phe Leu Ala
1910                1915                1920 cct cgc tcg gca gct gta cct ctt att aac cca gct gga ctt gga      6173
Pro Arg Ser Ala Ala Val Pro Leu Ile Asn Pro Ala Gly Leu Gly
1925                1930                1935 cct ggt ggg ccc ggg cat ctt ctt ctg aaa ccc atc tca gat gtt      6218
Pro Gly Gly Pro Gly His Leu Leu Leu Lys Pro Ile Ser Asp Val
1940                1945                1950 ttg ccc aca ttt aca cct ttg cca gcg tta cct gac aac agt gct      6263
Leu Pro Thr Phe Thr Pro Leu Pro Ala Leu Pro Asp Asn Ser Ala
1955                1960                1965 ggg gtt gtg ctg aaa gac ctt tta aag caa tag atgattctca           6306
Gly Val Val Leu Lys Asp Leu Leu Lys Gln
1970                1975 agccagagac aatctagcac tttaaagaaa ccatgaacac tatatgtatg tactttatca 6366 caaagtggcc tttggggaga aagtcatgta tttgttcgca attatgcttt ctctgaattt 6426 aataaaaata ttcctaatgc ttttag                                     6452

<210> SEQ ID NO 41
<211> LENGTH: 1979
<212> TYPE: PRT
<213> ORGANISM: Homo sapiens

<400> SEQUENCE: 41

Met Ser Ser Trp Leu Gly Gly Leu Gly Ser Gly Leu Gly Gln Ser Leu
```

-continued

```
1               5                   10                  15
Gly Gln Val Gly Gly Ser Leu Ala Ser Leu Thr Gly Gln Ile Ser Asn
            20                  25                  30
Phe Thr Lys Asp Met Leu Met Glu Gly Thr Glu Val Glu Ala Glu
            35                  40                  45
Leu Pro Asp Ser Arg Thr Lys Glu Ile Glu Ala Ile His Ala Ile Leu
 50                  55                  60
Arg Ser Glu Asn Glu Arg Leu Lys Lys Leu Cys Thr Asp Leu Glu Glu
 65                  70                  75                  80
Lys His Glu Ala Ser Glu Ile Gln Ile Lys Gln Gln Ser Thr Ser Tyr
                    85                  90                  95
Arg Asn Gln Leu Gln Gln Lys Glu Val Glu Ile Ser His Leu Lys Ala
            100                 105                 110
Arg Gln Ile Ala Leu Gln Asp Gln Leu Leu Lys Leu Gln Ser Ala Ala
            115                 120                 125
Gln Ser Val Pro Ser Gly Ala Gly Val Pro Ala Thr Thr Ala Ser Ser
            130                 135                 140
Ser Phe Ala Tyr Gly Ile Ser His His Pro Ser Ala Phe His Asp Asp
145                 150                 155                 160
Asp Met Asp Phe Gly Asp Ile Ile Ser Ser Gln Gln Glu Ile Asn Arg
                    165                 170                 175
Leu Ser Asn Glu Val Ser Arg Leu Glu Ser Glu Val Gly His Trp Arg
            180                 185                 190
His Ile Ala Gln Thr Ser Lys Ala Gln Gly Thr Asp Asn Ser Asp Gln
            195                 200                 205
Ser Glu Ile Cys Lys Leu Gln Asn Ile Ile Lys Glu Leu Lys Gln Asn
 210                 215                 220
Arg Ser Gln Glu Ile Asp Asp His Gln His Glu Met Ser Val Leu Gln
225                 230                 235                 240
Asn Ala His Gln Gln Lys Leu Thr Glu Ile Ser Arg Arg His Arg Glu
                    245                 250                 255
Glu Leu Ser Asp Tyr Glu Glu Arg Ile Glu Glu Leu Glu Asn Leu Leu
            260                 265                 270
Gln Gln Gly Gly Ser Gly Val Ile Glu Thr Asp Leu Ser Lys Ile Tyr
            275                 280                 285
Glu Met Gln Lys Thr Ile Gln Val Leu Gln Ile Glu Lys Val Glu Ser
            290                 295                 300
Thr Lys Lys Met Glu Gln Leu Glu Asp Lys Ile Lys Asp Ile Asn Lys
305                 310                 315                 320
Lys Leu Ser Ser Ala Glu Asn Asp Arg Asp Ile Leu Arg Arg Glu Gln
                    325                 330                 335
Glu Gln Leu Asn Val Glu Lys Arg Gln Ile Met Glu Glu Cys Glu Asn
            340                 345                 350
Leu Lys Leu Glu Cys Ser Lys Leu Gln Pro Ser Ala Val Lys Gln Ser
            355                 360                 365
Asp Thr Met Thr Glu Lys Glu Arg Ile Leu Ala Gln Ser Ala Ser Val
            370                 375                 380
Glu Glu Val Phe Arg Leu Gln Gln Ala Leu Ser Asp Ala Glu Asn Glu
385                 390                 395                 400
Ile Met Arg Leu Ser Ser Leu Asn Gln Asp Asn Ser Leu Ala Glu Asp
                    405                 410                 415
Asn Leu Lys Leu Lys Met Arg Ile Glu Val Leu Glu Lys Glu Lys Ser
            420                 425                 430
```

```
Leu Leu Ser Gln Glu Lys Glu Leu Gln Met Ser Leu Leu Lys Leu
        435                 440                 445

Asn Asn Glu Tyr Glu Val Ile Lys Ser Thr Ala Thr Arg Asp Ile Ser
    450                 455                 460

Leu Asp Ser Glu Leu His Asp Leu Arg Leu Asn Leu Glu Ala Lys Glu
465                 470                 475                 480

Gln Glu Leu Asn Gln Ser Ile Ser Glu Lys Glu Thr Leu Ile Ala Glu
                485                 490                 495

Ile Glu Glu Leu Asp Arg Gln Asn Gln Glu Ala Thr Lys His Met Ile
                500                 505                 510

Leu Ile Lys Asp Gln Leu Ser Lys Gln Gln Asn Glu Gly Asp Ser Ile
            515                 520                 525

Ile Ser Lys Leu Lys Gln Asp Leu Asn Asp Glu Lys Lys Arg Val His
    530                 535                 540

Gln Leu Glu Asp Asp Lys Met Asp Ile Thr Lys Glu Leu Asp Val Gln
545                 550                 555                 560

Lys Glu Lys Leu Ile Gln Ser Glu Val Ala Leu Asn Asp Leu His Leu
                565                 570                 575

Thr Lys Gln Lys Leu Glu Asp Lys Val Glu Asn Leu Val Asp Gln Leu
            580                 585                 590

Asn Lys Ser Gln Glu Ser Asn Val Ser Ile Gln Lys Glu Asn Leu Glu
            595                 600                 605

Leu Lys Glu His Ile Arg Gln Asn Glu Glu Leu Ser Arg Ile Arg
    610                 615                 620

Asn Glu Leu Met Gln Ser Leu Asn Gln Asp Ser Asn Ser Asn Phe Lys
625                 630                 635                 640

Asp Thr Leu Leu Lys Glu Arg Glu Ala Glu Val Arg Asn Leu Lys Gln
                645                 650                 655

Asn Leu Ser Glu Leu Glu Gln Leu Asn Glu Asn Leu Lys Lys Val Ala
            660                 665                 670

Phe Asp Val Lys Met Glu Asn Glu Lys Leu Val Leu Ala Cys Glu Asp
        675                 680                 685

Val Arg His Gln Leu Glu Glu Cys Leu Ala Gly Asn Asn Gln Leu Ser
    690                 695                 700

Leu Glu Lys Asn Thr Ile Val Glu Thr Leu Lys Met Glu Lys Gly Glu
705                 710                 715                 720

Ile Glu Ala Glu Leu Cys Trp Ala Lys Lys Arg Leu Leu Glu Glu Ala
                725                 730                 735

Asn Lys Tyr Glu Lys Thr Ile Glu Glu Leu Ser Asn Ala Arg Asn Leu
            740                 745                 750

Asn Thr Ser Ala Leu Gln Leu Glu His Glu His Leu Ile Lys Leu Asn
            755                 760                 765

Gln Lys Lys Asp Met Glu Ile Ala Glu Leu Lys Lys Asn Ile Glu Gln
        770                 775                 780

Met Asp Thr Asp His Lys Glu Thr Lys Asp Val Leu Ser Ser Ser Leu
785                 790                 795                 800

Glu Glu Gln Lys Gln Leu Thr Gln Leu Ile Asn Lys Lys Glu Ile Phe
                805                 810                 815

Ile Glu Lys Leu Lys Glu Arg Ser Ser Lys Leu Gln Glu Glu Leu Asp
            820                 825                 830

Lys Tyr Ser Gln Ala Leu Arg Lys Asn Glu Ile Leu Arg Gln Thr Ile
            835                 840                 845
```

```
Glu Glu Lys Asp Arg Ser Leu Gly Ser Met Lys Glu Asn Asn His
850                 855                 860

Leu Gln Glu Glu Leu Glu Arg Leu Arg Glu Gln Ser Arg Thr Ala
865                 870                 875                 880

Pro Val Ala Asp Pro Lys Thr Leu Asp Ser Val Thr Glu Leu Ala Ser
                885                 890                 895

Glu Val Ser Gln Leu Asn Thr Ile Lys Glu His Leu Glu Glu Glu Ile
                900                 905                 910

Lys His His Gln Lys Ile Ile Glu Asp Gln Asn Gln Ser Lys Met Gln
                915                 920                 925

Leu Leu Gln Ser Leu Gln Glu Gln Lys Lys Glu Met Asp Glu Phe Arg
930                 935                 940

Tyr Gln His Glu Gln Met Asn Ala Thr His Thr Gln Leu Phe Leu Glu
945                 950                 955                 960

Lys Asp Glu Glu Ile Lys Ser Leu Gln Lys Thr Ile Glu Gln Ile Lys
                965                 970                 975

Thr Gln Leu His Glu Arg Gln Asp Ile Gln Thr Asp Asn Ser Asp
                980                 985                 990

Ile Phe Gln Glu Thr Lys Val Gln  Ser Leu Asn Ile Glu  Asn Gly Ser
                995                1000                1005

Glu Lys  His Asp Leu Ser Lys  Ala Glu Thr Glu Arg  Leu Val Lys
     1010                1015                1020

Gly Ile  Lys Glu Arg Glu Leu  Glu Ile Lys Leu Leu  Asn Glu Lys
     1025                1030                1035

Asn Ile  Ser Leu Thr Lys Gln  Ile Asp Gln Leu Ser  Lys Asp Glu
     1040                1045                1050

Val Gly  Lys Leu Thr Gln Ile  Ile Gln Gln Lys Asp  Leu Glu Ile
     1055                1060                1065

Gln Ala  Leu His Ala Arg Ile  Ser Ser Thr Ser His  Thr Gln Asp
     1070                1075                1080

Val Val  Tyr Leu Gln Gln Gln  Leu Gln Ala Tyr Ala  Met Glu Arg
     1085                1090                1095

Glu Lys  Val Phe Ala Val Leu  Asn Glu Lys Thr Arg  Glu Asn Ser
     1100                1105                1110

His Leu  Lys Thr Glu Tyr His  Lys Met Met Asp Ile  Val Ala Ala
     1115                1120                1125

Lys Glu  Ala Ala Leu Ile Lys  Leu Gln Asp Glu Asn  Lys Lys Leu
     1130                1135                1140

Ser Thr  Arg Phe Glu Ser Ser  Gly Gln Asp Met Phe  Arg Glu Thr
     1145                1150                1155

Ile Gln  Asn Leu Ser Arg Ile  Ile Arg Glu Lys Asp  Ile Glu Ile
     1160                1165                1170

Asp Ala  Leu Ser Gln Lys Cys  Gln Thr Leu Leu Ala  Val Leu Gln
     1175                1180                1185

Thr Ser  Ser Thr Gly Asn Glu  Ala Gly Gly Val Asn  Ser His Gln
     1190                1195                1200

Phe Glu  Glu Leu Leu Gln Glu  Arg Asp Lys Leu Lys  Gln Gln Val
     1205                1210                1215

Lys Lys  Met Glu Glu Trp Lys  Gln Gln Val Met Thr  Thr Val Gln
     1220                1225                1230

Asn Met  Gln His Glu Ser Ala  Gln Leu Gln Glu Glu  Leu His Gln
     1235                1240                1245

Leu Gln  Ala Gln Val Leu Val  Asp Ser Asp Asn Asn  Ser Lys Leu
```

-continued

```
            1250                1255                1260

Gln Val Asp Tyr Thr Gly Leu Ile Gln Ser Tyr Glu Gln Asn Glu
            1265                1270                1275

Thr Lys Leu Lys Asn Phe Gly Gln Glu Leu Ala Gln Val Gln His
            1280                1285                1290

Ser Ile Gly Gln Leu Cys Asn Thr Lys Asp Leu Leu Leu Gly Lys
            1295                1300                1305

Leu Asp Ile Ile Ser Pro Gln Leu Ser Ser Ala Ser Leu Leu Thr
            1310                1315                1320

Pro Gln Ser Ala Glu Cys Leu Arg Ala Ser Lys Ser Glu Val Leu
            1325                1330                1335

Ser Glu Ser Ser Glu Leu Leu Gln Gln Glu Leu Glu Glu Leu Arg
            1340                1345                1350

Lys Ser Leu Gln Glu Lys Asp Ala Thr Ile Arg Thr Leu Gln Glu
            1355                1360                1365

Asn Asn His Arg Leu Ser Asp Ser Ile Ala Ala Thr Ser Glu Leu
            1370                1375                1380

Glu Arg Lys Glu His Glu Gln Thr Asp Ser Glu Ile Lys Gln Leu
            1385                1390                1395

Lys Glu Lys Gln Asp Val Leu Gln Lys Leu Leu Lys Glu Lys Asp
            1400                1405                1410

Leu Leu Ile Lys Ala Lys Ser Asp Gln Leu Leu Ser Ser Asn Glu
            1415                1420                1425

Asn Phe Thr Asn Lys Val Asn Glu Asn Glu Leu Leu Arg Gln Ala
            1430                1435                1440

Val Thr Asn Leu Lys Glu Arg Ile Leu Ile Leu Glu Met Asp Ile
            1445                1450                1455

Gly Lys Leu Lys Gly Glu Asn Glu Lys Ile Val Glu Thr Tyr Arg
            1460                1465                1470

Gly Lys Glu Thr Glu Tyr Gln Ala Leu Gln Glu Thr Asn Met Lys
            1475                1480                1485

Phe Ser Met Met Leu Arg Glu Lys Glu Phe Glu Cys His Ser Met
            1490                1495                1500

Lys Glu Lys Ala Leu Ala Phe Glu Gln Leu Leu Lys Glu Lys Glu
            1505                1510                1515

Gln Gly Lys Thr Gly Glu Leu Asn Gln Leu Leu Asn Ala Val Lys
            1520                1525                1530

Ser Met Gln Glu Lys Thr Val Val Phe Gln Gln Glu Arg Asp Gln
            1535                1540                1545

Val Met Leu Ala Leu Lys Gln Lys Gln Met Glu Asn Thr Ala Leu
            1550                1555                1560

Gln Asn Glu Val Gln Arg Leu Arg Asp Lys Glu Phe Arg Ser Asn
            1565                1570                1575

Gln Glu Leu Glu Arg Leu Arg Asn His Leu Leu Glu Ser Glu Asp
            1580                1585                1590

Ser Tyr Thr Arg Glu Ala Leu Ala Ala Glu Asp Arg Glu Ala Lys
            1595                1600                1605

Leu Arg Lys Lys Val Thr Val Leu Glu Glu Lys Leu Val Ser Ser
            1610                1615                1620

Ser Asn Ala Met Glu Asn Ala Ser His Gln Ala Ser Val Gln Val
            1625                1630                1635

Glu Ser Leu Gln Glu Gln Leu Asn Val Val Ser Lys Gln Arg Asp
            1640                1645                1650
```

```
Glu Thr Ala Leu Gln Leu Ser Val Ser Gln Glu Gln Val Lys Gln
    1655                1660                1665

Tyr Ala Leu Ser Leu Ala Asn Leu Gln Met Val Leu Glu His Phe
    1670                1675                1680

Gln Gln Glu Glu Lys Ala Met Tyr Ser Ala Glu Leu Glu Lys Gln
    1685                1690                1695

Lys Gln Leu Ile Ala Glu Trp Lys Lys Asn Ala Glu Asn Leu Glu
    1700                1705                1710

Gly Lys Val Ile Ser Leu Gln Glu Cys Leu Asp Glu Ala Asn Ala
    1715                1720                1725

Ala Leu Asp Ser Ala Ser Arg Leu Thr Glu Gln Leu Asp Val Lys
    1730                1735                1740

Glu Glu Gln Ile Glu Glu Leu Lys Arg Gln Asn Glu Leu Arg Gln
    1745                1750                1755

Glu Met Leu Asp Asp Val Gln Lys Lys Leu Met Ser Leu Ala Asn
    1760                1765                1770

Ser Ser Glu Gly Lys Val Asp Lys Val Leu Met Arg Asn Leu Phe
    1775                1780                1785

Ile Gly His Phe His Thr Pro Lys Asn Gln Arg His Glu Val Leu
    1790                1795                1800

Arg Leu Met Gly Ser Ile Leu Gly Val Arg Arg Glu Glu Met Glu
    1805                1810                1815

Gln Leu Phe His Asp Asp Gln Gly Ser Val Thr Arg Trp Met Thr
    1820                1825                1830

Gly Trp Leu Gly Gly Gly Ser Lys Ser Val Pro Asn Thr Pro Leu
    1835                1840                1845

Arg Pro Asn Gln Gln Ser Val Val Asn Ser Ser Phe Ser Glu Leu
    1850                1855                1860

Phe Val Lys Phe Leu Glu Thr Glu Ser His Pro Ser Ile Pro Pro
    1865                1870                1875

Pro Lys Leu Ser Val His Asp Met Lys Pro Leu Asp Ser Pro Gly
    1880                1885                1890

Arg Arg Lys Arg Asp Thr Asn Ala Pro Glu Ser Phe Lys Asp Thr
    1895                1900                1905

Ala Glu Ser Arg Ser Gly Arg Arg Thr Asp Val Asn Pro Phe Leu
    1910                1915                1920

Ala Pro Arg Ser Ala Ala Val Pro Leu Ile Asn Pro Ala Gly Leu
    1925                1930                1935

Gly Pro Gly Gly Pro Gly His Leu Leu Leu Lys Pro Ile Ser Asp
    1940                1945                1950

Val Leu Pro Thr Phe Thr Pro Leu Pro Ala Leu Pro Asp Asn Ser
    1955                1960                1965

Ala Gly Val Val Leu Lys Asp Leu Leu Lys Gln
    1970                1975

<210> SEQ ID NO 42
<211> LENGTH: 18
<212> TYPE: DNA
<213> ORGANISM: Artificial Sequence
<220> FEATURE:
<223> OTHER INFORMATION: Synthetic primer

<400> SEQUENCE: 42
gaagctacaa agcacatg                                                18
```

```
<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
tcctgtcttt cttcatgc                                                   18

<210> SEQ ID NO 44
<211> LENGTH: 24
<212> TYPE: DNA
<213> ORGANISM: Artificial Sequence
<220> FEATURE:
<223> OTHER INFORMATION: Synthetic primer

<400> SEQUENCE: 44
gtcgacatgt cgtcctggct cggg                                            24

<210> SEQ ID NO 45
<211> LENGTH: 24
<212> TYPE: DNA
<213> ORGANISM: Artificial Sequence
<220> FEATURE:
<223> OTHER INFORMATION: Synthetic primer

<400> SEQUENCE: 45
ctcgagctat tgctttaaaa ggtc                                            24

<210> SEQ ID NO 46
<211> LENGTH: 24
<212> TYPE: DNA
<213> ORGANISM: Artificial Sequence
<220> FEATURE:
<223> OTHER INFORMATION: Synthetic primer

<400> SEQUENCE: 46
catatgtcgt cctggcttgg gggc                                            24

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
ggtaccttgc tttaaaaggt ctttc                                           25
```

IMMUNE RESPONSE INDUCER

CROSS REFERENCE TO RELATED APPLICATIONS

This application is a Divisional of U.S. patent application Ser. No. 12/739,723 filed on Apr. 23, 2010, which is the National Stage of PCT International Application No. PCT/JP2008/069267, filed on Oct. 23, 2008, which claims priority to Patent Application Nos. 2007-277578, 2007-277611, 2007-277240 and 2007-279113, filed in Japan on Oct. 25, 2007, Oct. 25, 2007, Oct. 25, 2007 and Oct. 26, 2007, all of which are hereby expressly incorporated by reference into the present application.

TECHNICAL FIELD

The present invention relates to a novel immunity-inducing agent useful as a therapeutic and/or prophylactic agent for a cancer(s).

BACKGROUND ART

Cancers are the commonest cause for death among all of the causes for death, and the therapies therefor are mainly surgical treatment in combination with radiotherapy and chemotherapy. In spite of the developments of new surgical methods and discovery of new anti-cancer agents in recent years, treatment results of cancers are not improved very much at present except for some cancers. In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised (see Non-patent Literature 1). In immunotherapy, to reduce side effects, it is necessary that the peptide or protein recognized as the antigen exist hardly in normal cells and exist specifically in cancer cells. In 1991, Boon et al. of Ludwig Institute in Belgium isolated human melanoma antigen MAGE 1 recognized by CD8-positive T cells by a cDNA-expression cloning method using an autologous cancer cell line and cancer-reactive T cells (see Non-patent Literature 2). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Non-patent Literature 3; Patent Literature 1), and various cancer antigens have been isolated (see Non-patent Literatures 4 to 9). Using a part thereof as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, at present, no therapeutic, prophylactic or diagnostic agents exist which are effective for cancers in dogs and cats. Most of tumors in dogs and cats are realized by owners only after they advance to grow bigger, and in many cases, it is already too late to visit a hospital to receive surgical excision of the tumor or administration of a human drug (an anticancer preparation or the like), so that those dogs and cats die shortly after the treatment. Under such circumstances, if therapeutic agents, prophylactic agents and diagnostic agents for cancers effective for dogs and cats become available, their uses for canine cancers are expected to be developed.

Patent Literature 1: U.S. Pat. No. 5,698,396 B
Non-patent Literature 1: Tsuyoshi Akiyoshi, Cancer and Chemotherapy, 24, 551-519 (1997)
Non-patent Literature 2: Bruggen P. et al., Science, 254: 1643-1647 (1991)
Non-patent Literature 3: Proc. Natl. Acad. Sci. USA, 92:11810-11813 (1995)
Non-patent Literature 4: Int. J. Cancer, 72:965-971 (1997)
Non-patent Literature 5: Cancer Res., 58:1034-1041 (1998)
Non-patent Literature 6: Int. J. Cancer, 29:652-658 (1998)
Non-patent Literature 7: Int. J. Oncol., 14:703-708 (1999)
Non-patent Literature 8: Cancer Res., 56:4766-4772 (1996)
Non-patent Literature 9: Hum. Mol. Genet 6:33-39, 1997
Non-patent Literature 10: Naokazu Inoue, Ryo Yamaguchi and Masahito Ikawa, Protein, Nucleic Acid and Enzyme, Vol. 50, No. 11, 1405-1412
Non-patent Literature 11: J Cell Sci. 115:1825-35
Non-patent Literature 12: Blood. 95:1788-96
Non-patent Literature 13: Mol Endocrinol. 9:243-54 (1995)
Non-patent Literature 14: J Cell Biol. 145: 83-98 (1999)

DISCLOSURE OF THE INVENTION

Problems to be Solved by the Invention

An object of the present invention is to provide a novel immunity-inducing agent which is useful as a therapeutic and/or prophylactic agent for a cancer(s)

Means for Solving the Problems

The present inventors intensively studied to obtain a cDNA encoding a protein which binds to an antibody existing in serum derived from a cancer-bearing living body by the SEREX method using a cDNA library derived from canine testis and serum of a cancer-bearing dog, which cDNA was used to prepare a polypeptide having the amino acid sequence shown in SEQ ID NO:2, a canine calmegin protein having the amino acid sequence shown in SEQ ID NO:16, a canine centrosomal protein (which may be hereinafter abbreviated as CEP) having the amino acid sequence shown in SEQ ID NO:26, and the canine thyroid hormone receptor interactor 11 (which may be hereinafter described as "TRIP11") having the amino acid sequence shown in SEQ ID NO:39. Further, based on a registered canine gene having a high homology to the canine CEP of the above-described SEQ ID NO:26, a canine CEP having the amino acid sequence shown in SEQ ID NO:28 was prepared. Further, based on a human gene homologous to the obtained gene, a polypeptide having the amino acid sequence shown in SEQ ID NO:4, a human calmegin protein having the amino acid sequence shown in SEQ ID NO:18, a human CEP having the amino acid sequence shown in SEQ ID NO:30, and a human TRIP11 having the amino acid sequence shown in SEQ ID NO:41 were prepared. The inventors then discovered that these polypeptides can induce immunocytes in a living body and cause regression of an already occurred tumor when administered to the living body, thereby completing the present invention.

That is, the present invention provides an immunity-inducing agent comprising as an effective ingredient any one of the polypeptides (a) to (c) below, the polypeptide having an immunity-inducing activity, or as an effective ingredient a recombinant vector which comprises a polynucleotide encoding the polypeptide and is capable of expressing the polypeptide in vivo: (a) a polypeptide consisting of not less than 7 consecutive amino acids of the amino acid sequence shown in SEQ ID NO:2, 4, 16, 18, 26, 28, 30, 39 or 41 in SEQUENCE LISTING; (b) a polypeptide having a homology of not less than 80% to the polypeptide (a) and consisting of not less than 7 amino acids; and (c) a polypeptide comprising the polypeptide (a) or (b) as a partial sequence thereof. The present invention also provides a method for inducing immunity, the method comprising administering to an individual an effective amount of any one of the above-described polypeptides (a) to (c), the polypeptide having an immunity-inducing activity, or an effective amount of a recombinant vector which comprises a polynucleotide encoding the polypeptide and is capable of expressing the polypeptide in vivo. The present invention further provides a method for treating antigen-presenting cells, the method comprising bringing any one of the above-described polypeptides (a) to (c), the polypeptide having an immunity-inducing activity, into contact with antigen-presenting cells. The present invention further provides use of any one of the above-described polypeptides (a) to (c), the polypeptide having an immunity-inducing activity, or a recombinant vector which comprises a polynucleotide encoding the polypeptide and is capable of expressing the polypeptide in vivo, for production of an immunity-inducing agent.

Effect of the Invention

By the present invention, a novel immunity-inducing agent useful as a therapeutic and/or prophylactic agent for a cancer(s) was provided. As indicated in the Examples below, the polypeptide used in the present invention can induce immunocytes in a cancer-bearing dog and also can cause reduction or regression of an already occurred tumor when administered to a cancer-bearing dog. Therefore, the polypeptide is useful for therapy and prophylaxis of a cancer(s).

BEST MODE FOR CARRYING OUT THE INVENTION

Figures 1, 2:
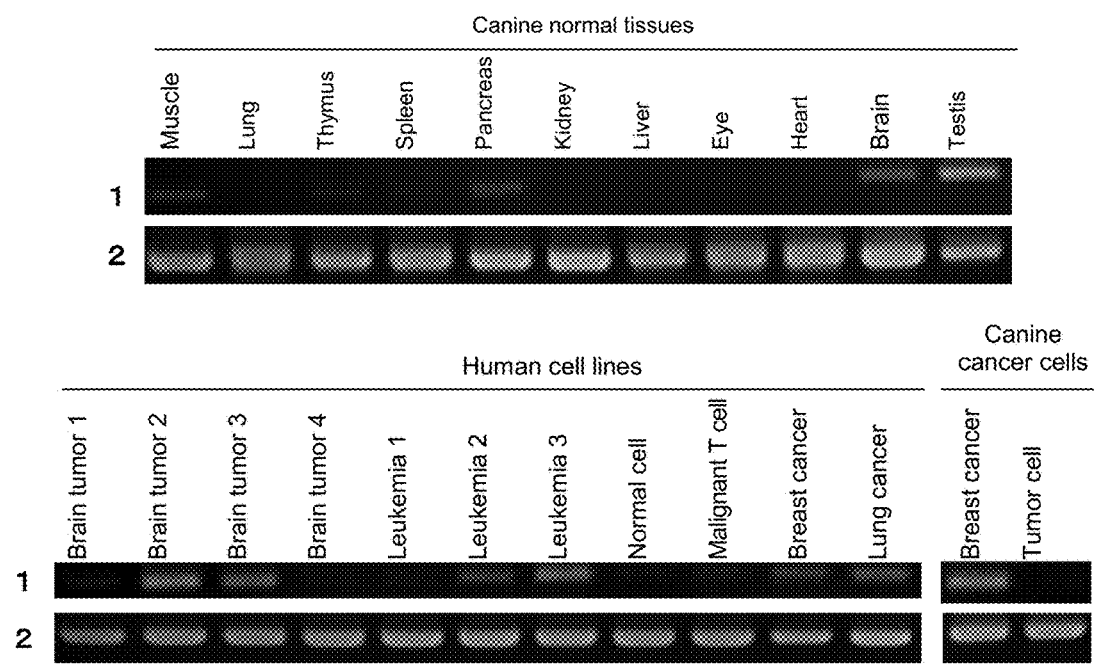
FIG. 1 shows the expression pattern of the gene identified in Example A-1 in normal tissues and tumor cell lines. Reference numeral 1: the expression pattern of the identified gene; Reference numeral 2: the expression pattern of the GAPDH gene.
FIG. 2 shows the detection by Coomassie staining of the canine-derived protein produced in E. coli and purified in Example A, which protein was identified in the present invention. Reference numeral 3: the band for the canine-derived protein of the present invention.

The polypeptides contained in the immunity-inducing agents of the present invention as effective ingredients are as follows. It should be noted that the term "polypeptide" in the present invention means a molecule formed by peptide bonding of a plurality of amino acids, and includes not only polypeptide molecules having large numbers of amino acids constituting them, but also low molecular weight molecules having small numbers of amino acids (oligopeptides) and full-length proteins. Thus, in the present invention, proteins consisting of the full length of SEQ ID NO:2, 4, 16, 18, 26, 28, 30, 39 or 41 are also included in "polypeptide".

(a) A polypeptide which consists of not less than 7 consecutive amino acids of a polypeptide having the amino acid sequence shown in SEQ ID NO:2, 4, 16, 18, 26, 28, 30, 39 or 41 in SEQUENCE LISTING and has an immunity-inducing activity.

(b) A polypeptide which has a homology of not less than 80% to the polypeptide (a), consists of not less than 7 amino acids, and has an immunity-inducing activity.

(c) A polypeptide which comprises the polypeptide (a) or (b) as a partial sequence thereof and has an immunity-inducing activity.

It should be noted that the term "having the amino acid sequence" in the present invention means that amino acid residues are aligned in that order.

Accordingly, for example, "a polypeptide having the amino acid sequence shown in SEQ ID NO:2" means a polypeptide having a size of 306 amino acid residues, whose amino acid sequence is Met Ala Ala Leu . . . (snip) . . . Ile Thr Ser Pro as shown in SEQ ID NO:2. Further, "a polypeptide having the amino acid sequence shown in SEQ ID NO:2" may be abbreviated as "a polypeptide of SEQ ID NO:2". This also applies to the term "having the base sequence".

As used herein, the term "immunity-inducing activity" means an ability to induce immunocytes which secrete cytokines such as interferon in a living body. Whether or not a polypeptide has an immunity-inducing activity can be confirmed using, for example, the known ELISPOT assay. More particularly, for example, as described in the Examples below, cells such as peripheral blood mononuclear cells are obtained from a living body to which a polypeptide whose immunity-inducing activity is to be evaluated was administered, which cells are then cocultivated with the polypeptide, followed by measuring the amount of a cytokine produced by the cells using a specific antibody, thereby measuring the number of immunocytes in the cells, which enables evaluation of the immunity-inducing activity. Further, as described in the Examples below, a recombinant polypeptide prepared based on the amino acid sequence of SEQ ID NO:2, 4, 16, 18, 26, 28, 30, 39 or 41 can cause regression of a tumor by its immunity-inducing activity when administered to a cancer-bearing living body. Therefore, the above-described immunity-inducing activity can be evaluated also as the ability to inhibit the growth of cancer cells expressing the polypeptide of SEQ ID NO:2, 4, 16, 18, 26, 28, 30, 39 or 41 or to cause reduction or disappearance of a cancer tissue (tumor) (hereinafter referred to as "anti-tumor activity"). The anti-tumor activity of a polypeptide can be confirmed by, for example, observation of whether or not the tumor is reduced when the polypeptide was administered to a cancer-bearing living body, as more particularly described in the Examples below. Further, the anti-tumor activity of a polypeptide can be evaluated also by observation of whether or not T cells stimulated with the polypeptide (that is, T cells brought into contact with antigen-presenting cells which present the polypeptide) show a cytotoxic activity against tumor cells in vitro. The contact between T cells and antigen-presenting cells can be carried out by cocultivation of the both in a liquid medium, as mentioned below. Measurement of the cytotoxic activity can be carried out by, for example, a known method called $^{51}$Cr release assay described in Int. J. Cancer, 58: p 317, 1994. In cases where a polypeptide is used for therapy and/or prophylaxis of a cancer(s), the evaluation of the immunity-inducing activity is preferably carried out using the anti-tumor activity as an index, although the index is not restricted.

The amino acid sequence shown in SEQ ID NO:2 in SEQUENCE LISTING is the amino acid sequence of the polypeptide with unknown function isolated as a polypeptide which binds to an antibody existing specifically in serum derived from a cancer-bearing dog, which isolation was carried out by the SEREX method using a canine testis-derived cDNA library and serum of a cancer-bearing dog (see Example A-1). It is registered in the NCBI database under Accession No. XP_535343 (protein) and Accession No. XM_535343 (coding gene), but its function has not been reported. Further, the amino acid sequence shown in SEQ ID NO:4 is an amino acid sequence of a human homologous factor of the polypeptide of SEQ ID NO:2 isolated as described above. This human homologous factor is also a protein whose function is unknown, which is registered in the NCBI database under Accession No. NP_689873 (protein) and Accession No. NM 152660 (coding gene). The homology between them is 93% in terms of base sequence and 99% in terms of amino acid sequence.

The respective amino acid sequences shown in SEQ ID NOs:16 and 18 are those of the calmegin protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example B-1). Calmegin was identified as a protein which is expressed specifically at the time of differentiation of a spermatid, and it has a chaperone activity in vitro. Since it is expressed only in testis and disappears in a mature sperm, calmegin is considered to have a function to fold proteins involved in differentiation of spermatid (Non-patent Literature 10, Naokazu Inoue, Ryo Yamaguchi and Masahito Ikawa, Protein, Nucleic Acid and Enzyme, Vol. 50, No. 11, 1405-1412). However, there has been no report showing that the protein is expressed in a cancer and useful for therapy or prophylaxis thereof. The homology between the canine calmegin gene and the human calmegin gene is 90% in terms of base sequence and 89% in terms of amino acid sequence.

The respective amino acid sequences shown in SEQ ID NOs:26, 28 and 30 are those of the CEP isolated as a polypeptide, a canine factor having a high homology to the polypeptide and a human homologous factor of the polypeptide, which polypeptide binds to an antibody existing specifically in serum derived from a cancer-bearing dog, which isolation was carried out by the SEREX method using a canine testis-derived cDNA library and serum of a cancer-bearing dog (see Example C-1). CEP is a protein which is required by the centrosome to control microtubules and also involved in maturation of the centrosome. It is known that chromosomal translocation frequently occurs in some of myeloproliferative disorders, and since the CEP gene exists at the point where the translocation occurs, CEP is considered to have a certain relationship with the disorders. However, there has been no report showing that the protein is expressed in a cancer and useful for therapy or prophylaxis thereof (Non-patent Literature 11: J Cell Sci. 115:1825-35; Non-patent Literature 12: Blood. 95:1788-96). The homology between the canine CEP gene encoding the CEP of SEQ ID NO:26 and the human CEP gene is 87% in terms of base sequence and 84% in terms of amino acid sequence.

The respective amino acid sequences shown in SEQ ID NOs:39 and 41 are those of the TRIP11 protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example D-1). TRIP11 (thyroid hormone receptor interactor 11) was first identified as a factor which interacts with the thyroid hormone receptor β, and its binding to Golgi bodies and microtubules also became evident, so that TRIP11 is considered to play a role in maintaining the shapes of these organelles. However, there has been no report showing that the protein is expressed in a cancer and useful for therapy or prophylaxis thereof (Non-patent Literature 13, Mol Endocrinol. 9:243-54 (1995); Non-patent Literature 14, J Cell Biol. 145: 83-98 (1999)). The homology between the canine TRIP11 gene and the human TRIP11 gene is 88% in terms of base sequence and 86% in terms of amino acid sequence.

The polypeptide (a) consists of not less than 7 consecutive, preferably not less than 9 consecutive amino acids of a polypeptide having the amino acid sequence shown in SEQ ID NO:2, 4, 16, 18, 26, 28, 30, 39 or 41, and has an immunity-inducing activity. The polypeptide especially preferably has the amino acid sequence shown in SEQ ID NO:2, 4, 16, 18, 26, 28, 30, 39 or 41. As known in the art, a polypeptide consists of not less than about 7 amino acid residues can exert its antigenicity. Thus, a polypeptide consists of not less than 7 consecutive amino acid residues of the amino acid sequence shown in SEQ ID NO:2, 4, 16, 18, 26, 28, 30, 39 or 41 can have an immunity-inducing activity, so that it can be used for preparation of the immunity-inducing agent of the present invention. However, in view of the fact that antibodies produced against antigenic substances in a living body are polyclonal antibodies, it is thought that an antigenic substance composed of larger number of amino acid residues can induce more types of antibodies which can recognize various sites on the antigenic substance, thereby attaining higher immunity-inducing activity. Therefore, in order to increase the immunity-inducing activity, in the case of SEQ ID NO:2 or 4, the number of the amino acid residues may be preferably not less than 30, more preferably not less than 100, still more preferably not less than 200, still more preferably not less than 250. In the case of SEQ ID NO:16 or 18, the number of the amino acid residues may be preferably not less than 30, more preferably not less than 100, still more preferably not less than 200, still more preferably not less than 400, still more preferably not less than 550. In the case of SEQ ID NO:26, 28 or 30, the number of the amino acid residues may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acid residues may be preferably not less than 30, more preferably not less than 100, still more preferably not less than 300, still more preferably not less than 600, still more preferably not less than 1000, still more preferably not less than 1500.

As a principle of immune induction by administration of a cancer antigenic polypeptide, the following process is known: the polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen.

The size of the polypeptide presented on the surface of the antigen-presenting cell is relatively small and about 7 to 30 amino acids. Therefore, from the view point of presenting thereof on the surface of the antigen-presenting cell, a polypeptide consisting of about 7 to 30, preferably about 9 to 30 consecutive amino acids of the amino acid sequence shown in SEQ ID NO:2, 4, 16, 18, 26, 28, 30, 39 or 41 is sufficient as the above-described polypeptide (a). In some cases, these relatively small polypeptides are presented directly on the surface of the antigen-presenting cells without incorporation thereof into the antigen-presenting cells.

However, as described above, since a polypeptide incorporated into an antigen-presenting cell is cleaved at random sites by peptidases in the cell to yield various polypeptide fragments, which are then presented on the surface of the antigen-presenting cell, administration of a large polypeptide such as the entire region of SEQ ID NO:2, 4, 16, 18, 26, 28, 30, 39 or 41 inevitably causes production of polypeptide fragments by degradation thereof in the antigen-presenting cell, which fragments are effective for immune induction via the antigen-presenting cell. Therefore, for immune induction via antigen-presenting cells, a large polypeptide can also be preferably used. In the case of SEQ ID NO:2 or 4, the number of the amino acids may be preferably not less than 30, more preferably not less than 100, still more preferably not less than 200, still more preferably not less than 250. In the case of SEQ ID NO:16 or 18, the number of the amino acids may be preferably not less than 30, more preferably not less than 100, still more preferably not less than 200, still more preferably not less than 400, still more preferably not less than 550. In the case of SEQ ID NO:26, 28 or 30, the number of the amino acids may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acids may be preferably not less than 30, more preferably not less than 100, still more preferably not less than 300, still more preferably not less than 600, still more preferably not less than 1000, still more preferably not less than 1500.

The above-described polypeptide (b) is the same polypeptide as the above-described polypeptide (a) except that a small number of amino acid residues are substituted, deleted and/or inserted, which has a homology of not less than 80%, preferably not less than 90%, more preferably not less than 95%, still more preferably not less than 98% to the original sequence, and has an immunity-inducing activity. It is well known in the art that, in general, there are cases where a protein antigen retains substantially the same antigenicity as the original even if the amino acid sequence of the protein is modified such that a small number of amino acids are substituted, deleted and/or inserted. Therefore, since the above-described polypeptide (b) may also exert an immunity-inducing activity, it can be used for preparation of the immunity-inducing agent of the present invention. Further, the above-described polypeptide (b) is also preferably the same polypeptide as one having the amino acid sequence shown in SEQ ID NO:2, 4, 16, 18, 26, 28, 30, 39 or 41 except that one or several amino acid residues are substituted, deleted and/or inserted.

As used herein, the term "homology" of amino acid sequences means a value expressed in percentage which is calculated by aligning two amino acid sequences to be compared such that the number of matched amino acid residues is the maximum, and dividing the number of the matched amino acid residues by the number of the total amino acid residues. When the above-described alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described number of the total amino acid residues is calculated by counting one gap as one amino acid residue. When the thus counted numbers of the total amino acid residues are different between the two sequences to be compared, the homology (%) is calculated by dividing the number of matched amino acid residues by the number of the total amino acid residues in the longer sequence.

The 20 types of amino acids constituting the naturally occurring proteins may be classified into groups each of which has similar properties, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptide. Therefore, in cases where amino acid residue(s) in the above described polypeptide (a) in the present invention is/are substituted, the probability that the immunity-inducing activity can be maintained may be made high by conducting the substitution(s) within the same group.

The above-described polypeptide (c) comprises the above-described polypeptide (a) or (b) as a partial sequence and has an immunity-inducing activity. That is, the polypeptide (c) has another/other amino acid(s) or polypeptide(s) added at one or both ends of the polypeptide (a) or (b), and has an immunity-inducing activity. Such a polypeptide can also be used for preparation of the immunity-inducing agent of the present invention.

For example, the above-described polypeptides can be synthesized by a chemical synthesis method such as the Fmoc method (fluorenylmethylcarbonyl method) or the tBoc method (t-butyloxycarbonyl method). Further, they can be synthesized by conventional methods using various commercially available peptide synthesizers. Further, the polypeptide of interest can be obtained by a known genetic engineering method wherein a polynucleotide encoding the above-described polypeptide is prepared and incorporated into an expression vector, which is then introduced into a host cell, in which the polypeptide is produced.

The polynucleotide encoding the above-described polypeptide can be easily prepared by a known genetic engineering method or a conventional method using a commercially available nucleic acid synthesizer. For example, DNA having the base sequence of SEQ ID NO:1, 15, 25, 27 or 38 can be prepared by carrying out PCR using the chromosomal DNA or a cDNA library of a dog as a template and using a pair of primers designed such that the primers can amplify the base sequence described in SEQ ID NO:1, 15, 25, 27 or 38, respectively. DNA having the base sequence of SEQ ID NO:3, 17, 29 or 40 can be prepared similarly by using as the above-described template the human chromosomal DNA or a cDNA library. Conditions for the PCR reaction can be selected as appropriate, and examples of the conditions include, but are not limited to, those wherein a cycle comprising the reaction steps of 94° C. for 30 seconds (denaturing), 55° C. for 30 seconds to 1 minute (annealing), and 72° C. for 2 minutes (extension) is repeated, for example, 30 times, followed by allowing the reaction to proceed at 72° C. for 7 minutes. Further, a desired DNA can be isolated by preparing an appropriate probe or primer based on the information of the base sequence and the amino acid sequence shown in SEQ ID NOs:1 to 4, 15 to 18, 25 to 30, 38 to 41 in SEQUENCE LISTING of the present specification and then using the probe or primer for screening of a cDNA library from a dog or a human. The cDNA library is preferably prepared from cells, an organ or a tissue expressing the protein of SEQ ID NO:2, 4, 16, 18, 26, 28, 30, 39 or 41. Operations such as the above-described preparation of a probe or a primer, construction of a cDNA library, screening of a cDNA library and cloning of a gene of interest are known to those skilled in the art, and can be carried out according to, for example, Molecular Cloning, 2nd Ed. or Current Protocols in Molecular Biology. From the thus obtained DNA, DNA encoding the above-described polypeptide (a) can be obtained. Further, since codons encoding each amino acid are known, the base sequence of a polynucleotide encoding a specific amino acid sequence can be easily specified. Therefore, the base sequences of polynucleotides encoding the above-described polypeptide (b) and polypeptide (c) can also be easily specified, so that such polynucleotides can also be easily synthesized using a commercially available nucleic acid synthesizer according to a conventional method.

The above-described host cells are not restricted as long as they can express the above-described polypeptide, and examples thereof include, but are not limited to, prokaryotic cells such as E. coli; and eukaryotic cells such as mammalian cultured cells including monkey kidney cells COS 1 and Chinese hamster ovary cells CHO, budding yeast, fission yeast, silkworm cells, and Xenopus laevis egg cells.

In cases where prokaryotic cells are used as the host cells, an expression vector having the origin that enables its replication in a prokaryotic cell, a promoter, a ribosome binding site, a DNA cloning site, a terminator and the like is used as the expression vector. Examples of the expression vector for E. coli include the pUC system, pBluescript II, pET expression system and pGEX expression system. By incorporating DNA encoding the above-described polypeptide into such an expression vector and transforming prokaryotic host cells with the vector, followed by culturing the obtained transformant, the polypeptide encoded by the above-described DNA can be expressed in the prokaryotic host cells. In this case, the polypeptide can also be expressed as a fusion protein with another protein.

In cases where eukaryotic cells are used as the host cells, an expression vector for eukaryotic cells having a promoter, splicing site, poly(A) addition site and the like is used as the expression vector. Examples of such an expression vector include pKA1, pCDM8, pSVK3, pMSG, pSVL, pBK-CMV, pBK-RSV, the EBV vector, pRS, pcDNA3, pMSG and pYES2. In the same manner as described above, by incorporating DNA encoding the above-described polypeptide into such an expression vector and transforming eukaryotic host cells with the vector, followed by culturing the obtained transformant, the polypeptide encoded by the above-described DNA can be expressed in the eukaryotic host cells. In cases where pIND/V5-His, pFLAG-CMV-2, pEGFP-N1 or pEGFP-C1 was used as the expression vector, the above-described polypeptide can be expressed as a fusion protein having various added tags such as His tag, FLAG tag, myc tag, HA tag or GFP.

Introduction of the expression vector to the host cells can be carried out using a well-known method such as electroporation, the calcium phosphate method, the liposome method or the DEAE dextran method.

Isolation and purification of a polypeptide of interest from the host cells can be carried out by a combination of known separation operations. Examples of the operations include, but are not limited to, treatment by a denaturant such as urea or by a surfactant; ultrasonication treatment; enzyme digestion; salting-out and solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method include, as mentioned above, those in the form of a fusion protein with another arbitrary protein. Examples thereof include fusion proteins with glutathion S-transferase (GST) and with a His tag. Such a polypeptide in the form of a fusion protein is also included within the scope of the present invention as the above-described polypeptide (c). Further, in some cases, a polypeptide expressed in a transformed cell is modified in various ways in the cell after translation thereof. Such a polypeptide having a post-translational modification is also included within the scope of the present invention as long as it has an immunity-inducing activity. Examples of such a post-translational modification include elimination of N-terminus methionine, N-terminus acetylation, glycosylation, limited degradation by an intracellular protease, myristoylation, isoprenylation and phosphorylation.

As described concretely in the following Examples, the above-described polypeptide having an immunity-inducing activity can cause regression of an already occurred tumor when administered to a cancer-bearing living body. Therefore, the immunity-inducing agent of the present invention can be used as a therapeutic and/or prophylactic agent for a cancer(s). In this case, cancers to be treated are those expressing the gene encoding the polypeptide of SEQ ID NO:2 or 4, and examples thereof include, but are not limited to, brain tumor; squamous cell carcinomas of head, neck, lung, uterus and esophagus; melanoma; adenocarcinomas of lung, breast and uterus; renal cancer; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); and leiomyosarcoma. The animals to be treated are mammals, especially preferably humans, dogs and cats.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of a cancer, it may be administered to a regional lymph node in the vicinity of the tumor to be treated, as described in the Examples below, in order to enhance its anticancer activity. The dose may be any dose as long as the dose is effective for immune induction, and in cases where the agent is used for therapy and/or prophylaxis of a cancer, the dose may be one effective for therapy and/or prophylaxis of the cancer. The dose effective for therapy and/or prophylaxis of a cancer is appropriately selected depending on the size of the tumor, the symptom and the like, and usually, 0.0001 µg to 1000 µg, preferably 0.001 µg to 1000 µg of the agent in terms of the effective ingredient may be administered once or in several times per day per animal to be treated. The agent is preferably administered in several times, every several days to several months. As concretely shown in the Examples below, the immunity-inducing agent of the present invention can cause regression of an already occurred tumor. Therefore, since the agent can exert its anticancer activity also against a small number of cancer cells in the early stage, development or recurrence of the cancer can be prevented by using the agent before development of a cancer or after therapy for a cancer. That is, the immunity-inducing agent of the present invention is effective for both therapy and prophylaxis of a cancer.

The immunity-inducing agent of the present invention may contain only a polypeptide or may be formulated by mixing as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additive include, but are not limited to, diluents such as physiological buffer solutions; vehicles such as sucrose, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the above-described immunoenhancer include adjuvants. Adjuvants can enhance the immune response by providing a reservoir of antigen (extracellularly or within macrophages), activating macrophages and stimulating specific sets of lymphocytes, thereby enhancing the anticancer activity. Therefore, especially in cases where the immunity-inducing agent of the present invention is used for therapy and/or prophylaxis of a cancer, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham) and homologues of *Salmonella minnesota* Re 595 lipopolysaccharide obtained after purification and acid hydrolysis of the lipopolysaccharide; QS21 (SmithKline Beecham), pure QA-21 saponin purified from extract of *Quillja saponaria*; DQS21 described in WO96/33739 (SmithKline Beecham); QS-7, QS-17, QS-18 and QS-L1 (So and 10 others, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 others, "Nature", Vol. 374, p. 546-549); poly-I:C and derivatives thereof (e.g., poly ICLC); and various water in oil emulsions prepared from biodegradable oils such as squalene and/or tocopherol. Among these, Freund's incomplete adjuvant; Montanide; poly-I:C and derivatives thereof, and CpG oligonucleotides are preferred. The mixing ratio between the above-described adjuvant and polypeptide is typically about 1:10 to 10:1, preferably about 1:5 to 5:1, more preferably about 1:1. However, the adjuvant is not limited to the above-described examples, and adjuvants known in the art other than the above-described ones (for example, see Goding, "Monoclonal Antibodies: Principles and Practice", 2nd edition, 1986) may be used when the immunity-inducing agent of the present invention is administered. Preparation methods for mixtures or emulsions of a polypeptide and an adjuvant are well-known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been shown to promote the prophylactic action of vaccines. Such factors may also be used as the above-described immunoenhancer, and can be contained in the immunity-inducing agent of the present invention, or can be prepared as a separate composition to be administered to a patient in combination with the immunity-inducing agent of the present invention.

Further, by bringing the above-described polypeptide into contact with antigen-presenting cells in vitro, the antigen-presenting cells can be made to present the polypeptide. That is, the above-described polypeptides (a) to (c) can be used as agents for treating antigen-presenting cells. As the antigen-presenting cells, dendritic cells or B cells, which have MHC class I molecules, may preferably be employed. Various MHC class I molecules have been identified and well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system. By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be a fresh sample, cold-stored sample or frozen sample. As for the peripheral blood, whole blood may be cultured or the leukocyte components alone may be separated and cultured, and the latter is efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted and naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced, and usually, the total concentration of the cytokine(s) is preferably about 10 to 1000 ng/mL, more preferably about 20 to 500 ng/mL. The culture may be carried out using a well-known medium usually used for the culture of leukocytes.

The culturing temperature is not restricted as long as the proliferation of the leukocytes is attained, and about 37° C. which is the body temperature of human is most preferred. The atmospheric environment during the culturing is not restricted as long as the proliferation of the leukocytes is attained, and to flow 5% $CO_2$ is preferred. The culturing period is not restricted as long as the necessary number of the cells is induced, and is usually 3 days to 2 weeks. As for the apparatuses used for separation and culturing of the cells, appropriate apparatuses, preferably those whose safety when applied to medical uses have been confirmed, and whose operations are stable and simple, may be employed. Particularly, as for the cell-culturing apparatus, not only the general vessels such as a Petri dish, flask and bottle, but also a layer type vessel, multistage vessel, roller bottle, spinner type bottle, bag type culturing vessel, hollow fiber column and the like may be used.

Bringing the above-described peptide of the present invention into contact with the antigen presenting cells in vitro may be carried out by a well-known method. For example, it may be carried out by culturing the antigen-presenting cells in a culture medium containing the above-described polypeptide. The concentration of the peptide in the medium is not restricted, and usually about 1 μg/ml to 100 μg/ml, preferably about 5 μg/ml to 20 μg/ml. The cell density during the culturing is not restricted and is usually about $10^3$ cells/ml to $10^7$ cells/ml, preferably about $5×10^4$ cells/ml to $5×10^6$ cells/ml. The culturing may be carried out according to a conventional method, and is preferably carried out at 37° C. under atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, and induce, and allow proliferation of, cytotoxic T cells specific to the polypeptide.

By bringing the antigen-presenting cells prepared as described above having the complex between the above-described polypeptide and the MHC molecule into contact with T cells in vitro, cytotoxic T cells specific to the polypeptide can be induced and allowed to proliferate. This may be carried out by cocultivating the above-described antigen-presenting cells and T cells in a liquid medium. For example, it may be attained by suspending the antigen-presenting cells in a liquid medium, placing the suspension in vessels such as wells of a microplate, adding thereto T cells and then culturing the cells. The mixing ratio of the antigen-presenting cells to the T cells in the cocultivation is not restricted, and is usually about 1:1 to 1:100, preferably about 1:5 to 1:20 in terms of the number of cells. The density of the antigen-presenting cells suspended in the liquid medium is not restricted, and is usually about 100 to 10,000,000 cells/ml, preferably about 10,000 to 1,000,000 cells/ml. The cocultivation is preferably carried out at 37° C. under atmosphere of 5% $CO_2$ in accordance with a conventional method. The culturing time is not restricted, and is usually 2 days to 3 weeks, preferably about 4 days to 2 weeks. The cocultivation is preferably carried out in the presence of one or more interleukins such as IL-2, IL-6, IL-7 and IL-12. In this case, the concentration of IL-2 and IL-7 is usually about 5 U/ml to 20 U/ml, the concentration of IL-6 is usually about 500 U/ml to 2000 U/ml, and the concentration of IL-12 is usually about 5 ng/ml to 20 ng/ml, but the concentrations of the interleukins are not restricted thereto. The above-described cocultivation may be repeated once to several times adding fresh antigen-presenting cells. For example, the operation of discarding the culture supernatant after the cocultivation and adding a fresh suspension of antigen-presenting cells to further conduct the cocultivation may be repeated once to several times. The conditions of the each cocultivation may be the same as described above.

By the above-described cocultivation, cytotoxic T cells specific to the polypeptide are induced and allowed to proliferate. Thus, using the above-described polypeptide, isolated T cells can be prepared which selectively bind the complex between the polypeptide and the MHC molecule.

As described in the Examples below, the genes encoding the polypeptides of SEQ ID NOs:2, 16, 26, 28 and 39 and SEQ ID NOs:4, 18, 30 and 41 are expressed specifically in cancer cells and testis of dogs and humans, respectively. Thus, in cancer cells, significantly higher numbers of the polypeptides of SEQ ID NOs:2, 16, 26, 28 and 39 or SEQ ID NOs:4, 18, 30 and 41 exist than in normal cells. When cytotoxic T cells prepared as described above are administered to a living body while a part of the polypeptides existing in cancer cells are presented by MHC molecules on the surfaces of the cancer cells, the cytotoxic T cells can damage the cancer cells using the presented polypeptides as markers. Since antigen-presenting cells presenting the above-described polypeptides can induce, and allow proliferation of, cytotoxic T cells specific to the polypeptides also in vivo, cancer cells can be damaged also by administering the antigen-presenting cells to a living body. That is, the above-described cytotoxic T cells and the above-described antigen-presenting cells prepared using the above-described polypeptide are also effective as therapeutic and/or prophylactic agents for a cancer(s).

In cases where the above-described isolated antigen-presenting cells or isolated T cells are administered to a living body, these are preferably prepared by treating antigen presenting cells or T cells collected from the patient to be treated with the polypeptide (a) to (c) as described above in order to avoid the immune response in the living body that attacks these cells as foreign bodies.

The therapeutic and/or prophylactic agent for a cancer(s) comprising as an effective ingredient the antigen-presenting cells or T cells is preferably administered via a parenteral administration route such as intravenous or intraarterial administration. The dose is appropriately selected depending on the symptom, the purpose of administration and the like, and is usually 1 cell to 10,000,000,000,000 cells, preferably 1,000,000 cells to 1,000,000,000 cells, which dose is preferably administered once per several days to once per several months. The formulation may be, for example, the cells suspended in physiological buffered saline, and the formulation may be used in combination with another/other anticancer preparation(s) and/or cytokine(s). Further, one or more additives well-known in the field of formulation of pharmaceuticals may also be added.

Also by expression of the polynucleotide encoding the above-described polypeptide (a) to (c) in the body of the animal to be treated, antibody production and cytotoxic T cells can be induced in the living body, and an effect comparable to the administration of a polypeptide can be obtained. That is, the immunity-inducing agent of the present invention may be one comprising as an effective ingredient a recombinant vector having a polynucleotide encoding the above-described polynucleotide (a) to (c), which recombinant vector is capable of expressing the polypeptide in a living body. Such a recombinant vector capable of expressing an antigenic polypeptide is also called gene vaccine. The vector used for production of a gene vaccine is not restricted as long as it is a vector capable of expressing a polypeptide in cells of the animal to be treated (preferably in a mammalian cell), and may be either a plasmid vector or a virus vector, and any known vector in the field of gene vaccines may be used. The polynucleotide such as DNA or RNA encoding the above-described polypeptide can be easily prepared, as mentioned above, by a conventional method. Incorporation of the polynucleotide into a vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and usually about 0.1 µg to 100 mg, preferably about 1 µg to 10 mg in terms of the weight of the gene vaccine per 1 kg of body weight.

Methods using a virus vector include those wherein a polynucleotide encoding the above-described polypeptide is incorporated into an RNA virus or DNA virus such as retrovirus, adenovirus, adeno-associated virus, herpes virus, vaccinia virus, pox virus, poliovirus or Sindbis virus, and then the animal to be treated is infected by the resulting virus. Among these methods, those using retrovirus, adenovirus, adeno-associated virus, vaccinia virus or the like are especially preferred.

Other methods include a method wherein an expression plasmid is directly intramuscularly administered (DNA vaccine method), the liposome method, lipofectin method, microinjection method, calcium phosphate method, electroporation method and the like, and the DNA vaccine method and liposome method are especially preferred.

Methods for actually making the gene encoding the above-described polypeptide of the present invention act as a pharmaceutical include the in vivo method wherein the gene is directly introduced into the body, and the ex vivo method wherein a kind of cells are collected from the animal to be treated, the gene is introduced into the cells ex vivo, and then the cells are returned to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these papers and the like). The in vivo method is more preferred.

In cases where the gene is administered by the in vivo method, the gene may be administered through an appropriate administration route depending on the disease to be treated, symptom and so on. It may be administered, for example, by intravenous, intraarterial, subcutaneous, intramuscular administration or the like. In cases where the gene is administered by the in vivo method, the gene may be formulated into a preparation such as a solution, and in general, it is formulated into an injection solution or the like containing the DNA encoding the above-described peptide of the present invention as an effective ingredient. A commonly used carrier(s) may be added as required. In the case of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence shown in SEQ ID NO:1" includes not only the base sequence expressly written in SEQ ID NO:1, but also the sequence complementary thereto. Thus, "a polynucleotide having the base sequence shown in SEQ ID NO:1" includes a single-stranded polynucleotide having the base sequence expressly written in SEQ ID NO:1, a single-stranded polynucleotide having the base sequence complementary thereto, and a double-stranded polynucleotide composed of these single strand polynucleotides. When the polynucleotide encoding the polypeptide used in the present invention is prepared, any one of these base sequences should be appropriately selected, and those skilled in the art can easily carry out the selection.

EXAMPLES

The present invention will now be described more concretely by way of Examples.

Example A-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host E. coli cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from squamous cell carcinoma was used. The serum was stored at −80° C. and pretreated immediately before use. The method of the pretreatment of the serum was as follows. That is, host E. coli cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an E. coli/phage extract. Thereafter, the collected E. coli/phage extract was allowed to flow through an NHS column (manufactured by GE Healthcare Bio-Science) to immobilize proteins derived from the E. coli/phage thereon. The serum from the canine patients was allowed to flow through and react with this protein-immobilized column to remove antibodies adsorbed on E. coli and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host E. coli (XL1-Blue MRF') such that the absorbance $OD_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host E. coli (SOLR) such that the absorbance $OD_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:1 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the gene (Accession No. XM_535343) encoding a protein (Accession No. XP_535343) whose function is unknown. The human homologous factor of this gene was the gene (Accession No. NM_152660) encoding a protein (Accession No. NP_689873) whose function is also unknown (homology: base sequence, 93%; amino acid sequence, 99%). The base sequence of the human homologous factor is shown in SEQ ID NO:3, and the amino acid sequence thereof is shown in SEQ ID NO:4.

(4) Analysis of Expression in Each Tissue

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:7 and 8) specific to the obtained canine gene and its human homologous gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 1 minute using Thermal Cycler (manufactured by BIO RAD). The gene-specific primers having the base sequences shown in the above-described SEQ ID NOs:7 and 8 were those which amplify the regions of the 87th to 606th bases of the base sequence of SEQ ID NO:1 and the 173rd to 695th bases of the base sequence of SEQ ID NO:3, and can be used for investigation of the expression of both the canine gene and its human homologous gene. As a control for comparison, primers (described in SEQ ID NOs:9 and 10) specific to GAPDH were used simultaneously. As a result, as shown in FIG. 1, strong expression of the obtained canine gene was observed in testis among the normal dog tissues, and on the other hand, strong expression was observed in the canine breast cancer cell line. Expression of the human homologous gene was confirmed, as is the case with the canine gene, only in testis among the human normal tissues, but the expression was detected in brain tumor, leukemia, breast cancer and lung cancer cells among human cancer cell lines. Thus, the human homologous gene was also confirmed to be specifically expressed in testis and cancer cells.

In FIG. 1, reference numeral 1 in the ordinate indicates the expression pattern of the above identified gene, and reference numeral 2 indicates the expression pattern of the GAPDH gene as a control for comparison.

Example A-2

Preparation of Novel Cancer Antigen Proteins (1) Preparation of Recombinant Protein Based on the gene of SEQ ID NO:1 obtained in Example A-1, a recombinant protein was prepared by the following method. Respective reagents and the attached buffer were mixed such that the mixture should contain 1 µl of the vector which was prepared from the phagemid solution obtained in Example A-1 and was subjected to the sequence analysis, 0.4 µM each of two kinds of primers having NdeI and XhoI restriction sites (described in SEQ ID NOs:11 and 12), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:2. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and XhoI and purified using QIAquick Gel Extraction Kit, followed by inserting the gene sequence of interest into an expression vector for *E. coli*, pET16b (manufactured by Novagen) that had been treated with NdeI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO:3, a recombinant protein of the human homologous gene was prepared by the following method. Respective reagents and the attached buffer were mixed such that the mixture should contain 1 µl of the cDNA prepared in Example A-1 whose expression could be confirmed by the RT-PCR method in various tissues/cells, 0.4 µM each of two kinds of primers having EcoRV and EcoRI restriction sites (described in SEQ ID NOs:13 and 14), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:4. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRV and EcoRI and purified using QIAquick Gel Extraction Kit, followed by inserting the gene sequence of interest into an expression vector for *E. coli*, pET30a (manufactured by Novagen) that had been treated with EcoRV and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:1 and SEQ ID NO:3, respectively, were cultured in 100 μg/ml ampicillin-containing LB medium at 37° C. until the absorbance at 600 nm reached about 0.7, and then isopropyl-β-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in 50 mM Tris-HCl buffer (pH 8.0) and subjected to sonication on ice. The sonicated solution of *E. coli* was centrifuged at 6,000 rpm for 20 minutes to obtain the supernatant as the soluble fraction and the precipitate as the insoluble fraction.

The insoluble fraction was suspended in 50 mM Tris-HCl buffer (pH 8.0) and centrifuged at 6,000 rpm for 15 minutes. This operation was repeated twice and an operation of removal of proteases was carried out.

The residue was suspended in 6M guanidine hydrochloride, 0.15 M sodium chloride-containing 50 mM Tris-HCl buffer (pH 8.0), and the resulting suspension was left to stand at 4° C. for 20 hours to denature proteins. Thereafter, the suspension was centrifuged at 6,000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride, 0.15 M sodium chloride-containing 50 mM Tris-HCl buffer (pH 8.0)), followed by leaving it to stand at 4° C. overnight to allow adsorption to the nickel-chelated carrier. The supernatant was recovered by centrifugation of this column carrier at 1,500 rpm for 5 minutes, and the column carrier was suspended in phosphate-buffered saline, followed by refilling the column with the resulting suspension.

The fraction that was not adsorbed to the column was washed away with 10 column volumes of 0.5 M sodium chloride-containing 0.1 M acetate buffer (pH 4.0), and elution was immediately carried out with 0.5 M sodium chloride-containing 0.1 M acetate buffer (pH 3.0) to obtain a purified fraction, which was used as the material for administration tests thereafter. The proteins of interest in respective eluted fractions were confirmed by Coomassie staining carried out according to a conventional method. Among these, the canine protein of interest is shown in FIG. 2.

The buffer contained in the purified preparation obtained by the above-described method was replaced with a reaction buffer (50 mM Tris-HCl, 100 mM NaCl, 5 mM $CaCl_2$; pH8.0), and cleavage of His tag by Factor Xa protease and purification of the protein of interest were carried out, using FactorXa Cleavage Capture Kit (manufactured by Novagen), in accordance with the protocols attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example A-3

Test of Administration of Recombinant Protein to Cancer-bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 μg (0.5 ml) of the recombinant polypeptides (derived from dog and human), respectively, to prepare two kinds of therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 25 $mm^3$ and 50 $mm^3$ at the time of administration of the therapeutic agents for a cancer(s) (derived from dog and human), respectively, were reduced in size to 20 $mm^3$ and 42 $mm^3$, respectively, 10 days after the first administration; 13 $mm^3$ and 26 $mm^3$, respectively, 20 days after the first administration; and to 5 $mm^3$ and 10 $mm^3$, respectively, 30 days after the first administration.

Further, to a canine patient suffering from malignant melanoma, a mixture of 100 μg (0.5 ml) of the above-described polypeptide derived from dog and 0.5 ml of Freund's incomplete adjuvant was administered intracutaneously at the periphery of the tumor a total of 3 times at the same intervals as described above. Further, concurrently with the respective administrations, 10 MU of "Intercat" which is a recombinant feline interferon was administered subcutaneously. As a result, the tumor with a size of about 142 $mm^3$ at the time of administration of the therapeutic agent for a cancer(s) completely regressed 29 days after the first administration.

Further, to a canine patient suffering from nasal adenocarcinoma, a mixture of 100 μg (0.5 ml) of the above-described polypeptide derived from dog and 0.5 ml of Freund's incomplete adjuvant was administered in the same manner as described above a total of 3 times. Further, concurrently with the respective administrations, 100 μg of canine interleukin 12 was administered subcutaneously. As a result, the tumor with a size of about 57 $mm^3$ at the time of administration of the therapeutic agent for a cancer(s) completely regressed 14 days after the first administration.

(2) Immune Inducibility Assay

Blood from the canine patient in which the anti-tumor effect was obtained in the administration test in the above-described (1) was collected before administration of the therapeutic agent for a cancer(s), and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5 \times 10^5$ cells/well of the canine peripheral blood mononuclear cells suspended in 10% fetal calf serum-containing RPMI medium were placed in the plate, and 10 μL/well of the canine-derived polypeptide or human-derived polypeptide used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-dog polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and the number of the appeared spots was counted using KS ELISPOT (manufactured by Carl Zeiss, Inc.).

As a result, in either canine patient to which the canine polypeptide or the human polypeptide was administered, peripheral blood mononuclear cells sampled before the administration of the polypeptide showed no spots. On the other hand, in the canine patient to which the canine polypeptide was administered, peripheral blood mononuclear cells sampled 10 days and 30 days after the administration showed 20 and 36 spots, respectively. In the canine patient to which the human polypeptide was administered, peripheral blood mononuclear cells sampled 10 days and 30 days after the administration showed 24 and 36 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example B-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from tumor proximal to the anus was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance OD$_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance OD$_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:15 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the calmegin gene. The human homologous factor of the canine calmegin gene was human calmegin (homology: base sequence, 90%; amino acid sequence, 89%). The base sequence of human calmegin is shown in SEQ ID NO:17, and the amino acid sequence thereof is shown in SEQ ID NO:18.

(4) Analysis of Expression in Each Tissue

Figure 3:
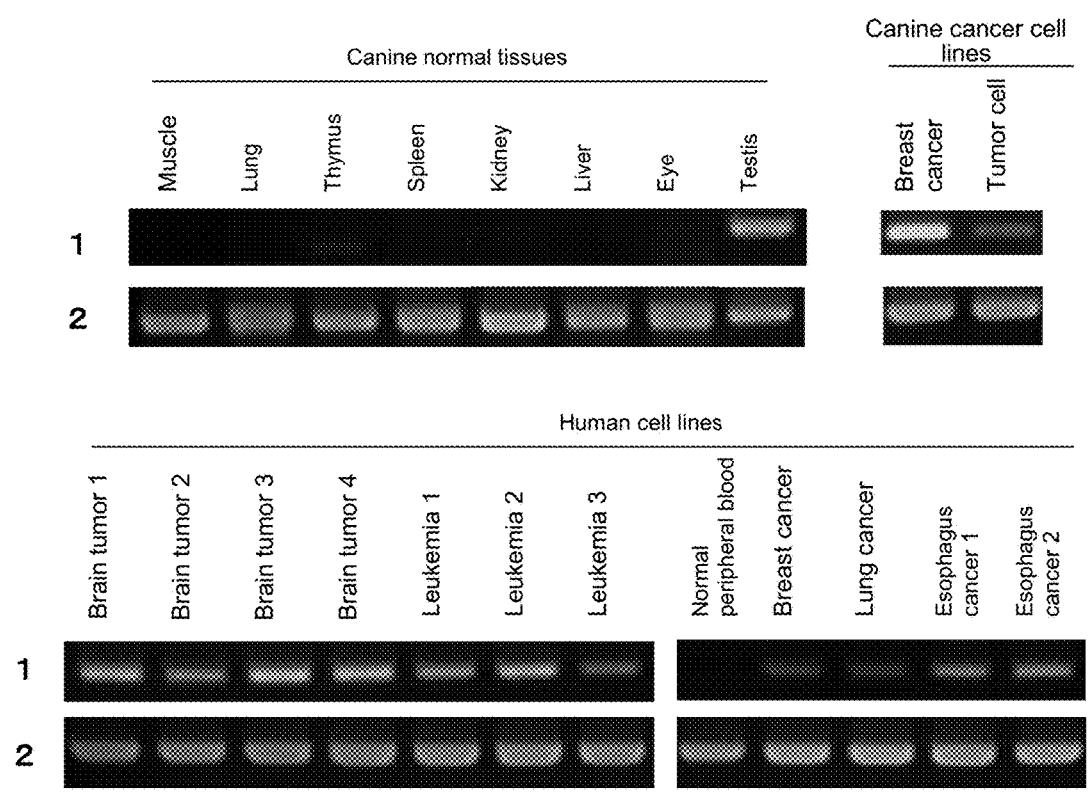
FIG. 3 shows the expression pattern of the calmegin gene identified in the present invention in normal tissues and tumor cell lines. Reference numeral 1: the expression pattern of the calmegin gene; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:19 and 20) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 1 minute using Thermal Cycler (manufactured by BIO RAD). The above-described gene-specific primers were those which amplify the regions of the 755th to 1318th bases of the base sequence of SEQ ID NO:15 (canine calmegin gene) and the 795th to 1358th bases of the base sequence of SEQ ID NO:17 (human calmegin gene), and can be used for investigation of the expression of both the canine calmegin gene and the human calmegin gene. As a control for comparison, primers (described in SEQ ID NOs:9 and 10) specific to GAPDH were used simultaneously. As a result, as shown in FIG. 3, strong expression of the canine calmegin gene was observed in testis among the normal dog tissues, and on the other hand, strong expression was observed in canine tumor cell lines. Expression of the human calmegin gene was confirmed, as is the case with the canine calmegin gene, only in testis among the human normal tissues, but the expression was detected in brain tumor, leukemia and esophagus cancer cells among human cancer cell lines. Thus, the human calmegin gene was also confirmed to be specifically expressed in testis and cancer cells.

In FIG. 3, reference numeral 1 in the ordinate indicates the expression pattern of the calmegin gene, and reference numeral 2 indicates the expression pattern of the GAPDH gene as a control for comparison.

Example B-2

Preparation of Canine and Human Calmegin Proteins (1) Preparation of Recombinant Protein Based on the gene of SEQ ID NO:15 obtained in Example B-1, a recombinant protein was prepared by the following method. Respective reagents and the attached buffer were mixed such that the mixture should contain 1 μl of the vector that was prepared from the phagemid solution obtained in Example B-1 and was subjected to the sequence analysis, 0.4 μM each of two kinds of primers having BamHI and EcoRI restriction sites (described in SEQ ID NOs:21 and 22), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:16. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and EcoRI and purified using QIAquick Gel Extraction Kit, followed by inserting the gene sequence of interest into an expression vector for *E. coli*, pET30a (manufactured by Novagen) that had been treated with BamHI and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO:17, a recombinant protein of the human homologous gene was prepared by the following method. Respective reagents and the attached buffer were mixed such that the mixture should contain 1 µl of the cDNA prepared in Example B-1 whose expression could be confirmed by the RT-PCR method in various tissues/cells, 0.4 µl each of two kinds of primers having EcoRI and XhoI restriction sites (described in SEQ ID NOs:23 and 24), 0.2 mM dNTP and 1.25 U of Prime-STAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:18. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRI and XhoI and purified using QIAquick Gel Extraction Kit, followed by inserting the gene sequence of interest into an expression vector for *E. coli*, pET30a (manufactured by Novagen) that had been treated with EcoRI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:15 and SEQ ID NO:17, respectively, were cultured in 30 µg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in 20 mM phosphate buffer (pH 7.0) and subjected to sonication on ice. The sonicated solution of *E. coli* was centrifuged at 6,000 rpm for 20 minutes to obtain the supernatant as the soluble fraction and the precipitate as the insoluble fraction.

The soluble fraction was placed in an ion-exchange column (carrier: SP Sepharose (trademark) Fast Flow (GE Health Care); column volume: 5 mL; equilibration buffer: 20 mM phosphate buffer (pH 7.0)). The column was washed with 10 column volumes of 20 mM phosphate buffer (pH 7.0), and elution was carried out with density gradient of salt by 0.3 M-1.0 M sodium chloride-containing 20 mM phosphate buffer (pH 7.0). Six column volumes of the eluted fraction was collected in each elution step.

Among these eluted fractions, the 1st to 6th fractions eluted with 0.3 M sodium chloride-containing 20 mM phosphate buffer (pH 7.0) and the 1st fraction eluted with 1.0 M sodium chloride-containing 20 mM phosphate buffer (pH 7.0) were combined, and the resulting solution was subjected to additional purification by a secondary column.

Figure 4:
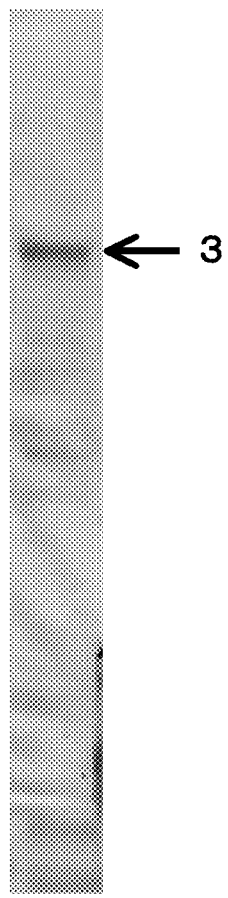
FIG. 4 shows the detection by Coomassie staining of the canine calmegin protein, which is an example of the polypeptide used in the present invention, produced in E. coli and purified in Example B. Reference numeral 3: the band for the canine calmegin protein.

For the secondary column, a column carrier Bio gel HT Type II (BioRad) was used. The column volume was 5 mL. The column was equilibrated with 10 column volumes of 0.3 M sodium chloride-containing 20 mM phosphate buffer (pH 7.0), and the above-described eluted fractions were placed in the column. The fractions that were not adsorbed to the column was washed away with 10 column volumes of 0.3 M sodium chloride-containing 20 mM phosphate buffer (pH 7.0) and 0.1 M phosphate buffer (pH 7.0), and elution was carried out with 0.2 M phosphate buffer (pH 7.0) to obtain a purified fraction, which was used as the material for administration tests thereafter. The proteins of interest in the eluted fractions were confirmed by Coomassie staining carried out according to a conventional method. Among these, the canine calmegin protein is shown in FIG. 4.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example B-3

Test of Administration of Recombinant Protein to Cancer-bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 µg (0.5 ml) of the recombinant canine calmegin and human calmegin proteins, respectively, to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 45 $mm^3$ and 78 $mm^3$, respectively, at the time of administration of the therapeutice agents were reduced to 27 $mm^3$ and 46 $mm^3$, respectively, 10 days after the first administration; 15 mm³ and 26 mm³, respectively, 20 days after the first administration; and to 7 mm³ and 15 mm³, respectively, 30 days after the first administration.

Further, to a canine patient suffering from malignant melanoma, a mixture of 100 µg (0.5 ml) of the above-described canine calmegin protein and 0.5 ml of Freund's incomplete adjuvant was administered a total of 3 times in the same manner as described above. Further, concurrently with the respective administrations, 100 µg of canine interleukin 12 was administered subcutaneously. As a result, the tumor with a size of about 38 mm³ at the time of administration of the therapeutic agent completely regressed 21 days after the first administration of the therapeutic agent.

(2) Immune Inducibility Assay

Blood from the canine patient in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 µl/well of 200 mM Sodium Bicarbonate (pH8.2) was placed therein. After leaving it to stand for 5 minutes, Sodium Bicarbonate was removed by aspiration, and then the plate was washed. Subsequently, 0.5 µg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 µL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 µL/well of 10% fetal calf serum-containing RPMI medium (manufactured by Invitrogen) was placed in the wells, and the plate was left to stand for 5 minutes, followed by removal of the medium by aspiration. Subsequently, 5×10⁵ cells/well of the canine peripheral blood mononuclear cells suspended in 10% fetal calf serum-containing RPMI medium were placed in the plate, and 10 µL/well of the canine calmegin or human calmegin protein used in each administration was added thereto, followed by culturing the cells under the conditions of 37° C. and 5% CO₂ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 µL of rabbit anti-dog polyclonal antibody 1000-fold diluted with the above-described blocking solution was placed, and the resulting mixture was incubated at 4° C. overnight. After washing the wells 3 times with the above-described washing solution, 100 µL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which canine calmegin or human calmegin was administered, peripheral blood mononuclear cells sampled before the administration showed no spots. On the other hand, in the canine patient to which canine calmegin was administered, peripheral blood mononuclear cells sampled 10 days and 30 days after the administration showed 15 and 45 spots, respectively. In the canine patient to which human calmegin was administered, peripheral blood mononuclear cells sampled 10 days and 30 days after the administration showed 12 and 39 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example C-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 µg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was 1.3×10⁶ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M NaHCO₃, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 µl of SM buffer (100 mM NaCl, 10 mM MgClSO₄, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host *E. coli* (XL1-Blue MRF') such that the absorbance OD$_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 µl of a solution prepared to contain a phagemid host *E. coli* (SOLR) such that the absorbance OD$_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:25 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene has 99% homology (which was calculated only in the overlapping region) to the CEP gene described in SEQ ID NO:27 in terms of base sequence and amino acid sequence, so that the gene was judged as the CEP gene. The human homologous factor of the canine CEP was human CEP (homology to the CEP gene described in SEQ ID NO:25: base sequence, 87%; amino acid sequence, 84%). The base sequence of human CEP is shown in SEQ ID NO:29, and the amino acid sequence thereof is shown in SEQ ID NO:30.

(4) Analysis of Expression in Each Tissue

Figure 5:
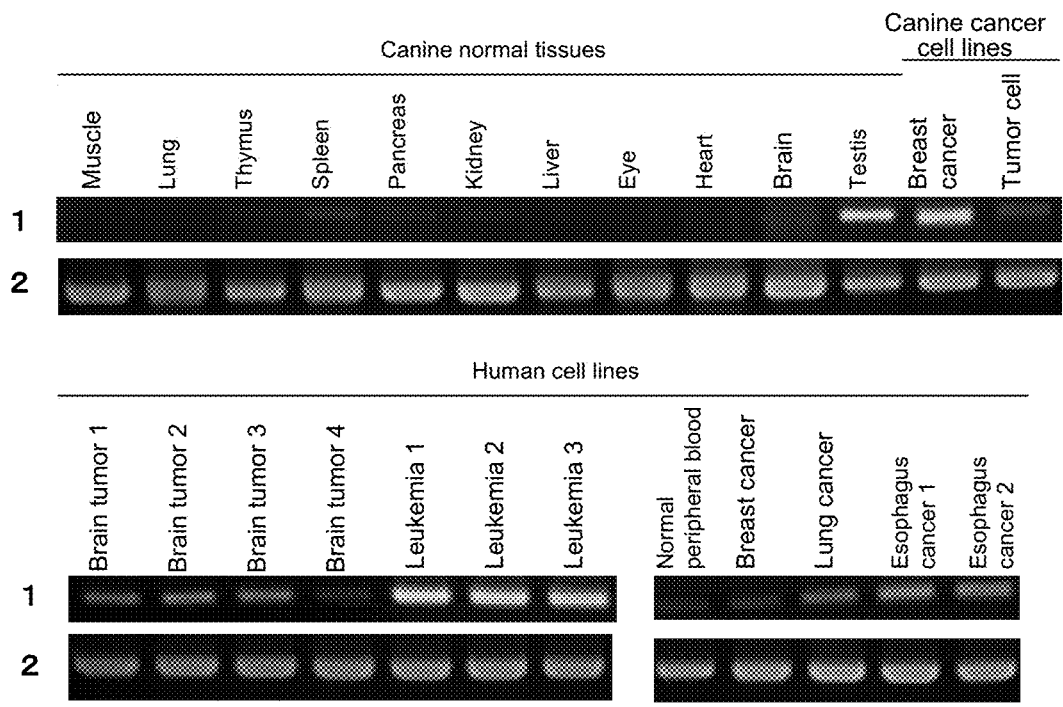
FIG. 5 shows the expression pattern of the gene encoding the CEP protein in normal tissues and tumor cell lines. Reference numeral 1: the expression pattern of the gene encoding the CEP protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10⁶ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:31 and 32) specific to the obtained gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 30 seconds using Thermal Cycler (manufactured by BIO RAD). The above-described gene-specific primers were those which amplify the regions of the 4582nd to 5124th bases of the base sequences of SEQ ID NOs:25 and 27 (canine CEP gene) and the 4610th to 5152nd bases of the base sequence of SEQ ID NO:29 (human CEP gene), and can be used for investigation of the expression of both the canine CEP gene and the human CEP gene. As a control for comparison, primers (described in SEQ ID NOs:9 and 10) specific to GAPDH were used simultaneously. As a result, as shown in FIG. 5, strong expression of the canine CEP gene was observed in testis among the normal dog tissues, and on the other hand, strong expression was observed in the canine breast cancer cell line. Expression of the human CEP gene was confirmed, as is the case with the canine CEP gene, only in testis among the human normal tissues, but the expression was detected in brain tumor, leukemia and esophagus cancer cells among human cancer cell lines, and especially, strong expression was observed in the leukemia cell line. Thus, the human CEP gene was also confirmed to be specifically expressed in testis and cancer cells.

In FIG. 5, reference numeral 1 in the ordinate indicates the expression pattern of the CEP gene, and reference numeral 2 indicates the expression pattern of the GAPDH gene as a control for comparison.

Example C-2

Preparation of Canine and Human CEPs (1) Preparation of Recombinant Protein

Based on the gene of SEQ ID NO:25 obtained in Example C-1, a recombinant protein was prepared by the following method. Respective reagents and the attached buffer were mixed such that the mixture should contain 1 µl of the vector that was prepared from the phagemid solution obtained in Example C-1 and was subjected to the sequence analysis, 0.4 µM each of two kinds of primers having BamHI and SalI restriction sites (described in SEQ ID NOs:33 and 34), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:26. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG. In the same manner, based on the gene of SEQ ID NO:27, using the canine testis cDNA as a template and two kinds of primers having BamHI and SalI restriction sites (SEQ ID NOs:33 and 35), a recombinant protein of the registered canine CEP gene was prepared. The above-described two kinds of primers were those which amplify the region of about 7.8 kbp encoding the entire amino acid sequence of SEQ ID NO:28.

Further, based on the gene of SEQ ID NO:29, a recombinant protein of the human homologous gene was prepared by the following method. Respective reagents and the attached buffer were mixed such that the mixture should contain 1 µl of the cDNA prepared in Example C-1 whose expression could be confirmed by the RT-PCR method in various tissues/cells, 0.4 µM each of two kinds of primers having BamHI and SalI restriction sites (described in SEQ ID NOs:36 and 37), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:30. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:25, SEQ ID NO:27, and SEQ ID NO:29, respectively, were cultured in 30 µg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7000 rpm for 20 minutes to obtain the supernatant as the soluble fraction and the precipitate as the insoluble fraction. The insoluble fraction was suspended in 4% Triton X-100 solution and the resulting suspension was centrifuged at 7000 rpm for 20 minutes. This operation was repeated twice and an operation of removal of proteases was carried out. The residue was suspended in 8 M urea-containing 10 mM Tris-HCl, 100 mM phosphate buffer (hereinafter referred to as 8 M urea solution) and a protease inhibitor cocktail solution, and the resulting suspension was left to stand at 4° C. for 20 hours to denature proteins.

Figure 6:
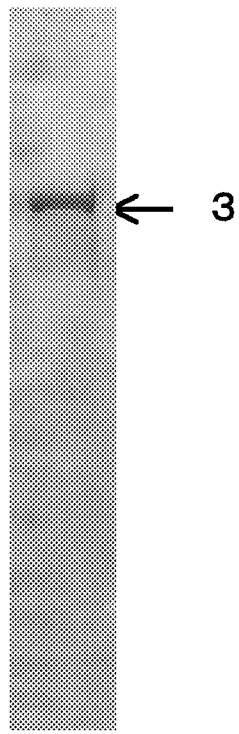
FIG. 6 shows the detection by Coomassie staining of the canine CEP of SEQ ID NO:26, which is an example of the polypeptide used in the present invention, produced in E. coli and purified in Example C. Reference numeral 3: the band for the canine CEP protein.

Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 8M urea solution), followed by leaving it to stand at 4° C. overnight. The supernatant was recovered by centrifugation of this column carrier at 1,500 rpm for 5 minutes, and the column carrier was suspended in phosphate-buffered saline, followed by refilling the column with the resulting suspension. The fraction that was not adsorbed to the column was washed away with 5 column volumes of 8 M urea solution, 10 column volumes of 0.5 M sodium chloride-containing 0.1 M acetate buffer (pH 5.0) and 10 mM imidazole-containing 20 mM phosphate buffer (pH 8.0), and elution was immediately carried out with a five-step density gradient of 100 mM-500 mM imidazole to obtain a purified fraction, which was used as the material for administration tests thereafter. The proteins of interest in respective eluted fractions were confirmed by Coomassie staining carried out according to a conventional method. Among these, the recombinant canine CEP described in SEQ ID NO:26 is shown in FIG. 6.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example C-3

Test of Administration of Recombinant Protein to Cancer-bearing Dogs (1) Antitumor Assay The anti-tumor effect of the two kinds of recombinant proteins which were purified as described above was assessed in two individuals of cancer-bearing dogs having epidermal tumor (2 individuals having perianal adenoma).

An equal amount of Freund's incomplete adjuvant (manufactured by Wako Pure Chemicals) was mixed with 100 µg (0.5 ml) each of the recombinant canine CEP described in SEQ ID NO:26 and human CEP purified as described above to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 87 mm$^3$ and 69 mm$^3$ at the time of administration of the therapeutic agents, respectively, were reduced to 69 mm$^3$ and 56 mm$^3$, respectively, 10 days after the first administration; 24 mm$^3$ and 31 mm$^3$, respectively, 20 days after the first administration; and to 10 mm$^3$ and 8 mm$^3$, respectively, 30 days after the first administration of the therapeutic agent.

Further, to a canine patient suffering from mammary adenocarcinoma, a mixture of 100 µg (0.5 ml) of the canine CEP protein described in SEQ ID NO:26 with 0.5 ml of Freund's incomplete adjuvant was administered a total of 3 times in the same manner as described above. Further, concurrently with the respective administrations, 10 MU of "Intercat" which is a recombinant feline interferon was administered subcutaneously. As a result, the tumor with a size of about 126 mm$^3$ at the time of administration of the therapeutic agent completely regressed 26 days after the first administration of the therapeutic agent. Similarly, in the case where the canine CEP described in SEQ ID NO:28 was used, an anti-tumor effect was also observed in a cancer-bearing dog.

Further, to a canine patient of mastocytoma, a mixture of 100 µg (0.5 ml) of the canine CEP protein described in SEQ ID NO:26 with 0.5 ml of Freund's incomplete adjuvant was administered a total of 3 times in the same manner as described above. Further, concurrently with the respective administrations, 100 µg of canine interleukin-12 was subcutaneously administered. As a result, the tumor with a size of about 83 mm$^3$ at the time of administration of the therapeutic agent completely regressed 18 days after the first administration of the therapeutic agent.

(2) Immune Inducibility Assay

Blood from the canine patient suffering from perianal adenoma in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 µl/well of 200 mM Sodium Bicarbonate (pH8.2) was placed therein. After leaving it to stand for 5 minutes, Sodium Bicarbonate was removed by aspiration, and then the plate was washed. Subsequently, 0.5 µl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 µL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 µL/well of 10% fetal calf serum-containing RPMI medium (manufactured by Invitrogen) was placed in the wells, and the plate was left to stand for 5 minutes, followed by removal of the medium by aspiration. Subsequently, 5×10$^5$ cells/well of the canine peripheral blood mononuclear cells suspended in 10% fetal calf serum-containing RPMI medium were placed in the plate, and 10 µL/well of the canine CEP described in SEQ ID NO:26 or the human CEP used in each administration was added thereto, followed by culturing the cells under the conditions of 37° C. and 5% CO$_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 µL of rabbit anti-canine polyclonal antibody 1000-fold diluted with the above-described blocking solution was placed, and the plate was incubated at 4° C. overnight. After washing the wells 3 times with the above-described washing solution, 100 µL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine CEP described in SEQ ID NO: 26 or the human CEP was administered, peripheral blood mononuclear cells sampled before the administration showed no spots. On the other hand, in the canine patient to which the canine CEP was administered, peripheral blood mononuclear cells sampled 10 days and 30 days after the administration showed 23 and 52 spots, respectively. In the canine patient to which the human CEP was administered, peripheral blood mononuclear cells sampled 10 days and 30 days after the administration showed 19 and 49 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example D-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host E. coli cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host E. coli cells (XL1-Blue MRF') were infected with λ ZAP Express phage to which no foreign gene was inserted, and then cultured on NZY plate medium at 37° C. overnight. Subsequently, the buffer of 0.2 M NaHCO$_3$, pH 8.3 containing 0.5 M NaCl was added to the plate, and the plate was left to stand at 4° C. for 15 hours, followed by collecting the supernatant as an E. coli/phage extract. Thereafter, the collected E. coli/phage extract was allowed to flow through an NHS column (manufactured by GE Healthcare Bio-Science) to immobilize proteins derived from the E. coli/phage thereon. The serum from the canine patients was allowed to flow through and react with this protein-immobilized column to remove antibodies adsorbed on E. coli and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host E. coli (XL1-Blue MRF') such that the absorbance OD$_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host E. coli (SOLR) such that the absorbance OD$_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:38 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the TRIP11 gene. The human homologous factor of canine TRIP11 was human TRIP11 (homology: base sequence, 88%; amino acid sequence, 86%). The base sequence of human TRIP11 is shown in SEQ ID NO:40, and the amino acid sequence thereof is shown in SEQ ID NO:41.

(4) Analysis of Expression in Each Tissue

Figure 7:
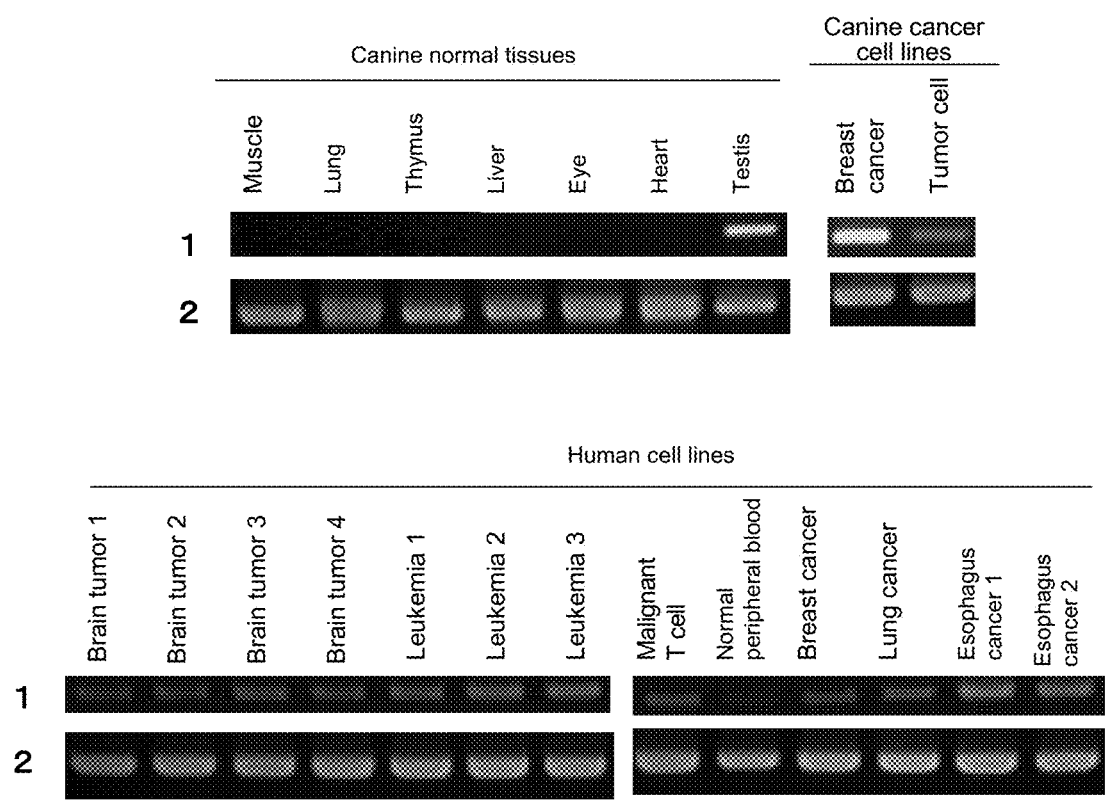
FIG. 7 shows the expression pattern of the gene encoding the TRIP11 protein in normal tissues and tumor cell lines. Reference numeral 1: the expression pattern of the gene encoding the TRIP11 protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10 \times 10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:42 and 43) specific to the obtained gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 1.5 minutes using Thermal Cycler (manufactured by BIO RAD). The above-described gene-specific primers were those which amplify the regions of the 1519th to 2957th bases of the base sequence of SEQ ID NO:38 (canine TRIP11 gene) and the 1872nd to 3310th bases of the base sequence of SEQ ID NO:40 (human TRIP11 gene), and can be used for investigation of the expression of both the canine TRIP11 gene and the human TRIP11 gene. As a control for comparison, primers (described in SEQ ID NOs:9 and 10) specific to GAPDH were used simultaneously. As a result, as shown in FIG. 7, strong expression of the canine TRIP11 gene was observed in testis among the normal dog tissues, and on the other hand, strong expression was observed in the canine breast cancer cell line. Expression of the human gene was confirmed, as is the case with the canine TRIP11 gene, only in testis among the human normal tissues, but the expression was detected in many types of cancer cell lines such as brain tumor, leukemia, breast cancer, lung cancer and esophagus cancer cell lines among human cancer cell lines. Thus, the human TRIP11 gene was also confirmed to be specifically expressed in testis and cancer cells.

In FIG. 7, reference numeral 1 in the ordinate indicates the expression pattern of the TRIP11 gene, and reference numeral 2 indicates the expression pattern of the GAPDH gene as a control for comparison.

Example D-2

Preparation of Canine and Human TRIP11 Proteins (1) Preparation of Recombinant Protein Based on the gene of SEQ ID NO:38 obtained in Example D-1, a recombinant protein was prepared by the following method. NO: Respective reagents and the attached buffer were mixed such that the mixture should contain 1 µl of the vector which was prepared from the phagemid solution obtained in Example D-1 and was subjected to the sequence analysis, 0.4 µM each of two kinds of primers having SalI and XhoI restriction sites (described in SEQ ID NOs:44 and 45), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:39. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). E. coli was transformed with the resulting ligation product, and plasmids were recovered thereafter, followed by confirming, by sequencing, that the amplified gene fragment matches the sequence of interest. The plasmid that matched the sequence of interest was treated with restriction enzymes SalI and XhoI and purified using QIAquick Gel Extraction Kit, followed by inserting the gene sequence of interest into an expression vector for E. coli, pET30b (manufactured by Novagen) that had been treated with SalI and XhoI. Usage of this vector enables production of a His-tag fusion recombinant protein. E. coli for expression, BL21 (DE3), was transformed with this plasmid, and expression of the protein of interest was induced in E. coli with 1 mM IPTG.

Further, based on the gene of SEQ ID NO:40, a recombinant protein of the human homologous gene was prepared by the following method. Respective reagents and the attached buffer were mixed such that the mixture should contain 1 µl of the cDNA prepared in Example D-1 whose expression could be confirmed by the RT-PCR method in various tissues/cells, 0.4 µM each of two kinds of primers having NdeI and KpnI restriction sites (described in SEQ ID NOs:46 and 47), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:41. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). E. coli was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and KpnI and purified using QIAquick Gel Extraction Kit, followed by inserting the gene sequence of interest into an expression vector for E. coli, pET30b (manufactured by Novagen) that had been treated with NdeI and KpnI. Usage of this vector enables production of a His-tag fusion recombinant protein. E. coli for expression, BL21 (DE3), was transformed with this plasmid, and expression of the protein of interest was induced in E. coli with 1 mM IPTG.

(2) Purification of Recombinant Proteins

The above-obtained recombinant E. coli cells that expressed SEQ ID NO:38 and SEQ ID NO:40, respectively, were cultured in 30 µg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of E. coli cells was suspended in phosphate-buffered saline and subjected to sonication on ice. The sonicated solution of E. coli was centrifuged at 7,000 rpm for 15 minutes to obtain the supernatant as the soluble fraction and the precipitate as the insoluble fraction.

The insoluble fraction was suspended in 4% Triton X-100 solution and the resulting suspension was centrifuged at 7,000 rpm for 10 minutes. This operation was repeated twice and an operation of removal of proteases was carried out. Thereafter, the residue was suspended in phosphate-buffered saline and an operation of removal of the surfactant was carried out.

Figure 8:
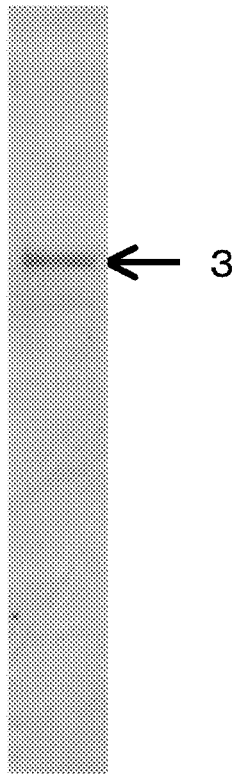
FIG. 8 shows the detection by Coomassie staining of the canine TRIP11 protein, which is one of the polypeptides used in the present invention, produced in E. coli and purified in Example D. Reference numeral 3: the band for the canine TRIP11 protein.

The residue was suspended in 6M guanidine hydrochloride-containing 20 mM phosphate buffer (pH 8.0), and the resulting suspension was left to stand at 4° C. for 20 hours to denature proteins. Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride-containing 20 mM phosphate buffer (pH 8.0)). The fraction that was not adsorbed to the column was washed away with 10 column volumes of 6 M sodium chloride-containing 20 mM phosphate buffer (pH 8.0) and 10 mM imidazole-containing 20 mM phosphate buffer (pH 8.0), and elution was immediately carried out with a four-step density gradient of 50 mM-500 mM imidazole to obtain a purified fraction, which was used as the material for administration tests thereafter. The proteins of interest in the eluted fractions were confirmed by Coomassie staining carried out according to a conventional method. Among these, the canine TRIP11 protein is shown in FIG. 8.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example D-3

Test of Administration of Recombinant Protein to Cancer-bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

Therapeutic agents for a cancer(s) were prepared by mixing 0.5 ml of Freund's incomplete adjuvant (manufactured by Wako Pure Chemicals) with 100 µg (0.5 ml) of the recombinant canine TRIP11 and human TRIP11 proteins, respectively, purified as described above. Each of these agents was administered to a regional lymph node in the vicinity of the tumor a total of 3 times, by carrying out the subsequent administrations 3 days and 7 days after the first administration. As a result, the tumors with a size of about 75 $mm^3$ and 102 $mm^3$, respectively, at the time of administration of the therapeutic agents were reduced to 63 $mm^3$ and 85 $mm^3$, respectively, 10 days after the first administration; 35 $mm^3$ and 42 $mm^3$, respectively, 20 days after the first administration; and to 15 $mm^3$ and 19 $mm^3$, respectively, 30 days after the first administration of the therapeutic agent for a cancer(s).

Further, to a canine patient suffering from mastocytoma, a mixture of 100 µg (0.5 ml) of the canine TRP11 protein with 0.5 ml of Freund's incomplete adjuvant was administered a total of 3 times in the same manner as described above. Concurrently with the respective administrations, 100 µg of canine interleukin-12 was subcutaneously administered. As a result, the tumor with a size of about 165 $mm^3$ at the time of administration of the therapeutic agent completely regressed 23 days after the first administration of the therapeutic agent.

(2) Immune Inducibility Assay

Blood from the canine patient suffering from mammary gland tumor in which the anti-tumor effect was obtained in the administration test in the above-described (1) was collected. Peripheral blood mononuclear cells were isolated according to a conventional method, and by the ELISPOT assay for IFNγ using it, the immune inducibility of each administered protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 µl/well of 200 mM Sodium Bicarbonate (pH8.2) was placed therein. After leaving it to stand for 5 minutes, Sodium Bicarbonate was removed by aspiration, and then the plate was washed. Subsequently, 0.5 µg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 µL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 µL/well of 10% fetal calf serum-containing RPMI medium (manufactured by Invitrogen) was placed in the wells and the plate was left to stand for 5 minutes, followed by removal of the medium by aspiration. Subsequently, $5 \times 10^5$ cells/well of the canine peripheral blood mononuclear cells suspended in 10% fetal calf serum-containing RPMI medium were placed in the plate, and 10 µL/well of the canine TRIP11 or the human TRIP11 protein used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 µL of rabbit anti-dog polyclonal antibody 1000-fold diluted with the above-described blocking solution was placed, and the plate was incubated at 4° C. overnight. After washing the wells 3 times with the above-described washing solution, 100 µL of HRP-labeled anti-rabbit antibody 1,000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine TRIP11 protein or the human TRIP11 protein was administered, peripheral blood mononuclear cells sampled before the administration showed no spots. On the other hand, in the canine patient to which the canine TRIP11 was administered, peripheral blood mononuclear cells sampled 10 days and 30 days after the administration showed 26 and 65 spots, respectively. In the canine patient to which the human TRIP11 was administered, peripheral blood mononuclear cells sampled 10 days and 30 days after the administration showed 31 and 72 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in the above-described (1) was exerted by immunoreactions in which these immunocytes are mainly involved.

The invention claimed is:

1. A method for exerting an anti-tumor effect, said method comprising administering an effective amount of any one of the polypeptides (a) to (b) below to an individual having a cancer, said polypeptide having an immunity-inducing activity:
   (a) a polypeptide comprising the amino acid sequence shown in SEQ ID NO: 39 or 41; and
   (b) a polypeptide having a homology of not less than 90% to the polypeptide (a);
   wherein said cancer is a thyroid hormone receptor interactor 11-expressing cancer.

2. A method for exerting an anti-tumor effect, said method comprising administering an effective amount of a recombinant vector which comprises a polynucleotide encoding an immunity-inducing polypeptide selected from any one of the polypeptides (a) to (b) below, said recombinant vector being capable of expressing said polypeptide in vivo:
   (a) a polypeptide comprising the amino acid sequence shown in SEQ ID NO: 39 or 41; and
   (b) a polypeptide having a homology of not less than 90% to the polypeptide (a);
   wherein said cancer is a thyroid hormone receptor interactor 11-expressing cancer.

3. The method according to claim 1, wherein said polypeptide (b) has a homology of not less than 95% to said polypeptide (a).

4. The method according to claim 1, wherein said polypeptide having an immunity-inducing activity has the amino acid sequence shown in SEQ ID NO: 39 or 41.

5. The method according to claim 1, which is a method of therapy for the cancer.

6. The method according to claim 5, wherein said individual is a human, a dog or a cat.

7. The method according to claim 5, further comprising administering an immunoenhancer.

8. The method according to claim 7, wherein said immunoenhancer is at least one selected from the group consisting of Freund's incomplete adjuvant; Montanide; poly I:C and derivatives thereof; CpG oligonucleotides; interleukin-12; interleukin-18; interferon-α; interferon-β; interferon-ω; interferon-γ; and Flt3 ligand.

9. The method according to claim 2, wherein said polypeptide (b) has a homology of not less than 95% to said polypeptide (a).

10. The method according to claim 2, wherein said polypeptide having an immunity-inducing activity has the amino acid sequence shown in SEQ ID NO: 39 or 41.

11. The method according to claim 2, which is a method of therapy of the cancer.

12. The method according to claim 11, wherein said individual is a human, a dog or a cat.

13. The method according to claim 11, further comprising administering an immunoenhancer.

14. The method according to claim 13, wherein said immunoenhancer is at least one selected from the group consisting of Freund's incomplete adjuvant; Montanide; poly I:C and derivatives thereof; CpG oligonucleotides; interleukin-12; interleukin-18; interferon-α; interferon-β; interferon-ω; interferon-γ; and Flt3 ligand.

* * * * *